US012528800B2

(12) United States Patent
Maity et al.

(10) Patent No.: US 12,528,800 B2
(45) Date of Patent: Jan. 20, 2026

(54) PESTICIDAL COMPOUNDS

(71) Applicant: BASF SE, Ludwigshafen (DE)

(72) Inventors: Pulakesh Maity, Navi Mumbai (IN); Arun Narine, Ludwigshafen (DE); Rupsha Chaudhuri, Navi Mumbai (IN); Sunderraman Sambasivan, Mumbai (IN); Ashokkumar Adisechan, Navi Mumbai (IN); Rizwan Shabbir Shaikh, Navi Mumbai (IN); Devendra Vyas, Research Triangle Park, NC (US)

(73) Assignee: BASF SE, Ludwigshafen (DE)

( * ) Notice: Subject to any disclaimer, the term of this patent is extended or adjusted under 35 U.S.C. 154(b) by 1101 days.

(21) Appl. No.: 17/283,293

(22) PCT Filed: Oct. 17, 2019

(86) PCT No.: PCT/EP2019/078163
§ 371 (c)(1),
(2) Date: Apr. 7, 2021

(87) PCT Pub. No.: WO2020/083733
PCT Pub. Date: Apr. 30, 2020

(65) Prior Publication Data

US 2021/0395243 A1 Dec. 23, 2021

(30) Foreign Application Priority Data

Oct. 24, 2018 (EP) .................................... 18202182

(51) Int. Cl.

| | |
|---|---|
| ***C07D 417/12*** | (2006.01) |
| ***A01N 43/78*** | (2006.01) |
| ***A01N 47/34*** | (2006.01) |
| ***C07D 231/20*** | (2006.01) |
| ***C07D 231/40*** | (2006.01) |
| ***C07H 15/26*** | (2006.01) |

(52) U.S. Cl.
CPC ........... *C07D 417/12* (2013.01); *A01N 43/78* (2013.01); *A01N 47/34* (2013.01); *C07D 231/20* (2013.01); *C07D 231/40* (2013.01); *C07H 15/26* (2013.01)

(58) Field of Classification Search
None
See application file for complete search history.

(56) References Cited

U.S. PATENT DOCUMENTS 11,160,280 B2 * 11/2021 Narine .................. A01N 47/18
2017/0066756 A1 * 3/2017 Giampietro ............ A01N 47/36

FOREIGN PATENT DOCUMENTS

WO WO-2006/033943 A2 3/2006
WO WO-2007/107758 A1 9/2007
WO WO-2016/116445 A1 7/2016
WO WO-2016/156076 A1 10/2016
WO WO-2017/040060 A1 3/2017
WO WO-2018/177781 A1 10/2018

OTHER PUBLICATIONS

Database Registry [Online], Chemical Abstracts Service, retrieved from STN Database accession No. 1114868-16-4, XP002788235, Mar. 3, 2009, 1 page.
Database Registry [Online], Chemical Abstracts Service, retrieved from STN Database accession No. 1114914-36-1, XP002788234, Mar. 3, 2009, 1 page.
Database Registry [Online], Chemical Abstracts Service, retrieved from STN Database accession No. 1115250-50-4, XP002788233, Mar. 4, 2009, 1 page.
European Search Report for EP Patent Application No. 18202182.4, Issued on Feb. 7, 2019, 4 pages.
International Application No. PCT/EP2019/078163, International Search Report and Written Opinion, mailed Dec. 10, 2019.

* cited by examiner

*Primary Examiner* — Erin E Hirt
(74) *Attorney, Agent, or Firm* — MARSHALL, GERSTEIN & BORUN LLP

(57) ABSTRACT

The present invention relates to the compounds of formula (I), and the N-oxides, stereoisomers, tautomers and agriculturally or veterinarily acceptable salts thereof wherein the variables are defined according to the description, (I) The compounds of formula (I), as well as the N-oxides, stereoisomers, tautomers and agriculturally or veterinarily acceptable salts thereof, are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

(I)

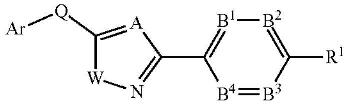

13 Claims, No Drawings

PESTICIDAL COMPOUNDS

CROSS-REFERENCE TO RELATED APPLICATIONS

This is the U.S. national phase of International Application No. PCT/EP2019/078163, filed Oct. 17, 2019, which claims the benefit of European Patent Application No. 18202182.4, filed on Oct. 24, 2018.

Invertebrate pests and in particular insects, arachnids and nematodes destroy growing and harvested crops and attack wooden dwelling and commercial structures, thereby causing large economic loss to the food supply and to property. Accordingly, there is an ongoing need for new agents for combating invertebrate pests.

Carbamoylated and thiocarbamoylated oxime derivatives are known for pesticidal use, for example, in patent publications WO 2016/156076, semi-carbazones and thiosemicarbazones derivatives are known for pesticidal use in patent publication WO 2016/116445.

Due to the ability of target pests to develop resistance to pesticidally-active agents, there is an ongoing need to identify further compounds, which are suitable for combating invertebrate pests such as insects, arachnids and nematodes. Furthermore, there is a need for new compounds having a high pesticidal activity and showing a broad activity spectrum against a large number of different invertebrate pests, especially against difficult to control insects, arachnids and nematodes.

It is therefore an object of the present invention to identify and provide compounds, which exhibit a high pesticidal activity and have a broad activity spectrum against invertebrate pests.

It has been found that these objects can be achieved by substituted bicyclic compounds of formula I, as depicted and defined below, including their stereoisomers, their salts, in particular their agriculturally or veterinarily acceptable salts, their tautomers and their N-oxides.

In a first aspect, the present invention relates to the compounds of formula I, (I)

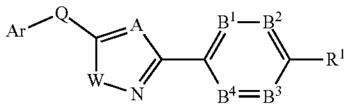

wherein

A is N or $CR^{A}$;

$B^1$ is N or $CR^{B1}$;

$B^2$ is N or $CR^{B2}$;

$B^3$ is N or $CR^{B3}$;

$B^4$ is N or $CR^{B4}$;

W is O, $S(=O)_m$, or $NR^6$;

$R^A$ is H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, $C(=O)—OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, $C(=O)—NR^bR^c$, $C(=O)—R^d$, $SO_2NR^bR^c$, or $S(=O)_mR^e$, phenyl, phenoxy, phenylcarbonyl, phenylthio, or —$CH_2$-phenyl, wherein the phenyl rings are unsubstituted or substituted with $R^f$;

$R^{B1}$, $R^{B2}$, $R^{B3}$, and $R^{B4}$ independently of each other are H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, $C(=O)—OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, $C(=O)—NR^bR^c$, $C(=O)—R^d$, $SO_2NR^bR^c$, or $S(=O)_mR^e$, phenyl, phenoxy, phenylcarbonyl, phenylthio, or —$CH_2$-phenyl, wherein the phenyl rings are unsubstituted or substituted with $R^f$;

Q is —$C(R^4R^5)$—O—, —C(=O)—O—, —$S(=O)_m$—$C(R^7R^8)$—, —$N(R^2)$—$S(=O)_m$—, —$N(R^2)$—$C(R^9R^{10})$—, —C(=O)—$C(R^{19}R^{20})$—, —$N(R^2)$—C(=O)—, —$N(R^2)$—C(=S)—, —$C(R^{13}R^{14})$—$C(R^{15}R^{16})$—, —N=C(X)—, or —$N(R^2)$—C(=NR)—; wherein Ar is bound to either side of Q;

m is 0, 1, or 2;

X is H, halogen, $SR^7$, $OR^8$, or $N(R^3)_2$;

R is H, CN, $C_1$-$C_6$-alkyl, $C_2$-$C_6$-alkenyl, $C_2$-$C_6$-alkynyl, or $C_3$-$C_6$-cycloalkyl, wherein the alkyl, alkenyl, and cycloalkyl moieties are unsubstituted or substituted with halogen, $OR^8$, $N(R^3)_2$;

$R^3$ is H, $C_1$-$C_6$-alkyl, $C_1$-$C_6$-alkoxy-$C_1$-$C_4$-alkyl;

$R^2$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $C(=O)—OR^a$, $C_1$-$C_6$-alkylene-$NR^bR^c$, $C_1$-$C_6$-alkylene-CN, $C(=O)—NR^bR^c$, $C(=O)—R^d$, $SO_2NR^bR^c$, $S(=O)_mR^e$, phenyl, or —$CH_2$-phenyl, wherein the phenyl rings are unsubstituted or substituted with $R^f$;

$R^4$, $R^5$, $R^7$, $R^8$, $R^9$, $R^{10}$, $R^{13}$, $R^{14}$, $R^{15}$, $R^{16}$, $R^{19}$, $R^{20}$ are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $C(=O)—OR^a$, $C_1$-$C_6$-alkylene-$NR^bR^c$, $C_1$-$C_6$-alkylene-CN, $C(=O)—NR^bR^c$, $C(=O)—R^d$, $SO_2NR^bR^c$, $S(=O)_mR^e$, phenyl, or —$CH_2$-phenyl, wherein the phenyl rings are unsubstituted or substituted with $R^f$;

$R^6$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $C(=O)—OR^a$, $C_1$-$C_6$-alkylene-$NR^bR^c$, $C_1$-$C_6$-alkylene-CN, $C(=O)—NR^bR^c$, $C(=O)—R^d$, $SO_2NR^bR^c$, $S(=O)_mR^e$, phenyl, —$CH_2$—C(=O)—$OR^a$, or —$CH_2$-phenyl, wherein the phenyl rings are unsubstituted or substituted with $R^f$;

Ar is phenyl or 5- or 6-membered hetaryl, which are unsubstituted or substituted with $R^{Ar}$, wherein $R^{Ar}$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$, phenyl, phenoxy, phenylcarbonyl, phenylthio or —$CH_2$-phenyl, wherein phenyl rings are unsubstituted or substituted with $R^f$;

$R^1$ is a moiety of formula Y—Z-T-$R^{11}$ or Y—Z-T-$R^{12}$; wherein

Y is —$CR^{ya}$═N—, wherein the N is bound to Z;

—$NR^{yc}$—C(═O)—, wherein C(═O) is bound to Z; or

—$NR^{yc}$—C(═S)—, wherein C(═S) is bound to Z;

Z is a single bond;

—$NR^{zc}$—C(═O)—, wherein C(═O) is bound to T;

—$NR^{zc}$—C(═S)—, wherein C(═S) is bound to T;

—N═C(S—$R^{za}$)—, wherein T is bound to the carbon atom;

—O—C(═O)—, wherein T is bound to the carbon atom; or

—$NR^{zc}$—C(S—$R^{za}$)═, wherein T is bound to the carbon atom;

wherein if Y is other than —$CR^{ya}$═N—, Z is other than —N═C(S—$R^{za}$)—;

T is O, N or N—$R^T$;

$R^{11}$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, $C_1$-$C_6$-alkylene-$NR^bR^c$, $C_1$-$C_6$-alkylene-CN, C(═O)—$NR^bR^c$, C(═O)—$R^d$, aryl, aryl-carbonyl, aryl-$C_1$-$C_4$-alkyl, aryloxy-$C_1$-$C_4$-alkyl, hetaryl, carbonyl-hetaryl, hetaryl-$C_1$-$C_4$-alkyl or hetaryloxy-$C_1$-$C_4$-alkyl, wherein the phenyl rings are unsubstituted or substituted with $R^g$ and wherein the hetaryl is a 5- or 6-membered monocyclic hetaryl or a 8-, 9- or 10-membered bicyclic hetaryl;

$R^{12}$ is a radical of the formula $A^1$;

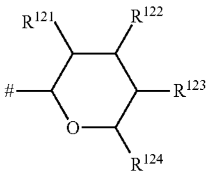

($A^1$)

wherein # indicates the point of attachment to T;

$R^{121}$, $R^{122}$, $R^{123}$ are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy, $C_2$-$C_6$-alkenyloxy, $C_2$-$C_6$-alkynyloxy, $C_1$-$C_6$-alkoxy-$C_1$-$C_4$-alkoxy, $C_1$-$C_6$-alkylcarbonlyoxy, $C_1$-$C_6$-alkenylcarbonlyoxy, $C_3$-$C_6$-cycloalkylcarbonlyoxy, wherein the alkyl, alkoxy, alkenyl, alkenyloxy, alkynyl, alkynyloxy and cycloalkyl moieties are unsubstituted or substituted with halogen, or $NR^bR^c$, or one of $R^{121}$, $R^{122}$, $R^{123}$ may also be oxo;

$R^{124}$ is H, $C_1$-$C_6$-alkyl, $C_1$-$C_6$-alkoxy-$C_1$-$C_4$-alkyl, $C_1$-$C_6$-alkoxy, or $C_2$-$C_6$-alkenyloxy, wherein the alkyl, alkoxy, alkenyl and alkenyloxy moieties are unsubstituted or substituted with halogen;

and where $R^{ya}$ is H, halogen, $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_1$-$C_4$-alkyl-$C_3$-$C_6$-cycloalkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, $S(═O)_mR^e$, phenyl, or —$CH_2$-phenyl, wherein the phenyl rings are unsubstituted or substituted with $R^f$;

$R^{yc}$, $R^{zc}$ are, identical or different, H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkyl, or $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen;

$R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, $S(═O)_mR^e$, phenyl, or —$CH_2$-phenyl, wherein the phenyl rings are unsubstituted or substituted with $R^f$;

$R^{zc}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^{za}$ is H, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkoxy, $C_1$-$C_4$-alkyl-$C_3$-$C_6$-cycloalkyl, wherein the alkyl, alkoxy, alkenyl, alkynyl, cycloalkyl and cycloalkoxy moieties are unsubstituted or substituted with halogen, $C_1$-$C_6$-alkylene-$NR^bR^c$, $C_1$-$C_6$-alkylene-CN, C(═O)—$NR^bR^c$, C(═O)—$R^d$, phenyl, phenylcarbonyl, or —$CH_2$-phenyl, wherein the phenyl rings are unsubstituted or substituted with $R^f$;

$R^{za}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^a$, $R^b$ and $R^c$ are, identical or different, H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cyclo-alkoxy-$C_1$-$C_4$-alkyl, wherein the alkyl, alkoxy, alkenyl, alkynyl, cycloalkyl and cycloalkoxy moieties are unsubstituted or substituted with halogen, $C_1$-$C_6$-alkylene-CN, phenyl, or —$CH_2$-phenyl, wherein the phenyl rings are unsubstituted or substituted with $R^f$;

$R^d$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are un-substituted or substituted with halogen, phenyl, or —$CH_2$-phenyl, wherein the phenyl rings are unsubstituted or substituted with $R^f$;

$R^e$ is $C_1$-$C_6$-alkyl, $C_3$-$C_6$-cycloalkyl, $C_3$-$C_6$-cycloalkyl-$C_1$-$C_4$-alkyl, wherein the alkyl, cycloalkyl moieties are unsubstituted or substituted with halogen, phenyl and —$CH_2$-phenyl, wherein the phenyl rings are unsubstituted or substituted with $R^f$;

$R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, wherein the alkyl, alkoxy, alkenyl, alkynyl, cycloalkyl and cycloalkoxy moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$;

$R^g$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$;

$R^h$ is halogen, OH, $C_1$-$C_6$-alkyl, $C_3$-$C_6$-cycloalkyl, or CN;

except the compound tert-Butyl N-[4-(5-[3-(aminocarbonyl)-2,4-difluorophenoxy]methyl-1,2,4-oxadiazol-3-yl)phenyl]carbamate;

and the N-oxides, stereoisomers, tautomers and agriculturally or veterinarily acceptable salts thereof.

Moreover, the present invention also relates to processes and intermediates for preparing compounds of formula I and to active compound combinations comprising them. Moreover, the present invention relates to agricultural or veterinary compositions comprising the compounds of formula I, and to the use of the compounds of formula I or compositions comprising them for combating or controlling invertebrate pests and/or for protecting crops, plants, plant propagation material and/or growing plants from attack and/or infestation by invertebrate pests. The present invention also relates to methods of applying the compounds of formula I. Furthermore, the present invention relates to seed comprising compounds of formula I. Wherein the compounds of formula I includes N-oxides, stereoisomers, tautomers and agriculturally or veterinarily acceptable salts thereof.

General Procedure:

With due modification of the starting compounds, the compounds of formula I can be prepared by procedures as given in below schemes.

General Procedure:

The compounds of the formula (I) can be prepared by methods of organic chemistry, e.g, by the methods described herein after in schemes 1 to 21 and in the synthesis description of the examples. In the schemes 1 to 21, the radicals Ar, A, $B^1$, $B^2$, $B^3$, $B^4$, Q and $R^1$, $R^2$, $R^4$, $R^5$, $R^6$, $R^7$, $R^8$, $R^9$, $R^{10}$, $R^{ya}$, $R^{zc}$, $R^{yc}$, $R^{yz}$, $R^{11}$, $R^{12}$, $R^{13}$, $R^{14}$, $R^{15}$, $R^{16}$, $R^{19}$ and $R^{20}$ are as defined above for formula (1), unless otherwise specified.

Compounds of formula (I), wherein Z is a single bond or —$NR^{zc}$—C(═S)— or —$NR^{zc}$—C(═O) and T is O, N or N—$R^T$, are the compounds of formula (Ia) and can be prepared by analogy to the methods described in WO 2011/017504 or WO 2015/007682 or methods described in Scheme 1.

Scheme 1

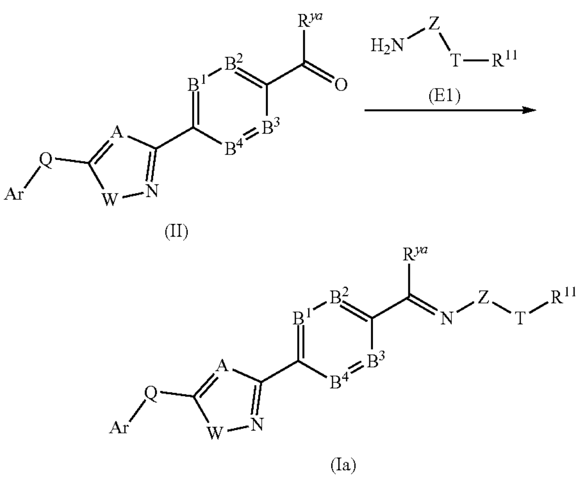

(II)

(Ia)

In one embodiment of Scheme 1, an aldehyde or ketone of the formula (II) is reacted with a compound of formula (E1) wherein Z is —$NR^{zc}$—C(═S) or —$NR^{zc}$—C(═O) and T is N, in the presence or in the absence of a solvent. Suitable solvents are polar protic solvents. If the reaction is performed in the absence of a solvent, the compound of the formula (E1) usually also act as solvent. Compounds of the formula (E1) are commercially available or can be prepared using organic reactions analogy to method as described in March's Advanced Organic Chemistry 6th edition, Michael B. Smith and Jerry March.

According to another embodiment of Scheme 1, an aldehyde or ketone compound of the formula (II) is first reacted with a hydrazine of the formula $R^{zc}NHNH_2$ followed by the reaction with an isocyanate of the formula $R^{11}$—NCO or with an isothiocyanate $R^{11}$—NCS to yield a compound of the formula (Ia), wherein Z is —$N(R^{zc})$—C(═O) or —$N(R^{zc})$—C(═S) and T is N.

According to another embodiment of Scheme 1, an aldehyde or ketone compound of the formula (II) is first reacted with a hydroxylamine followed by the reaction with a compound $R^{12}$-L, where L is a suitable leaving group, such as halogen or activated OH. Thereby, a compound of the formula (Ia) will result, wherein Z is a single bond and T is O.

According to another embodiment of the above reaction, an aldehyde or ketone compound of formula (II) is first reacted with a hydroxylamine followed by reaction with an isocyanate of the formula $R^{11}$—NCO or with an isothiocyanate $R^{11}$—NCS to yield a compound of the formula (Ia), wherein Z is —O—C(═O)— or —O—C(═S)— and T is N.

Compounds of formula (Ib) wherein Z is $NR^{zc}C(═S)$ or $NR^{zc}C(═O)$, wherein C(═S) or C(═O) is bound to T and T is O, N or N—$R^T$, can be prepared by analogy to the method described in Synthesis, 2010, 2990-296 or as shown in Scheme 2.

Scheme 2

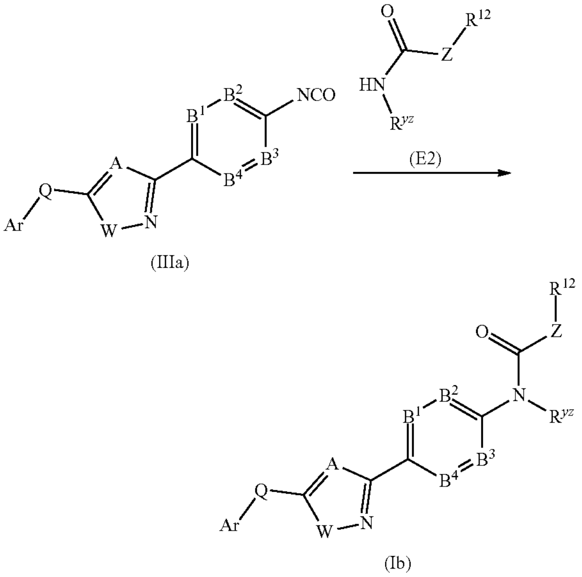

(IIIa)

(Ib)

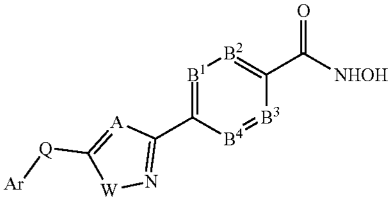

(IVa)

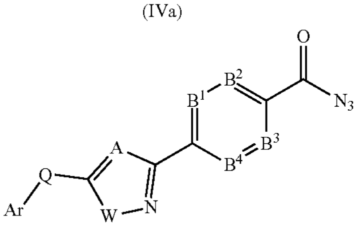

(IVb)

According to the method depicted in scheme 2, an isocyanate compound of the formula (IIIa) is reacted with the compound of formula (E2) by methods of isocyanate chemistry. The isocyanate of the formula (IIIa) can be obtained e.g. via Lossen rearrangement of the corresponding hydroxamic acid (IVa). The hydroxamic acid (IVa) is reacted with 1-propanephosphonic acid cyclic anhydride (T3P) in the presence of a base. The base is preferably N-methylmorpholine. The isocyanate of the formula (IIIa) may also be obtained via Curtius rearrangement of the corresponding azide of the formula (IVb), e.g. by analogy to the method described in WO 2014/204622.

For converting compounds of formula (Ia) and (Ib) wherein $R^{yz}$ or $R^{zc}$ is H into compounds (I) wherein $R^{yz}$ or $R^{zc}$ is different from H, compounds of formula (Ia) and (Ib) wherein $R^{yz}$ or $R^{zc}$ is H can be reacted with compounds of formulae $R^{yz}$-Lg or $R^{zc}$-Lg wherein $R^{yz}$ or $R^{zc}$ is not H and Lg is a leaving group, such as a bromine, chlorine or iodine atom or a tosylate, mesylate or triflate, to yield compounds of formula (Ia) and (Ib), wherein $R^{yz}$ or $R^{zc}$ is different from H. The reaction is suitably carried out in the presence of a base such as sodium hydride or potassium hydride, suitably in a polar aprotic solvent such as N,N-dimethylformamide, tetrahydrofuran, dioxane, acetonitrile, dimethylsulfoxide or pyridine, or mixtures of these solvents, in a temperature range of from 0° C. and 100° C.

Compounds of the formula (Ic) can be prepared from compounds of formula (IIc) by the reactions shown below.

Scheme 3

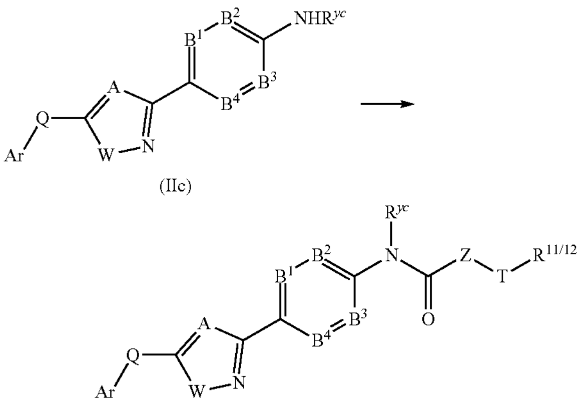

(IIc)

(Ic)

$R^{11/12}$ corresponds to radicals $R^{11}$ or $R^{12}$ respectively. The reaction shown above can be performed by analogy to conventional methods of preparing carbamates. According to a first embodiment, the amine of the formula (IIc) is converted into either an isocyanate or p-nitrophenyl carbamate followed by treatment with an alcohol of the formula $R^{11}$—OH or $R^{12}$—OH, respectively, in the presence of an organic or inorganic base. According to another embodiment, the compound of the formula (IIc) is reacted with a chloroformate of the formula $R^{11/12}$—O—C(═O)—Cl. The chloroformate is prepared from the alcohols $R^{11/12}$—OH by treatment with phosgene or triphosgene in the presence of a base, e.g. pyridine. Compounds of formula (Ic), wherein Z is —N($R^{zc}$)—C(═O)— or —N($R^{zc}$)—C(═S)— can be prepared by analogy to the methods described in WO 2013/009791 or by analogy to methods described in US 2012/0202687.

Compounds of formula (IIb) and (IIc) can be prepared from compounds of formula (IIa) by the reactions shown below.

Scheme 4

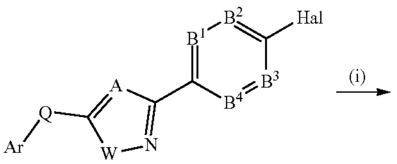

(IIa)

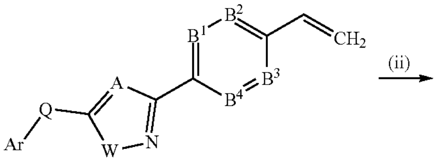

(IIa-1)

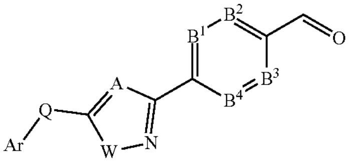

(IIb)

$R^{ya}$ = H

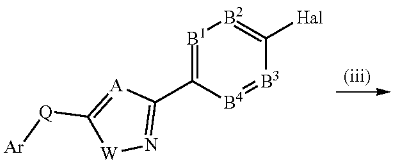

(IIa)

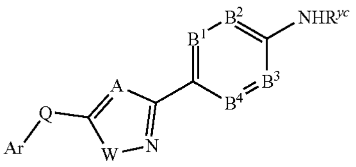

(IIc)

Reaction step (i) can be performed by analogy to method described in WO 2015/051341. Reaction step (ii) can be performed by analogy to method described in *E. J. Med. Chem.,* 2012, 49, 310-323. Compounds of the formula (IIc) [reaction step (iii) of the above reaction] can be prepared by reacting compounds of the formula (IIa) with ammonia or amines of the formula $R^{yc}NH_2$ in the presence of a metal catalyst or its salts, preferably copper or its salts as described in *Chem. Commun.,* 2009, 3035-3037.

Compounds of formula (IId-3), (IId-4), (IId-5), (IId-6), (IId-7) and (IId-9), where Q is —N($R^2$)—C(═O)— or —N$R^2$—C($R^9R^{10}$)— or —N($R^2$)—C(═S)— or —O—C(═O)— —C($R^4R^5$)—O— or —C($R^7R^8$)—S— or and W is N($R^6$) and A is CH can be prepared by the reactions shown below.

Scheme 5

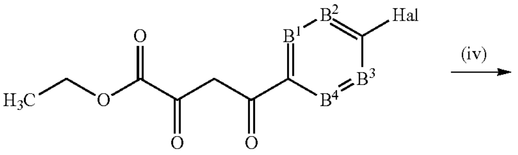

(IId)

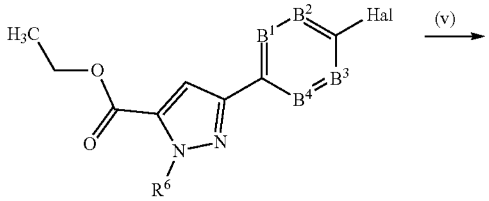

(IId-1)

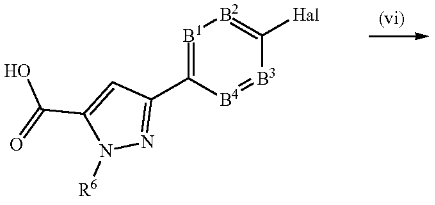

(IId-2)

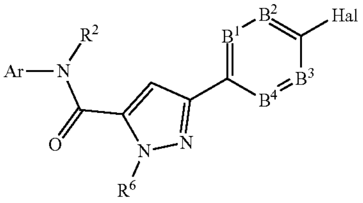

(IId-3)

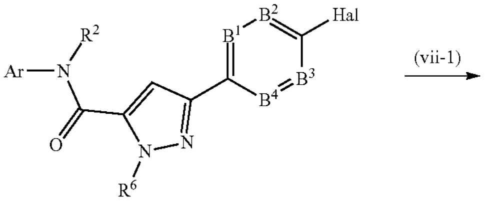

(IId-3)

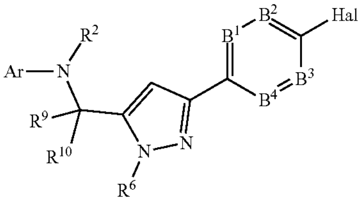

(IId-4)

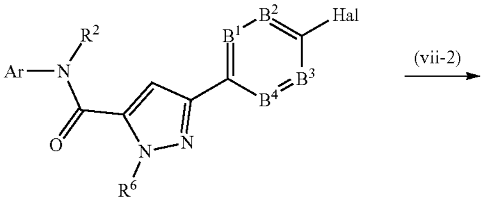

(IId-3)

-continued

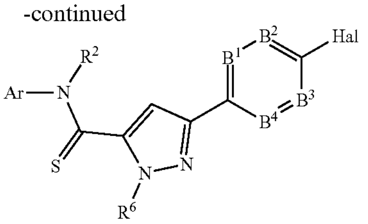

(IId-5)

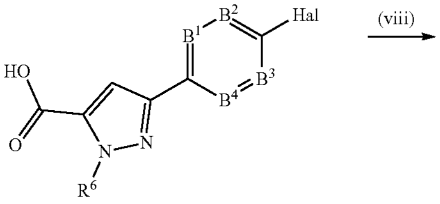

(IId-2)

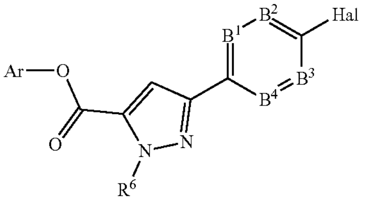

(IId-6)

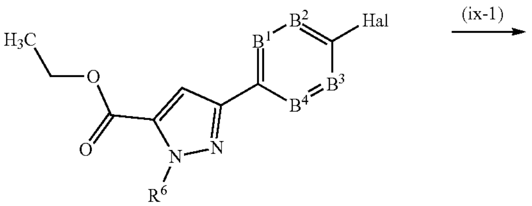

(IId-1)

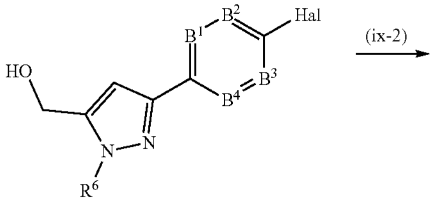

(IId-6)

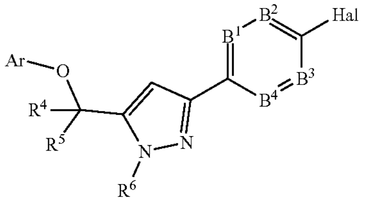

(IId-7)

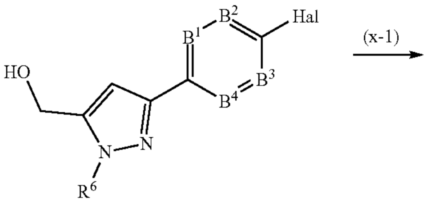

(IId-6)

-continued

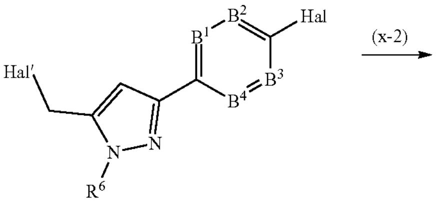

(IId-8)

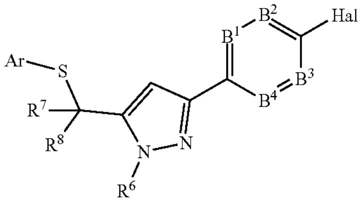

(IId-9)

Compounds of formula (IId-1) can be prepared from a suitable starting point 2,4 dioxo-4-aryl-butyric acid ethyl ester derivative (IId, commercially available) in two steps as described in Chem. Central Journal, 2016, 10, 40/1-40/6. Compounds of formula (IId-2) can be prepared from ester intermediate (IId-1) by hydrolysis with suitable base like LiOH, NaOH, as mentioned in WO 2011/050245. Common intermediate of formula (IId-3) can be prepared via amide formation by reacting the compounds of formula (IId-2) with Ar—$NH_2$ in presence of suitable coupling reagent like HATU and base like DIPEA. Compounds of formula (IId-5) can be prepared by reaction of compounds of formula (IId-3) with $P_2S_5$ or Lawesson's reagent as described by, for example, Strong et al, *J. Med. Chem.*, 2017, 60, 5556-5585. Compounds of formula (IId-4) can be prepared from a common intermediate of formula (IId-3) via amide reduction with LAH as described in *Tet. Lett.*, 2015, 56 (16), 2062-2066. Compounds of formula (IId-6) can be prepared from a common intermediate of formula (IId-2) via esterification by reacting the compound of formula (IId-2) with ArOH in presence of acid. Common intermediate of formula (IId-7) can be prepared from formula (IId-1) by reduction in presence of suitable reducing agents like $LiAlH_4$ or DIBAL-H. Common intermediate of formula (IId-8) can be prepared from formula (IId-7) via etherification reaction through Mitsunobu reaction condition. The compounds of formula (IId-9) can be prepared from compounds of formula (IId-6) via two steps sequence involving intermediate of compounds of formula (IId-8). and Hal' is chlorine, bromine, iodine, tosylate, mesylate or triflate. Steps (vi), (vii), (viii), (ix-1), (ix-2) and (x-1), (x-2) can be performed analogous to process as described in March's Advanced Organic Chemistry 6th edition, Michael B. Smith and Jerry March.

Compounds of formula (IIe-1), (IIe-2), (IIe-3), (IIe-4), (IIe-5), (IIe-6), (IIf-1), (IIf-2), (IIf-3), (IIf-4), (IIf-5) and (IIf-6) where Q is —N($R^2$)—C(═O)— or —N($R^2$)—C(═S)— or —C($R^4R^5$)—O— and W is O or S and A is CH can be prepared by the reactions shown below.

Scheme 6
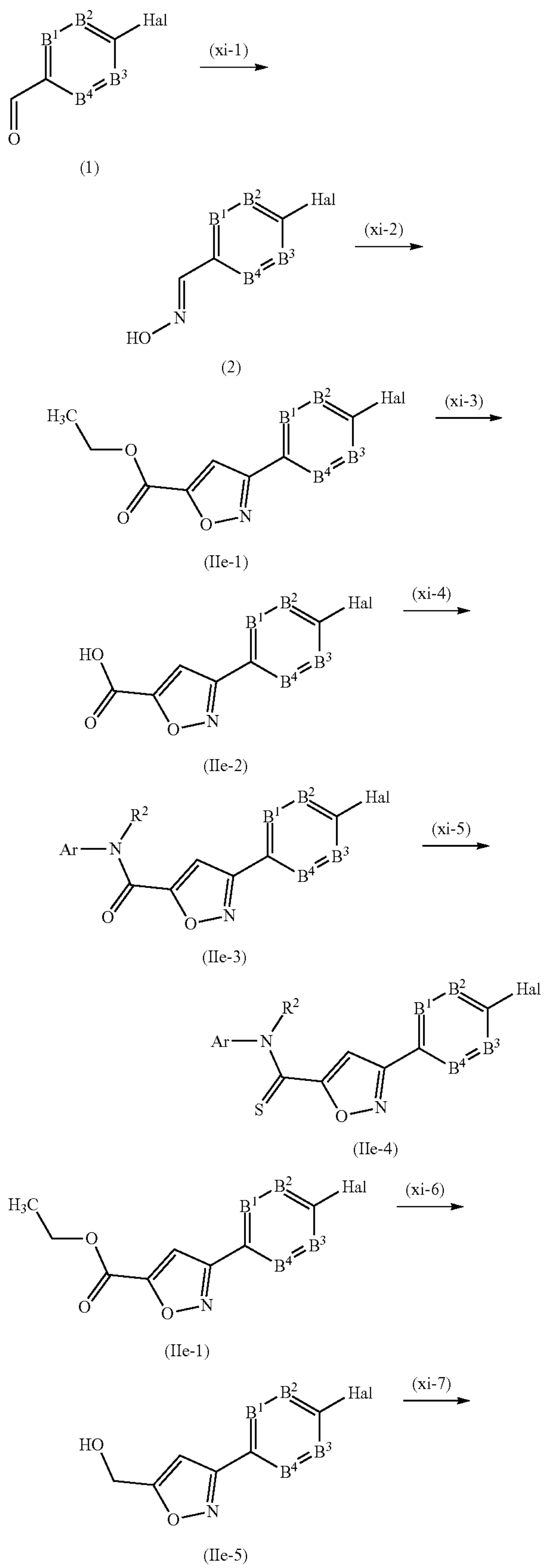
-continued
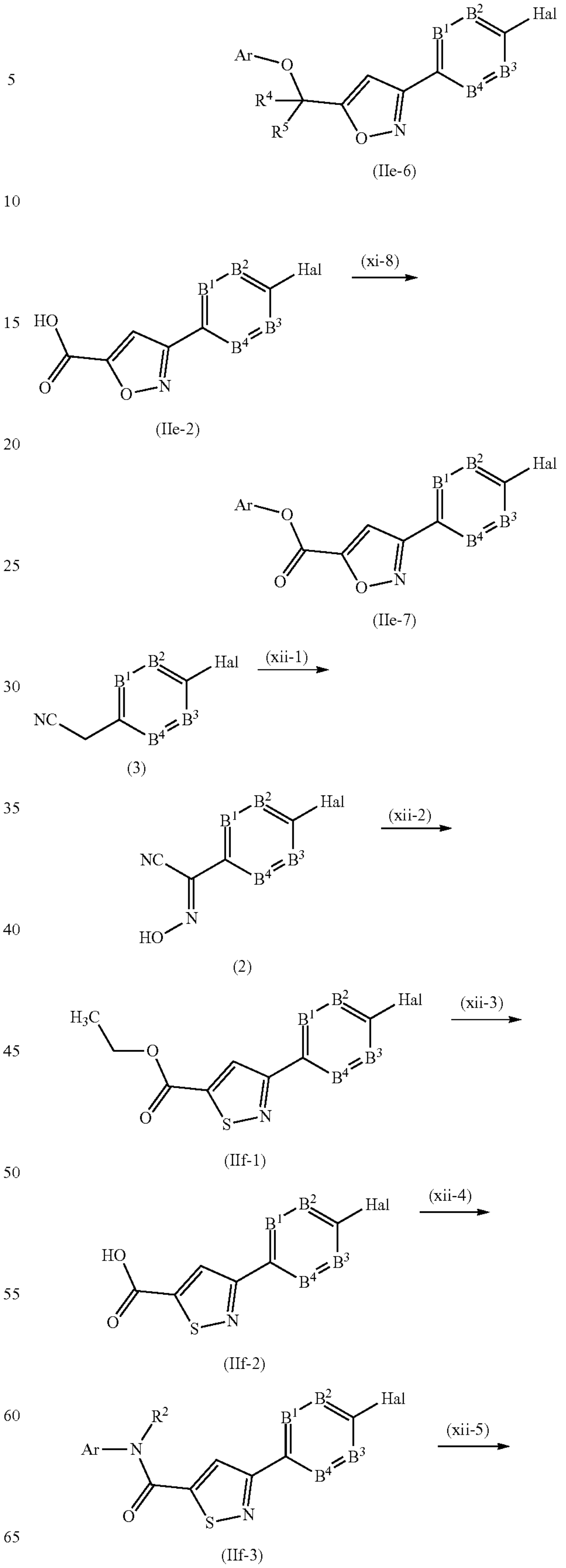

-continued

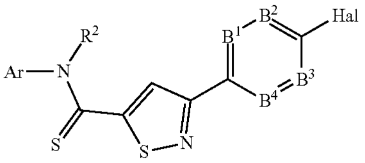

(IIf-4)

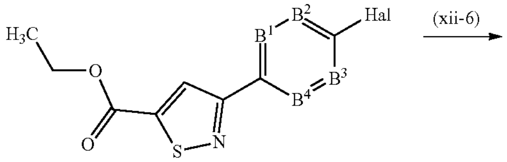

(IIf-1)

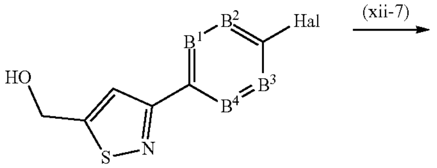

(IIf-5)

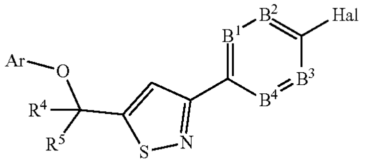

(IIf-6)

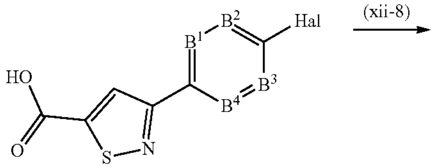

(IIf-2)

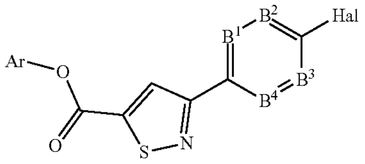

(IIf-7)

Compounds of formula (IIe-1) could be synthesized from a benzadehyde derivative (1) via an oxime derivative (2) in two steps as described in *Tet. Lett.*, 2016, 57(7), 719-722. Compounds of formula (IIe-2), (IIe-3), (IIe-4), (IIe-5), (IIe-6) and (IIe-7) can be prepared from a common intermediate (IIe-1) as described in Scheme-5.

Compounds of formula (IIf-1) can be synthesized from an acetonitrile precursor (3) via cyano-oxime intermediate (4) as described in *Eur., J. Med. Chem.*, 2017, 125, 527-584. Similarly, compounds of formula (IIf-2), (IIf-3), (IIf-4), (IIf-5), (IIf-6) and (IIf-7) can be prepared from a common intermediate (IIf-1) as described in Scheme-5.

Compounds of formula (IIg-1), (IIg-2) and (IIg-3) where Q is —N═C(X)—, X is Cl or F and W is $N(R^6)$ or S or O and A is CH can be prepared by the reactions shown below.

Scheme 7

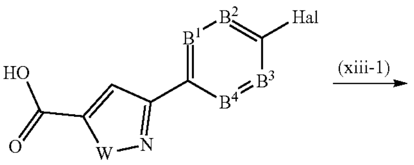

(IId-2; W = $NR^6$)
(IIe-2, W = O)
(IIf-2, W = S)

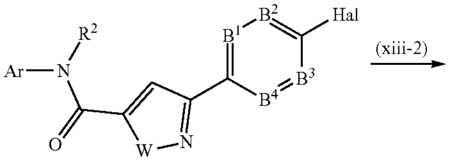

(IIg-1)

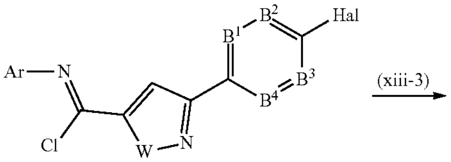

(IIg-2)

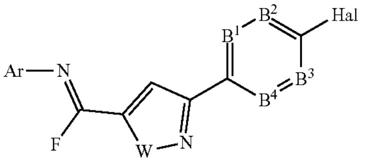

(IIg-3)

Compounds of formula (IIg-1) can be prepared using the method analogous to step (vi) of scheme 5. Compounds of formula (IIg-2) can be prepared using thionyl chloride as described in *Angew. Chem. Int. Ed.*, 2014, 53, 9068-9071. Compounds of formula (IIg-3) can be prepared from compounds of formula (IIg-2) by a method described in *Australian Journal of Chemistry*, 1999, 52, 807-811.

Compounds of formula (IIg-4), (IIg-5), (IIg-6) and (IIg-7) where Q is N═C(X)—, X is $OR^8$ or $SR^7$ or $N(R^3)_2$ or $NH_2CN$ and W is $N(R^6)$ and A is CH can be prepared by the reactions shown below.

Scheme 8

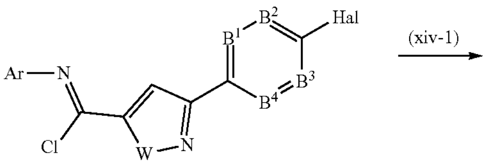

(IIg-2)

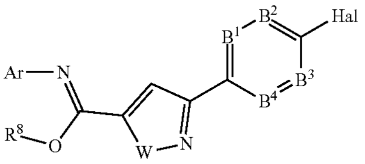

(IIg-4)

-continued

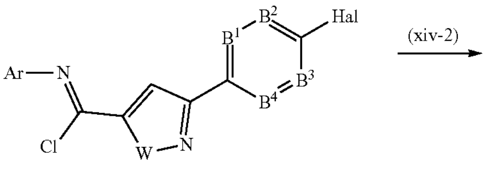

(IIg-2)

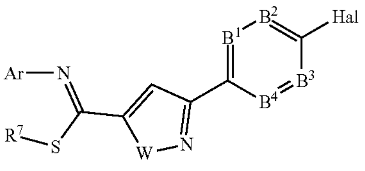

(IIg-5)

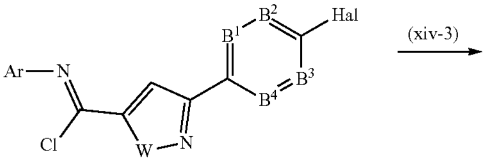

(IIg-2)

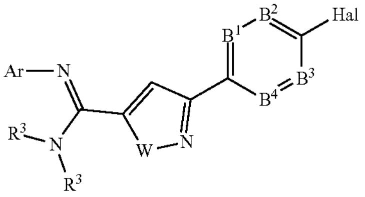

(IIg-6)

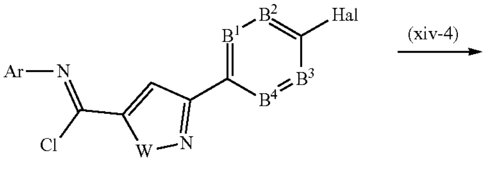

(IIg-2)

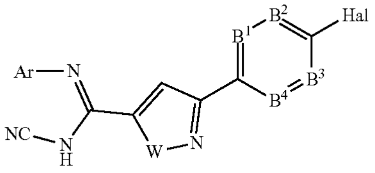

(IIg-7)

Compounds of formula (IIg-4), (IIg-5), (IIg-6) and (IIg-7) can be prepared by heating compounds of formula (IIg-2) with compounds of the formula $R^8$—OH or $R^7$—SH or $NH(R^3)_2$ or $NH_2CN$ in a polar protic or aprotic solvents in an acidic, basic or neutral conditions as described in WO2010129053, WO2007146824 or *Chem. Commun.*, 2014, 50, 1465.

Compounds of formula (IIh-1) and (IIh-4), where Q is —$C(R^{19}R^{20})$—C(═O)— or —C(═O)—$C(R^{19}R^{20})$— and W is $N(R^6)$ or O or S and A is CH can be prepared by the reactions shown below.

Scheme 9

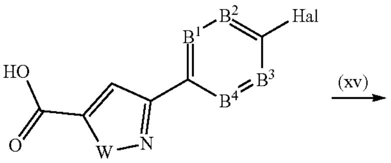

(IId-2; W = $NR^6$)
(IIe-2, W = O)
(IIf-2, W = S)

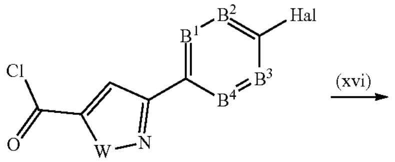

(IIg-8)

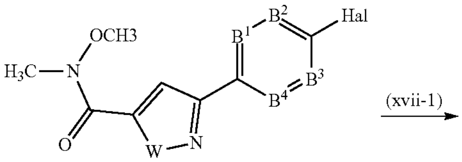

(IIg-9)

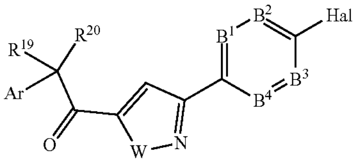

(IIh-1)

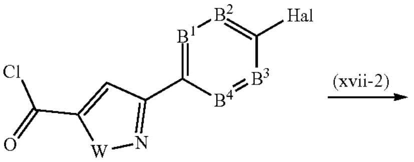

(IIg-8)

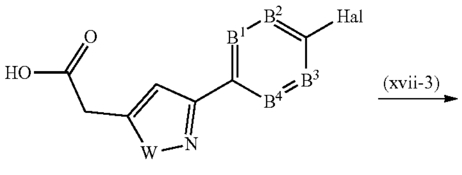

(IIh-2)

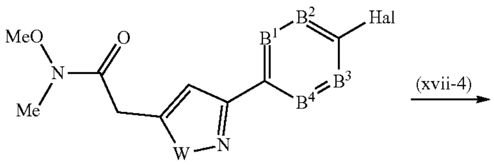

(IIh-3)

-continued

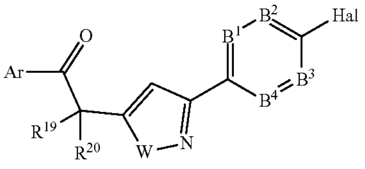

(IIh-4)

Compounds of formula (IIh-1) can be prepared from compounds of formula (IId-2) or (IIe-2) or (IIf-2) in two steps via intermediary of (IIg-8) and (IIg-9) as per methods described in *Org. Lett.*, 2016, 18(23), 6026-6029. Compounds of formula (IIh-4) can be prepared starting from compounds of formula (IIg-8) in three steps via intermediary of (IIh-2) and (IIh-3). The first step (xvii-2) involve Arndt-Eistert homologation from (IIg-8) followed by Weinreb amide formation (step-xvii-3) and addition of an aryl Grignard reagent (step-xvii-4) as per methods described in Photochemical & Photobiological Sciences, 2014, 13(2), 324-341.

Compounds of formula (IIi-1) and (IIj-1) where Q is —$NR^2$—$C(R^9R^{10})$ or —$S(=O)_m$—$C(R^7R^8)$; W is O or S and A is CH can be prepared by the reactions shown below.

Scheme 10

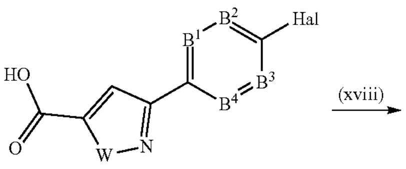

(IIe-2, W = O)
(IIf-2, W = S)

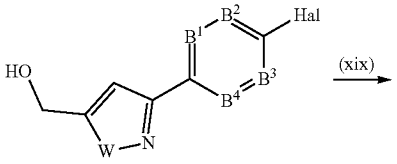

(IIg-10)

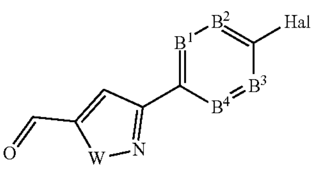

(IIg-11)

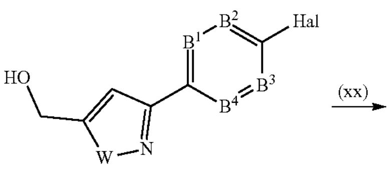

(IIg-10)

-continued

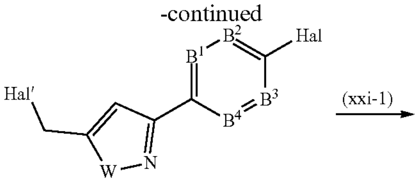

(IIg-12)

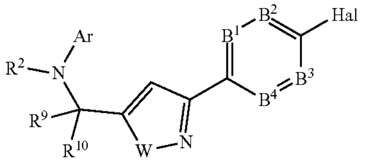

(IIi-1)

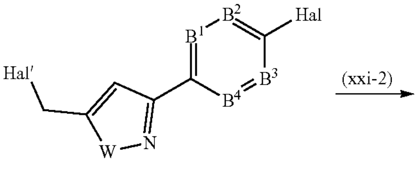

(IIg-12)

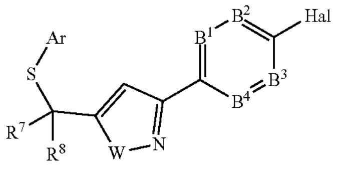

(IIj-1)

The compounds of formula (IIg-11) can be prepared from compounds of formula formula or (IIe-2) or (IIf-2) via two steps sequence involving intermediate of compounds of formula (IIg-10). Step (xviii) involves acid reduction to alcohol using LAH or $BH_3$-THF as reducing agent. Step (xix) involves oxidation of alcohol to aldehyde using Dess-Martin periodinane or Swern oxidation condition to afford the compounds of formula (IIg-11). Compounds of the formula (IIi-1) and (IIj-1) can be prepared from compounds of formula (IIg-12) by reacting with compounds of the formula Ar—$NHR^2$ or Ar—SH by heating in a polar protic or aprotic solvents in an acidic, basic or neutral conditions as described in WO 2010/129053, WO 2007/146824 or *Chem. Commun.*, 2014, 50, 1465. Moreover, compounds of formula (IIj-1) can be further oxidised using mCPBA for preparing compounds with different oxidation states on sulphur, as described in March's Advanced Organic Chemistry 6th edition, Michael B. Smith and Jerry March. Compounds of formula (IIg-12) can be prepared from compounds of formula (IIg-10) using analogy to methods described in March's Advanced Organic Chemistry 6th edition, Michael B. Smith and Jerry March.

Compounds of formula (III-1) and (III-2) where Q is —$C(R^{13}R^{14})$—$C(R^{15}R^{16})$— and W is $N(R^6)$ or O or S and A is CH can be prepared as per below reactions.

Scheme 11

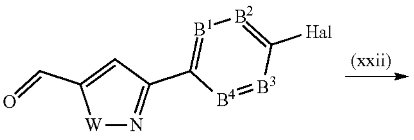

(IIg-11)

-continued

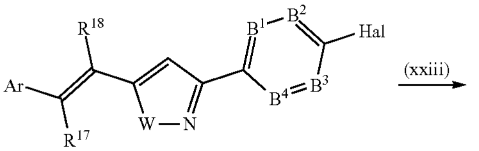

(III-1)

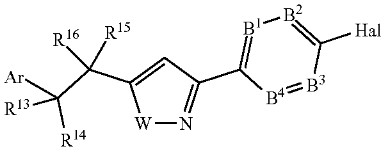

(III-2)

Two compounds of formula (III-1) and (III-2) can be prepared from compounds of formula (IIg-11) by Wittig reactions (step-xxii) using phosphorous Wittig ylide and bases like $^{t}$BuOK in THF, followed by hydrogenation process (step-xxiii) known in organic chemistry such as using hydrogen gas and a suitable metal catalyst as described in Marchs Advanced Organic Chemistry 6th edition, Michael B. Smith and Jerry March.

Compounds of formula (IIm-2) and (IIm-6) where Q is —C(═O)—O— and W is N($R^6$) or O and A is CH can be prepared as per below reactions.

Scheme 12

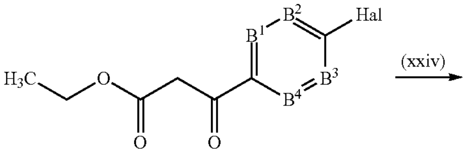

(5)

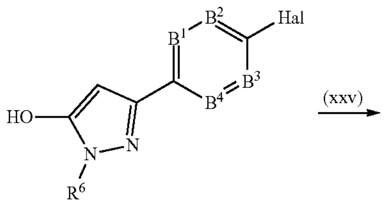

(IIm-1)

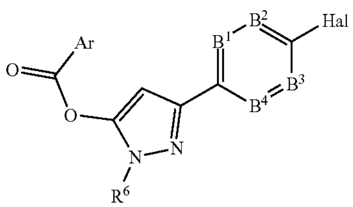

(IIm-2)

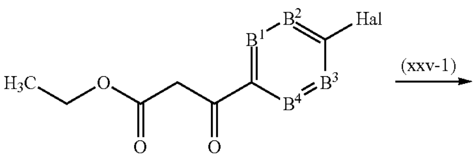

(5)

-continued

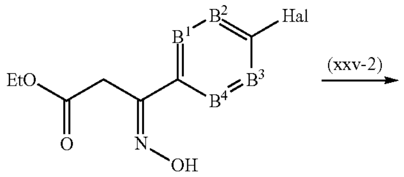

(IIm-4)

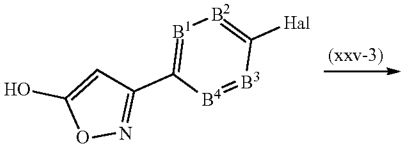

(IIm-5)

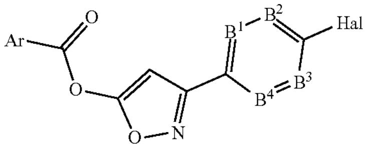

(IIm-6)

Compounds of formula (IIm-1) can be prepared from a commercially available beta keto ester derivative (5) by reacting it with substituted hydrazines ($R^6NHNH_2$) in protic solvents like EtOH and irradiating in microwave as described in *Bioorg. Med. Chem. Lett.,* 2007, 17(5), 1189-1192. Compounds of formula (IIm-2) can be prepared from (IIm-1) by esterification process analogous to as described in March's Advanced Organic Chemistry 6th edition, Michael B. Smith and Jerry March. Compounds of formula (IIm-6) can be prepared from a beta keto ester (5) in three steps involving through the intermediary of (IIm-4) and (IIp-5) as described in *Science of Synthesis,* 2002, 11, 229-288.

Compounds of formula (IIn-1), (IIn-2), (IIk-1) and (IIk-3), where Q is —C($R^4R^5$)—O— or —C($R^7R^8$)—S(═O)$_m$— and W is N($R^6$) or O and A is CH can be prepared as per below reactions.

Scheme 13

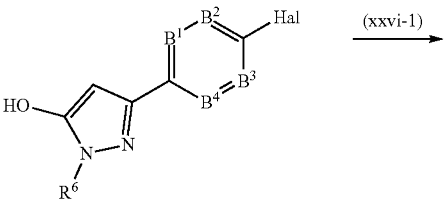

(IIm-1)

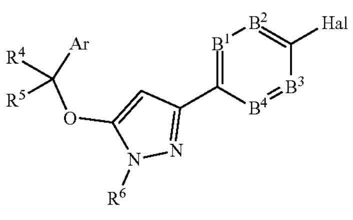

(IIn-1)

-continued

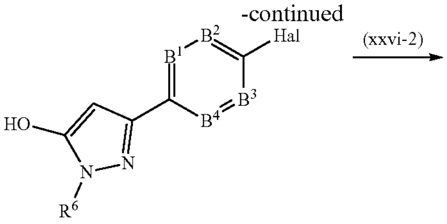

(IIm-1)

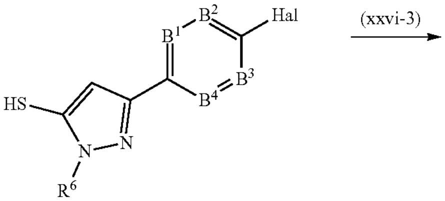

(IIm-3)

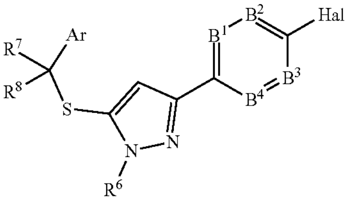

(IIn-2)

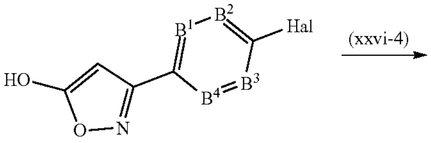

(IIm-5)

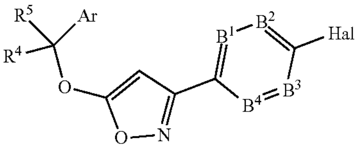

(IIk-1)

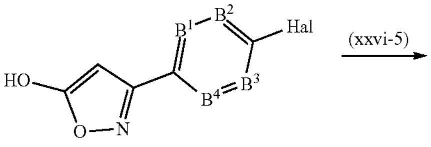

(IIm-5)

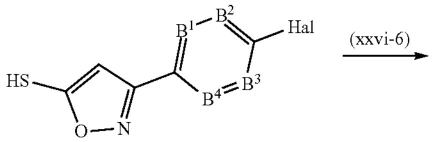

(IIk-2)

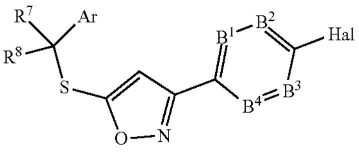

(IIk-3)

Compounds of the formula (IIn-1) can be prepared from compounds of formula (IIm-1) by reacting with compounds of the formula $ArC(R^4R^5)$-Lg (where Lg is bromine, chlorine, iodine, tosylate, or mesylate) with compounds of formula (IIm-1) in polar and aprotic solvents in presence of a base like NaH or $K_2CO_3$. Compounds of the formula (IIm-3) can be prepared from compounds of formula (IIm-1) by reacting with Lawesson's reagent as described in *J. Med. Chem.,* 1992, 35(2), 368-374. Compounds of the formula (IIn-2) can be prepared from compounds of formula (IIm-3) by reacting with compounds of the formula $ArC(R^7R^8)$-Lg (where Lg is bromine, chlorine, iodine) in polar and aprotic solvents in presence of a base like NaH or $K_2CO_3$ etc. Compounds of formula (IIn-2) can be further oxidised using mCPBA for preparing compounds with different oxidation states on sulphur, as described in March's Advanced Organic Chemistry 6th edition, Michael B. Smith and Jerry March. Steps (xxvi-4), (xxvi-5) and (xxvi-6) are analogous to steps (xxvi-1), (xxvi-2) and (xxvi-3).

Compounds of formula (IIn-5), where Q is $—N(R^2)—S(═O)_m—$ and W is $N(R^6)$ or O and A is CH can be prepared as per below reactions.

Scheme 14

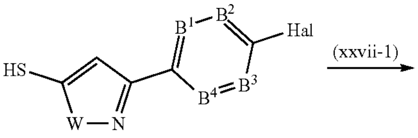

(IIm-3); W = $NR^6$ (IIk-2); W = O

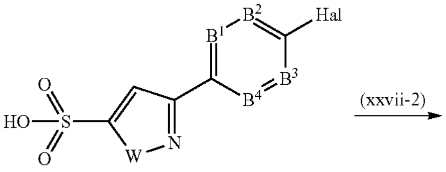

(IIn-3)

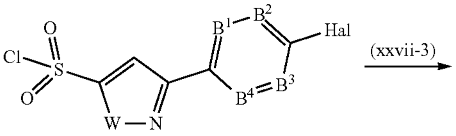

(IIn-4)

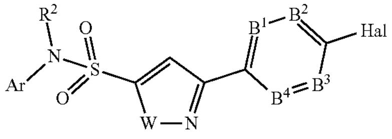

(IIn-5)

Compounds of formula (IIn-5) can be prepared starting from compounds of formula (IIm-3) in three steps involving through the intermediary of (IIn-3) and (IIn-4) using the suitable reaction conditions as described in *Chemistry Select,* 2016, 3, 490-494, (step (xxvii-1), EP1992/524634 [step(xxvii-2)], *Chemistry—A European Journal,* 2014, 20(1), 317-322 (step-xxvii-3).

Compounds of formula (IIo), (IIo-1), (IIo-2), (IIo-3), (IIo-4), (IIo-6), (IIo-7), (IIo-9) and (IIo-12), where Q is $—C(R^9R^{10})—N(R^2)—$ or $—C(═O)—N(R^2)—$ or $—C(═S)—N(R^2)—$ or $—S(═O)_m—N(R^2)—$ or $—O—C(═O)—$ or $—C(R^4R^5)—O—$ or $—C(R^7R^8)—S(═O)_m—$ or $—N(R^2)—S(═O)_m—$ and W is S and A is CH can be prepared as per below reactions.

Scheme 15
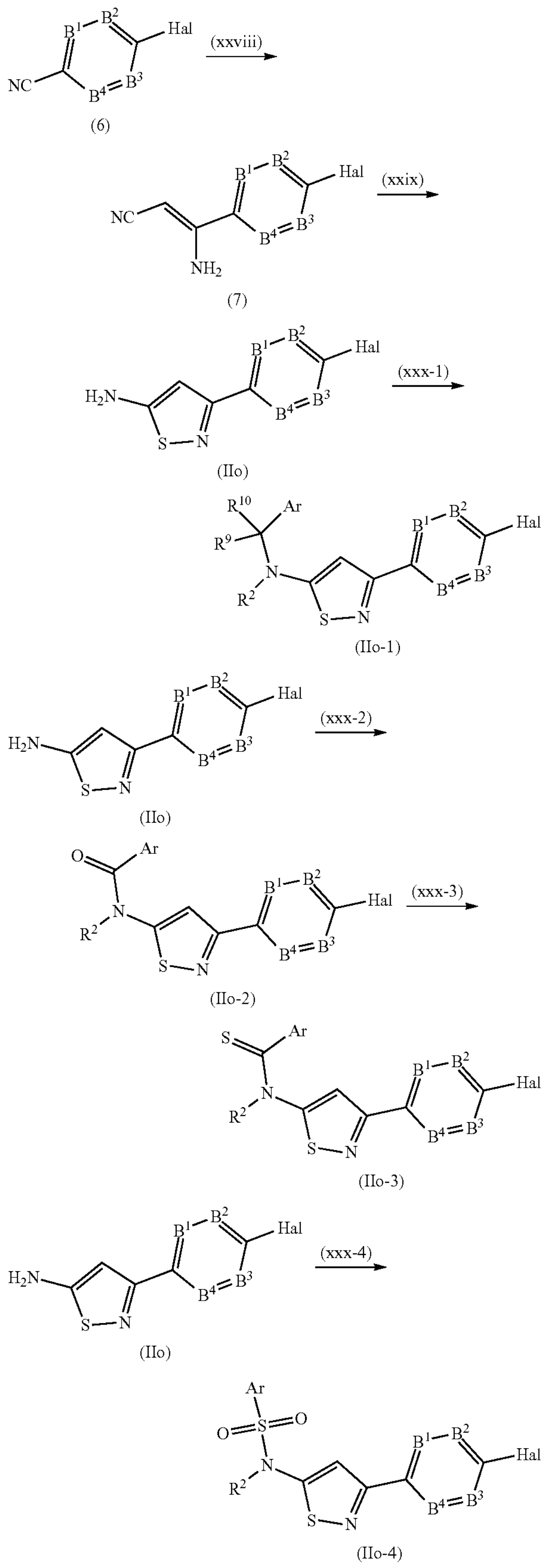
(6)
(7)
(IIo)
(IIo-1)
(IIo)
(IIo-2)
(IIo-3)
(IIo)
(IIo-4)
-continued
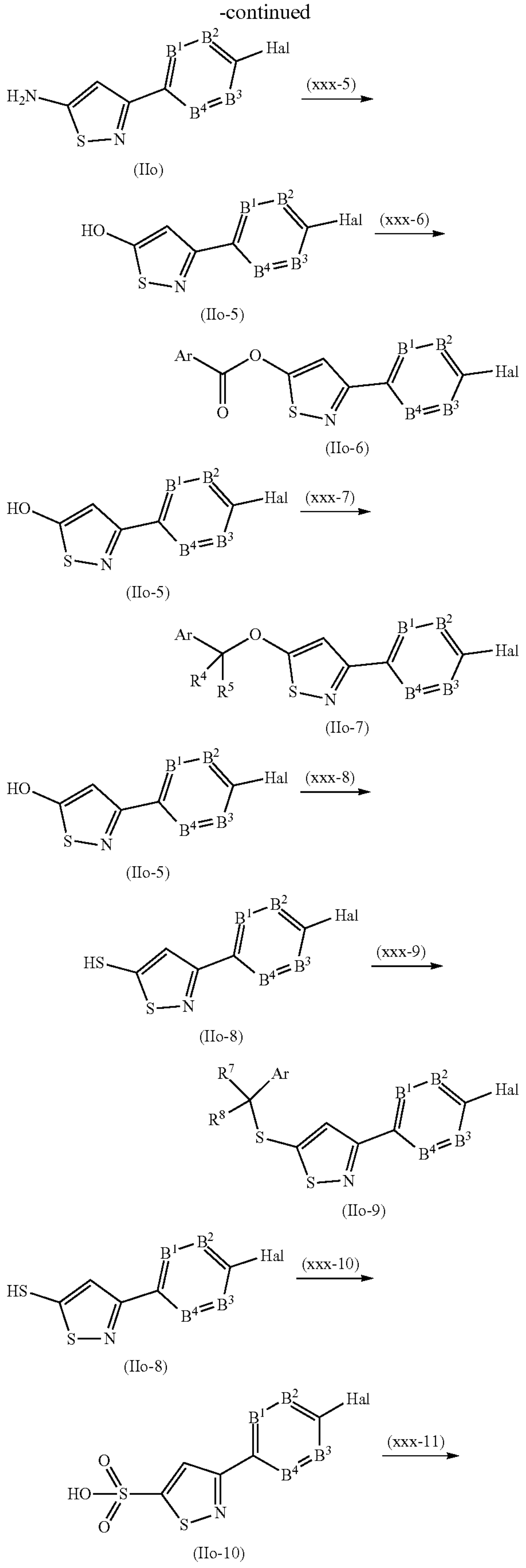
(IIo)
(IIo-5)
(IIo-6)
(IIo-5)
(IIo-7)
(IIo-5)
(IIo-8)
(IIo-9)
(IIo-8)
(IIo-10)

-continued

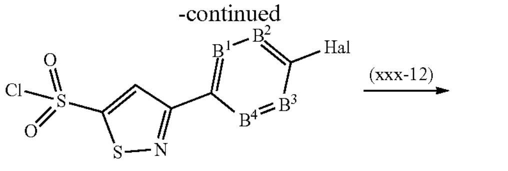

(IIo-11)

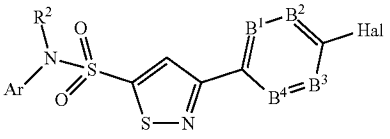

(IIo-12)

Compounds of formula (IIo-1), (IIo-2), (IIo-3) and (IIo-4) can be prepared from a common intermediate (IIo). The intermediate (IIo) can be synthesized from commercially available benzonitrile derivative (6) in two steps (steps xxviii and xxix) involving through an acetonitrile intermediate (7), as described *Tet. Lett.* 2015, 56, 2605-2607. Compounds of formula (IIo-1, IIo-2, IIo-3 and IIo-4) can be synthesized from compounds of formula (IIo) following known procedure (steps: xxx-1, xxx-2, xxx-3 and xxx-4) as described in March's Advanced Organic Chemistry 6th edition, Michael B. Smith and Jerry March. Step (xxx-5) can be performed as described in *Heteroatom Chemistry,* 2015, 26(6), 411-416. Compounds of formula (IIo-6) and (IIo-7) can be synthesized from compounds of formula (IIo-5) following known procedure as described in March's Advanced Organic Chemistry 6th edition, Michael B. Smith and Jerry March. Compounds of formula (IIo-9) and (IIo-12) can be prepared by the method mentioned in scheme 13 and scheme 14.

Compounds of formula (IIp-1), (IIp-2), (IIp-3), (IIp-4) and (IIp-7), where Q is —C($R^9R^{10}$)—N($R^2$)— or —C(═O)—N($R^2$)— —C(═S)—N($R^2$)— or —S(═O)$_m$—N($R^2$)— or —C(═O)—O— and W is N($R^6$) or O and A is CH can be prepared as per below reactions.

Scheme 16

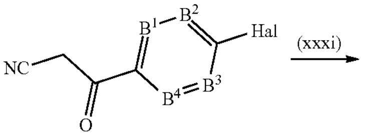

(7)

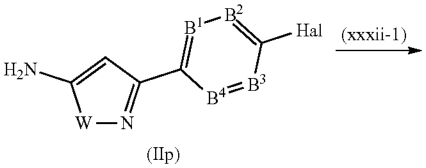

(IIp)

W = $NR^6$,
= O

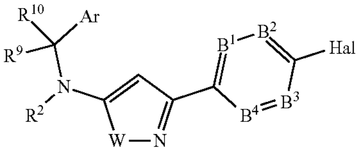

(IIp-1)

-continued

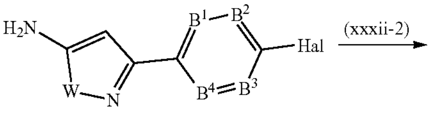

(IIp)

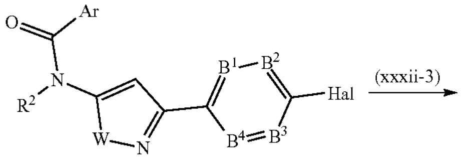

(IIp-2)

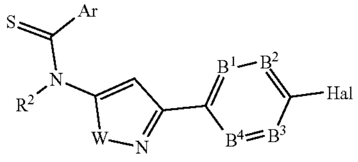

(IIp-3)

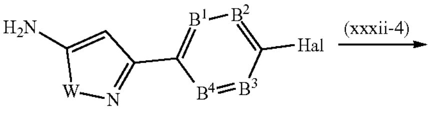

(IIp)

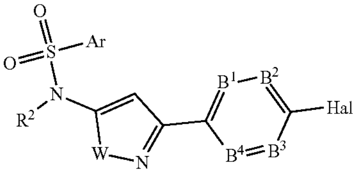

(IIp-4)

Compounds of formula (IIp) can be prepared from a suitably substituted and commercially available benzoyl acetonitrile derivative (7) by reacting it with substituted hydrazines under sealed tube condition (step-xxxi) as described in *Org. Lett.,* 2017, 19 (4), 934-937. Compounds of formula (IIp-1) can be prepared by heating compounds of the formula Ar—C($R^9R^{10}$)-Lg (where Lg is bromine, chlorine, tosylate, or mesylate with compounds of formula (IIp) in a polar protic or aprotic solvents in an acidic, basic or neutral conditions as described in WO 2010/129053, WO 2007/146824 or *Chem. Commun.,* 2014, 50, 1465, shown in step (xxxii-1). Compounds of formula (IIp-2) can be prepared from compounds of formula (IIp) by using amide coupling reactions analogous to as described in March's Advanced Organic Chemistry 6th edition, Michael B. Smith and Jerry March, shown in step (xxxii-3). Compounds of formula (IIp-3) can be prepared by reaction of compounds of formula (IIp-2) with $P_2S_5$ or Lawesson's reagent as described by, for example, Strong. et al, *J. Med. Chem.,* 2017, 60, 5556-5585 as shown in step (xxxii-3). Compounds of formula (IIp-4) can be prepared from compounds of formula (IIp) by treating with suitable Ar—$SO_3Cl$ in presence of bases like pyridine and coupling reagents like DMAP, as described in *Chemistry—A European Journal,* 2014, 20(1), 317-322 (step-xxxii-4).

Compounds of formula (IIq-1) and IIq-2), where W is N($R^6$) and A is N can be prepared as per below reactions.

Scheme 17

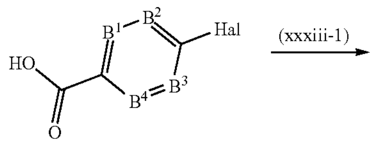

(8)

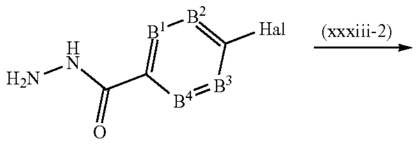

(9)

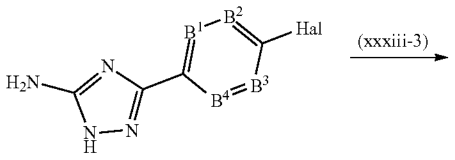

(IIq-1)

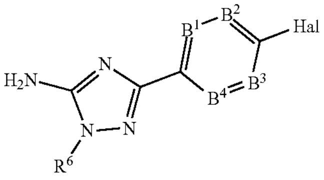

(IIq-2)

Compounds of formula (IIg-1) and (IIg-2) can be prepared from commercially available a benzoic acid derivative (8) through intermediary of compounds of formula (9) and (IIg-1) in three steps (steps-xxxiii-1, xxxiii-2 and xxxiii-3) as described in *Eur. J. of Med. Chem.*, 2016, 113, 11-27.

Compounds of formula (IIr-1) and (IIs-1), where W is O or S and A is N can be prepared as per below reactions.

Scheme 18

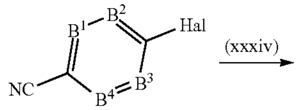

(10)

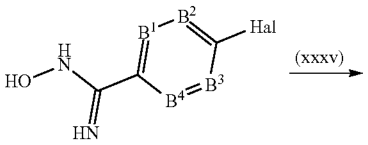

(11)

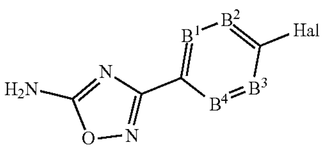

(IIr-1)

-continued

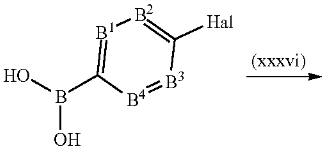

(12)

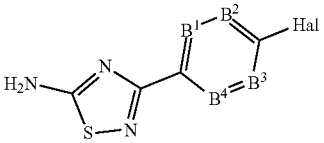

(IIs-1)

Compounds of formula (IIr-1) can be prepared from commercially available benzonitrile derivative (10) in two steps (xxxiv and xxxv) via an intermediate (11), as described in *Zeitschrift fuer Chemie,* 1975, 15(2), 57. Similarly, compounds of formula (115-1) can be prepared from commercially available starting materials like a phenyl boronic acid (12) and a thiadiazole halide under the Suzuki cross coupling reaction (step-xxxvi) condition as described in *Org. Lett.*, 2009, 11(24), 5666-5669.

Compounds of formula (IIt-1), (IIt-2) and (IIt-3), where Q is —C($R^9R^{10}$)—N($R^2$)— or —C(═O)—N($R^2$)— or C(═S)—N($R^2$)— or —S(═O)$_m$—N($R^2$)— and W is N($R^6$) or O or S and A is N can be prepared as per below reactions.

Scheme 19

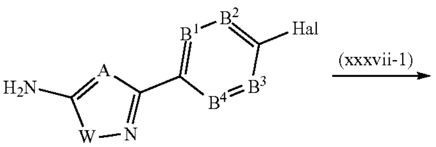

(IIt)

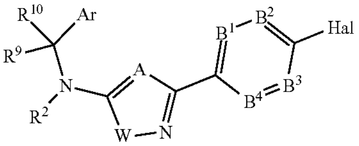

(IIt-1)

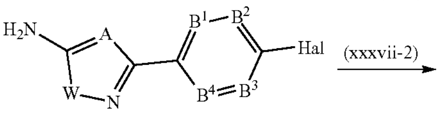

(iit)

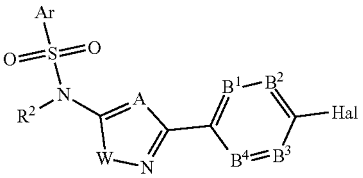

(IIt-2)

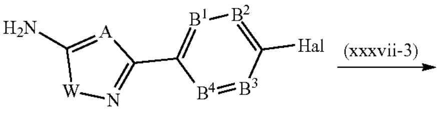

(IIt)

-continued

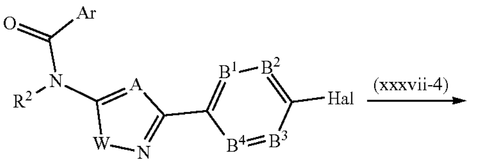

(IIt-3)

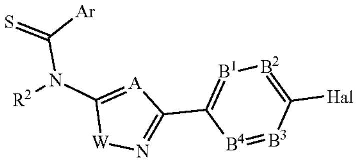

(IIt-4)

Compounds of formula (IIt-1) can be prepared by heating compounds of the formula Ar—C($R^9R^{10}$)-Lg (where Lg can be bromine, chlorine, tosylate, mesylate) with the common intermediate of compounds of formula (IIt) in a polar protic or aprotic solvents in an acidic, basic or neutral conditions analogous to as described in WO 2010/129053, WO 2007/0146824 or *Chem. Comnun.*, 2014, 50, 1465, shown in step (xxxvii-1). Compounds of formula (IIt-2) can be prepared from compounds of formula (IIt) by treating with suitable Ar—$SO_2Cl$ in presence of bases like pyridine and coupling reagents like DMAP, as described in *Chemistry—A European Journal,* 2014, 20(1), 317-322, (step-xxxvii-2). Compounds of formula (IIt-3) can be prepared from compounds of formula (IIt) by using amide coupling reactions analogous to as described in March's Advanced Organic Chemistry 6th edition, Michael B. Smith and Jerry March, shown in step (xxxvii-3). Compounds of formula (IIt-4) can be prepared by reaction of compounds of formula (IIt-3) with P2S5 or Lawesson's reagent as described by, for example, Strong. et al, *J. Med. Chem.,* 2017, 60, 5556-5585 as shown in step (xxxvii-4).

Compounds of formula (IIu-1) and (IIu-2), where Q is —N═C(X)—, X is Cl or F and W is O or S or N($R^6$) and A is N or CH can be prepared by the reactions shown below.

Scheme 20

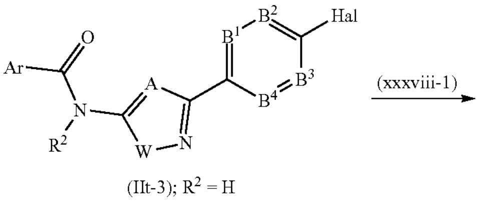

(IIt-3); $R^2$ = H

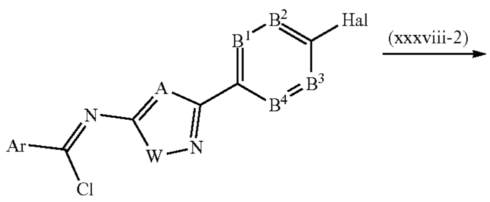

(IIu-1)

-continued

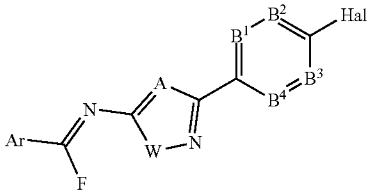

(IIu-2)

In the above reactions compounds of formula (IIu-1) can be prepared from compounds of formula (11t-3) using thionyl chloride as described in *Angew. Chem. Int. Ed.,* 2014, 53, 9068-9071. Compounds of formula (IIu-2) can be prepared from compounds of formula (IIu-1) by a method described in *Aust. J. Chem.,* 1999, 52, 807-811.

Compounds of formula (IIu-3), (IIu-4), (IIu-5) and (IIu-6), where Q is —C(X)═N—, X is $OR^8$ or $SR^7$ or $N(R^3)_2$ or —NHCN and W is S or O or N($R^6$) and A is N or CH can be prepared as per below reactions.

Scheme 21

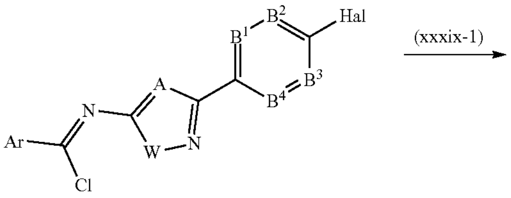

(IIu-1)

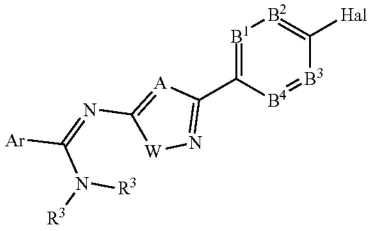

(IIu-3)

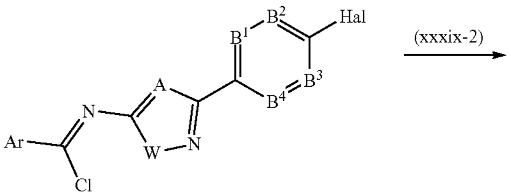

(IIu-1)

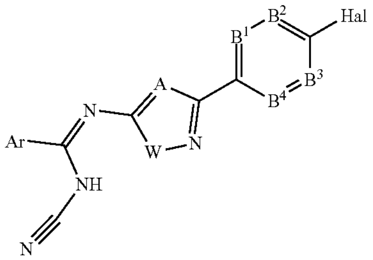

(IIu-4)

-continued

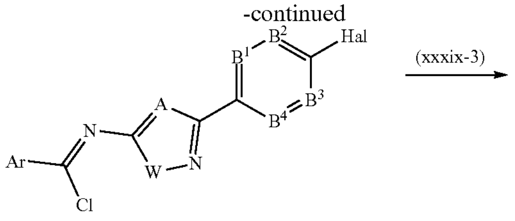

(IIu-1)

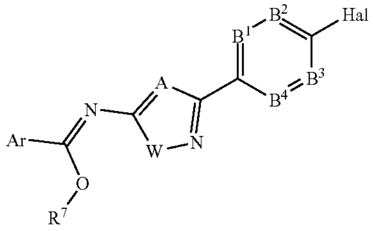

(IIu-5)

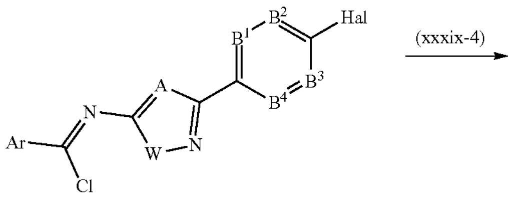

(IIu-1)

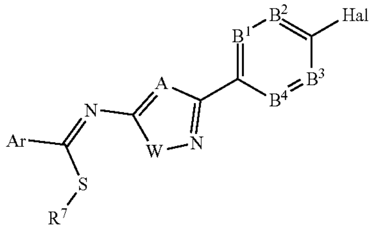

(IIu-6)

Compounds of formula (IIu-3), (IIu-4), (IIu-5) and (IIu-6) can be prepared by heating compounds of formula (IIu-1) with compounds of the formula $NH(R^3)_2$ or $NH_2CN$ or $R^8$—OH or $R^7$—SH in a polar protic or aprotic solvents in an acidic, basic or neutral conditions as described in WO2010129053, WO2007146824 or *Chem. Commun.*, 2014, 50, 1465.

Compounds of formula (IIv-1), (IIv-2), (IIv-3), (IIv-4), (IIv-5), (IIv-6), (IIv-7), (IIv-8), (IIv-9), (IIv-10), (IIv-11), (IIv-12), (IIv-14), (IIv-15) and (IIv-16), where Q is —$C(R^4R^5)$—O— or —$C(R^7R^8)$—$S(=O)_m$ or —O—C(=O)— or —$C(R^{19}R^{20})$—C(=O)— or —$N(R^2)$—$S(=O)_m$— or —$N(R^2)$—$C(R^9R^{10})$— or —C(=O)—$C(R^{19}R^{20})$— or —$N(R^2)$—C(=O)— or —$N(R^2)$—C(=S)— or —$C(R^{13}R^{14})$—$C(R^{15}R^{16})$— or —N=C(X)— or —$N(R^2)$—C(=NR)— or —O—$C(R^4R^5)$— or —$S(=O)_m$—$C(R^7R^8)$— or —C(=O)—O— and W is S or O or $N(R^6)$ and A is N and X is $OR^8$ or $SR^7$ or $N(R^3)_2$ or —NHCN can be prepared from suitable commercially available products following the methods mentioned in the previous schemes.

a (IIv-1)

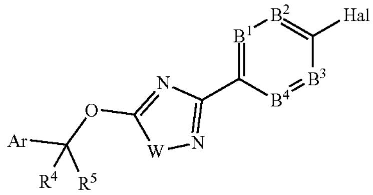

(IIv-2)

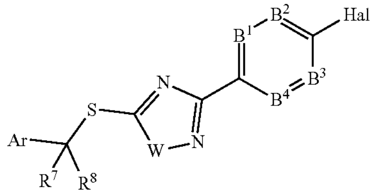

(IIv-3)

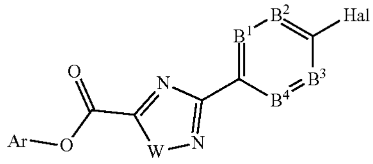

(IIv-4)

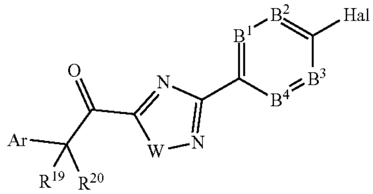

(IIv-5)

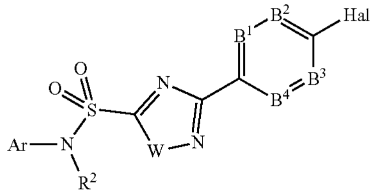

(IIv-6)

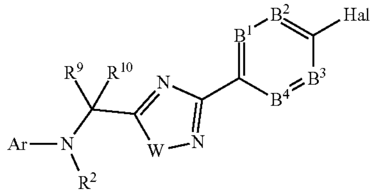

(IIv-7)

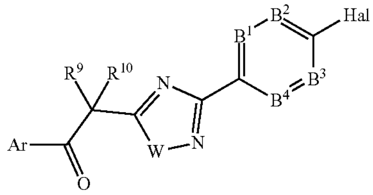

(IIv-8)

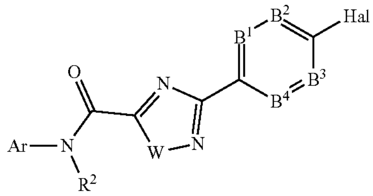

-continued (IIv-9)

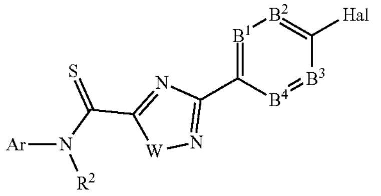

(IIv-10)

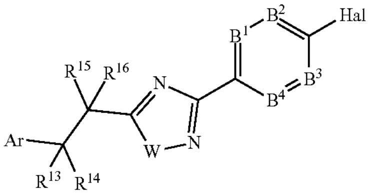

(IIv-11)

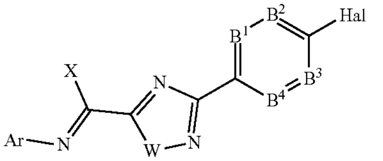

(IIv-12)

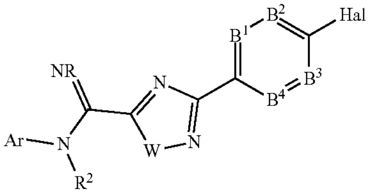

(IIv-14)

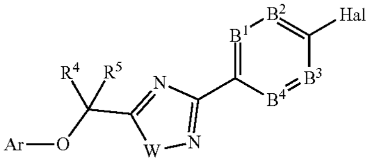

(IIv-15)

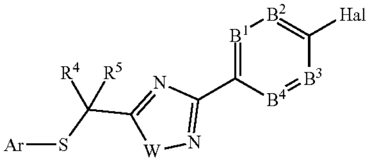

(IIv-16)

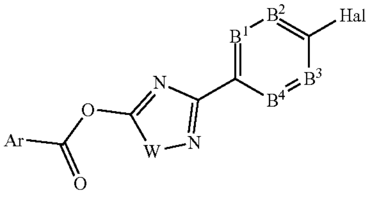

Individual compounds of formula I can also be prepared by derivatisation of other compounds of formula I or the intermediates thereof.

If the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus to be controlled.

A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

Unless otherwise indicated, the term "compound(s) according to the invention" or "compound(s) of the invention" or "compound(s) of formula (I)", refers to the compounds of formula I.

The term "compound(s) according to the invention", or "compounds of formula I" comprises the compound(s) as defined herein as well as a stereoisomer, salt, tautomer or N-oxide thereof. The term "compound(s) of the present invention" is to be understood as equivalent to the term "compound(s) according to the invention", therefore also comprising a stereoisomer, salt, tautomer or N-oxide thereof.

The term "composition(s) according to the invention" or "composition(s) of the present invention" encompasses composition(s) comprising at least one compound of formula I according to the invention as defined above. The compositions of the invention are preferably agricultural or veterinary compositions.

Depending on the substitution pattern, the compounds according to the invention may have one or more centers of chirality, in which case they are present as mixtures of enantiomers or diastereomers. The invention provides both the single pure enantiomers or pure diastereomers of the compounds according to the invention, and their mixtures and the use according to the invention of the pure enantiomers or pure diastereomers of the compounds according to the invention or their mixtures. Suitable compounds according to the invention also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula I, i.e. to single enantiomers or diastereomers, as well as to mixtures thereof.

The compounds according to the invention may be amorphous or may exist in one or more different crystalline states (polymorphs) which may have different macroscopic properties such as stability or show different biological properties such as activities. The present invention relates to amorphous and crystalline compounds according to the invention, mixtures of different crystalline states of the respective compounds according to the invention, as well as amorphous or crystalline salts thereof.

The term "tautomers" encompasses isomers, which are derived from the compounds of formula I by the shift of an H-atom involving at least one H-atom located at a nitrogen, oxygen or sulphur atom. Examples of tautomeric forms are keto-enol forms, imine-enamine forms, ureaisourea forms, thiourea-isothiourea forms, (thio)amide-(thio)imidate forms etc.

The term "stereoisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isothiazoline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by oxidizing e.g. the ring nitrogen atom of an N-heterocycle, e.g. a pyridine or pyrimidine ring present in Ar or $R^{11}$, or an imino-nitrogen present in central tricyclic core, with a suitable oxidizing agent, such as peroxo carboxylic acids or other peroxides. The person skilled in the art knows if and in which positions compounds of the present invention may form N-oxides.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally or veterinarily acceptable salts are especially the salts of those cations or the acid addition salts of those acids whose cations and anions, which are known and accepted in the art for the formation of salts for agricultural or veterinary use respectively, and do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or $CH_2$-phenyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Suitable acid addition veterinarily acceptable salts, e.g. formed by compounds of formula I containing a basic nitrogen atom, e.g. an amino group, include salts with inorganic acids, for example hydrochlorides, sulphates, phosphates, and nitrates and salts of organic acids for example acetic acid, maleic acid, dimaleic acid, fumaric acid, difumaric acid, methane sulfenic acid, methane sulfonic acid, and succinic acid.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "modified plants" and in particular "cultivated plants".

The term "modified plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The organic moieties mentioned in the above definitions of the variables are—like the term halogen—collective terms for individual listings of the individual members. The prefix $C_n$-$C_m$ indicates in each case the possible number of carbon atoms in the group.

The term halogen denotes in each case F, Br, Cl or I, in particular F, Cl or Br.

The term "alkyl" as used herein and in the alkyl moieties of alkoxy, alkylthio, and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is $CH_3$ or $C_2H_5$. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl") or 1 to 6 ("$C_1$-$C_6$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

The term "alkylene" (or alkanediyl) as used herein in each case denotes an alkyl radical as defined above, wherein one hydrogen atom at any position of the carbon backbone is replaced by one further binding site, thus forming a bivalent moiety. Alkylene has preferably 1 to 6 carbon atoms ($C_1$-$C_6$-alkylene), 2 to 6 carbon atoms ($C_2$-$C_6$-alkylene), in particular 1 to 4 carbon atoms ($C_1$-$C_4$-alkylene) or 2 to 4 carbon atoms ($C_2$-$C_4$-alkylene). Examples of alkylene are methylene ($CH_2$), 1,1-ethandiyl, 1,2-ethandiyl, 1,3-propandiyl, 1,2-propandiyl, 2,2-propandiyl, 1,4-butandiyl, 1,2-butandiyl, 1,3-butandiyl, 2,3-butandiyl, 2,2-butandiyl, 1,5-pentandiyl, 2,2-dimethylpropan-1,3-diyl, 1,3-dimethyl-1,3-propandiyl, 1,6-hexandiyl etc.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl") carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "cycloalkyl" as used herein refers to mono- or bi- or polycyclic saturated hydrocarbon radicals having in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "cycloalkoxy" as used herein refers to a cycloalkyl radical, in particular a monocyclic cycloalkyl radical, as defined above having in particular 3 to 6 ("$C_3$-$C_6$-cycloalkoxy") or 3 to 5 ("$C_3$-$C_5$-cycloalkoxy") or 3 to 4 ("$C_3$-$C_4$-cycloalksoxy") carbon atoms, which is bound via an oxygen atom to the remainder of the molecule.

The term "cycloalkyl-$C_1$-$C_4$-alkyl" refers to a $C_3$-$C_8$-cycloalkyl ("$C_3$-$C_8$-cycloalkyl-$C_1$-$C_4$-alkyl"), preferably a $C_3$-$C_6$-cycloalkyl ("$C_3$-$C_6$-cycloalkyl-$C_1$-$C_4$-alkyl"), more preferably a $C_3$-$C_4$-cycloalkyl ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cyclo-alkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is $OCH_3$ or $OC_2H_5$. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methyl-butoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-d ifluoropropoxy, 2,3-d ifluoropropoxy, 2-chloropropoxy, 3-chloropropoxy, 2,3-d ichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_6$-alkoxy-$C_1$-$C_4$-alkyl" as used herein, refers to a straight-chain or branched alkyl having 1 to 4 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tertbutoxymethyl, 1-methoxyethyl, 1-ethoxyethyl, 1-propoxyethyl, 1-isopropoxyethyl, 1-n-butoxy-ethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "alkoxyalkoxy" as used herein refers to an alkoxyalkyl radical, in particular a $C_1$-$C_6$-alkoxy-$C_1$-$C_4$-alkyl radical, as defined above, which is bound via an oxygen atom to the remainder of the molecule. Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, etc.

The substituent "oxo" replaces a $CH_2$ by a C(═O) group.

The term "aryl" relates to phenyl and bi- or polycyclic carbocycles having at least one fused phenylene ring, which is bound to the remainder of the molecule. Examples of bi- or polycyclic carbocycles having at least one phenylene ring include naphthyl, tetrahydronaphthyl, indanyl, indenyl, anthracenyl, fluorenyl etc.

The term "aryl-$C_1$-$C_4$-alkyl" relates to $C_1$-$C_4$-alkyl, as defined above, wherein one hydrogen atom has been replaced by an aryl radical, in particular a phenyl radical. Particular examples of aryl-$C_1$-$C_4$-alkyl include —$CH_2$-phenyl, 1-phenethyl, 2-phenetyl, 1-phenylpropyl, 2-phenylpropyl, 3-phenyl-1-propyl and 2-phenyl-2-propyl.

The term "aryloxy-$C_1$-$C_4$-alkyl" relates to $C_1$-$C_4$-alkyl, as defined above, wherein one hydrogen atom has been replaced by an aryloxy radical, in particular a phenoxy radical. Particular examples of aryloxy-$C_1$-$C_4$-alkyl include phenoxymethyl, 1-phenoxyethyl, 2-phenoxyetyl, 1-phenoxypropyl, 2-phenoxypropyl, 3-phenoxy-1-propyl and 2-phenoxy-2-propyl.

The term "aryl-$C_1$-$C_4$-carbonyl" relates to aryl as defined above, in particular a phenyl radical, which is bound by a carbonyl to the remainder of the molecule. Particular examples of arylcarbonyl include benzoyl, 1-naphthoyl and 2-naphthoyl.

The term "hetaryl" relates to aromatic heterocycles having either 5 or 6 ring atoms (5- or 6-membered hetaryl) and being monocyclic or 8, 9 or 10 ring atoms and bing bicyclic. Hetaryl will generally have at least one ring atom selected from O, S and N, which in case of N may be an imino-nitrogen or an amino-nitrogen, which carries hydrogen or a radical different from hydrogen. Hetaryl may have 1, 2, 3 or 4 further nitrogen atoms as ring members, which are imino nitrogens. Examples of 5- or 6-membered hetaryl include 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-ox-azolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 1,3,4-oxadiazolyl-2-yl, 1,3,4-thiadiazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl and 1,3,5-triazin-2-yl. Examples of 8-, 9- or 10-membered hetaryl include, for example, quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Examples of N-bound 5-, 6-, 7 or 8-membered saturated heterocycles include: pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 1-oxothiomorpholin-4-yl, 1,1-dioxothiomorpholin-4-yl, azepan-1-yl and the like.

The term "hetaryl-$C_1$-$C_4$-alkyl" relates to $C_1$-$C_4$-alkyl, as defined above, wherein one hydrogen atom has been replaced by a hetaryl radical, in particular a pyridyl radical. Particular examples of hetaryl-$C_1$-$C_4$-alkyl include 2-pyridylmethyl, 3-pyridylmethyl, 4-pyridylmethyl, 1-(2-pyridyl)ethyl, 2-(2-pyridyl)ethyl, 1-(3-pyridyl)ethyl, 2-(3-pyridyl)ethyl, 1-(4-pyridyl)ethyl, 2-(4-pyridyl)ethyl etc.

The term "hetaryloxy-$C_1$-$C_4$-alkyl" relates to $C_1$-$C_4$-alkyl, as defined above, wherein one hydrogen atom has been replaced by an hetaryloxy radical, in particular a pyridyloxy radical. Particular examples of hetaryloxy-$C_1$-$C_4$-alkyl include 2-pyridyloxymethyl, 3-pyridyloxymethyl, 4-pyridyloxymethyl, 1-(2-pyridyloxy)ethyl, 2-(2-pyridyloxy)ethyl, 1-(3-pyridyloxy)ethyl, 2-(3-pyridyloxy)ethyl, 1-(4-pyridyloxy)ethyl, 2-(4-pyridyloxy)ethyl etc.

The term "hetaryl-$C_1$-$C_4$-carbonyl" relates to hetaryl as defined above, in particular a C-bound hetaryl radical, e.g. 2-, 3- or 4-pyridyl, 2- or 3-thienyl, 2- or 3-furyl, 1-, 2- or 3-pyrrolyl, 2- or 4-pyrimidinyl, pyridazinyl, 1-, 3- or 4-pyrazolyl, 1-, 2- or 4-imidazolyl radical, which is bound by a carbonyl to the remainder of the molecule.

The term "substituted" if not specified otherwise refers to substituted with 1, 2 or maximum possible number of substituents. If substituents as defined in compounds of formula I are more than one then they are independently from each other are same or different if not mentioned otherwise.

With respect to the variables, the embodiments of the compounds of the formula I are, In one preferred embodiment, W is O.

In another preferred embodiment, W is $NR^6$.

In another preferred embodiment, W is $S(=O)_m$.

In another preferred embodiment, A is $CR^A$.

In another preferred embodiment, A is N.

In another preferred embodiment, W is O, A is $CR^A$;

In another preferred embodiment, W is O, A is N;

In another preferred embodiment, W is $S(=O)_m$, A is $CR^A$;

In another preferred embodiment, W is $S(=O)_m$, A is N;

In another preferred embodiment, W is $NR^6$, A is $CR^A$;

In another preferred embodiment, W is $NR^6$, A is N;

In one preferred embodiment, $B^1$ is $CR^{B1}$, $B^2$ is $CR^{B2}$, $B^3$ is $CR^{B3}$, and $B^4$ is $CR^{B4}$;

In another preferred embodiment, $B^1$ is N, $B^2$ is $CR^{B2}$, $B^3$ is $CR^{B3}$, $B^4$ is $CR^{B4}$;

In another preferred embodiment, $B^1$ is $CR^{B1}$, $B^2$ is N, $B^3$ is $CR^{B3}$, $B^4$ is $CR^{B4}$;

In another preferred embodiment, $B^1$ is N, $B^2$ is N, $B^3$ is $CR^{B3}$, $B^4$ is $CR^{B4}$;

In another preferred embodiment, $B^1$ is N, $B^2$ is N, $B^3$ is N, $B^4$ is $CR^{B4}$;

In another preferred embodiment, W is O, A is $CR^A$, $B^1$ is $CR^{B1}$, $B^2$ is $CR^{B2}$, $B^3$ is $CR^{B3}$, and $B^4$ is $CR^{B4}$;

In another preferred embodiment, W is O, A is $CR^A$, $B^1$ is N, $B^2$ is $CR^{B2}$, $B^3$ is $CR^{B3}$, $B^4$ is $CR^{B4}$;

In another preferred embodiment, W is O, A is $CR^A$, $B^1$ is $CR^{B1}$, $B^2$ is N, $B^3$ is $CR^{B3}$, $B^4$ is $CR^{B4}$;

In another preferred embodiment, W is O, A is $CR^A$, $B^1$ is N, $B^2$ is N, $B^3$ is $CR^{B3}$, $B^4$ is $CR^{B4}$;

In another preferred embodiment, W is O, A is $CR^A$, $B^1$ is N, $B^2$ is N, $B^3$ is N, $B^4$ is $CR^{B4}$;

In another preferred embodiment, W is O, A is N, $B^1$ is $CR^{B1}$, $B^2$ is $CR^{B2}$, $B^3$ is $CR^{B3}$, and $B^4$ is $CR^{B4}$;

In another preferred embodiment, W is O, A is N, $B^1$ is N, $B^2$ is $CR^{B2}$, $B^3$ is $CR^{B3}$, $B^4$ is $CR^{B4}$;

In another preferred embodiment, W is O, A is N, $B^1$ is $CR^{B1}$, $B^2$ is N, $B^3$ is $CR^{B3}$, $B^4$ is $CR^{B4}$;

In another preferred embodiment, W is O, A is N, $B^1$ is N, $B^2$ is N, $B^3$ is $CR^{B3}$, $B^4$ is $CR^{B4}$;

In another preferred embodiment, W is O, A is N, $B^1$ is N, $B^2$ is N, $B^3$ is N, $B^4$ is $CR^{B4}$;

In another preferred embodiment, W is $S(=O)_m$, A is $CR^A$, B1 is $CR^{B1}$, $B^2$ is $CR^{B2}$, $B^3$ is $CR^{B3}$, and $B^4$ is $CR^{B4}$;

In another preferred embodiment, W is $S(=O)_m$, A is $CR^A$, $B^1$ is N, $B^2$ is $CR^{B2}$, $B^3$ is $CR^{B3}$, $B^4$ is $CR^{B4}$;

In another preferred embodiment, W is $S(=O)_m$, A is $CR^A$, $B^1$ is $CR^{B1}$, $B^2$ is N, $B^3$ is $CR^{B3}$, $B^4$ is $CR^{B4}$;

In another preferred embodiment, W is $S(=O)_m$, A is $CR^A$, $B^1$ is N, $B^2$ is N, $B^3$ is $CR^{B3}$, $B^4$ is $CR^{B4}$;

In another preferred embodiment, W is $S(=O)_m$, A is $CR^A$, $B^1$ is N, $B^2$ is N, $B^3$ is N, $B^4$ is $CR^{B4}$;

In another preferred embodiment, W is $S(=O)_m$, A is N, $B^1$ is $CR^{B1}$, $B^2$ is $CR^{B2}$, $B^3$ is $CR^{B3}$, and $B^4$ is $CR^{B4}$;

In another preferred embodiment, W is $S(=O)_m$, A is N, $B^1$ is N, $B^2$ is $CR^{B2}$, $B^3$ is $CR^{B3}$, $B^4$ is $CR^{B4}$;

In another preferred embodiment, W is $S(=O)_m$, A is N, $B^1$ is $CR^{B1}$, $B^2$ is N, $B^3$ is $CR^{B3}$, $B^4$ is $CR^{B4}$;

In another preferred embodiment, W is $S(=O)_m$, A is N, $B^1$ is N, $B^2$ is N, $B^3$ is $CR^{B3}$, $B^4$ is $CR^{B4}$;

In another preferred embodiment, W is $S(=O)_m$, A is N, $B^1$ is N, $B^2$ is N, $B^3$ is N, $B^4$ is $CR^{B4}$;

In another preferred embodiment, W is $NR^6$, A is $CR^A$, $B^1$ is $CR^{B1}$, $B^2$ is $CR^{B2}$, $B^3$ is $CR^{B3}$, and $B^4$ is $CR^{B4}$;

In another preferred embodiment, W is $NR^6$, A is $CR^A$, $B^1$ is N, $B^2$ is $CR^{B2}$, $B^3$ is $CR^{B3}$, $B^4$ is $CR^{B4}$;

In another preferred embodiment, W is $NR^6$, A is $CR^A$, $B^1$ is $CR^{B1}$, $B^2$ is N, $B^3$ is $CR^{B3}$, $B^4$ is $CR^{B4}$;

In another preferred embodiment, W is $NR^6$, A is $CR^A$, $B^1$ is N, $B^2$ is N, $B^3$ is $CR^{B3}$, $B^4$ is $CR^{B4}$;

In another preferred embodiment, W is $NR^6$, A is $CR^A$, $B^1$ is N, $B^2$ is N, $B^3$ is N, $B^4$ is $CR^{B4}$;

In another preferred embodiment, W is $NR^6$, A is N, $B^1$ is $CR^{B1}$, $B^2$ is $CR^{B2}$, $B^3$ is $CR^{B3}$, and $B^4$ is $CR^{B4}$;

In another preferred embodiment, W is $NR^6$, A is N, $B^1$ is N, $B^2$ is $CR^{B2}$, $B^3$ is $CR^{B3}$, $B^4$ is $CR^{B4}$;

In another preferred embodiment, W is $NR^6$, A is N, $B^1$ is $CR^{B1}$, $B^2$ is N, $B^3$ is $CR^{B3}$, $B^4$ is $CR^{B4}$;

In another preferred embodiment, W is $NR^6$, A is N, $B^1$ is N, $B^2$ is N, $B^3$ is $CR^{B3}$, $B^4$ is $CR^{B4}$;

In another preferred embodiment, W is $NR^6$, A is N, $B^1$ is N, $B^2$ is N, $B^3$ is N, $B^4$ is $CR^{B4}$;

In one preferred embodiment, $R^A$ is H, halogen, OH, CN, $C_1$-$C_6$-alkyl, $C_1$-$C_6$-alkoxy, tri-$C_1$-$C_6$-alkylsilyl, $C_1$-$C_6$-alkoxy-$C_1$-$C_4$-alkyl, $C_3$-$C_6$-cycloalkyl, wherein the alkyl, alkoxy, cycloalkyl moieties are unsubstituted or substituted with halogen, $C(=O)-OR^a$, $NR^bR^c$, $C(=O)-NR^bR^c$, $C(=O)-R^d$, $SO_2NR^bR^c$, or $S(=O)_mR^e$;

In another preferred embodiment, $R^A$ is H, halogen, $C_1$-$C_6$-alkyl, $C_3$-$C_6$-cycloalkyl, wherein the alkyl or cycloalkyl moieties are unsubstituted or substituted with halogen.

In another preferred embodiment, $R^A$ is H, Cl, Br, F, $CH_3$, $C_2H_5$, n-$C_3H_7$, isopropyl, cyclopropyl, $CH_2F$, $CHF_2$, or $CF_3$.

In one preferred embodiment, $R^{B1}$, $R^{B2}$, $R^{B3}$, and $R^{B4}$ independently of each other are H, halogen, or $C_1$-$C_6$-alkyl;

In another preferred embodiment, $R^{B1}$, $R^{B2}$, $R^{B3}$, and $R^{B4}$ independently of each other are H, Cl, Br, F, $CH_3$, $C_2H_5$, n-$C_3H_7$, or isopropyl.

In one preferred embodiment, Q is —C($R^4R^5$)—O—, wherein C is bound to Ar.

In another preferred embodiment, Q is —C($R^4R^5$)—O—, wherein O is bound to Ar.

In another preferred embodiment, Q is —C(═O)—O—, wherein C is bound to Ar.

In another preferred embodiment, Q is —C(═O)—O—, wherein O is bound to Ar.

In another preferred embodiment, Q is —S(═O)$_m$—C($R^7R^8$)—, wherein S is bound to Ar.

In another preferred embodiment, Q is —S(═O)$_m$—C($R^7R^8$)—, wherein C is bound to Ar.

In another preferred embodiment, Q is —N($R^2$)—S(═O)$_m$—, wherein N is bound to Ar.

In another preferred embodiment, Q is —N($R^2$)—S(═O)$_m$—, wherein S is bound to Ar.

In another preferred embodiment, Q is —N($R^2$)—C($R^9R^{10}$)—, wherein N is bound to Ar.

In another preferred embodiment, Q is —N($R^2$)—C($R^9R^{10}$)—, wherein C is bound to Ar.

In another preferred embodiment, Q is —C(═O)—C($R^{19}R^{20}$)—, wherein C(═O) is bound to Ar.

In another preferred embodiment, Q is —C(═O)—C($R^{19}R^{20}$)—, wherein C($R^{19}R^{20}$) is bound to Ar.

In another preferred embodiment, Q is —N($R^2$)—C(═O)—, wherein N is bound to Ar.

In another preferred embodiment, Q is —N($R^2$)—C(═O)—, wherein C is bound to Ar.

In another preferred embodiment, Q is —N($R^2$)—C(═S)—, wherein N is bound to Ar.

In another preferred embodiment, Q is —N($R^2$)—C(═S)—, wherein C is bound to Ar.

In another preferred embodiment, Q is —N═C(X)—, wherein N is bound to Ar.

In another preferred embodiment, Q is —N═C(X)—, wherein C is bound to Ar.

In another preferred embodiment, Q is —N($R^2$)—C(═NR)—, wherein N is bound to Ar.

In another preferred embodiment, Q is —N($R^2$)—C(═NR)—, wherein C is bound to Ar.

In another preferred embodiment, Q is —C($R^{13}R^{14}$)—C($R^{15}R^{16}$)—.

In another preferred embodiment, Q is —C($R^4R^5$)—O—, —N($R^2$)—S(═O)$_m$—, —N($R^2$)—C($R^9R^{10}$)—, —N($R^2$)—C(═O)—, —N($R^2$)—C(═S)—, —N═C(X)—, or —N($R^2$)—C(═NR)—, wherein Ar is bound to either side of Q;

In another preferred embodiment, Q is —C($R^4R^5$)—O—, —N($R^2$)—C($R^9R^{10}$)—, —N($R^2$)—C(═O)—, —N($R^2$)—C(═NR)—, wherein Ar is bound to either side of Q;

In one preferred embodiment, X is H or N($R^3$)$_2$;

In another preferred embodiment, X is H;

In another preferred embodiment, X is N($R^3$)$_2$, preferably $NH_2$ or N($CH_3$)$_2$;

In one preferred embodiment, $R^3$ is H, $C_1$-$C_6$-alkyl, or $C_1$-$C_6$-alkoxy-$C_1$-$C_4$-alkyl;

In another preferred embodiment, $R^3$ is H, or $C_1$-$C_6$-alkyl;

In another preferred embodiment, $R^3$ is $C_1$-$C_6$-alkyl;

In another preferred embodiment, $R^3$ is H;

In one preferred embodiment, R is H, CN, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $OR^8$, or N($R^3$)$_2$;

In another preferred embodiment, R is H, CN, $C_1$-$C_6$-alkyl, or $OR^8$;

In another preferred embodiment, R is H, or $C_1$-$C_6$-alkyl;

In another preferred embodiment, R is H, $CH_3$, $C_2H_5$, n-$C_3H_7$, or isopropyl;

In one preferred embodiment, $R^6$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, S(═O)$_m$$R^e$, phenyl, or —$CH_2$-phenyl, wherein the phenyl rings are unsubstituted or substituted with $R^f$;

In another preferred embodiment, $R^6$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, In another preferred embodiment, $R^6$ is C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, S(═O)$_m$$R^e$, phenyl, or —$CH_2$-phenyl, wherein the phenyl rings are unsubstituted or substituted with $R^f$;

In another preferred embodiment, $R^6$ is H, $C_1$-$C_6$-alkyl, $C_1$-$C_6$-haloalkyl, —$CH_2$—C(═O)—$OR^a$, or —$CH_2$-phenyl;

In another preferred embodiment, $R^6$ is H, $C_1$-$C_6$-alkyl, $C_1$-$C_6$-haloalkyl, or —$CH_2$-phenyl;

In another preferred embodiment, $R^6$ is H, $C_1$-$C_6$-alkyl, $C_1$-$C_6$-haloalkyl, or —$CH_2$—C(═O)—$OR^a$;

In another preferred embodiment, $R^6$ is H, $C_1$-$C_6$-alkyl, or $C_1$-$C_6$-haloalkyl;

In another preferred embodiment, $R^6$ is H;

In another preferred embodiment, $R^6$ is $C_1$-$C_6$-alkyl;

In another preferred embodiment, $R^6$ is $C_1$-$C_6$-haloalkyl;

In another preferred embodiment, $R^6$ is H, $CH_3$, $C_2H_5$, $CH_2CF_3$, or $CHF_2$;

In another preferred embodiment, $R^6$ is H, $CH_3$, $C_2H_5$, or $CH_2CF_3$;

In one preferred embodiment, $R^4$, $R^5$, $R^7$, $R^8$, $R^9$, $R^{10}$, $R^{13}$, $R^{14}$, $R^{15}$, $R^{16}$, $R^{19}$, $R^{20}$ are, identical or different, H, halogen, $C_1$-$C_6$-alkyl, $C_1$-$C_6$-haloalkylalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-cycloalkoxy-$C_1$-$C_4$-alkyl, C(═O)—$OR^a$, C(═O)—$NR^bR^c$, C(═O)—$R^d$, $SO_2NR^bR^c$, S(═O)$_m$$R^e$, phenyl, or —$CH_2$-phenyl, wherein the phenyl rings are unsubstituted or substituted with $R^f$;

In another preferred embodiment, $R^4$, $R^5$, $R^7$, $R^8$, $R^9$, $R^{10}$, $R^{13}$, $R^{14}$, $R^{15}$, $R^{16}$, $R^{19}$, $R^{20}$ are, identical or different, H, halogen, $C_1$-$C_6$-alkyl, $C_1$-$C_6$-haloalkylalkyl, $C_3$-$C_6$-cycloalkyl, $C_3$-$C_6$-halo-cycloalkyl, C(═O)—$OR^a$, C(═O)—$NR^bR^c$, C(═O)—$R^d$, phenyl, or —$CH_2$-phenyl, wherein the phenyl rings are unsubstituted or substituted with $R^f$;

In another preferred embodiment, $R^4$, $R^5$, $R^7$, $R^8$, $R^9$, $R^{10}$, $R^{13}$, $R^{14}$, $R^{15}$, $R^{16}$, $R^{19}$, $R^{20}$ are, identical or different, H, halogen, $C_1$-$C_6$-alkyl, or $C_1$-$C_6$-haloalkylalkyl;

In another preferred embodiment, $R^4$, $R^5$, $R^7$, $R^8$, $R^9$, $R^{10}$, $R^{13}$, $R^{14}$, $R^{15}$, $R^{16}$, $R^{19}$, $R^{20}$ are, identical or different, H, halogen, or $C_1$-$C_6$-alkyl;

In another preferred embodiment, $R^4$, $R^5$, $R^7$, $R^8$, $R^9$, $R^{10}$, $R^{13}$, $R^{14}$, $R^{15}$, $R^{16}$, $R^{19}$, $R^{20}$ are, identical or different, H or $C_1$-$C_6$-alkyl;

In one preferred embodiment, Ar is phenyl which is unsubstituted or substituted with $R^{Ar}$.

In another preferred embodiment, Ar is 5- or 6-membered hetaryl, which is unsubstituted or substituted with $R^{Ar}$.

In more preferred embodiment, Ar is phenyl, pyrimidinyl, pyridazinyl, or pyridyl, which are unsubstituted or substituted with $R^{Ar}$.

In one preferred embodiment, $R^{Ar}$ is halogen, OH, CN, $NO_2$, SCN, $C_1$-$C_6$-alkyl, $C_1$-$C_6$-haloalkyl, $C_1$-$C_6$-alkoxy, $C_1$-$C_6$-haloalkoxy, or S—$R^e$.

In more preferred embodiment, $R^{Ar}$ is F, Cl, Br, OH, CN, $NO_2$, SCN, $CH_3$, $C_2H_5$, n-$C_3H_7$, isopropyl, $CH_2F$, $CHF_2$, $CF_3$, $CH_2CF_3$, $CF_2CHF_2$, $C_2F_5$, $CH_2CH_2CF_3$, $CH_2CF_2CHF_2$, $CH_2CF_2CF_3$, $OCH_3$, $OC_2H_5$, n-propyloxy, isopropyloxy, $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, $OCH_2CF_2CF_3$, or S—$R^e$, where $R^e$ is $C_1$-$C_6$-alkyl, in particular $C_1$-$C_3$-alkyl such as $CH_3$, $C_2H_5$, n-$C_3H_7$ or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$.

Particularly preferred Ar are listed in Table A below.

TABLE A

| | |
|---|---|
| 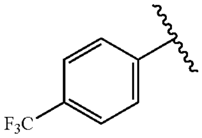 | Ar-1 |
| 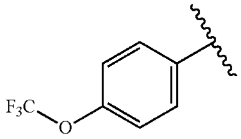 [SMILES: *c1ccc(OC(F)(F)F)cc1] | Ar-2 |
| 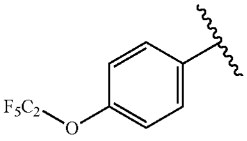 | Ar-3 |
| 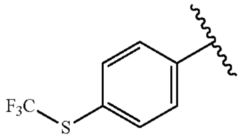 [SMILES: *c1ccc(SC(F)(F)F)cc1] | Ar-4 |
| 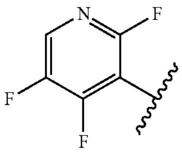 [SMILES: *c1c(F)ncc(F)c1F] | Ar-5 |
| 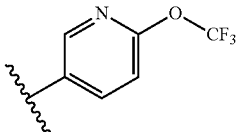 [SMILES: *c1ccc(OC(F)(F)F)nc1] | Ar-6 |
| 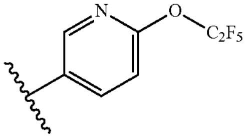 | Ar-7 |

TABLE A-continued

| | |
|---|---|
| 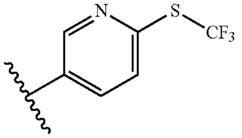 [SMILES: *c1ccc(SC(F)(F)F)nc1] | Ar-8 |
| 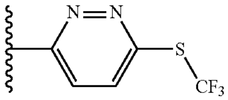 | Ar-9 |
| 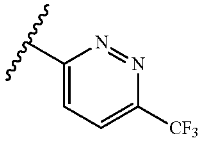 | Ar-10 |
| 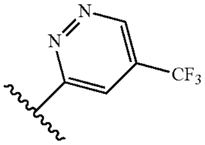 [SMILES: *c1cc(C(F)(F)F)cnn1] | Ar-11 |
| 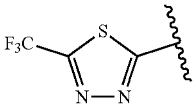 | Ar-12 |
| 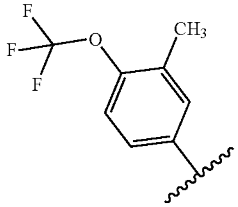 [SMILES: *c1ccc(OC(F)(F)F)c(C)c1] | Ar-13 |
| 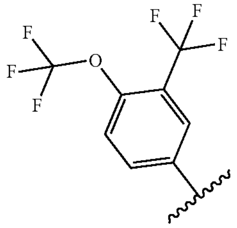 [SMILES: *c1ccc(OC(F)(F)F)c(C(F)(F)F)c1] | Ar-14 |
| 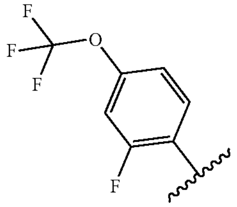 [SMILES: *c1ccc(OC(F)(F)F)cc1F] | Ar-15 |
| 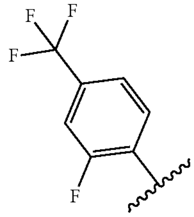 [SMILES: *c1ccc(C(F)(F)F)cc1F] | Ar-16 |

TABLE A-continued

| | |
|---|---|
| 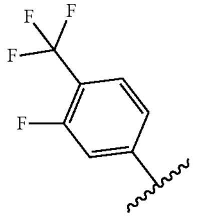 [SMILES: *c1ccc(C(F)(F)F)c(F)c1] | Ar-17 |
| 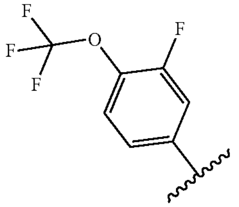 [SMILES: *c1ccc(OC(F)(F)F)c(F)c1] | Ar-18 |
| 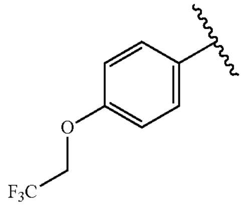 [SMILES: *c1ccc(OCC(F)(F)F)cc1] | Ar-19 |
| 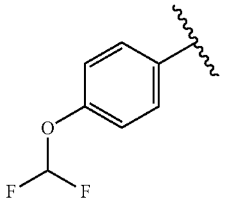 | Ar-20 |
| 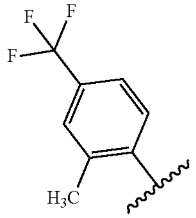 [SMILES: *c1ccc(C(F)(F)F)cc1C] | Ar-21 |
| 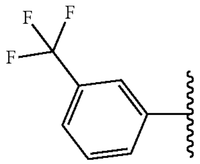 [SMILES: *c1cccc(C(F)(F)F)c1] | Ar-22 |

Particularly preferred Ar is selected from Ar-1 to Ar-20;

also particularly preferred Ar is selected from Ar-1 to Ar-13;

also particularly preferred Ar is selected from Ar-1 to Ar-13 and Ar-17 to Ar-18;

also particularly preferred Ar is selected from Ar-1, Ar-2, Ar-3, Ar-4, Ar-10, Ar-17, and Ar-18.

also particularly preferred Ar is selected from Ar-17 and Ar-18;

also particularly preferred Ar is Ar-17;

also particularly preferred Ar is Ar-18;

In one preferred embodiment, $R^1$ is Y—Z-T-$R^{11}$.

In another preferred embodiment, $R^1$ is Y—Z-T-$R^{12}$.

In one preferred embodiment, Y is —$CR^{ya}$═N—, wherein the N is bound to Z.

In another preferred embodiment, Y is —$NR^{yc}$—C(═S)—, wherein C(═S) is bound to Z.

In another preferred embodiment, Y is —$NR^{yc}$—C(═O)—, wherein C(═O) is bound to Z.

In one preferred embodiment, Z is a single bond;

—$NR^{zc}$—C(═O)—, wherein C(═O) is bound to T;

—$NR^{zc}$—C(═S)—, wherein C(═S) is bound to T;

—N═C(S—$R^{za}$)—, wherein T is bound to the carbon atom; or

—$NR^{zc}$—C(S—$R^{za}$)═, wherein T is bound to the carbon atom;

In another preferred embodiment, Z is —$NR^{zc}$—C(═S)—, wherein C(═S) is bound to T.

In another preferred embodiment, Z is —$NR^{zc}$—C(═O)—, wherein C(═O) is bound to T.

In another preferred embodiment, Z is —N═C(S—$R^{za}$)—, wherein T is bound to the carbon atom.

In another preferred embodiment, Z is —$NR^{zc}$—C(S—$R^{za}$)═, wherein T is bound to the carbon atom.

In another preferred embodiment, Z is —O—C(═O)—, wherein T is bound to the carbon atom;

In another preferred embodiment, Z is a single bond.

In one preferred embodiment, T is O.

In another preferred embodiment, T is N—$R^T$.

In another preferred embodiment, T is N.

In one preferred embodiment, $R^{ya}$ is H, halogen, $C_1$-$C_6$-alkyl, $C_1$-$C_6$-alkoxy, which are unsubstituted or substituted with halogen, phenyl, or —$CH_2$-phenyl, wherein the phenyl rings are unsubstituted or substituted with $R^f$.

In more preferred embodiment, $R^{ya}$ is H, halogen, $C_1$-$C_6$-alkyl, $C_1$-$C_6$-alkoxy, which are unsubstituted or substituted with halogen, or phenyl which is unsubstituted or substituted with $R^f$.

In most preferred embodiment, $R^{ya}$ is H, F, Cl, Br, $CH_3$, $C_2H_5$, n-$C_3H_7$, isopropyl, $CH_2F$, $CHF_2$, $CF_3$, $CH_2CF_3$, $CF_2CHF_2$, $C_2F_5$, $CH_2CH_2CF_3$, $CH_2CF_2CHF_2$, $CH_2CF_2CF_3$, $OCH_3$, $OC_2H_5$, n-propyloxy, isopropyloxy, $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, $OCH_2CF_2CF_3$, or phenyl which is unsubstituted or substituted with $R^f$.

In further most preferred embodiment, $R^{ya}$ is H or $CH_3$;

In one embodiment, $R^{yc}$, $R^{zc}$ are H, $C_1$-$C_6$-alkyl, $C_3$-$C_6$-cycloalkyl, which are unsubstituted or substituted with halogen, phenyl, or —$CH_2$-phenyl, wherein the rings are unsubstituted or substituted with $R^f$.

In more preferred embodiment, $R^{yc}$ and $R^{zc}$ are H, $C_1$-$C_6$-alkyl, $C_1$-$C_6$-haloalkyl, or phenyl which is unsubstituted or substituted with $R^f$.

In most preferred embodiment, $R^{yc}$ and $R^{zc}$ are H, $CH_3$, $C_2H_5$, n-$C_3H_7$, isopropyl, $CH_2F$, $CHF_2$, $CF_3$, $CH_2CF_3$, $CF_2CHF_2$, $C_2F_5$, $CH_2CH_2CF_3$, $CH_2CF_2CHF_2$, $CH_2CF_2CF_3$, or phenyl which is unsubstituted or substituted with $R^f$.

In further most preferred embodiment, $R^{yc}$ and $R^{zc}$ are H or $CH_3$;

In one preferred embodiment, $R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, which are unsubstituted or substituted with halogen, C(═O)—$NR^bR^c$, C(═O)$R^d$, $SO_2NR^bR^c$, S(═O)$_m R^e$, phenyl, or —$CH_2$-phenyl, wherein the phenyl rings are unsubstituted or substituted with $R^f$.

In more preferred embodiment, $R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, which are unsubstituted or substituted with halogen.

In most preferred embodiment, $R^T$ is H or $C_1$-$C_6$-alkyl.

In another preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a carbonyl group.

In another more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a C═N—R' and wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In another more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene 1 or 2 $CH_2$ moieties are replaced by O or S and/or wherein the linear $C_1$-$C_6$-alkylene and the linear $C_2$-$C_6$-alkenylene may be unsubstituted or substituted with $R^h$.

In one preferred embodiment, $R^{za}$ is H, $C_1$-$C_6$-alkyl, $C_1$-$C_6$-haloalkyl, $C_1$-$C_6$-alkylene-$NR^bR^c$, $C_1$-$C_6$—C(═O)—$R^d$, phenyl, phenylcarbonyl, or —$CH_2$-phenyl, wherein the phenyl rings are unsubstituted or substituted with $R^f$;

In more preferred embodiment, $R^{za}$ is H, $C_1$-$C_6$-alkyl, or $C_1$-$C_6$-haloalkyl;

In most preferred embodiment, $R^{za}$ is H, $C_1$-$C_6$-alkyl.

In another preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

In more preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a carbonyl group.

In another more preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a C═N—R' and wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In another more preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene 1 or 2 $CH_2$ moieties are replaced by O or S and/or wherein the linear $C_1$-$C_6$-alkylene and the linear $C_2$-$C_6$-alkenylene may be unsubstituted or substituted with $R^h$.

In a preferred embodiment, $R^a$, $R^b$ and $R^c$ are H, $C_1$-$C_6$-alkyl, $C_2$-$C_6$-alkenyl, $C_2$-$C_6$-alkynyl, which are unsubstituted or substituted with halogen, $C_1$-$C_6$-alkylene-CN, phenyl, or —$CH_2$-phenyl, wherein the phenyl rings are unsubstituted or substituted with $R^f$;

In more preferred embodiment, $R^a$, $R^b$ and $R^c$ are H, $C_1$-$C_6$-alkyl, $C_2$-$C_6$-alkenyl, $C_2$-$C_6$-alkynyl, which are unsubstituted or substituted with halogen, phenyl, or —$CH_2$-phenyl, wherein the phenyl rings are unsubstituted or substituted with $R^f$.

In a preferred embodiment, $R^e$ is H, $C_1$-$C_6$-alkyl, $C_2$-$C_6$-alkenyl, $C_2$-$C_6$-alkynyl, which are unsubstituted or substituted with halogen, phenyl, or —$CH_2$-phenyl, wherein the phenyl rings are unsubstituted or substituted with $R^f$.

In more preferred embodiment, $R^e$ is H, $C_1$-$C_6$-alkyl, $C_1$-$C_6$-haloalkyl, or phenyl which is unsubstituted or substituted with $R^f$.

In one preferred embodiment, $R^e$ is $C_1$-$C_6$-alkyl, $C_1$-$C_6$-haloalkyl, $C_3$-$C_6$-cycloalkyl, $C_3$-$C_6$-halocycloalkyl, phenyl, or —$CH_2$-phenyl, wherein the phenyl rings are unsubstituted or substituted with $R^f$.

In more preferred embodiment, $R^e$ is H, $C_1$-$C_6$-alkyl, $C_1$-$C_6$-haloalkyl, or phenyl unsubstituted or substituted with $R^f$.

In one preferred embodiment, $R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen, C(═O)—$OR^a$, $NR^bR^c$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, or $S(═O)_mR^e$.

In more preferred embodiment, $R^f$ is halogen, $N_3$, OH, CN, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen, C(═O)—$OR^a$, $NR^bR^c$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, or $S(═O)_mR^e$.

In a preferred embodiment, $R^g$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen, C(═O)—$OR^a$, $NR^bR^c$, $C_1$-$C_6$-alkylene-$NR^bR^c$, NH—$C_1$-$C_6$-alkylene-$NR^bR^c$, C(═O)—$NR^bR^c$, C(═O)—$R^d$, $SO_2NR^bR^c$, or $S(═O)_mR^e$.

In more preferred embodiment, $R^g$ is halogen, $N_3$, OH, CN, $NO_2$, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkoxy, which are unsubstituted or substituted with halogen, C(═O)—$OR^a$, $NR^bR^c$, $C_1$-$C_6$-alkylene-$NR^bR^c$, C(═O)—$NR^bR^c$, C(═O)—$R^d$, $SO_2NR^bR^c$, or $S(═O)_mR^e$.

In one embodiment, m is 0.

In another embodiment, m is 1.

In another embodiment, m is 2.

In another embodiment, m is 0 or 1.

In another embodiment, m is 1 or 2.

In more preferred embodiment, $R^1$ are formulas Y-1 to Y-9 wherein

denotes attachment to the 6 membered ring, D is $R^{11}$ or $R^{12}$ and wherein $R^T$, $R^{11}$, $R^{12}$, $R^{ya}$, $R^{yc}$, $R^{za}$ and $R^{zc}$ are as defined in compounds of formula I.

Y-1

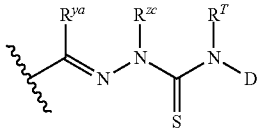

Y-2

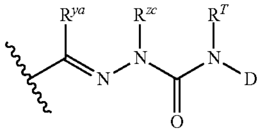

Y-3

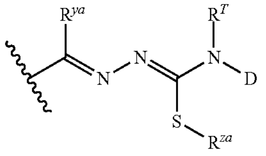

Y-4

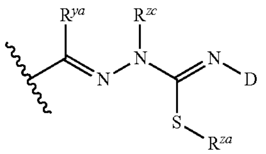

Y-5

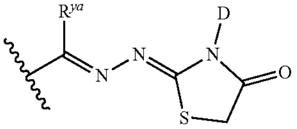

Y-6

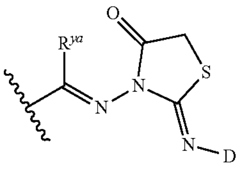

Y-7

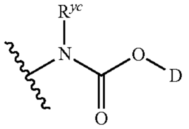

Y-8

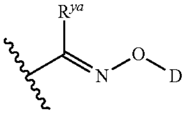

Y-9

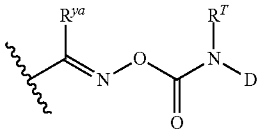

In more preferred embodiment, $R^1$ are formulas Y-1 to Y-8 wherein

denotes attachment to the 6 membered ring, D is $R^{11}$ or $R^{12}$ and wherein $R^T$, $R^{11}$, $R^{12}$, $R^{ya}$, $R^{yc}$, $R^{za}$ and $R^{zc}$ are as defined in compounds of formula I.

In another more preferred embodiment, $R^1$ are formulas YZT-1 to YZT-9, wherein

denotes attachment to the 6 membered ring and $R^{11}$, $R^{12}$, $R^T$, $R^{ya}$, $R^{za}$ and $R^{zc}$ are as defined in compounds of formula I.

YZT-1

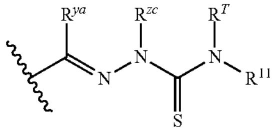

YZT-2

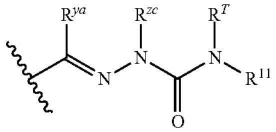

YZT-3

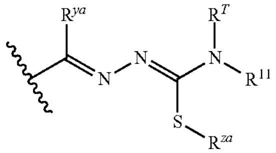

YZT-4

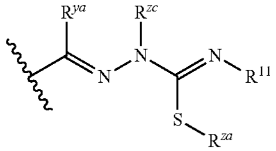

YZT-5

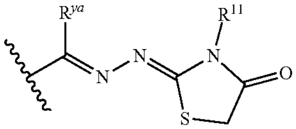

YZT-6

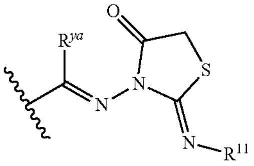

YZT-7

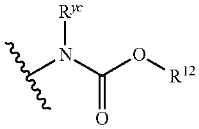

YZT-8

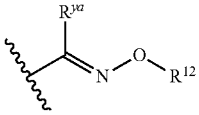

-continued

YZT-9

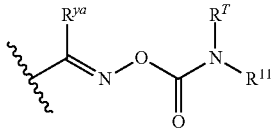

In another more preferred embodiment, $R^1$ are formulas YZT-1 to YZT-8, wherein

denotes attachment to the 6 membered ring and $R^{11}$, $R^{12}$, $R^T$, $R^{ya}$, $R^{za}$ and $R^{zc}$ are as defined in compounds of formula I.

In most preferred embodiment, $R^1$ are formulas Y-1A to Y-9A, wherein

denotes attachment to the 6 membered ring, D is $R^{11}$ or $R^{12}$.

Y-1A

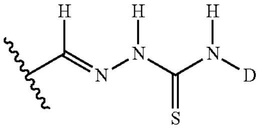

Y-1B

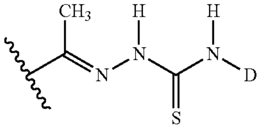

Y-2A

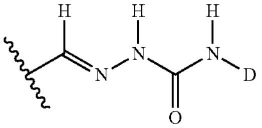

Y-2B

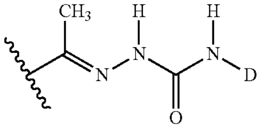

Y-3A

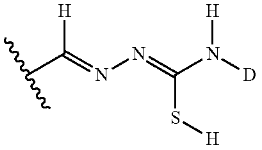

Y-3B

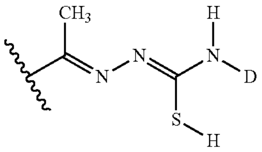

-continued

Y-3C

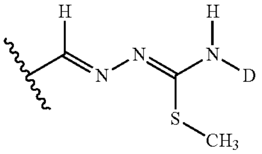

Y-3D

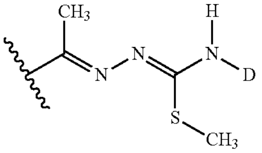

Y-4A

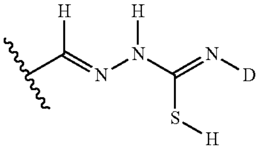

Y-4B

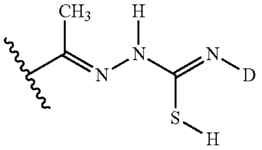

Y-4C

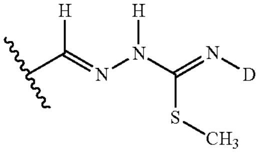

Y-4D

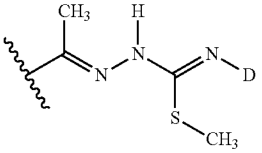

Y-5A

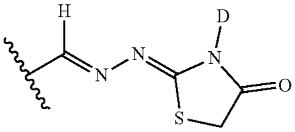

Y-5B

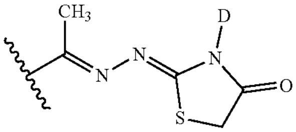

Y-6A

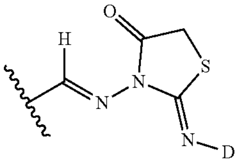

Y-6B

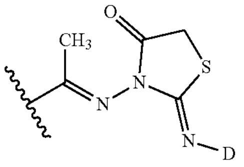

-continued

Y-7A

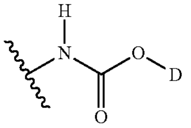

Y-7B

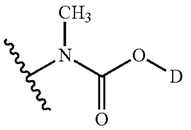

Y-8A

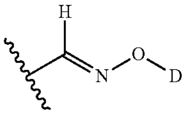

Y-8B

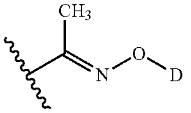

Y-9A

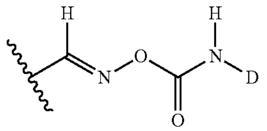

In most preferred embodiment, $R^1$ are formulas Y-1A to Y-8B, wherein

denotes attachment to the 6 membered ring, D is $R^{11}$ or $R^{12}$.

In one preferred embodiment, $R^{11}$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_1$-$C_4$-alkyl-$C_3$-$C_6$-cycloalkoxy, which are unsubstituted or substituted with halogen, aryl, arylcarbonyl, aryloxy-$C_1$-$C_4$-alkyl, hetaryl, carbonylhetaryl, $C_1$-$C_4$-alkyl-hetaryl and $C_1$-$C_4$-alkyl-hetaryloxy, wherein the aryl or hetaryl rings are unsubstituted or substituted with $R^g$ and wherein the hetaryl is a 5- or 6-membered monocyclic hetaryl or a 8-, 9- or 10-membered bicyclic hetaryl.

In more preferred embodiment, $R^{11}$ is $C_1$-$C_6$-alkyl, $C_2$-$C_6$-alkenyl, $C_2$-$C_6$-alkynyl, $C_3$-$C_6$-cycloalkyl, which are unsubstituted or substituted with halogen, aryl, arylcarbonyl, aryloxy-$C_1$-$C_4$-alkyl, hetaryl, carbonylhetaryl, $C_1$-$C_4$-alkyl-hetaryl and $C_1$-$C_4$-alkyl-hetaryloxy, where the rings are unsubstituted or substituted with $R^g$ and wherein the hetaryl is a 5- or 6-membered monocyclic hetaryl or a 8-, 9- or 10-membered bicyclic hetaryl.

In most preferred embodiment, $R^{11}$ is aryl, aryl-$C_1$-$C_4$-alkyl, hetaryl, or hetaryl-$C_1$-$C_4$-alkyl, wherein the rings are unsubstituted or substituted with $R^g$ and where hetaryl in hetaryl or hetaryl-$C_1$-$C_4$-alkyl, is preferably a 5- or 6-membered monocyclic hetaryl such as pyridyl, pyrimidinyl, pyridazinyl, pyrrolyl, pyrazolyl, imidazolyl, oxazolyl, thiazolyl, isoxazolyl or isothiazolyl which is unsubstituted or substituted with $R^g$.

Examples of particularly preferred radicals $R^{11}$ are the radicals $R^{11}$-1 to $R^{11}$-29 summarized in Table A-1 below.

TABLE A-1

| | |
|---|---|
| 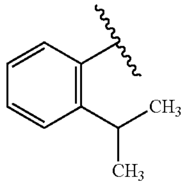 [SMILES: *c1ccccc1C(C)C] | $R^{11}$-1 |
| 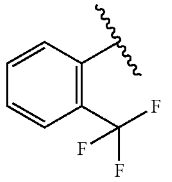 [SMILES: *c1ccccc1C(F)(F)F] | $R^{11}$-2 |
| 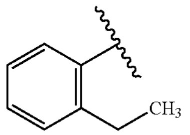 [SMILES: *c1ccccc1CC] | $R^{11}$-3 |
| 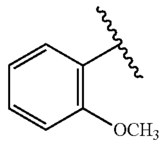 [SMILES: *c1ccccc1OC] | $R^{11}$-4 |
| 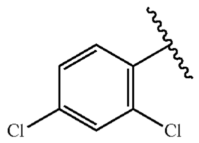 [SMILES: *c1ccc(Cl)cc1Cl] | $R^{11}$-5 |
| 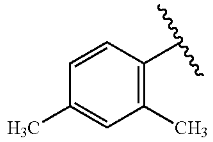 | $R^{11}$-6 |
| 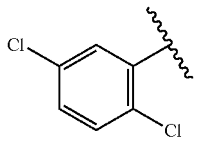 [SMILES: *c1cc(Cl)ccc1Cl] | $R^{11}$-7 |
| 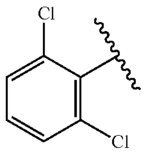 [SMILES: *c1c(Cl)cccc1Cl] | $R^{11}$-8 |
| 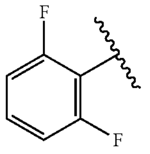 [SMILES: *c1c(F)cccc1F] | $R^{11}$-9 |
| 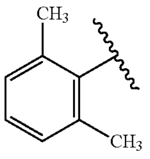 | $R^{11}$-10 |

TABLE A-1-continued
| | |
|---|---|
| 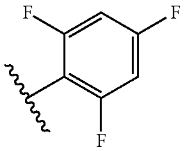 [SMILES: *c1c(F)cc(F)cc1F] | $R^{11}$-11 |
| 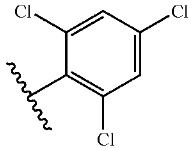 [SMILES: *c1c(Cl)cc(Cl)cc1Cl] | $R^{11}$-12 |
| 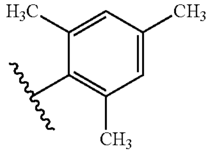 | $R^{11}$-13 |
| 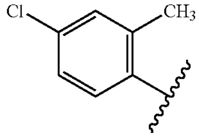 [SMILES: *c1ccc(Cl)cc1C] | $R^{11}$-14 |
| 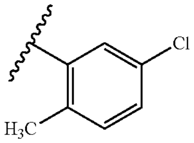 | $R^{11}$-15 |
| 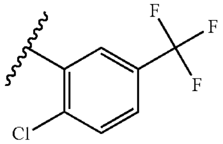 [SMILES: *c1cc(C(F)(F)F)ccc1Cl] | $R^{11}$-16 |
| 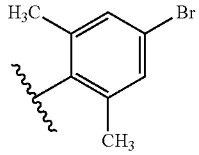 | $R^{11}$-17 |
| 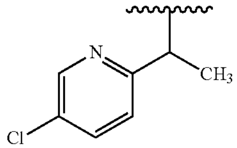 [SMILES: *C(C)c1ccc(Cl)cn1] | $R^{11}$-18 |
| 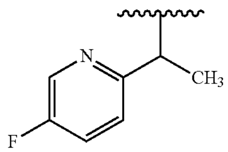 [SMILES: *C(C)c1ccc(F)cn1] | $R^{11}$-19 |
| 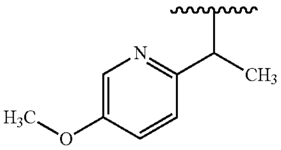 [SMILES: *C(C)c1ccc(OC)cn1] | $R^{11}$-20 |
TABLE A-1-continued
| | |
|---|---|
| 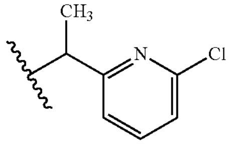 [SMILES: *C(C)c1cccc(Cl)n1] | $R^{11}$-21 |
| 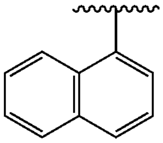 [SMILES: *c1cccc2ccccc12] | $R^{11}$-22 |
| 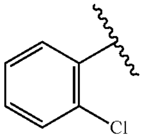 [SMILES: *c1ccccc1Cl] | $R^{11}$-23 |
| 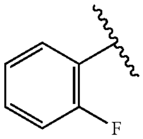 [SMILES: *c1ccccc1F] | $R^{11}$-24 |
| 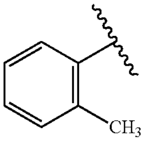 | $R^{11}$-25 |
| 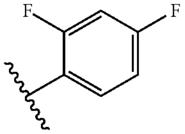 [SMILES: *c1ccc(F)cc1F] | $R^{11}$-26 |
| 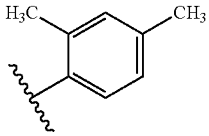 | $R^{11}$-27 |
| 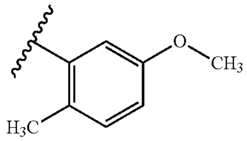 | $R^{11}$-28 |
| 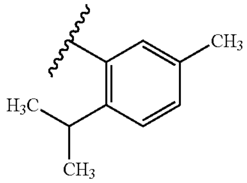 [SMILES: *c1cc(C)ccc1C(C)C] | $R^{11}$-29 |

In one embodiment, $R^{12}$ is a radical of the formula ($A^1$), ($A^1$)

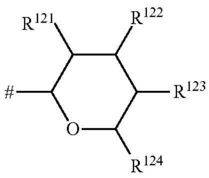

wherein # indicates the point of attachment to T and wherein $R^{121}$, $R^{122}$, $R^{123}$ and $R^{124}$ are as defined above and wherein $R^{121}$, $R^{122}$, $R^{123}$ and $R^{124}$ independently of each other and especially in combination preferably have the following meanings:

$R^{121}$ is $C_1$-$C_4$-alkoxy, in particular $OCH_3$, $OC_2H_5$;

$R^{122}$ is $C_1$-$C_4$-alkoxy, such as $OCH_3$, $OC_2H_5$, n-propoxyx or isopropoxy, or $C_3$-$C_4$-alkenyloxy, such as allyloxy, with $R^{122}$ in particular being $OCH_3$, $OC_2H_5$, or n-propoxy;

$R^{123}$ is OH, $C_1$-$C_4$-alkoxy, such as $OCH_3$, $OC_2H_5$, or $C_3$-$C_4$-alkenyloxy, such as allyloxy, with $R^{123}$ in particular being $OCH_3$, $OC_2H_5$;

$R^{124}$ is $C_1$-$C_4$-alkyl, such as $CH_3$ or $C_2H_5$, or $C_1$-$C_4$-alkoxy-$C_1$-$C_4$-alkyl, such as methoxymethyl, ethoxymethyl, 2-methoxyethyl or 2-ethoxyethyl, with $R^{124}$ in particular being methyl;.

In more preferred embodiment, $R^{12}$ is in particular a radical of the formula ($A^{11}$), e.g. ($A^{11}$-a) or ($A^{11}$-b)

($A^{11}$)

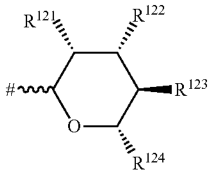

($A^{11}$-a)

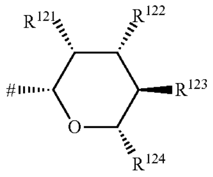

($A^{11}$-b)

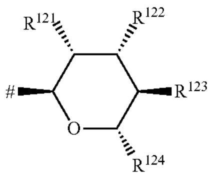

wherein # indicates the point of attachment to T and wherein $R^{121}$, $R^{122}$, $R^{123}$ and $R^{124}$ are as defined above and wherein $R^{121}$, $R^{122}$, $R^{123}$ and $R^{124}$ independently of each other and especially in combination preferably have the following meanings:

$R^{121}$ is $C_1$-$C_4$-alkoxy, in particular $OCH_3$ or $OC_2H_5$;

$R^{122}$ is $C_1$-$C_4$-alkoxy, such as $OCH_3$, $OC_2H_5$, n-propoxyx or isopropoxy, or $C_3$-$C_4$-alkenyloxy, such as allyloxy, with $R^{122}$ in particular being $OCH_3$, $OC_2H_5$ or n-propoxy;

$R^{123}$ is OH, $C_1$-$C_4$-alkoxy, such as $OCH_3$ or $OC_2H_5$, or $C_3$-$C_4$-alkenyloxy, such as allyloxy, with $R^{123}$ in particular being $OCH_3$ or $OC_2H_5$;

$R^{124}$ is $C_1$-$C_4$-alkyl, such as $CH_3$ or $C_2H_5$, or $C_1$-$C_4$-alkoxy-$C_1$-$C_4$-alkyl, such as methoxymethyl, ethoxymethyl, 2-methoxyethyl or 2-ethoxyethyl, with $R^{124}$ in particular being methyl.

Particular examples of radicals $R^{12}$ are the following radicals $A^{11}$-1, $A^{11}$-1a, $A^{11}$-1b, $A^{11}$-2, $A^{11}$-2a, $A^{11}$-2b, $A^{11}$-3, $A^{11}$-3a and $A^{11}$-3b:

($A^{11}$-1)

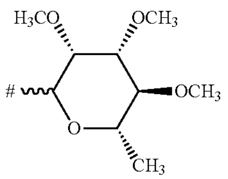

($A^{11}$-1a)

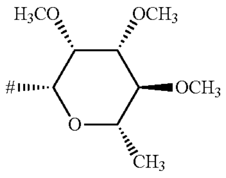

($A^{11}$-1b)

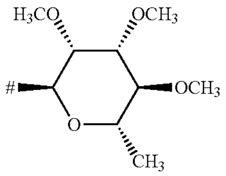

($A^{11}$-2)

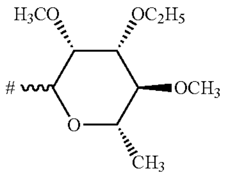

($A^{11}$-2a)

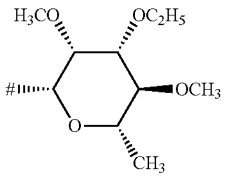

($A^{11}$-2b)

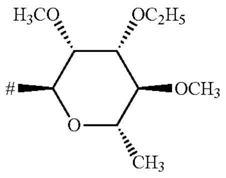

($A^{11}$-3)

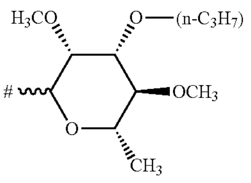

-continued
(A11-3a)
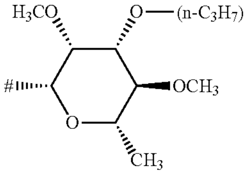
(A11-3b)
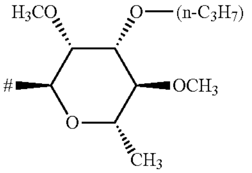
In a more preferred embodiment compounds of formula I are selected from compounds of formula A.1 to A.50.
A.1
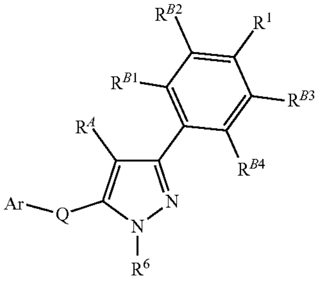
A.2
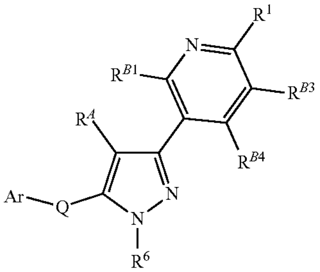
A.3
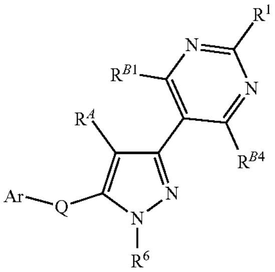
A.4
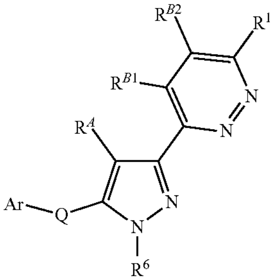
-continued
A.5
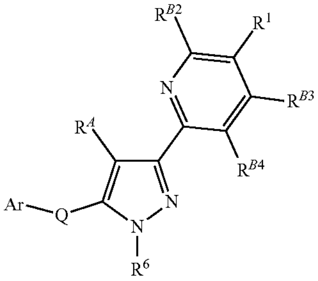
A.6
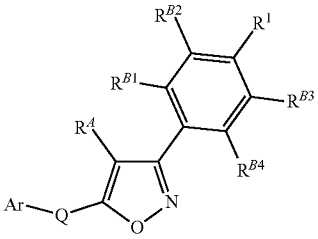
A.7
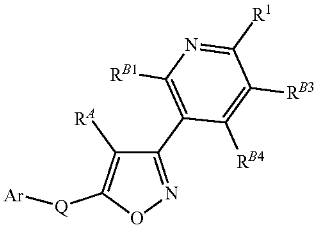
A.8
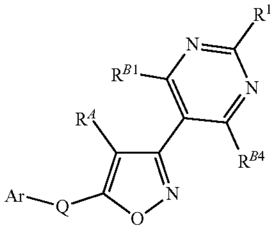
A.9
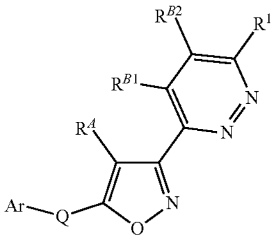
A.10
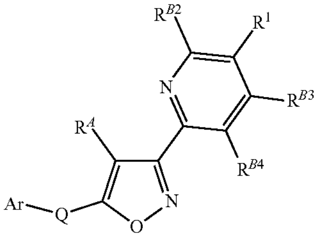

-continued
A.11
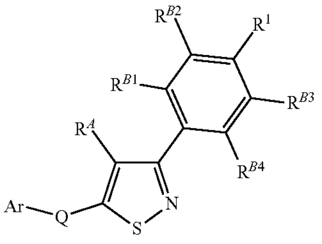
A.12
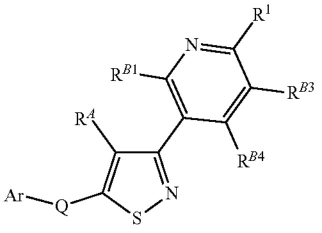
A.13
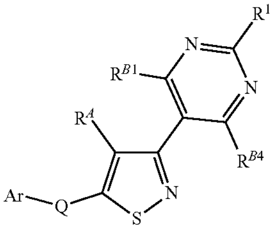
A.14
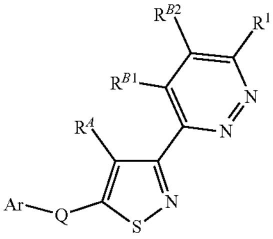
A.15
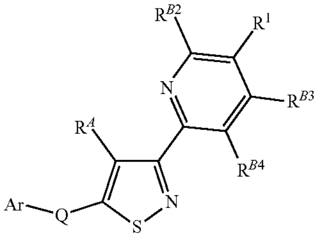
A.16
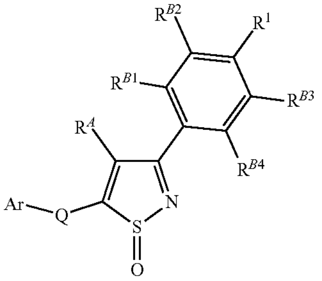
-continued
A.17
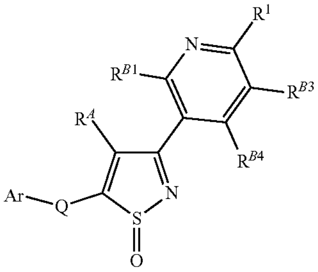
A.18
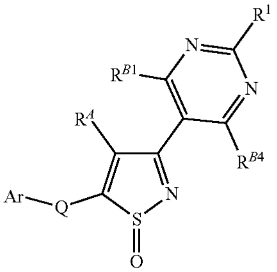
A.19
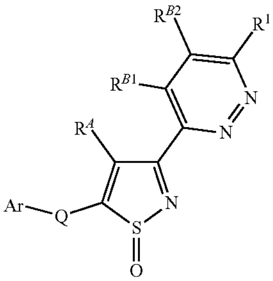
A.20
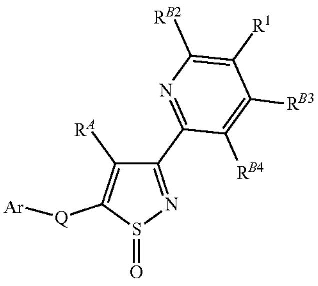
A.21
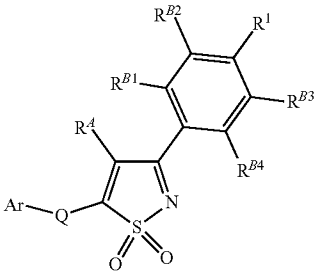

-continued
A.22
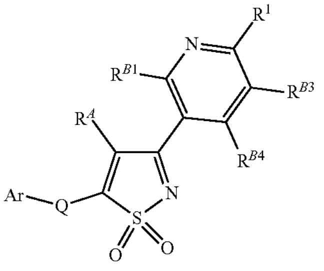
A.23
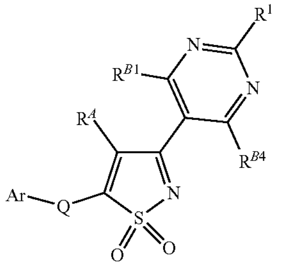
A.24
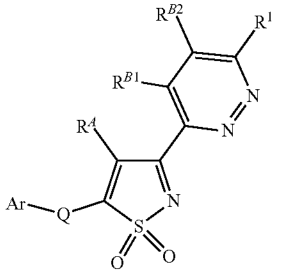
A.25
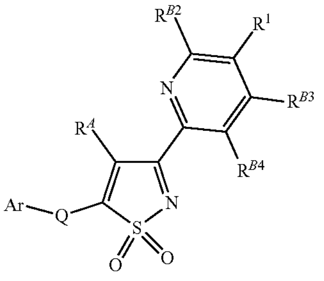
A.26
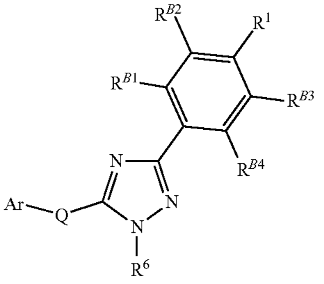
-continued
A.27
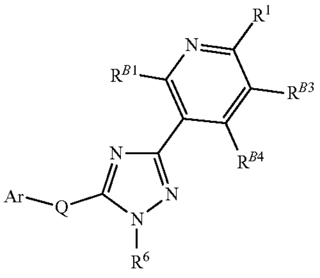
A.28
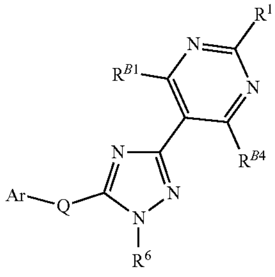
A.29
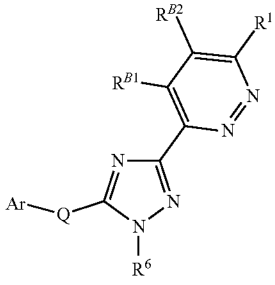
A.30
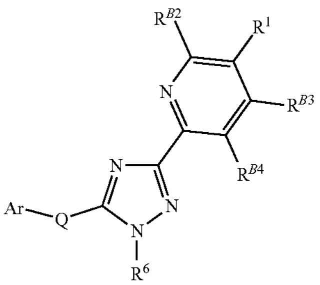
A.31
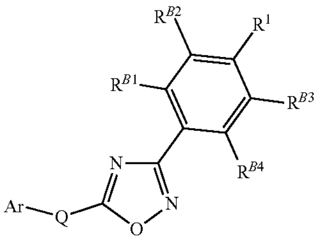
A.32
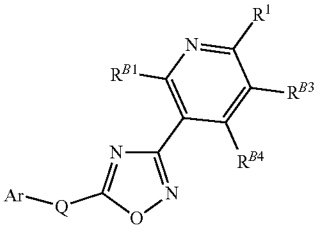

-continued
A.33
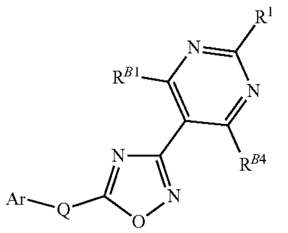
A.34
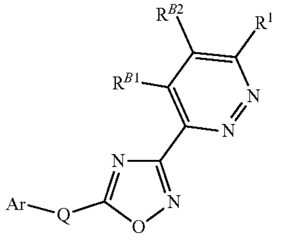
A.35
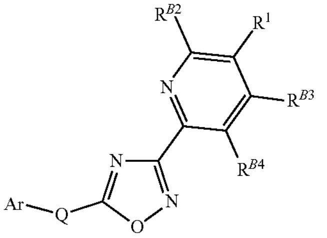
A.36
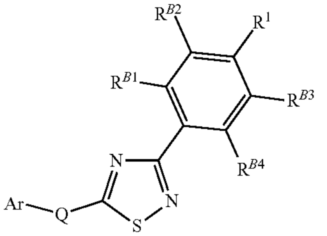
A.37
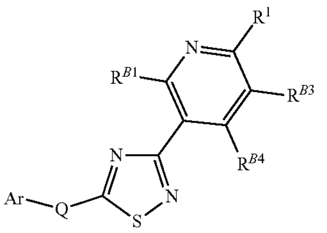
A.38
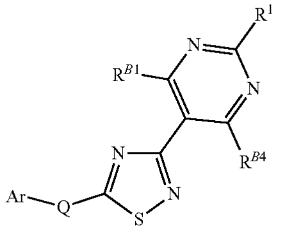
-continued
A.39
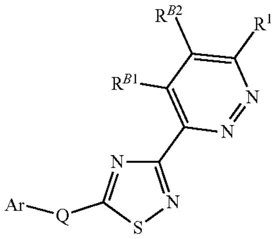
A.40
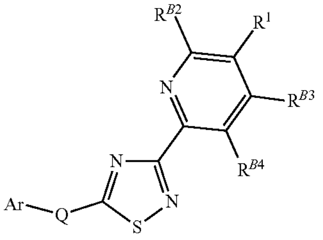
A.41
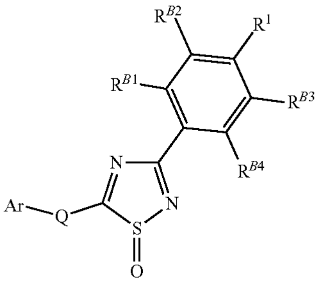
A.42
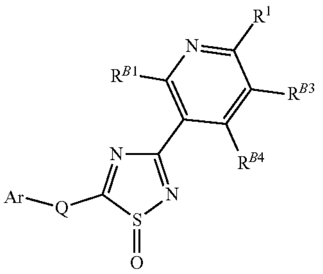
A.43
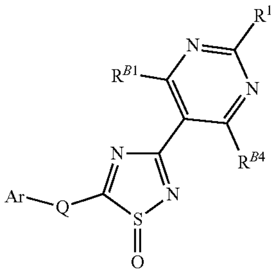
A.44
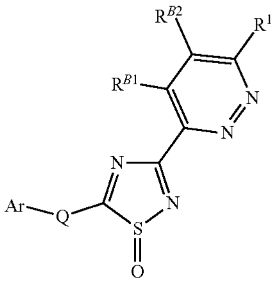

-continued

A.45

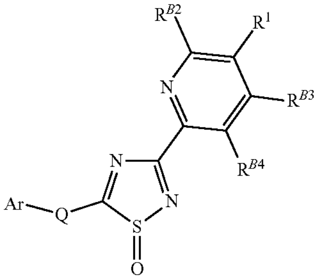

A.46

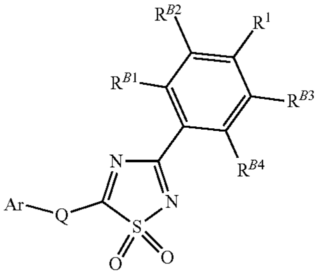

A.47

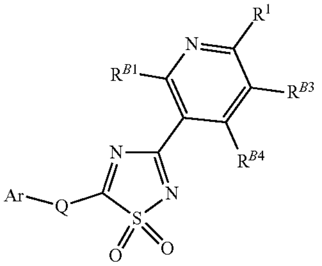

A.48

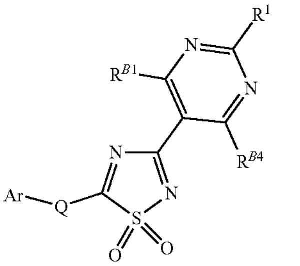

A.49

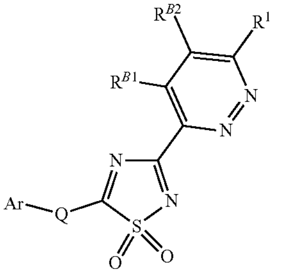

-continued

A.50

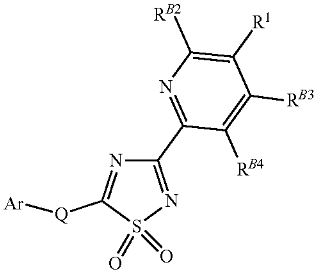

wherein, Ar is phenyl or 5- or 6-membered hetaryl ring which is substituted with $R^{Ar}$;

$R^{Ar}$ is halogen, OH, CN, $NO_2$, SCN, $C_1$-$C_6$-alkyl, $C_1$-$C_6$-alkoxy, or S—$R^e$, wherein the alkyl and alkoxy are unsubstituted or substituted with halogen;

$R^A$ is H, halogen, $C_1$-$C_6$-alkyl, $C_1$-$C_6$-haloalkyl, $C_3$-$C_6$-cycloalkyl, or $C_3$-$C_6$-halocycloalkyl;

$R^{B1}$, $R^{B2}$, $R^{B3}$, and $R^{B4}$ independently of each other are H, halogen, or $C_1$-$C_6$-alkyl;

Q is —C($R^4R^5$)—O—, —N($R^2$)—S(═O)$_m$—, —N($R^2$)—C($R^9R^{10}$)—, —N($R^2$)—C(═O)—, —N($R^2$)—C(═S)—, —N═C(X)—, —N($R^2$)—C(═NR)—; wherein Ar is bound to either side of Q;

X is N($R^3$)$_2$;

and $R^1$ is Y—Z-T-$R^{11}$ or Y—Z-T-$R^{12}$, as defined in formula I.

more preferred compounds of formula I are compounds of formula I.1 to I.24, wherein $R^1$ is selected from Y-1A, Y-1B, Y-2A, Y-2B, Y-3A, Y-3B, Y-3C, Y-3D, Y-4A, Y-4B, Y-4C, Y-4D, Y-5A, Y-5B, Y-6A, Y-6B, Y-7A, Y-7B, Y-8A, and Y-8B; wherein D is $R^{11}$ or $R^{12}$, and other variables are as defined herein.

I.1

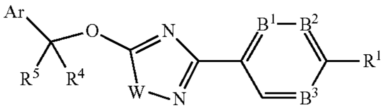

I.2

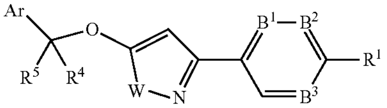

I.3

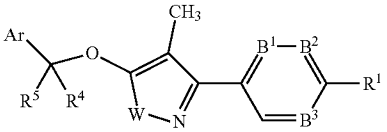

I.4

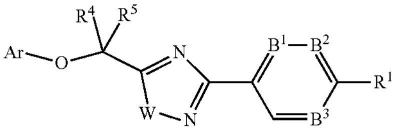

I.5

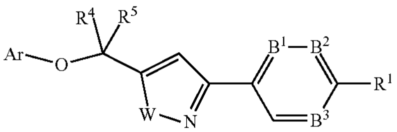

-continued

I.6

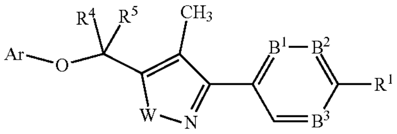

I.7

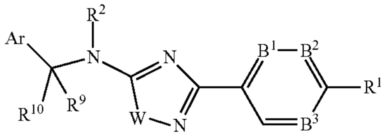

I.8

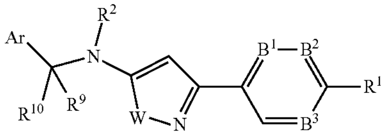

I.9

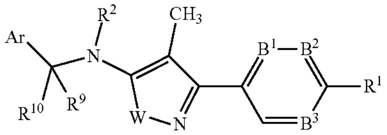

I.10

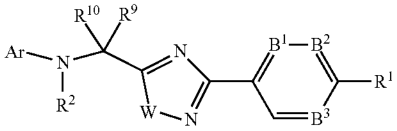

I.11

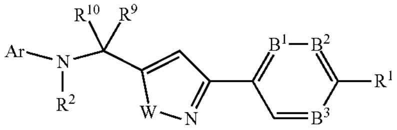

I.12

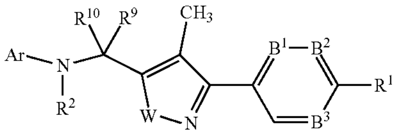

I.13

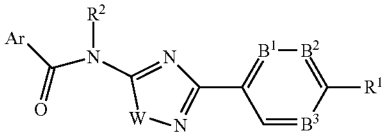

I.14

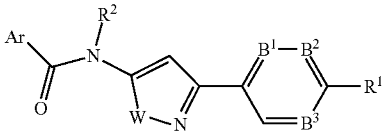

I.15

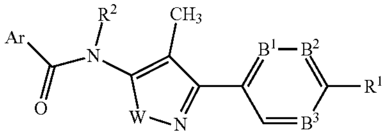

I.16

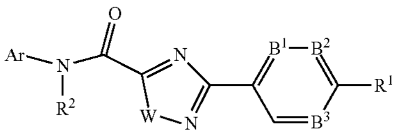

-continued

I.17

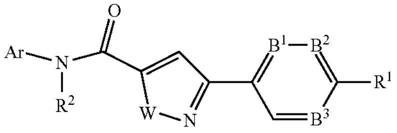

I.18

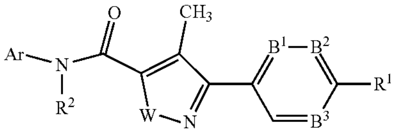

I.19

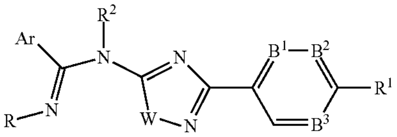

I.20

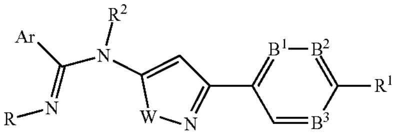

I.21

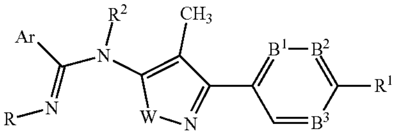

I.22

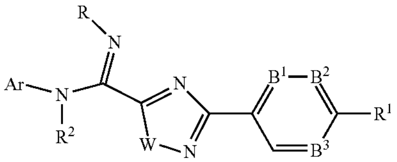

I.23

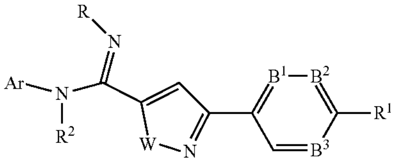

I.24

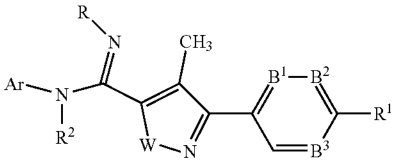

Also more preferred are the compound of formula I, wherein

A $CR^A$;

W is O, $S(=O)_m$, or $NR^6$;

$B^1$ is $CR^{B1}$, $B^2$ is $CR^{B2}$, $B^3$ is $CR^{B3}$, and $B^4$ is $CR^{B4}$ $R^{B1}$, $R^{B2}$, $R^{B3}$, and $R^{B4}$ independently of each other are H, halogen, $C_1$-$C_6$-alkyl;

Q is —$C(R^4R^5)$—O—, —$N(R^2)$—$C(R^9R^{10})$—, —$N(R^2)$—C(=O)—, —$N(R^2)$—C(=NR)—; wherein Ar is bound to either side of Q;

m is 0, 1, or 2;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

$R^6$ is H, $C_1$-$C_6$-alkyl, $C_1$-$C_6$-haloalkyl, or $CH_2$-phenyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-7A, Y-8A, or Y-9A;

D is $R^{11}$ or $R^{12}$;

$R^{11}$ is $R^{11}$-1 or $R^{11}$-10;

$R^{12}$ is $A^{11}$-1b or $A^{11}$-3b;

Also more preferred are the compound of formula I, wherein

A N;

W is O, S(═O)$_m$, or $NR^6$;

$B^1$ is $CR^{B1}$, $B^2$ is $CR^{B2}$, $B^3$ is $CR^{B3}$, and $B^4$ is $CR^{B4}$ $R^{B1}$, $R^{B2}$, $R^{B3}$, and $R^{B4}$ independently of each other are H, halogen, $C_1$-$C_6$-alkyl;

Q is —C($R^4R^5$)—O—, —N($R^2$)—C($R^9R^{10}$)—, —N($R^2$)—C(═O)—, —N($R^2$)—C(═NR)—; wherein Ar is bound to either side of Q;

m is 0, 1, or 2;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

$R^6$ is H, $C_1$-$C_6$-alkyl, $C_1$-$C_6$-haloalkyl, or —$CH_2$-phenyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-7A, Y-8A, or Y-9A;

D is $R^{11}$ or $R^{12}$;

$R^{11}$ is $R^{11}$-1 or $R^{11}$-10;

$R^{12}$ is $A^{11}$-1b or $A^{11}$-3b;

Also more preferred are the compound of formula I, wherein

A N or $R^A$;

W is O, S, NH, N—$CH_3$, N—$CH(CH_3)_2$, N—$CH_2(C_6H_5)$, N—$CH_2CHF_2$, or N—$C_2H_5$;

$B^1$ is $CR^{B1}$, $B^2$ is $CR^{B2}$, $B^3$ is $CR^{B3}$, and $B^4$ is $CR^{B4}$ $R^A$ is H, halogen, $C_1$-$C_6$-alkyl, $C_1$-$C_6$-haloalkyl, $C_3$-$C_6$-cycloalkyl, or $C_3$-$C_6$-halocycloalkyl;

$R^{B1}$, $R^{B2}$, $R^{B3}$, and $R^{B4}$ independently of each other are H, halogen, $C_1$-$C_6$-alkyl;

Q is —C($R^4R^5$)—O—, —N($R^2$)—C($R^9R^{10}$)—, —N($R^2$)—C(═O)—, —N($R^2$)—C(═NR)—; wherein Ar is bound to either side of Q;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-7A, Y-8A, or Y-9A;

D is $R^{11}$ or $R^{12}$;

$R^{11}$ is $R^{11}$-1 or $R^{11}$-10;

$R^{12}$ is $A^{11}$-1b or $A^{11}$-3b;

Also more preferred are the compound of formula I, wherein

A N or $R^A$;

W is O, S, NH, N—$CH_3$, N—$CH(CH_3)_2$, N—$CH_2(C_6H_5)$, N—$CH_2CHF_2$, or N—$C_2H_5$;

$B^1$ is $CR^{B1}$, $B^2$ is N, $B^3$ is $CR^{B3}$, and $B^4$ is $CR^{B4}$ $R^A$ is H, halogen, $C_1$-$C_6$-alkyl, $C_1$-$C_6$-haloalkyl, $C_3$-$C_6$-cycloalkyl, or $C_3$-$C_6$-halocycloalkyl;

$R^{B1}$, $R^{B3}$, and $R^{B4}$ independently of each other are H, halogen, $C_1$-$C_6$-alkyl;

Q is —C($R^4R^5$)—O—, —N($R^2$)—C($R^9R^{10}$)—, —N($R^2$)—C(═O)—, —N($R^2$)—C(═NR)—; wherein Ar is bound to either side of Q;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-7A, Y-8A, or Y-9A;

D is $R^{11}$ or $R^{12}$;

$R^{11}$ is $R^{11}$-1 or $R^{11}$-10;

$R^{12}$ is $A^{11}$-1b or $A^{11}$-3b;

Also more preferred are the compound of formula I, wherein

A N or $R^A$;

W is O, S, NH, N—$CH_3$, N—$CH(CH_3)_2$, N—$CH_2(C_6H_5)$, N—$CH_2CHF_2$, or N—$C_2H_5$;

$B^1$ is $CR^{B1}$, $B^2$ is N, $B^3$ is N, and $B^4$ is $CR^{B4}$ $R^A$ is H, halogen, $C_1$-$C_6$-alkyl, $C_1$-$C_6$-haloalkyl, $C_3$-$C_6$-cycloalkyl, or $C_3$-$C_6$-halocycloalkyl;

$R^{B1}$, $R^{B3}$, and $R^{B4}$ independently of each other are H, halogen, $C_1$-$C_6$-alkyl;

Q is —C($R^4R^5$)—O—, —N($R^2$)—C($R^9R^{10}$)—, —N($R^2$)—C(═O)—, —N($R^2$)—C(═NR)—; wherein Ar is bound to either side of Q;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-7A, Y-8A, or Y-9A;

D is $R^{11}$ or $R^{12}$;

$R^{11}$ is $R^{11}$-1 or $R^{11}$-10;

$R^{12}$ is $A^{11}$-1b or $A^{11}$-3b;

Also more preferred are the compound of formula I, wherein

A N or $R^A$;

W is O, S, NH, N—$CH_3$, N—$CH(CH_3)_2$, N—$CH_2(C_6H_5)$, N—$CH_2CHF_2$, or N—$C_2H_5$;

$B^1$ is N, $B^2$ is N, $B^3$ is $CR^{B3}$, and $B^4$ is $CR^{B4}$ $R^A$ is H, halogen, $C_1$-$C_6$-alkyl, $C_1$-$C_6$-haloalkyl, $C_3$-$C_6$-cycloalkyl, or $C_3$-$C_6$-halocycloalkyl;

$R^{B3}$, and $R^{B4}$ independently of each other are H, halogen, $C_1$-$C_6$-alkyl;

Q is —C($R^4R^5$)—O—, —N($R^2$)—C($R^9R^{10}$)—, —N($R^2$)—C(═O)—, —N($R^2$)—C(═NR)—; wherein Ar is bound to either side of Q;

$R^2$ is H or $C_1$-$C_6$-alkyl;

R is H, CN, or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-7A, Y-8A, or Y-9A;

D is $R^{11}$ or $R^{12}$;

$R^{11}$ is $R^{11}$-1 or $R^{11}$-10;

$R^{12}$ is $A^{11}$-1b or $A^{11}$-3b;

In another preferred embodiment, the compound of formula I are compounds of formula I.1 to I.24, wherein Ar is $Ar^1$, $Ar^2$, $Ar^3$, $Ar^4$, $Ar^{10}$, $Ar^{17}$, or $Ar^{18}$;

$B^1$ is N or CH;

$B^2$ is N or CH;

$B^3$ is N or CH;

W is NH, $NCH_3$, $NC_2H_5$, O, or S;

$R^1$ is Y-1A, Y-1B, Y-2A, Y-2B, Y-3A, Y-3B, Y-3C, Y-3D, Y-4A, Y-4B, Y-4C, Y-4D, Y-5A, Y-5B, Y-6A, Y-6B, Y-7A, Y-7B, Y-8A, or Y-8B; wherein D is $R^{11}$ or $R^{12}$;

$R^{11}$ is $R^{11}$-1, $R^{11}$-2, $R^{11}$-3, $R^{11}$-5, $R^{11}$-6, $R^{11}$-7, $R^{11}$-8, $R^{11}$-9, $R^{11}$-10, $R^{11}$-11, $R^{11}$-12, $R^{11}$-13, $R^{11}$-14, $R^{11}$-15, $R^{11}$-16, $R^{11}$-17, $R^{11}$-18, $R^{11}$-19, $R^{11}$-20, $R^{11}$-21, $R^{11}$-22, $R^{11}$-23, $R^{11}$-25, $R^{11}$- 26, $R^{11}$-27, $R^{11}$-28, or $R^{11}$-29;

$R^{12}$ is ($A^{11}$-1), ($A^{11}$-2), or ($A^{11}$-3).

$R^4$ and $R^5$ independently are H or $CH_3$, $R^9$ and $R^{10}$ independently are H or $CH_3$, $R^2$ is H, $CH_3$, or c-$C_3H_5$ R is NH, $NCH_3$, or NCN;

In another preferred embodiment, the compound of formula I are compounds wherein Ar is $Ar^1$, $Ar^2$, $Ar^4$, $Ar^{10}$, $Ar^{18}$, $Ar^{21}$, or $Ar^{22}$;

Q is —C($R^4R^5$)—O—, —N($R^2$)—C($R^9R^{10}$)—, —N($R^2$)—C(=O)—, or —N=C(X)—; wherein Ar is bound to either side of Q;

$R^2$ is H or $C_1$-$C_6$-alkyl;

$R^4$, $R^5$, $R^9$, $R^{10}$, are identical or different H or $C_1$-$C_6$-alkyl;

$B^1$ is $CR^{B1}$, $B^2$ is $CR^{B2}$, $B^3$ is $CR^{B3}$, and $B^4$ is $CR^{B4}$ $R^{B1}$, $R^{B2}$, $R^{B3}$, and $R^{B4}$ independently of each other are H, halogen, $C_1$-$C_6$-alkyl;

A is $CR^A$ or N, wherein $R^A$ is selected from CH, $CH_3$, and Cl;

W is NH, $NCH_3$, or $NC_2H_5$;

$R^1$ is Y-1A, Y-5A, Y-6A, or Y-7A; wherein D is $R^{11}$ or $R^{12}$;

$R^{11}$ is $R^{11}$-1 or $R^{11}$-29;

$R^{12}$ is $A^{11}$ wherein $R^{121}$, $R^{122}$, $R^{123}$, $R^{124}$ independently are selected from $OCH_3$, $OC_2H_5$, and O-n$C_3H_7$;

$R^4$ and $R^5$ independently are H or $CH_3$, $R^9$ and $R^{10}$ independently are H or $CH_3$, $R^2$ is H, $CH_3$, or c-$C_3H_5$ X is H, $NH_2$ or $N(CH_3)_2$;

Particular compounds of formula I are the compounds of the formulae I.1 to I.24 that are compiled in the following tables 1 to 3240, wherein the combination of variables W, $B^1$, $B^2$, $B^3$, Ar, and D for each compound of tables 1 to 3240 corresponds to each line of Table B. Each of the groups mentioned for a substituent in the tables is furthermore per se, independently of the combination in which it is mentioned, a particularly preferred aspect of the substituent in question.

Table 1. Compounds of formula I.1 wherein $R^1$ is Y-1A, $R^4$ is H and $R^5$ is H.

Table 2. Compounds of formula I.1 wherein $R^1$ is Y-1B, $R^4$ is H and $R^5$ is H.

Table 3. Compounds of formula I.1 wherein $R^1$ is Y-2A, $R^4$ is H and $R^5$ is H.

Table 4. Compounds of formula I.1 wherein $R^1$ is Y-2B, $R^4$ is H and $R^5$ is H.

Table 5. Compounds of formula I.1 wherein $R^1$ is Y-3A, $R^4$ is H and $R^5$ is H.

Table 6. Compounds of formula I.1 wherein $R^1$ is Y-3B, $R^4$ is H and $R^5$ is H.

Table 7. Compounds of formula I.1 wherein $R^1$ is Y-3C, $R^4$ is H and $R^5$ is H.

Table 8. Compounds of formula I.1 wherein $R^1$ is Y-3D, $R^4$ is H and $R^5$ is H.

Table 9. Compounds of formula I.1 wherein $R^1$ is Y-4A, $R^4$ is H and $R^5$ is H.

Table 10. Compounds of formula I.1 wherein $R^1$ is Y-4B, $R^4$ is H and $R^5$ is H.

Table 11. Compounds of formula I.1 wherein $R^1$ is Y-4C, $R^4$ is H and $R^5$ is H.

Table 12. Compounds of formula I.1 wherein $R^1$ is Y-4D, $R^4$ is H and $R^5$ is H.

Table 13. Compounds of formula I.1 wherein $R^1$ is Y-5A, $R^4$ is H and $R^5$ is H.

Table 14. Compounds of formula I.1 wherein $R^1$ is Y-5B, $R^4$ is H and $R^5$ is H.

Table 15. Compounds of formula I.1 wherein $R^1$ is Y-6A, $R^4$ is H and $R^5$ is H.

Table 16. Compounds of formula I.1 wherein $R^1$ is Y-6B, $R^4$ is H and $R^5$ is H.

Table 17. Compounds of formula I.1 wherein $R^1$ is Y-7A, $R^4$ is H and $R^5$ is H.

Table 18. Compounds of formula I.1 wherein $R^1$ is Y-7B, $R^4$ is H and $R^5$ is H.

Table 19. Compounds of formula I.1 wherein $R^1$ is Y-8A, $R^4$ is H and $R^5$ is H.

Table 20. Compounds of formula I.1 wherein $R^1$ is Y-8B, $R^4$ is H and $R^5$ is H.

Table 21. Compounds of formula I.1 wherein $R^1$ is Y-1A, $R^4$ is $CH_3$ and $R^5$ is H.

Table 22. Compounds of formula I.1 wherein $R^1$ is Y-1B, $R^4$ is $CH_3$ and $R^5$ is H.

Table 23. Compounds of formula I.1 wherein $R^1$ is Y-2A, $R^4$ is $CH_3$ and $R^5$ is H.

Table 24. Compounds of formula I.1 wherein $R^1$ is Y-2B, $R^4$ is $CH_3$ and $R^5$ is H.

Table 25. Compounds of formula I.1 wherein $R^1$ is Y-3A, $R^4$ is $CH_3$ and $R^5$ is H.

Table 26. Compounds of formula I.1 wherein $R^1$ is Y-3B, $R^4$ is $CH_3$ and $R^5$ is H.

Table 27. Compounds of formula I.1 wherein $R^1$ is Y-3C, $R^4$ is $CH_3$ and $R^5$ is H.

Table 28. Compounds of formula I.1 wherein $R^1$ is Y-3D, $R^4$ is $CH_3$ and $R^5$ is H.

Table 29. Compounds of formula I.1 wherein $R^1$ is Y-4A, $R^4$ is $CH_3$ and $R^5$ is H.

Table 30. Compounds of formula I.1 wherein $R^1$ is Y-4B, $R^4$ is $CH_3$ and $R^5$ is H.

Table 31. Compounds of formula I.1 wherein $R^1$ is Y-4C, $R^4$ is $CH_3$ and $R^5$ is H.

Table 32. Compounds of formula I.1 wherein $R^1$ is Y-4D, $R^4$ is $CH_3$ and $R^5$ is H.

Table 33. Compounds of formula I.1 wherein $R^1$ is Y-5A, $R^4$ is $CH_3$ and $R^5$ is H.

Table 34. Compounds of formula I.1 wherein $R^1$ is Y-5B, $R^4$ is $CH_3$ and $R^5$ is H.

Table 35. Compounds of formula I.1 wherein $R^1$ is Y-6A, $R^4$ is $CH_3$ and $R^5$ is H.

Table 36. Compounds of formula I.1 wherein $R^1$ is Y-6B, $R^4$ is $CH_3$ and $R^5$ is H.

Table 37. Compounds of formula I.1 wherein $R^1$ is Y-7A, $R^4$ is $CH_3$ and $R^5$ is H.

Table 38. Compounds of formula I.1 wherein $R^1$ is Y-7B, $R^4$ is $CH_3$ and $R^5$ is H.

Table 39. Compounds of formula I.1 wherein $R^1$ is Y-8A, $R^4$ is $CH_3$ and $R^5$ is H.

Table 40. Compounds of formula I.1 wherein $R^1$ is Y-8B, $R^4$ is $CH_3$ and $R^5$ is H.

Table 41. Compounds of formula I.1 wherein $R^1$ is Y-1A, $R^4$ is $CH_3$ and $R^5$ is $CH_3$.

Table 42. Compounds of formula I.1 wherein $R^1$ is Y-1B, $R^4$ is $CH_3$ and $R^5$ is $CH_3$.

Table 43. Compounds of formula I.1 wherein $R^1$ is Y-2A, $R^4$ is $CH_3$ and $R^5$ is $CH_3$.

Table 44. Compounds of formula I.1 wherein $R^1$ is Y-2B, $R^4$ is $CH_3$ and $R^5$ is $CH_3$.

Table 45. Compounds of formula I.1 wherein $R^1$ is Y-3A, $R^4$ is $CH_3$ and $R^5$ is $CH_3$.

Table 46. Compounds of formula I.1 wherein $R^1$ is Y-3B, $R^4$ is $CH_3$ and $R^5$ is $CH_3$.

Table 47. Compounds of formula I.1 wherein $R^1$ is Y-3C, $R^4$ is $CH_3$ and $R^5$ is $CH_3$.

Table 48. Compounds of formula I.1 wherein $R^1$ is Y-3D, $R^4$ is $CH_3$ and $R^5$ is $CH_3$.

Table 49. Compounds of formula I.1 wherein $R^1$ is Y-4A, $R^4$ is $CH_3$ and $R^5$ is $CH_3$.

Table 50. Compounds of formula I.1 wherein $R^1$ is Y-4B, $R^4$ is $CH_3$ and $R^5$ is $CH_3$.

Table 51. Compounds of formula I.1 wherein $R^1$ is Y-4C, $R^4$ is $CH_3$ and $R^5$ is $CH_3$.

Table 52. Compounds of formula I.1 wherein $R^1$ is Y-4D, $R^4$ is $CH_3$ and $R^5$ is $CH_3$.

Table 53. Compounds of formula I.1 wherein $R^1$ is Y-5A, $R^4$ is $CH_3$ and $R^5$ is $CH_3$.

Table 54. Compounds of formula I.1 wherein $R^1$ is Y-5B, $R^4$ is $CH_3$ and $R^5$ is $CH_3$.

Table 55. Compounds of formula I.1 wherein $R^1$ is Y-6A, $R^4$ is $CH_3$ and $R^5$ is $CH_3$.

Table 56. Compounds of formula I.1 wherein $R^1$ is Y-6B, $R^4$ is $CH_3$ and $R^5$ is $CH_3$.

Table 57. Compounds of formula I.1 wherein $R^1$ is Y-7A, $R^4$ is $CH_3$ and $R^5$ is $CH_3$.

Table 58. Compounds of formula I.1 wherein $R^1$ is Y-7B, $R^4$ is $CH_3$ and $R^5$ is $CH_3$.

Table 59. Compounds of formula I.1 wherein $R^1$ is Y-8A, $R^4$ is $CH_3$ and $R^5$ is $CH_3$.

Table 60. Compounds of formula I.1 wherein $R^1$ is Y-8B, $R^4$ is $CH_3$ and $R^5$ is $CH_3$.

Table 61. Compounds of formula I.2 wherein $R^1$ is Y-1A, $R^4$ is H and $R^5$ is H.

Table 62. Compounds of formula I.2 wherein $R^1$ is Y-1B, $R^4$ is H and $R^5$ is H.

Table 63. Compounds of formula I.2 wherein $R^1$ is Y-2A, $R^4$ is H and $R^5$ is H.

Table 64. Compounds of formula I.2 wherein $R^1$ is Y-2B, $R^4$ is H and $R^5$ is H.

Table 65. Compounds of formula I.2 wherein $R^1$ is Y-3A, $R^4$ is H and $R^5$ is H.

Table 66. Compounds of formula I.2 wherein $R^1$ is Y-3B, $R^4$ is H and $R^5$ is H.

Table 67. Compounds of formula I.2 wherein $R^1$ is Y-3C, $R^4$ is H and $R^5$ is H.

Table 68. Compounds of formula I.2 wherein $R^1$ is Y-3D, $R^4$ is H and $R^5$ is H.

Table 69. Compounds of formula I.2 wherein $R^1$ is Y-4A, $R^4$ is H and $R^5$ is H.

Table 70. Compounds of formula I.2 wherein $R^1$ is Y-4B, $R^4$ is H and $R^5$ is H.

Table 71. Compounds of formula I.2 wherein $R^1$ is Y-4C, $R^4$ is H and $R^5$ is H.

Table 72. Compounds of formula I.2 wherein $R^1$ is Y-4D, $R^4$ is H and $R^5$ is H.

Table 73. Compounds of formula I.2 wherein $R^1$ is Y-5A, $R^4$ is H and $R^5$ is H.

Table 74. Compounds of formula I.2 wherein $R^1$ is Y-5B, $R^4$ is H and $R^5$ is H.

Table 75. Compounds of formula I.2 wherein $R^1$ is Y-6A, $R^4$ is H and $R^5$ is H.

Table 76. Compounds of formula I.2 wherein $R^1$ is Y-6B, $R^4$ is H and $R^5$ is H.

Table 77. Compounds of formula I.2 wherein $R^1$ is Y-7A, $R^4$ is H and $R^5$ is H.

Table 78. Compounds of formula I.2 wherein $R^1$ is Y-7B, $R^4$ is H and $R^5$ is H.

Table 79. Compounds of formula I.2 wherein $R^1$ is Y-8A, $R^4$ is H and $R^5$ is H.

Table 80. Compounds of formula I.2 wherein $R^1$ is Y-8B, $R^4$ is H and $R^5$ is H.

Table 81. Compounds of formula I.2 wherein $R^1$ is Y-1A, $R^4$ is $CH_3$ and $R^5$ is H.

Table 82. Compounds of formula I.2 wherein $R^1$ is Y-1B, $R^4$ is $CH_3$ and $R^5$ is H.

Table 83. Compounds of formula I.2 wherein $R^1$ is Y-2A, $R^4$ is $CH_3$ and $R^5$ is H.

Table 84. Compounds of formula I.2 wherein $R^1$ is Y-2B, $R^4$ is $CH_3$ and $R^5$ is H.

Table 85. Compounds of formula I.2 wherein $R^1$ is Y-3A, $R^4$ is $CH_3$ and $R^5$ is H.

Table 86. Compounds of formula I.2 wherein $R^1$ is Y-3B, $R^4$ is $CH_3$ and $R^5$ is H.

Table 87. Compounds of formula I.2 wherein $R^1$ is Y-3C, $R^4$ is $CH_3$ and $R^5$ is H.

Table 88. Compounds of formula I.2 wherein $R^1$ is Y-3D, $R^4$ is $CH_3$ and $R^5$ is H.

Table 89. Compounds of formula I.2 wherein $R^1$ is Y-4A, $R^4$ is $CH_3$ and $R^5$ is H.

Table 90. Compounds of formula I.2 wherein $R^1$ is Y-4B, $R^4$ is $CH_3$ and $R^5$ is H.

Table 91. Compounds of formula I.2 wherein $R^1$ is Y-4C, $R^4$ is $CH_3$ and $R^5$ is H.

Table 92. Compounds of formula I.2 wherein $R^1$ is Y-4D, $R^4$ is $CH_3$ and $R^5$ is H.

Table 93. Compounds of formula I.2 wherein $R^1$ is Y-5A, $R^4$ is $CH_3$ and $R^5$ is H.

Table 94. Compounds of formula I.2 wherein $R^1$ is Y-5B, $R^4$ is $CH_3$ and $R^5$ is H.

Table 95. Compounds of formula I.2 wherein $R^1$ is Y-6A, $R^4$ is $CH_3$ and $R^5$ is H.

Table 96. Compounds of formula I.2 wherein $R^1$ is Y-6B, $R^4$ is $CH_3$ and $R^5$ is H.

Table 97. Compounds of formula I.2 wherein $R^1$ is Y-7A, $R^4$ is $CH_3$ and $R^5$ is H.

Table 98. Compounds of formula I.2 wherein $R^1$ is Y-7B, $R^4$ is $CH_3$ and $R^5$ is H.

Table 99. Compounds of formula I.2 wherein $R^1$ is Y-8A, $R^4$ is $CH_3$ and $R^5$ is H.

Table 100. Compounds of formula I.2 wherein $R^1$ is Y-8B, $R^4$ is $CH_3$ and $R^5$ is H.

Table 101. Compounds of formula I.2 wherein $R^1$ is Y-1A, $R^4$ is $CH_3$ and $R^5$ is $CH_3$.

Table 102. Compounds of formula I.2 wherein $R^1$ is Y-1B, $R^4$ is $CH_3$ and $R^5$ is $CH_3$.

Table 103. Compounds of formula I.2 wherein $R^1$ is Y-2A, $R^4$ is $CH_3$ and $R^5$ is $CH_3$.

Table 104. Compounds of formula I.2 wherein $R^1$ is Y-2B, $R^4$ is $CH_3$ and $R^5$ is $CH_3$.

Table 105. Compounds of formula I.2 wherein $R^1$ is Y-3A, $R^4$ is $CH_3$ and $R^5$ is $CH_3$.

Table 106. Compounds of formula I.2 wherein $R^1$ is Y-3B, $R^4$ is $CH_3$ and $R^5$ is $CH_3$.

Table 107. Compounds of formula I.2 wherein $R^1$ is Y-3C, $R^4$ is $CH_3$ and $R^5$ is $CH_3$.

Table 108. Compounds of formula I.2 wherein $R^1$ is Y-3D, $R^4$ is $CH_3$ and $R^5$ is $CH_3$.

Table 109. Compounds of formula I.2 wherein $R^1$ is Y-4A, $R^4$ is $CH_3$ and $R^5$ is $CH_3$.

Table 110. Compounds of formula I.2 wherein $R^1$ is Y-4B, $R^4$ is $CH_3$ and $R^5$ is $CH_3$.

Table 111. Compounds of formula I.2 wherein $R^1$ is Y-4C, $R^4$ is $CH_3$ and $R^5$ is $CH_3$.

Table 112. Compounds of formula I.2 wherein $R^1$ is Y-4D, $R^4$ is $CH_3$ and $R^5$ is $CH_3$.

Table 113. Compounds of formula I.2 wherein $R^1$ is Y-5A, $R^4$ is $CH_3$ and $R^5$ is $CH_3$.

Table 114. Compounds of formula I.2 wherein $R^1$ is Y-5B, $R^4$ is $CH_3$ and $R^5$ is $CH_3$.

Table 115. Compounds of formula I.2 wherein $R^1$ is Y-6A, $R^4$ is $CH_3$ and $R^5$ is $CH_3$.

Table 116. Compounds of formula I.2 wherein $R^1$ is Y-6B, $R^4$ is $CH_3$ and $R^5$ is $CH_3$.

Table 117. Compounds of formula I.2 wherein $R^1$ is Y-7A, $R^4$ is $CH_3$ and $R^5$ is $CH_3$.

Table 118. Compounds of formula I.2 wherein $R^1$ is Y-7B, $R^4$ is $CH_3$ and $R^5$ is $CH_3$.

Table 119. Compounds of formula I.2 wherein $R^1$ is Y-8A, $R^4$ is $CH_3$ and $R^5$ is $CH_3$.

Table 120. Compounds of formula I.2 wherein $R^1$ is Y-8B, $R^4$ is $CH_3$ and $R^5$ is $CH_3$.

Table 121. Compounds of formula I.3 wherein $R^1$ is Y-1A, $R^4$ is H and $R^5$ is H.

Table 122. Compounds of formula I.3 wherein $R^1$ is Y-1B, $R^4$ is H and $R^5$ is H.

Table 123. Compounds of formula I.3 wherein $R^1$ is Y-2A, $R^4$ is H and $R^5$ is H.

Table 124. Compounds of formula I.3 wherein $R^1$ is Y-2B, $R^4$ is H and $R^5$ is H.

Table 125. Compounds of formula I.3 wherein $R^1$ is Y-3A, $R^4$ is H and $R^5$ is H.

Table 126. Compounds of formula I.3 wherein $R^1$ is Y-3B, $R^4$ is H and $R^5$ is H.

Table 127. Compounds of formula I.3 wherein $R^1$ is Y-3C, $R^4$ is H and $R^5$ is H.

Table 128. Compounds of formula I.3 wherein $R^1$ is Y-3D, $R^4$ is H and $R^5$ is H.

Table 129. Compounds of formula I.3 wherein $R^1$ is Y-4A, $R^4$ is H and $R^5$ is H.

Table 130. Compounds of formula I.3 wherein $R^1$ is Y-4B, $R^4$ is H and $R^5$ is H.

Table 131. Compounds of formula I.3 wherein $R^1$ is Y-40, $R^4$ is H and $R^5$ is H.

Table 132. Compounds of formula I.3 wherein $R^1$ is Y-4D, $R^4$ is H and $R^5$ is H.

Table 133. Compounds of formula I.3 wherein $R^1$ is Y-5A, $R^4$ is H and $R^5$ is H.

Table 134. Compounds of formula I.3 wherein $R^1$ is Y-5B, $R^4$ is H and $R^5$ is H.

Table 135. Compounds of formula I.3 wherein $R^1$ is Y-6A, $R^4$ is H and $R^5$ is H.

Table 136. Compounds of formula I.3 wherein $R^1$ is Y-6B, $R^4$ is H and $R^5$ is H.

Table 137. Compounds of formula I.3 wherein $R^1$ is Y-7A, $R^4$ is H and $R^5$ is H.

Table 138. Compounds of formula I.3 wherein $R^1$ is Y-7B, $R^4$ is H and $R^5$ is H.

Table 139. Compounds of formula I.3 wherein $R^1$ is Y-8A, $R^4$ is H and $R^5$ is H.

Table 140. Compounds of formula I.3 wherein $R^1$ is Y-8B, $R^4$ is H and $R^5$ is H.

Table 141. Compounds of formula I.3 wherein $R^1$ is Y-1A, $R^4$ is $CH_3$ and $R^5$ is H.

Table 142. Compounds of formula I.3 wherein $R^1$ is Y-1B, $R^4$ is $CH_3$ and $R^5$ is H.

Table 143. Compounds of formula I.3 wherein $R^1$ is Y-2A, $R^4$ is $CH_3$ and $R^5$ is H.

Table 144. Compounds of formula I.3 wherein $R^1$ is Y-2B, $R^4$ is $CH_3$ and $R^5$ is H.

Table 145. Compounds of formula I.3 wherein $R^1$ is Y-3A, $R^4$ is $CH_3$ and $R^5$ is H.

Table 146. Compounds of formula I.3 wherein $R^1$ is Y-3B, $R^4$ is $CH_3$ and $R^5$ is H.

Table 147. Compounds of formula I.3 wherein $R^1$ is Y-3C, $R^4$ is $CH_3$ and $R^5$ is H.

Table 148. Compounds of formula I.3 wherein $R^1$ is Y-3D, $R^4$ is $CH_3$ and $R^5$ is H.

Table 149. Compounds of formula I.3 wherein $R^1$ is Y-4A, $R^4$ is $CH_3$ and $R^5$ is H.

Table 150. Compounds of formula I.3 wherein $R^1$ is Y-4B, $R^4$ is $CH_3$ and $R^5$ is H.

Table 151. Compounds of formula I.3 wherein $R^1$ is Y-4C, $R^4$ is $CH_3$ and $R^5$ is H.

Table 152. Compounds of formula I.3 wherein $R^1$ is Y-4D, $R^4$ is $CH_3$ and $R^5$ is H.

Table 153. Compounds of formula I.3 wherein $R^1$ is Y-5A, $R^4$ is $CH_3$ and $R^5$ is H.

Table 154. Compounds of formula I.3 wherein $R^1$ is Y-5B, $R^4$ is $CH_3$ and $R^5$ is H.

Table 155. Compounds of formula I.3 wherein $R^1$ is Y-6A, $R^4$ is $CH_3$ and $R^5$ is H.

Table 156. Compounds of formula I.3 wherein $R^1$ is Y-6B, $R^4$ is $CH_3$ and $R^5$ is H.

Table 157. Compounds of formula I.3 wherein $R^1$ is Y-7A, $R^4$ is $CH_3$ and $R^5$ is H.

Table 158. Compounds of formula I.3 wherein $R^1$ is Y-7B, $R^4$ is $CH_3$ and $R^5$ is H.

Table 159. Compounds of formula I.3 wherein $R^1$ is Y-8A, $R^4$ is $CH_3$ and $R^5$ is H.

Table 160. Compounds of formula I.3 wherein $R^1$ is Y-8B, $R^4$ is $CH_3$ and $R^5$ is H.

Table 161. Compounds of formula I.3 wherein $R^1$ is Y-1A, $R^4$ is $CH_3$ and $R^5$ is $CH_3$.

Table 162. Compounds of formula I.3 wherein $R^1$ is Y-1B, $R^4$ is $CH_3$ and $R^5$ is $CH_3$.

Table 163. Compounds of formula I.3 wherein $R^1$ is Y-2A, $R^4$ is $CH_3$ and $R^5$ is $CH_3$.

Table 164. Compounds of formula I.3 wherein $R^1$ is Y-2B, $R^4$ is $CH_3$ and $R^5$ is $CH_3$.

Table 165. Compounds of formula I.3 wherein $R^1$ is Y-3A, $R^4$ is $CH_3$ and $R^5$ is $CH_3$.

Table 166. Compounds of formula I.3 wherein $R^1$ is Y-3B, $R^4$ is $CH_3$ and $R^5$ is $CH_3$.

Table 167. Compounds of formula I.3 wherein $R^1$ is Y-3C, $R^4$ is $CH_3$ and $R^5$ is $CH_3$.

Table 168. Compounds of formula I.3 wherein $R^1$ is Y-3D, $R^4$ is $CH_3$ and $R^5$ is $CH_3$.

Table 169. Compounds of formula I.3 wherein $R^1$ is Y-4A, $R^4$ is $CH_3$ and $R^5$ is $CH_3$.

Table 170. Compounds of formula I.3 wherein $R^1$ is Y-4B, $R^4$ is $CH_3$ and $R^5$ is $CH_3$.

Table 171. Compounds of formula I.3 wherein $R^1$ is Y-4C, $R^4$ is $CH_3$ and $R^5$ is $CH_3$.

Table 172. Compounds of formula I.3 wherein $R^1$ is Y-4D, $R^4$ is $CH_3$ and $R^5$ is $CH_3$.

Table 173. Compounds of formula I.3 wherein $R^1$ is Y-5A, $R^4$ is $CH_3$ and $R^5$ is $CH_3$.

Table 174. Compounds of formula I.3 wherein $R^1$ is Y-5B, $R^4$ is $CH_3$ and $R^5$ is $CH_3$.

Table 175. Compounds of formula I.3 wherein $R^1$ is Y-6A, $R^4$ is $CH_3$ and $R^5$ is $CH_3$.

Table 176. Compounds of formula I.3 wherein $R^1$ is Y-6B, $R^4$ is $CH_3$ and $R^5$ is $CH_3$.

Table 177. Compounds of formula I.3 wherein $R^1$ is Y-7A, $R^4$ is $CH_3$ and $R^5$ is $CH_3$.

Table 178. Compounds of formula I.3 wherein $R^1$ is Y-7B, $R^4$ is $CH_3$ and $R^5$ is $CH_3$.

Table 179. Compounds of formula I.3 wherein $R^1$ is Y-8A, $R^4$ is $CH_3$ and $R^5$ is $CH_3$.

Table 180. Compounds of formula I.3 wherein $R^1$ is Y-8B, $R^4$ is $CH_3$ and $R^5$ is $CH_3$.

Table 181. Compounds of formula I.4 wherein $R^1$ is Y-1A, $R^4$ is H and $R^5$ is H.

Table 182. Compounds of formula I.4 wherein $R^1$ is Y-1B, $R^4$ is H and $R^5$ is H.

Table 183. Compounds of formula I.4 wherein $R^1$ is Y-2A, $R^4$ is H and $R^5$ is H.

Table 184. Compounds of formula I.4 wherein $R^1$ is Y-2B, $R^4$ is H and $R^5$ is H.

Table 185. Compounds of formula I.4 wherein $R^1$ is Y-3A, $R^4$ is H and $R^5$ is H.

Table 186. Compounds of formula I.4 wherein $R^1$ is Y-3B, $R^4$ is H and $R^5$ is H.

Table 187. Compounds of formula I.4 wherein $R^1$ is Y-3C, $R^4$ is H and $R^5$ is H.

Table 188. Compounds of formula I.4 wherein $R^1$ is Y-3D, $R^4$ is H and $R^5$ is H.

Table 189. Compounds of formula I.4 wherein $R^1$ is Y-4A, $R^4$ is H and $R^5$ is H.

Table 190. Compounds of formula I.4 wherein $R^1$ is Y-4B, $R^4$ is H and $R^5$ is H.

Table 191. Compounds of formula I.4 wherein $R^1$ is Y-4C, $R^4$ is H and $R^5$ is H.

Table 192. Compounds of formula I.4 wherein $R^1$ is Y-4D, $R^4$ is H and $R^5$ is H.

Table 193. Compounds of formula I.4 wherein $R^1$ is Y-5A, $R^4$ is H and $R^5$ is H.

Table 194. Compounds of formula I.4 wherein $R^1$ is Y-5B, $R^4$ is H and $R^5$ is H.

Table 195. Compounds of formula I.4 wherein $R^1$ is Y-6A, $R^4$ is H and $R^5$ is H.

Table 196. Compounds of formula I.4 wherein $R^1$ is Y-6B, $R^4$ is H and $R^5$ is H.

Table 197. Compounds of formula I.4 wherein $R^1$ is Y-7A, $R^4$ is H and $R^5$ is H.

Table 198. Compounds of formula I.4 wherein $R^1$ is Y-7B, $R^4$ is H and $R^5$ is H.

Table 199. Compounds of formula I.4 wherein $R^1$ is Y-8A, $R^4$ is H and $R^5$ is H.

Table 200. Compounds of formula I.4 wherein $R^1$ is Y-8B, $R^4$ is H and $R^5$ is H.

Table 201. Compounds of formula I.4 wherein $R^1$ is Y-1A, $R^4$ is $CH_3$ and $R^5$ is H.

Table 202. Compounds of formula I.4 wherein $R^1$ is Y-1B, $R^4$ is $CH_3$ and $R^5$ is H.

Table 203. Compounds of formula I.4 wherein $R^1$ is Y-2A, $R^4$ is $CH_3$ and $R^5$ is H.

Table 204. Compounds of formula I.4 wherein $R^1$ is Y-2B, $R^4$ is $CH_3$ and $R^5$ is H.

Table 205. Compounds of formula I.4 wherein $R^1$ is Y-3A, $R^4$ is $CH_3$ and $R^5$ is H.

Table 206. Compounds of formula I.4 wherein $R^1$ is Y-3B, $R^4$ is $CH_3$ and $R^5$ is H.

Table 207. Compounds of formula I.4 wherein $R^1$ is Y-3C, $R^4$ is $CH_3$ and $R^5$ is H.

Table 208. Compounds of formula I.4 wherein $R^1$ is Y-3D, $R^4$ is $CH_3$ and $R^5$ is H.

Table 209. Compounds of formula I.4 wherein $R^1$ is Y-4A, $R^4$ is $CH_3$ and $R^5$ is H.

Table 210. Compounds of formula I.4 wherein $R^1$ is Y-4B, $R^4$ is $CH_3$ and $R^5$ is H.

Table 211. Compounds of formula I.4 wherein $R^1$ is Y-4C, $R^4$ is $CH_3$ and $R^5$ is H.

Table 212. Compounds of formula I.4 wherein $R^1$ is Y-4D, $R^4$ is $CH_3$ and $R^5$ is H.

Table 213. Compounds of formula I.4 wherein $R^1$ is Y-5A, $R^4$ is $CH_3$ and $R^5$ is H.

Table 214. Compounds of formula I.4 wherein $R^1$ is Y-5B, $R^4$ is $CH_3$ and $R^5$ is H.

Table 215. Compounds of formula I.4 wherein $R^1$ is Y-6A, $R^4$ is $CH_3$ and $R^5$ is H.

Table 216. Compounds of formula I.4 wherein $R^1$ is Y-6B, $R^4$ is $CH_3$ and $R^5$ is H.

Table 217. Compounds of formula I.4 wherein $R^1$ is Y-7A, $R^4$ is $CH_3$ and $R^5$ is H.

Table 218. Compounds of formula I.4 wherein $R^1$ is Y-7B, $R^4$ is $CH_3$ and $R^5$ is H.

Table 219. Compounds of formula I.4 wherein $R^1$ is Y-8A, $R^4$ is $CH_3$ and $R^5$ is H.

Table 220. Compounds of formula I.4 wherein $R^1$ is Y-8B, $R^4$ is $CH_3$ and $R^5$ is H.

Table 221. Compounds of formula I.4 wherein $R^1$ is Y-1A, $R^4$ is $CH_3$ and $R^5$ is $CH_3$.

Table 222. Compounds of formula I.4 wherein $R^1$ is Y-1B, $R^4$ is $CH_3$ and $R^5$ is $CH_3$.

Table 223. Compounds of formula I.4 wherein $R^1$ is Y-2A, $R^4$ is $CH_3$ and $R^5$ is $CH_3$.

Table 224. Compounds of formula I.4 wherein $R^1$ is Y-2B, $R^4$ is $CH_3$ and $R^5$ is $CH_3$.

Table 225. Compounds of formula I.4 wherein $R^1$ is Y-3A, $R^4$ is $CH_3$ and $R^5$ is $CH_3$.

Table 226. Compounds of formula I.4 wherein $R^1$ is Y-3B, $R^4$ is $CH_3$ and $R^5$ is $CH_3$.

Table 227. Compounds of formula I.4 wherein $R^1$ is Y-3C, $R^4$ is $CH_3$ and $R^5$ is $CH_3$.

Table 228. Compounds of formula I.4 wherein $R^1$ is Y-3D, $R^4$ is $CH_3$ and $R^5$ is $CH_3$.

Table 229. Compounds of formula I.4 wherein $R^1$ is Y-4A, $R^4$ is $CH_3$ and $R^5$ is $CH_3$.

Table 230. Compounds of formula I.4 wherein $R^1$ is Y-4B, $R^4$ is $CH_3$ and $R^5$ is $CH_3$.

Table 231. Compounds of formula I.4 wherein $R^1$ is Y-4C, $R^4$ is $CH_3$ and $R^5$ is $CH_3$.

Table 232. Compounds of formula I.4 wherein $R^1$ is Y-4D, $R^4$ is $CH_3$ and $R^5$ is $CH_3$.

Table 233. Compounds of formula I.4 wherein $R^1$ is Y-5A, $R^4$ is $CH_3$ and $R^5$ is $CH_3$.

Table 234. Compounds of formula I.4 wherein $R^1$ is Y-5B, $R^4$ is $CH_3$ and $R^5$ is $CH_3$.

Table 235. Compounds of formula I.4 wherein $R^1$ is Y-6A, $R^4$ is $CH_3$ and $R^5$ is $CH_3$.

Table 236. Compounds of formula I.4 wherein $R^1$ is Y-6B, $R^4$ is $CH_3$ and $R^5$ is $CH_3$.

Table 237. Compounds of formula I.4 wherein $R^1$ is Y-7A, $R^4$ is $CH_3$ and $R^5$ is $CH_3$.

Table 238. Compounds of formula I.4 wherein $R^1$ is Y-7B, $R^4$ is $CH_3$ and $R^5$ is $CH_3$.

Table 239. Compounds of formula I.4 wherein $R^1$ is Y-8A, $R^4$ is $CH_3$ and $R^5$ is $CH_3$.

Table 240. Compounds of formula I.4 wherein $R^1$ is Y-8B, $R^4$ is $CH_3$ and $R^5$ is $CH_3$.

Table 241. Compounds of formula I.5 wherein $R^1$ is Y-1A, $R^4$ is H and $R^5$ is H.

Table 242. Compounds of formula I.5 wherein $R^1$ is Y-1B, $R^4$ is H and $R^5$ is H.

Table 243. Compounds of formula I.5 wherein $R^1$ is Y-2A, $R^4$ is H and $R^5$ is H.

Table 244. Compounds of formula I.5 wherein $R^1$ is Y-2B, $R^4$ is H and $R^5$ is H.

Table 245. Compounds of formula I.5 wherein $R^1$ is Y-3A, $R^4$ is H and $R^5$ is H.

Table 246. Compounds of formula I.5 wherein $R^1$ is Y-3B, $R^4$ is H and $R^5$ is H.

Table 247. Compounds of formula I.5 wherein $R^1$ is Y-3C, $R^4$ is H and $R^5$ is H.

Table 248. Compounds of formula I.5 wherein $R^1$ is Y-3D, $R^4$ is H and $R^5$ is H.

Table 249. Compounds of formula I.5 wherein $R^1$ is Y-4A, $R^4$ is H and $R^5$ is H.

Table 250. Compounds of formula I.5 wherein $R^1$ is Y-4B, $R^4$ is H and $R^5$ is H.

Table 251. Compounds of formula I.5 wherein $R^1$ is Y-4C, $R^4$ is H and $R^5$ is H.

Table 252. Compounds of formula I.5 wherein $R^1$ is Y-4D, $R^4$ is H and $R^5$ is H.

Table 253. Compounds of formula I.5 wherein $R^1$ is Y-5A, $R^4$ is H and $R^5$ is H.

Table 254. Compounds of formula I.5 wherein $R^1$ is Y-5B, $R^4$ is H and $R^5$ is H.

Table 255. Compounds of formula I.5 wherein $R^1$ is Y-6A, $R^4$ is H and $R^5$ is H.

Table 256. Compounds of formula I.5 wherein $R^1$ is Y-6B, $R^4$ is H and $R^5$ is H.

Table 257. Compounds of formula I.5 wherein $R^1$ is Y-7A, $R^4$ is H and $R^5$ is H.

Table 258. Compounds of formula I.5 wherein $R^1$ is Y-7B, $R^4$ is H and $R^5$ is H.

Table 259. Compounds of formula I.5 wherein $R^1$ is Y-8A, $R^4$ is H and $R^5$ is H.

Table 260. Compounds of formula I.5 wherein $R^1$ is Y-8B, $R^4$ is H and $R^5$ is H.

Table 261. Compounds of formula I.5 wherein $R^1$ is Y-1A, $R^4$ is $CH_3$ and $R^5$ is H.

Table 262. Compounds of formula I.5 wherein $R^1$ is Y-1B, $R^4$ is $CH_3$ and $R^5$ is H.

Table 263. Compounds of formula I.5 wherein $R^1$ is Y-2A, $R^4$ is $CH_3$ and $R^5$ is H.

Table 264. Compounds of formula I.5 wherein $R^1$ is Y-2B, $R^4$ is $CH_3$ and $R^5$ is H.

Table 265. Compounds of formula I.5 wherein $R^1$ is Y-3A, $R^4$ is $CH_3$ and $R^5$ is H.

Table 266. Compounds of formula I.5 wherein $R^1$ is Y-3B, $R^4$ is $CH_3$ and $R^5$ is H.

Table 267. Compounds of formula I.5 wherein $R^1$ is Y-3C, $R^4$ is $CH_3$ and $R^5$ is H.

Table 268. Compounds of formula I.5 wherein $R^1$ is Y-3D, $R^4$ is $CH_3$ and $R^5$ is H.

Table 269. Compounds of formula I.5 wherein $R^1$ is Y-4A, $R^4$ is $CH_3$ and $R^5$ is H.

Table 270. Compounds of formula I.5 wherein $R^1$ is Y-4B, $R^4$ is $CH_3$ and $R^5$ is H.

Table 271. Compounds of formula I.5 wherein $R^1$ is Y-4C, $R^4$ is $CH_3$ and $R^5$ is H.

Table 272. Compounds of formula I.5 wherein $R^1$ is Y-4D, $R^4$ is $CH_3$ and $R^5$ is H.

Table 273. Compounds of formula I.5 wherein $R^1$ is Y-5A, $R^4$ is $CH_3$ and $R^5$ is H.

Table 274. Compounds of formula I.5 wherein $R^1$ is Y-5B, $R^4$ is $CH_3$ and $R^5$ is H.

Table 275. Compounds of formula I.5 wherein $R^1$ is Y-6A, $R^4$ is $CH_3$ and $R^5$ is H.

Table 276. Compounds of formula I.5 wherein $R^1$ is Y-6B, $R^4$ is $CH_3$ and $R^5$ is H.

Table 277. Compounds of formula I.5 wherein $R^1$ is Y-7A, $R^4$ is $CH_3$ and $R^5$ is H.

Table 278. Compounds of formula I.5 wherein $R^1$ is Y-7B, $R^4$ is $CH_3$ and $R^5$ is H.

Table 279. Compounds of formula I.5 wherein $R^1$ is Y-8A, $R^4$ is $CH_3$ and $R^5$ is H.

Table 280. Compounds of formula I.5 wherein $R^1$ is Y-8B, $R^4$ is $CH_3$ and $R^5$ is H.

Table 281. Compounds of formula I.5 wherein $R^1$ is Y-1A, $R^4$ is $CH_3$ and $R^5$ is $CH_3$.

Table 282. Compounds of formula I.5 wherein $R^1$ is Y-1B, $R^4$ is $CH_3$ and $R^5$ is $CH_3$.

Table 283. Compounds of formula I.5 wherein $R^1$ is Y-2A, $R^4$ is $CH_3$ and $R^5$ is $CH_3$.

Table 284. Compounds of formula I.5 wherein $R^1$ is Y-2B, $R^4$ is $CH_3$ and $R^5$ is $CH_3$.

Table 285. Compounds of formula I.5 wherein $R^1$ is Y-3A, $R^4$ is $CH_3$ and $R^5$ is $CH_3$.

Table 286. Compounds of formula I.5 wherein $R^1$ is Y-3B, $R^4$ is $CH_3$ and $R^5$ is $CH_3$.

Table 287. Compounds of formula I.5 wherein $R^1$ is Y-3C, $R^4$ is $CH_3$ and $R^5$ is $CH_3$.

Table 288. Compounds of formula I.5 wherein $R^1$ is Y-3D, $R^4$ is $CH_3$ and $R^5$ is $CH_3$.

Table 289. Compounds of formula I.5 wherein $R^1$ is Y-4A, $R^4$ is $CH_3$ and $R^5$ is $CH_3$.

Table 290. Compounds of formula I.5 wherein $R^1$ is Y-4B, $R^4$ is $CH_3$ and $R^5$ is $CH_3$.

Table 291. Compounds of formula I.5 wherein $R^1$ is Y-4C, $R^4$ is $CH_3$ and $R^5$ is $CH_3$.

Table 292. Compounds of formula I.5 wherein $R^1$ is Y-4D, $R^4$ is $CH_3$ and $R^5$ is $CH_3$.

Table 293. Compounds of formula I.5 wherein $R^1$ is Y-5A, $R^4$ is $CH_3$ and $R^5$ is $CH_3$.

Table 294. Compounds of formula I.5 wherein $R^1$ is Y-5B, $R^4$ is $CH_3$ and $R^5$ is $CH_3$.

Table 295. Compounds of formula I.5 wherein $R^1$ is Y-6A, $R^4$ is $CH_3$ and $R^5$ is $CH_3$.

Table 296. Compounds of formula I.5 wherein $R^1$ is Y-6B, $R^4$ is $CH_3$ and $R^5$ is $CH_3$.

Table 297. Compounds of formula I.5 wherein $R^1$ is Y-7A, $R^4$ is $CH_3$ and $R^5$ is $CH_3$.

Table 298. Compounds of formula I.5 wherein $R^1$ is Y-7B, $R^4$ is $CH_3$ and $R^5$ is $CH_3$.

Table 299. Compounds of formula I.5 wherein $R^1$ is Y-8A, $R^4$ is $CH_3$ and $R^5$ is $CH_3$.

Table 300. Compounds of formula I.5 wherein $R^1$ is Y-8B, $R^4$ is $CH_3$ and $R^5$ is $CH_3$.

Table 301. Compounds of formula I.6 wherein $R^1$ is Y-1A, $R^4$ is H and $R^5$ is H.

Table 302. Compounds of formula I.6 wherein $R^1$ is Y-1B, $R^4$ is H and $R^5$ is H.

Table 303. Compounds of formula I.6 wherein $R^1$ is Y-2A, $R^4$ is H and $R^5$ is H.

Table 304. Compounds of formula I.6 wherein $R^1$ is Y-2B, $R^4$ is H and $R^5$ is H.

Table 305. Compounds of formula I.6 wherein $R^1$ is Y-3A, $R^4$ is H and $R^5$ is H.

Table 306. Compounds of formula I.6 wherein $R^1$ is Y-3B, $R^4$ is H and $R^5$ is H.

Table 307. Compounds of formula I.6 wherein $R^1$ is Y-3C, $R^4$ is H and $R^5$ is H.

Table 308. Compounds of formula I.6 wherein $R^1$ is Y-3D, $R^4$ is H and $R^5$ is H.

Table 309. Compounds of formula I.6 wherein $R^1$ is Y-4A, $R^4$ is H and $R^5$ is H.

Table 310. Compounds of formula I.6 wherein $R^1$ is Y-4B, $R^4$ is H and $R^5$ is H.

Table 311. Compounds of formula I.6 wherein $R^1$ is Y-4C, $R^4$ is H and $R^5$ is H.

Table 312. Compounds of formula I.6 wherein $R^1$ is Y-4D, $R^4$ is H and $R^5$ is H.

Table 313. Compounds of formula I.6 wherein $R^1$ is Y-5A, $R^4$ is H and $R^5$ is H.

Table 314. Compounds of formula I.6 wherein $R^1$ is Y-5B, $R^4$ is H and $R^5$ is H.

Table 315. Compounds of formula I.6 wherein $R^1$ is Y-6A, $R^4$ is H and $R^5$ is H.

Table 316. Compounds of formula I.6 wherein $R^1$ is Y-6B, $R^4$ is H and $R^5$ is H.

Table 317. Compounds of formula I.6 wherein $R^1$ is Y-7A, $R^4$ is H and $R^5$ is H.

Table 318. Compounds of formula I.6 wherein $R^1$ is Y-7B, $R^4$ is H and $R^5$ is H.

Table 319. Compounds of formula I.6 wherein $R^1$ is Y-8A, $R^4$ is H and $R^5$ is H.

Table 320. Compounds of formula I.6 wherein $R^1$ is Y-8B, $R^4$ is H and $R^5$ is H.

Table 321. Compounds of formula I.6 wherein $R^1$ is Y-1A, $R^4$ is $CH_3$ and $R^5$ is H.

Table 322. Compounds of formula I.6 wherein $R^1$ is Y-1B, $R^4$ is $CH_3$ and $R^5$ is H.

Table 323. Compounds of formula I.6 wherein $R^1$ is Y-2A, $R^4$ is $CH_3$ and $R^5$ is H.

Table 324. Compounds of formula I.6 wherein $R^1$ is Y-2B, $R^4$ is $CH_3$ and $R^5$ is H.

Table 325. Compounds of formula I.6 wherein $R^1$ is Y-3A, $R^4$ is $CH_3$ and $R^5$ is H.

Table 326. Compounds of formula I.6 wherein $R^1$ is Y-3B, $R^4$ is $CH_3$ and $R^5$ is H.

Table 327. Compounds of formula I.6 wherein $R^1$ is Y-3C, $R^4$ is $CH_3$ and $R^5$ is H.

Table 328. Compounds of formula I.6 wherein $R^1$ is Y-3D, $R^4$ is $CH_3$ and $R^5$ is H.

Table 329. Compounds of formula I.6 wherein $R^1$ is Y-4A, $R^4$ is $CH_3$ and $R^5$ is H.

Table 330. Compounds of formula I.6 wherein $R^1$ is Y-4B, $R^4$ is $CH_3$ and $R^5$ is H.

Table 331. Compounds of formula I.6 wherein $R^1$ is Y-4C, $R^4$ is $CH_3$ and $R^5$ is H.

Table 332. Compounds of formula I.6 wherein $R^1$ is Y-4D, $R^4$ is $CH_3$ and $R^5$ is H.

Table 333. Compounds of formula I.6 wherein $R^1$ is Y-5A, $R^4$ is $CH_3$ and $R^5$ is H.

Table 334. Compounds of formula I.6 wherein $R^1$ is Y-5B, $R^4$ is $CH_3$ and $R^5$ is H.

Table 335. Compounds of formula I.6 wherein $R^1$ is Y-6A, $R^4$ is $CH_3$ and $R^5$ is H.

Table 336. Compounds of formula I.6 wherein $R^1$ is Y-6B, $R^4$ is $CH_3$ and $R^5$ is H.

Table 337. Compounds of formula I.6 wherein $R^1$ is Y-7A, $R^4$ is $CH_3$ and $R^5$ is H.

Table 338. Compounds of formula I.6 wherein $R^1$ is Y-7B, $R^4$ is $CH_3$ and $R^5$ is H.

Table 339. Compounds of formula I.6 wherein $R^1$ is Y-8A, $R^4$ is $CH_3$ and $R^5$ is H.

Table 340. Compounds of formula I.6 wherein $R^1$ is Y-8B, $R^4$ is $CH_3$ and $R^5$ is H.

Table 341. Compounds of formula I.6 wherein $R^1$ is Y-1A, $R^4$ is $CH_3$ and $R^5$ is $CH_3$.

Table 342. Compounds of formula I.6 wherein $R^1$ is Y-1B, $R^4$ is $CH_3$ and $R^5$ is $CH_3$.

Table 343. Compounds of formula I.6 wherein $R^1$ is Y-2A, $R^4$ is $CH_3$ and $R^5$ is $CH_3$.

Table 344. Compounds of formula I.6 wherein $R^1$ is Y-2B, $R^4$ is $CH_3$ and $R^5$ is $CH_3$.

Table 345. Compounds of formula I.6 wherein $R^1$ is Y-3A, $R^4$ is $CH_3$ and $R^5$ is $CH_3$.

Table 346. Compounds of formula I.6 wherein $R^1$ is Y-3B, $R^4$ is $CH_3$ and $R^5$ is $CH_3$.

Table 347. Compounds of formula I.6 wherein $R^1$ is Y-3C, $R^4$ is $CH_3$ and $R^5$ is $CH_3$.

Table 348. Compounds of formula I.6 wherein $R^1$ is Y-3D, $R^4$ is $CH_3$ and $R^5$ is $CH_3$.

Table 349. Compounds of formula I.6 wherein $R^1$ is Y-4A, $R^4$ is $CH_3$ and $R^5$ is $CH_3$.

Table 350. Compounds of formula I.6 wherein $R^1$ is Y-4B, $R^4$ is $CH_3$ and $R^5$ is $CH_3$.

Table 351. Compounds of formula I.6 wherein $R^1$ is Y-4C, $R^4$ is $CH_3$ and $R^5$ is $CH_3$.

Table 352. Compounds of formula I.6 wherein $R^1$ is Y-4D, $R^4$ is $CH_3$ and $R^5$ is $CH_3$.

Table 353. Compounds of formula I.6 wherein $R^1$ is Y-5A, $R^4$ is $CH_3$ and $R^5$ is $CH_3$.

Table 354. Compounds of formula I.6 wherein $R^1$ is Y-5B, $R^4$ is $CH_3$ and $R^5$ is $CH_3$.

Table 355. Compounds of formula I.6 wherein $R^1$ is Y-6A, $R^4$ is $CH_3$ and $R^5$ is $CH_3$.

Table 356. Compounds of formula I.6 wherein $R^1$ is Y-6B, $R^4$ is $CH_3$ and $R^5$ is $CH_3$.

Table 357. Compounds of formula I.6 wherein $R^1$ is Y-7A, $R^4$ is $CH_3$ and $R^5$ is $CH_3$.

Table 358. Compounds of formula I.6 wherein $R^1$ is Y-7B, $R^4$ is $CH_3$ and $R^5$ is $CH_3$.

Table 359. Compounds of formula I.6 wherein $R^1$ is Y-8A, $R^4$ is $CH_3$ and $R^5$ is $CH_3$.

Table 360. Compounds of formula I.6 wherein $R^1$ is Y-8B, $R^4$ is $CH_3$ and $R^5$ is $CH_3$.

Table 361. Compounds of formula I.7 wherein $R^1$ is Y-1A, $R^2$ is H, $R^9$ is H and $R^{10}$ is H.

Table 362. Compounds of formula I.7 wherein $R^1$ is Y-1A, $R^2$ is H, $R^9$ is $CH_3$ and, $R^{10}$ is H.

Table 363. Compounds of formula I.7 wherein $R^1$ is Y-1A, $R^2$ is H, $R^9$ is $CH_3$ and $R^{10}$ is $CH_3$.

Table 364. Compounds of formula I.7 wherein $R^1$ is Y-1B, $R^2$ is H, $R^9$ is H and $R^{10}$ is H.

Table 365. Compounds of formula I.7 wherein $R^1$ is Y-1B, $R^2$ is H, $R^9$ is $CH_3$ and $R^{10}$ is H.

Table 366. Compounds of formula I.7 wherein $R^1$ is Y-1B, $R^2$ is H, $R^9$ is $CH_3$ and $R^{10}$ is $CH_3$.

Table 367. Compounds of formula I.7 wherein $R^1$ is Y-2A, $R^2$ is H, $R^9$ is H and $R^{10}$ is H.

Table 368. Compounds of formula I.7 wherein $R^1$ is Y-2A, $R^2$ is H, $R^9$ is $CH_3$ and $R^{10}$ is H.

Table 369. Compounds of formula I.7 wherein $R^1$ is Y-2A, $R^2$ is H, $R^9$ is $CH_3$ and $R^{10}$ is $CH_3$.

Table 370. Compounds of formula I.7 wherein $R^1$ is Y-2B, $R^2$ is H, $R^9$ is H and $R^{10}$ is H.

Table 371. Compounds of formula I.7 wherein $R^1$ is Y-2B, $R^2$ is H, $R^9$ is $CH_3$ and $R^{10}$ is H.

Table 372. Compounds of formula I.7 wherein $R^1$ is Y-2B, $R^2$ is H, $R^9$ is $CH_3$ and $R^{10}$ is $CH_3$.

Table 373. Compounds of formula I.7 wherein $R^1$ is Y-3A, $R^2$ is H, $R^9$ is H and $R^{10}$ is H.

Table 374. Compounds of formula I.7 wherein $R^1$ is Y-3A, $R^2$ is H, $R^9$ is $CH_3$ and $R^{10}$ is H.

Table 375. Compounds of formula I.7 wherein $R^1$ is Y-3A, $R^2$ is H, $R^9$ is $CH_3$ and $R^{10}$ is $CH_3$.

Table 376. Compounds of formula I.7 wherein $R^1$ is Y-3B, $R^2$ is H, $R^9$ is H and $R^{10}$ is H.

Table 377. Compounds of formula I.7 wherein $R^1$ is Y-3B, $R^2$ is H, $R^9$ is $CH_3$ and $R^{10}$ is H.

Table 378. Compounds of formula I.7 wherein $R^1$ is Y-3B, $R^2$ is H, $R^9$ is $CH_3$ and $R^{10}$ is $CH_3$.

Table 379. Compounds of formula I.7 wherein $R^1$ is Y-3C, $R^2$ is H, $R^9$ is H and $R^{10}$ is H.

Table 380. Compounds of formula I.7 wherein $R^1$ is Y-3C, $R^2$ is H, $R^9$ is $CH_3$ and $R^{10}$ is H.

Table 381. Compounds of formula I.7 wherein $R^1$ is Y-3C, $R^2$ is H, $R^9$ is $CH_3$ and $R^{10}$ is $CH_3$.

Table 382. Compounds of formula I.7 wherein $R^1$ is Y-3D, $R^2$ is H, $R^9$ is H and $R^{10}$ is H.

Table 383. Compounds of formula I.7 wherein $R^1$ is Y-3D, $R^2$ is H, $R^9$ is $CH_3$ and $R^{10}$ is H.

Table 384. Compounds of formula I.7 wherein $R^1$ is Y-3D, $R^2$ is H, $R^9$ is $CH_3$ and $R^{10}$ is $CH_3$.

Table 385. Compounds of formula I.7 wherein $R^1$ is Y-4A, $R^2$ is H, $R^9$ is H and $R^{10}$ is H.

Table 386. Compounds of formula I.7 wherein $R^1$ is Y-4A, $R^2$ is H, $R^9$ is $CH_3$ and $R^{10}$ is H.

Table 387. Compounds of formula I.7 wherein $R^1$ is Y-4A, $R^2$ is H, $R^9$ is $CH_3$ and $R^{10}$ is $CH_3$.

Table 388. Compounds of formula I.7 wherein $R^1$ is Y-4B, $R^2$ is H, $R^9$ is H and $R^{10}$ is H.

Table 389. Compounds of formula I.7 wherein $R^1$ is Y-4B, $R^2$ is H, $R^9$ is $CH_3$ and $R^{10}$ is H.

Table 390. Compounds of formula I.7 wherein $R^1$ is Y-4B, $R^2$ is H, $R^9$ is $CH_3$ and $R^{10}$ is $CH_3$.

Table 391. Compounds of formula I.7 wherein $R^1$ is Y-4C, $R^2$ is H, $R^9$ is H and $R^{10}$ is H.

Table 392. Compounds of formula I.7 wherein $R^1$ is Y-4C, $R^2$ is H, $R^9$ is $CH_3$ and $R^{10}$ is H.

Table 393. Compounds of formula I.7 wherein $R^1$ is Y-4C, $R^2$ is H, $R^9$ is $CH_3$ and $R^{10}$ is $CH_3$.

Table 394. Compounds of formula I.7 wherein $R^1$ is Y-4D, $R^2$ is H, $R^9$ is H and $R^{10}$ is H.

Table 395. Compounds of formula I.7 wherein $R^1$ is Y-4D, $R^2$ is H, $R^9$ is $CH_3$ and $R^{10}$ is H.

Table 396. Compounds of formula I.7 wherein $R^1$ is Y-4D, $R^2$ is H, $R^9$ is $CH_3$ and $R^{10}$ is $CH_3$.

Table 397. Compounds of formula I.7 wherein $R^1$ is Y-5A, $R^2$ is H, $R^9$ is H and $R^{10}$ is H.

Table 398. Compounds of formula I.7 wherein $R^1$ is Y-5A, $R^2$ is H, $R^9$ is $CH_3$ and $R^{10}$ is H.

Table 399. Compounds of formula I.7 wherein $R^1$ is Y-5A, $R^2$ is H, $R^9$ is $CH_3$ and $R^{10}$ is $CH_3$.

Table 400. Compounds of formula I.7 wherein $R^1$ is Y-5B, $R^2$ is H, $R^9$ is H and $R^{10}$ is H.

Table 401. Compounds of formula I.7 wherein $R^1$ is Y-5B, $R^2$ is H, $R^9$ is $CH_3$ and $R^{10}$ is H.

Table 402. Compounds of formula I.7 wherein $R^1$ is Y-5B, $R^2$ is H, $R^9$ is $CH_3$ and $R^{10}$ is $CH_3$.

Table 403. Compounds of formula I.7 wherein $R^1$ is Y-6A, $R^2$ is H, $R^9$ is H and $R^{10}$ is H.

Table 404. Compounds of formula I.7 wherein $R^1$ is Y-6A, $R^2$ is H, $R^9$ is $CH_3$ and $R^{10}$ is H.

Table 405. Compounds of formula I.7 wherein $R^1$ is Y-6A, $R^2$ is H, $R^9$ is $CH_3$ and $R^{10}$ is $CH_3$.

Table 406. Compounds of formula I.7 wherein $R^1$ is Y-6B, $R^2$ is H, $R^9$ is H and $R^{10}$ is H.

Table 407. Compounds of formula I.7 wherein $R^1$ is Y-6B, $R^2$ is H, $R^9$ is $CH_3$ and $R^{10}$ is H.

Table 408. Compounds of formula I.7 wherein $R^1$ is Y-6B, $R^2$ is H, $R^9$ is $CH_3$ and $R^{10}$ is $CH_3$.

Table 409. Compounds of formula I.7 wherein $R^1$ is Y-7A, $R^2$ is H, $R^9$ is H and $R^{10}$ is H.

Table 410. Compounds of formula I.7 wherein $R^1$ is Y-7A, $R^2$ is H, $R^9$ is $CH_3$ and $R^{10}$ is H.

Table 411. Compounds of formula I.7 wherein $R^1$ is Y-7A, $R^2$ is H, $R^9$ is $CH_3$ and $R^{10}$ is $CH_3$.

Table 412. Compounds of formula I.7 wherein $R^1$ is Y-7B, $R^2$ is H, $R^9$ is H and $R^{10}$ is H.

Table 413. Compounds of formula I.7 wherein $R^1$ is Y-7B, $R^2$ is H, $R^9$ is $CH_3$ and $R^{10}$ is H.

Table 414. Compounds of formula I.7 wherein $R^1$ is Y-7B, $R^2$ is H, $R^9$ is $CH_3$ and $R^{10}$ is $CH_3$.

Table 415. Compounds of formula I.7 wherein $R^1$ is Y-8A, $R^2$ is H, $R^9$ is H and $R^{10}$ is H.

Table 416. Compounds of formula I.7 wherein $R^1$ is Y-8A, $R^2$ is H, $R^9$ is $CH_3$ and $R^{10}$ is H.

Table 417. Compounds of formula I.7 wherein $R^1$ is Y-8A, $R^2$ is H, $R^9$ is $CH_3$ and $R^{10}$ is $CH_3$.

Table 418. Compounds of formula I.7 wherein $R^1$ is Y-8B, $R^2$ is H, $R^9$ is H and $R^{10}$ is H.

Table 419. Compounds of formula I.7 wherein $R^1$ is Y-8B, $R^2$ is H, $R^9$ is $CH_3$ and $R^{10}$ is H.

Table 420. Compounds of formula I.7 wherein $R^1$ is Y-8B, $R^2$ is H, $R^9$ is $CH_3$ and $R^{10}$ is $CH_3$.

Table 421. Compounds of formula I.7 wherein $R^1$ is Y-1A, $R^2$ is $CH_3$, $R^9$ is H and $R^{10}$ is H.

Table 422. Compounds of formula I.7 wherein $R^1$ is Y-1A, $R^2$ is $CH_3$, $R^9$ is $CH_3$ and $R^{10}$ is H.

Table 423. Compounds of formula I.7 wherein $R^1$ is Y-1A, $R^2$ is $CH_3$, $R^9$ is $CH_3$ and $R^{10}$ is $CH_3$.

Table 424. Compounds of formula I.7 wherein $R^1$ is Y-1B, $R^2$ is $CH_3$, $R^9$ is H and $R^{10}$ is H.

Table 425. Compounds of formula I.7 wherein $R^1$ is Y-1B, $R^2$ is $CH_3$, $R^9$ is $CH_3$ and $R^{10}$ is H.

Table 426. Compounds of formula I.7 wherein $R^1$ is Y-1B, $R^2$ is $CH_3$, $R^9$ is $CH_3$ and $R^{10}$ is $CH_3$.

Table 427. Compounds of formula I.7 wherein $R^1$ is Y-2A, $R^2$ is $CH_3$, $R^9$ is H and $R^{10}$ is H.

Table 428. Compounds of formula I.7 wherein $R^1$ is Y-2A, $R^2$ is $CH_3$, $R^9$ is $CH_3$ and $R^{10}$ is H.

Table 429. Compounds of formula I.7 wherein $R^1$ is Y-2A, $R^2$ is $CH_3$, $R^9$ is $CH_3$ and $R^{10}$ is $CH_3$.

Table 430. Compounds of formula I.7 wherein $R^1$ is Y-2B, $R^2$ is $CH_3$, $R^9$ is H and $R^{10}$ is H.

Table 431. Compounds of formula I.7 wherein $R^1$ is Y-2B, $R^2$ is $CH_3$, $R^9$ is $CH_3$ and $R^{10}$ is H.

Table 432. Compounds of formula I.7 wherein $R^1$ is Y-2B, $R^2$ is $CH_3$, $R^9$ is $CH_3$ and $R^{10}$ is $CH_3$.

Table 433. Compounds of formula I.7 wherein $R^1$ is Y-3A, $R^2$ is $CH_3$, $R^9$ is H and $R^{10}$ is H.

Table 434. Compounds of formula I.7 wherein $R^1$ is Y-3A, $R^2$ is $CH_3$, $R^9$ is $CH_3$ and $R^{10}$ is H.

Table 435. Compounds of formula I.7 wherein $R^1$ is Y-3A, $R^2$ is $CH_3$, $R^9$ is $CH_3$ and $R^{10}$ is $CH_3$.

Table 436. Compounds of formula I.7 wherein $R^1$ is Y-3B, $R^2$ is $CH_3$, $R^9$ is H and $R^{10}$ is H.

Table 437. Compounds of formula I.7 wherein $R^1$ is Y-3B, $R^2$ is $CH_3$, $R^9$ is $CH_3$ and $R^{10}$ is H.

Table 438. Compounds of formula I.7 wherein $R^1$ is Y-3B, $R^2$ is $CH_3$, $R^9$ is $CH_3$ and $R^{10}$ is $CH_3$.

Table 439. Compounds of formula I.7 wherein $R^1$ is Y-3C, $R^2$ is $CH_3$, $R^9$ is H and $R^{10}$ is H.

Table 440. Compounds of formula I.7 wherein $R^1$ is Y-3C, $R^2$ is $CH_3$, $R^9$ is $CH_3$ and $R^{10}$ is H.

Table 441. Compounds of formula I.7 wherein $R^1$ is Y-3C, $R^2$ is $CH_3$, $R^9$ is $CH_3$ and $R^{10}$ is $CH_3$.

Table 442. Compounds of formula I.7 wherein $R^1$ is Y-3D, $R^2$ is $CH_3$, $R^9$ is H and $R^{10}$ is H.

Table 443. Compounds of formula I.7 wherein $R^1$ is Y-3D, $R^2$ is $CH_3$, $R^9$ is $CH_3$ and $R^{10}$ is H.

Table 444. Compounds of formula I.7 wherein $R^1$ is Y-3D, $R^2$ is $CH_3$, $R^9$ is $CH_3$ and $R^{10}$ is $CH_3$.

Table 445. Compounds of formula I.7 wherein $R^1$ is Y-4A, $R^2$ is $CH_3$, $R^9$ is H and $R^{10}$ is H.

Table 446. Compounds of formula I.7 wherein $R^1$ is Y-4A, $R^2$ is $CH_3$, $R^9$ is $CH_3$ and $R^{10}$ is H.

Table 447. Compounds of formula I.7 wherein $R^1$ is Y-4A, $R^2$ is $CH_3$, $R^9$ is $CH_3$ and $R^{10}$ is $CH_3$.

Table 448. Compounds of formula I.7 wherein $R^1$ is Y-4B, $R^2$ is $CH_3$, $R^9$ is H and $R^{10}$ is H.

Table 449. Compounds of formula I.7 wherein $R^1$ is Y-4B, $R^2$ is $CH_3$, $R^9$ is $CH_3$ and $R^{10}$ is H.

Table 450. Compounds of formula I.7 wherein $R^1$ is Y-4B, $R^2$ is $CH_3$, $R^9$ is $CH_3$ and $R^{10}$ is $CH_3$.

Table 451. Compounds of formula I.7 wherein $R^1$ is Y-4C, $R^2$ is $CH_3$, $R^9$ is H and $R^{10}$ is H.

Table 452. Compounds of formula I.7 wherein $R^1$ is Y-4C, $R^2$ is $CH_3$, $R^9$ is $CH_3$ and $R^{10}$ is H.

Table 453. Compounds of formula I.7 wherein $R^1$ is Y-4C, $R^2$ is $CH_3$, $R^9$ is $CH_3$ and $R^{10}$ is $CH_3$.

Table 454. Compounds of formula I.7 wherein $R^1$ is Y-4D, $R^2$ is $CH_3$, $R^9$ is H and $R^{10}$ is H.

Table 455. Compounds of formula I.7 wherein $R^1$ is Y-4D, $R^2$ is $CH_3$, $R^9$ is $CH_3$ and $R^{10}$ is H.

Table 456. Compounds of formula I.7 wherein $R^1$ is Y-4D, $R^2$ is $CH_3$, $R^9$ is $CH_3$ and $R^{10}$ is $CH_3$.

Table 457. Compounds of formula I.7 wherein $R^1$ is Y-5A, $R^2$ is $CH_3$, $R^9$ is H and $R^{10}$ is H.

Table 458. Compounds of formula I.7 wherein $R^1$ is Y-5A, $R^2$ is $CH_3$, $R^9$ is $CH_3$ and $R^{10}$ is H.

Table 459. Compounds of formula I.7 wherein $R^1$ is Y-5A, $R^2$ is $CH_3$, $R^9$ is $CH_3$ and $R^{10}$ is $CH_3$.

Table 460. Compounds of formula I.7 wherein $R^1$ is Y-5B, $R^2$ is $CH_3$, $R^9$ is H and $R^{10}$ is H.

Table 461. Compounds of formula I.7 wherein $R^1$ is Y-5B, $R^2$ is $CH_3$, $R^9$ is $CH_3$ and $R^{10}$ is H.

Table 462. Compounds of formula I.7 wherein $R^1$ is Y-5B, $R^2$ is $CH_3$, $R^9$ is $CH_3$ and $R^{10}$ is $CH_3$.

Table 463. Compounds of formula I.7 wherein $R^1$ is Y-6A, $R^2$ is $CH_3$, $R^9$ is H and $R^{10}$ is H.

Table 464. Compounds of formula I.7 wherein $R^1$ is Y-6A, $R^2$ is $CH_3$, $R^9$ is $CH_3$ and $R^{10}$ is H.

Table 465. Compounds of formula I.7 wherein $R^1$ is Y-6A, $R^2$ is $CH_3$, $R^9$ is $CH_3$ and $R^{10}$ is $CH_3$.

Table 466. Compounds of formula I.7 wherein $R^1$ is Y-6B, $R^2$ is $CH_3$, $R^9$ is H and $R^{10}$ is H.

Table 467. Compounds of formula I.7 wherein $R^1$ is Y-6B, $R^2$ is $CH_3$, $R^9$ is $CH_3$ and $R^{10}$ is H.

Table 468. Compounds of formula I.7 wherein $R^1$ is Y-6B, $R^2$ is $CH_3$, $R^9$ is $CH_3$ and $R^{10}$ is $CH_3$.

Table 469. Compounds of formula I.7 wherein $R^1$ is Y-7A, $R^2$ is $CH_3$, $R^9$ is H and $R^{10}$ is H.

Table 470. Compounds of formula I.7 wherein $R^1$ is Y-7A, $R^2$ is $CH_3$, $R^9$ is $CH_3$ and $R^{10}$ is H.

Table 471. Compounds of formula I.7 wherein $R^1$ is Y-7A, $R^2$ is $CH_3$, $R^9$ is $CH_3$ and $R^{10}$ is $CH_3$.

Table 472. Compounds of formula I.7 wherein $R^1$ is Y-7B, $R^2$ is $CH_3$, $R^9$ is H and $R^{10}$ is H.

Table 473. Compounds of formula I.7 wherein $R^1$ is Y-7B, $R^2$ is $CH_3$, $R^9$ is $CH_3$ and $R^{10}$ is H.

Table 474. Compounds of formula I.7 wherein $R^1$ is Y-7B, $R^2$ is $CH_3$, $R^9$ is $CH_3$ and $R^{10}$ is $CH_3$.

Table 475. Compounds of formula I.7 wherein $R^1$ is Y-8A, $R^2$ is $CH_3$, $R^9$ is H and $R^{10}$ is H.

Table 476. Compounds of formula I.7 wherein $R^1$ is Y-8A, $R^2$ is $CH_3$, $R^9$ is $CH_3$ and $R^{10}$ is H.

Table 477. Compounds of formula I.7 wherein $R^1$ is Y-8A, $R^2$ is $CH_3$, $R^9$ is $CH_3$ and $R^{10}$ is $CH_3$.

Table 478. Compounds of formula I.7 wherein $R^1$ is Y-8B, $R^2$ is $CH_3$, $R^9$ is H and $R^{10}$ is H.

Table 479. Compounds of formula I.7 wherein $R^1$ is Y-8B, $R^2$ is $CH_3$, $R^9$ is $CH_3$ and $R^{10}$ is H.

Table 480. Compounds of formula I.7 wherein $R^1$ is Y-8B, $R^2$ is $CH_3$, $R^9$ is $CH_3$ and $R^{10}$ is $CH_3$.

Table 481. Compounds of formula I.7 wherein $R^1$ is Y-1A, $R^2$ is $C_2H_5$, $R^9$ is H and $R^{10}$ is H.

Table 482. Compounds of formula I.7 wherein $R^1$ is Y-1A, $R^2$ is $C_2H_5$, $R^9$ is $CH_3$ and $R^{10}$ is H.

Table 483. Compounds of formula I.7 wherein $R^1$ is Y-1A, $R^2$ is $C_2H_5$, $R^9$ is $CH_3$ and $R^{10}$ is $CH_3$.

Table 484. Compounds of formula I.7 wherein $R^1$ is Y-1B, $R^2$ is $C_2H_5$, $R^9$ is H and $R^{10}$ is H.

Table 485. Compounds of formula I.7 wherein $R^1$ is Y-1B, $R^2$ is $C_2H_5$, $R^9$ is $CH_3$ and $R^{10}$ is H.

Table 486. Compounds of formula I.7 wherein $R^1$ is Y-1B, $R^2$ is $C_2H_5$, $R^9$ is $CH_3$ and $R^{10}$ is $CH_3$.

Table 487. Compounds of formula I.7 wherein $R^1$ is Y-2A, $R^2$ is $C_2H_5$, $R^9$ is H and $R^{10}$ is H.

Table 488. Compounds of formula I.7 wherein $R^1$ is Y-2A, $R^2$ is $C_2H_5$, $R^9$ is $CH_3$ and $R^{10}$ is H.

Table 489. Compounds of formula I.7 wherein $R^1$ is Y-2A, $R^2$ is $C_2H_5$, $R^9$ is $CH_3$ and $R^{10}$ is $CH_3$.

Table 490. Compounds of formula I.7 wherein $R^1$ is Y-2B, $R^2$ is $C_2H_5$, $R^9$ is H and $R^{10}$ is H.

Table 491. Compounds of formula I.7 wherein $R^1$ is Y-2B, $R^2$ is $C_2H_5$, $R^9$ is $CH_3$ and $R^{10}$ is H.

Table 492. Compounds of formula I.7 wherein $R^1$ is Y-2B, $R^2$ is $C_2H_5$, $R^9$ is $CH_3$ and $R^{10}$ is $CH_3$.

Table 493. Compounds of formula I.7 wherein $R^1$ is Y-3A, $R^2$ is $C_2H_5$, $R^9$ is H and $R^{10}$ is H.

Table 494. Compounds of formula I.7 wherein $R^1$ is Y-3A, $R^2$ is $C_2H_5$, $R^9$ is $CH_3$ and $R^{10}$ is H.

Table 495. Compounds of formula I.7 wherein $R^1$ is Y-3A, $R^2$ is $C_2H_5$, $R^9$ is $CH_3$ and $R^{10}$ is $CH_3$.

Table 496. Compounds of formula I.7 wherein $R^1$ is Y-3B, $R^2$ is $C_2H_5$, $R^9$ is H and $R^{10}$ is H.

Table 497. Compounds of formula I.7 wherein $R^1$ is Y-3B, $R^2$ is $C_2H_5$, $R^9$ is $CH_3$ and $R^{10}$ is H.

Table 498. Compounds of formula I.7 wherein $R^1$ is Y-3B, $R^2$ is $C_2H_5$, $R^9$ is $CH_3$ and $R^{10}$ is $CH_3$.

Table 499. Compounds of formula I.7 wherein $R^1$ is Y-3C, $R^2$ is $C_2H_5$, $R^9$ is H and $R^{10}$ is H.

Table 500. Compounds of formula I.7 wherein $R^1$ is Y-3C, $R^2$ is $C_2H_5$, $R^9$ is $CH_3$ and $R^{10}$ is H.

Table 501. Compounds of formula I.7 wherein $R^1$ is Y-3C, $R^2$ is $C_2H_5$, $R^9$ is $CH_3$ and $R^{10}$ is $CH_3$.

Table 502. Compounds of formula I.7 wherein $R^1$ is Y-3D, $R^2$ is $C_2H_5$, $R^9$ is H and $R^{10}$ is H.

Table 503. Compounds of formula I.7 wherein $R^1$ is Y-3D, $R^2$ is $C_2H_5$, $R^9$ is $CH_3$ and $R^{10}$ is H.

Table 504. Compounds of formula I.7 wherein $R^1$ is Y-3D, $R^2$ is $C_2H_5$, $R^9$ is $CH_3$ and $R^{10}$ is $CH_3$.

Table 505. Compounds of formula I.7 wherein $R^1$ is Y-4A, $R^2$ is $C_2H_5$, $R^9$ is H and $R^{10}$ is H.

Table 506. Compounds of formula I.7 wherein $R^1$ is Y-4A, $R^2$ is $C_2H_5$, $R^9$ is $CH_3$ and $R^{10}$ is H.

Table 507. Compounds of formula I.7 wherein $R^1$ is Y-4A, $R^2$ is $C_2H_5$, $R^9$ is $CH_3$ and $R^{10}$ is $CH_3$.

Table 508. Compounds of formula I.7 wherein $R^1$ is Y-4B, $R^2$ is $C_2H_5$, $R^9$ is H and $R^{10}$ is H.

Table 509. Compounds of formula I.7 wherein $R^1$ is Y-4B, $R^2$ is $C_2H_5$, $R^9$ is $CH_3$ and $R^{10}$ is H.

Table 510. Compounds of formula I.7 wherein $R^1$ is Y-4B, $R^2$ is $C_2H_5$, $R^9$ is $CH_3$ and $R^{10}$ is $CH_3$.

Table 511. Compounds of formula I.7 wherein $R^1$ is Y-4C, $R^2$ is $C_2H_5$, $R^9$ is H and $R^{10}$ is H.

Table 512. Compounds of formula I.7 wherein $R^1$ is Y-4C, $R^2$ is $C_2H_5$, $R^9$ is $CH_3$ and $R^{10}$ is H.

Table 513. Compounds of formula I.7 wherein $R^1$ is Y-4C, $R^2$ is $C_2H_5$, $R^9$ is $CH_3$ and $R^{10}$ is $CH_3$.

Table 514. Compounds of formula I.7 wherein $R^1$ is Y-4D, $R^2$ is $C_2H_5$, $R^9$ is H and $R^{10}$ is H.

Table 515. Compounds of formula I.7 wherein $R^1$ is Y-4D, $R^2$ is $C_2H_5$, $R^9$ is $CH_3$ and $R^{10}$ is H.

Table 516. Compounds of formula I.7 wherein $R^1$ is Y-4D, $R^2$ is $C_2H_5$, $R^9$ is $CH_3$ and $R^{10}$ is $CH_3$.

Table 517. Compounds of formula I.7 wherein $R^1$ is Y-5A, $R^2$ is $C_2H_5$, $R^9$ is H and $R^{10}$ is H.

Table 518. Compounds of formula I.7 wherein $R^1$ is Y-5A, $R^2$ is $C_2H_5$, $R^9$ is $CH_3$ and $R^{10}$ is H.

Table 519. Compounds of formula I.7 wherein $R^1$ is Y-5A, $R^2$ is $C_2H_5$, $R^9$ is $CH_3$ and $R^{10}$ is $CH_3$.

Table 520. Compounds of formula I.7 wherein $R^1$ is Y-5B, $R^2$ is $C_2H_5$, $R^9$ is H and $R^{10}$ is H.

Table 521. Compounds of formula I.7 wherein $R^1$ is Y-5B, $R^2$ is $C_2H_5$, $R^9$ is $CH_3$ and $R^{10}$ is H.

Table 522. Compounds of formula I.7 wherein $R^1$ is Y-5B, $R^2$ is $C_2H_5$, $R^9$ is $CH_3$ and $R^{10}$ is $CH_3$.

Table 523. Compounds of formula I.7 wherein $R^1$ is Y-6A, $R^2$ is $C_2H_5$, $R^9$ is H and $R^{10}$ is H.

Table 524. Compounds of formula I.7 wherein $R^1$ is Y-6A, $R^2$ is $C_2H_5$, $R^9$ is $CH_3$ and $R^{10}$ is H.

Table 525. Compounds of formula I.7 wherein $R^1$ is Y-6A, $R^2$ is $C_2H_5$, $R^9$ is $CH_3$ and $R^{10}$ is $CH_3$.

Table 526. Compounds of formula I.7 wherein $R^1$ is Y-6B, $R^2$ is $C_2H_5$, $R^9$ is H and $R^{10}$ is H.

Table 527. Compounds of formula I.7 wherein $R^1$ is Y-6B, $R^2$ is $C_2H_5$, $R^9$ is $CH_3$ and $R^{10}$ is H.

Table 528. Compounds of formula I.7 wherein $R^1$ is Y-6B, $R^2$ is $C_2H_5$, $R^9$ is $CH_3$ and $R^{10}$ is $CH_3$.

Table 529. Compounds of formula I.7 wherein $R^1$ is Y-7A, $R^2$ is $C_2H_5$, $R^9$ is H and $R^{10}$ is H.

Table 530. Compounds of formula I.7 wherein $R^1$ is Y-7A, $R^2$ is $C_2H_5$, $R^9$ is $CH_3$ and $R^{10}$ is H.

Table 531. Compounds of formula I.7 wherein $R^1$ is Y-7A, $R^2$ is $C_2H_5$, $R^9$ is $CH_3$ and $R^{10}$ is $CH_3$.

Table 532. Compounds of formula I.7 wherein $R^1$ is Y-7B, $R^2$ is $C_2H_5$, $R^9$ is H and $R^{10}$ is H.

Table 533. Compounds of formula I.7 wherein $R^1$ is Y-7B, $R^2$ is $C_2H_5$, $R^9$ is $CH_3$ and $R^{10}$ is H.

Table 534. Compounds of formula I.7 wherein $R^1$ is Y-7B, $R^2$ is $C_2H_5$, $R^9$ is $CH_3$ and $R^{10}$ is $CH_3$.

Table 535. Compounds of formula I.7 wherein $R^1$ is Y-8A, $R^2$ is $C_2H_5$, $R^9$ is H and $R^{10}$ is H.

Table 536. Compounds of formula I.7 wherein $R^1$ is Y-8A, $R^2$ is $C_2H_5$, $R^9$ is $CH_3$ and $R^{10}$ is H.

Table 537. Compounds of formula I.7 wherein $R^1$ is Y-8A, $R^2$ is $C_2H_5$, $R^9$ is $CH_3$ and $R^{10}$ is $CH_3$.

Table 538. Compounds of formula I.7 wherein $R^1$ is Y-8B, $R^2$ is $C_2H_5$, $R^9$ is H and $R^{10}$ is H.

Table 539. Compounds of formula I.7 wherein $R^1$ is Y-8B, $R^2$ is $C_2H_5$, $R^9$ is $CH_3$ and $R^{10}$ is H.

Table 540. Compounds of formula I.7 wherein $R^1$ is Y-8B, $R^2$ is $C_2H_5$, $R^9$ is $CH_3$ and $R^{10}$ is $CH_3$.

Table 541. Compounds of formula I.7 wherein $R^1$ is Y-1A, $R^2$ is c-$C_3H_5$, $R^9$ is H and $R^{10}$ is H.

Table 542. Compounds of formula I.7 wherein $R^1$ is Y-1A, $R^2$ is c-$C_3H_5$, $R^9$ is $CH_3$ and $R^{10}$ is H.

Table 543. Compounds of formula I.7 wherein $R^1$ is Y-1A, $R^2$ is c-$C_3H_5$, $R^9$ is $CH_3$ and $R^{10}$ is $CH_3$.

Table 544. Compounds of formula I.7 wherein $R^1$ is Y-1B, $R^2$ is c-$C_3H_5$, $R^9$ is H and $R^{10}$ is H.

Table 545. Compounds of formula I.7 wherein $R^1$ is Y-1B, $R^2$ is c-$C_3H_5$, $R^9$ is $CH_3$, $R^{10}$ is H.

Table 546. Compounds of formula I.7 wherein $R^1$ is Y-1B, $R^2$ is c-$C_3H_5$, $R^9$ is $CH_3$ and $R^{10}$ is $CH_3$.

Table 547. Compounds of formula I.7 wherein $R^1$ is Y-2A, $R^2$ is c-$C_3H_5$, $R^9$ is H and $R^{10}$ is H.

Table 548. Compounds of formula I.7 wherein $R^1$ is Y-2A, $R^2$ is c-$C_3H_5$, $R^9$ is $CH_3$ and $R^{10}$ is H.

Table 549. Compounds of formula I.7 wherein $R^1$ is Y-2A, $R^2$ is c-$C_3H_5$, $R^9$ is $CH_3$ and $R^{10}$ is $CH_3$.

Table 550. Compounds of formula I.7 wherein $R^1$ is Y-2B, $R^2$ is c-$C_3H_5$, $R^9$ is H and $R^{10}$ is H.

Table 551. Compounds of formula I.7 wherein $R^1$ is Y-2B, $R^2$ is c-$C_3H_5$, $R^9$ is $CH_3$ and $R^{10}$ is H.

Table 552. Compounds of formula I.7 wherein $R^1$ is Y-2B, $R^2$ is c-$C_3H_5$, $R^9$ is $CH_3$ and $R^{10}$ is $CH_3$.

Table 553. Compounds of formula I.7 wherein $R^1$ is Y-3A, $R^2$ is c-$C_3H_5$, $R^9$ is H and $R^{10}$ is H.

Table 554. Compounds of formula I.7 wherein $R^1$ is Y-3A, $R^2$ is c-$C_3H_5$, $R^9$ is $CH_3$ and $R^{10}$ is H.

Table 555. Compounds of formula I.7 wherein $R^1$ is Y-3A, $R^2$ is c-$C_3H_5$, $R^9$ is $CH_3$ and $R^{10}$ is $CH_3$.

Table 556. Compounds of formula I.7 wherein $R^1$ is Y-3B, $R^2$ is c-$C_3H_5$, $R^9$ is H and $R^{10}$ is H.

Table 557. Compounds of formula I.7 wherein $R^1$ is Y-3B, $R^2$ is c-$C_3H_5$, $R^9$ is $CH_3$ and $R^{10}$ is H.

Table 558. Compounds of formula I.7 wherein $R^1$ is Y-3B, $R^2$ is c-$C_3H_5$, $R^9$ is $CH_3$ and $R^{10}$ is $CH_3$.

Table 559. Compounds of formula I.7 wherein $R^1$ is Y-3C, $R^2$ is c-$C_3H_5$, $R^9$ is H and $R^{10}$ is H.

Table 560. Compounds of formula I.7 wherein $R^1$ is Y-3C, $R^2$ is c-$C_3H_5$, $R^9$ is $CH_3$ and $R^{10}$ is H.

Table 561. Compounds of formula I.7 wherein $R^1$ is Y-3C, $R^2$ is c-$C_3H_5$, $R^9$ is $CH_3$ and $R^{10}$ is $CH_3$.

Table 562. Compounds of formula I.7 wherein $R^1$ is Y-3D, $R^2$ is c-$C_3H_5$, $R^9$ is H and $R^{10}$ is H.

Table 563. Compounds of formula I.7 wherein $R^1$ is Y-3D, $R^2$ is c-$C_3H_5$, $R^9$ is $CH_3$ and $R^{10}$ is H.

Table 564. Compounds of formula I.7 wherein $R^1$ is Y-3D, $R^2$ is c-$C_3H_5$, $R^9$ is $CH_3$ and $R^{10}$ is $CH_3$.

Table 565. Compounds of formula I.7 wherein $R^1$ is Y-4A, $R^2$ is c-$C_3H_5$, $R^9$ is H and $R^{10}$ is H.

Table 566. Compounds of formula I.7 wherein $R^1$ is Y-4A, $R^2$ is c-$C_3H_5$, $R^9$ is $CH_3$ and $R^{10}$ is H.

Table 567. Compounds of formula I.7 wherein $R^1$ is Y-4A, $R^2$ is c-$C_3H_5$, $R^9$ is $CH_3$ and $R^{10}$ is $CH_3$.

Table 568. Compounds of formula I.7 wherein $R^1$ is Y-4B, $R^2$ is c-$C_3H_5$, $R^9$ is H and $R^{10}$ is H.

Table 569. Compounds of formula I.7 wherein $R^1$ is Y-4B, $R^2$ is c-$C_3H_5$, $R^9$ is $CH_3$ and $R^{10}$ is H.

Table 570. Compounds of formula I.7 wherein $R^1$ is Y-4B, $R^2$ is c-$C_3H_5$, $R^9$ is $CH_3$ and $R^{10}$ is $CH_3$.

Table 571. Compounds of formula I.7 wherein $R^1$ is Y-4C, $R^2$ is c-$C_3H_5$, $R^9$ is H and $R^{10}$ is H.

Table 572. Compounds of formula I.7 wherein $R^1$ is Y-4C, $R^2$ is c-$C_3H_5$, $R^9$ is $CH_3$ and $R^{10}$ is H.

Table 573. Compounds of formula I.7 wherein $R^1$ is Y-4C, $R^2$ is c-$C_3H_5$, $R^9$ is $CH_3$ and $R^{10}$ is $CH_3$.

Table 574. Compounds of formula I.7 wherein $R^1$ is Y-4D, $R^2$ is c-$C_3H_5$, $R^9$ is H and $R^{10}$ is H.

Table 575. Compounds of formula I.7 wherein $R^1$ is Y-4D, $R^2$ is c-$C_3H_5$, $R^9$ is $CH_3$ and $R^{10}$ is H.

Table 576. Compounds of formula I.7 wherein $R^1$ is Y-4D, $R^2$ is c-$C_3H_5$, $R^9$ is $CH_3$ and $R^{10}$ is $CH_3$.

Table 577. Compounds of formula I.7 wherein $R^1$ is Y-5A, $R^2$ is c-$C_3H_5$, $R^9$ is H and $R^{10}$ is H.

Table 578. Compounds of formula I.7 wherein $R^1$ is Y-5A, $R^2$ is c-$C_3H_5$, $R^9$ is $CH_3$ and $R^{10}$ is H.

Table 579. Compounds of formula I.7 wherein $R^1$ is Y-5A, $R^2$ is c-$C_3H_5$, $R^9$ is $CH_3$ and $R^{10}$ is $CH_3$.

Table 580. Compounds of formula I.7 wherein $R^1$ is Y-5B, $R^2$ is c-$C_3H_5$, $R^9$ is H and $R^{10}$ is H.

Table 581. Compounds of formula I.7 wherein $R^1$ is Y-5B, $R^2$ is c-$C_3H_5$, $R^9$ is $CH_3$ and $R^{10}$ is H.

Table 582. Compounds of formula I.7 wherein $R^1$ is Y-5B, $R^2$ is c-$C_3H_5$, $R^9$ is $CH_3$ and $R^{10}$ is $CH_3$.

Table 583. Compounds of formula I.7 wherein $R^1$ is Y-6A, $R^2$ is c-$C_3H_5$, $R^9$ is H and $R^{10}$ is H.

Table 584. Compounds of formula I.7 wherein $R^1$ is Y-6A, $R^2$ is c-$C_3H_5$, $R^9$ is $CH_3$ and $R^{10}$ is H.

Table 585. Compounds of formula I.7 wherein $R^1$ is Y-6A, $R^2$ is c-$C_3H_5$, $R^9$ is $CH_3$ and $R^{10}$ is $CH_3$.

Table 586. Compounds of formula I.7 wherein $R^1$ is Y-6B, $R^2$ is c-$C_3H_5$, $R^9$ is H and $R^{10}$ is H.

Table 587. Compounds of formula I.7 wherein $R^1$ is Y-6B, $R^2$ is c-$C_3H_5$, $R^9$ is $CH_3$ and $R^{10}$ is H.

Table 588. Compounds of formula I.7 wherein $R^1$ is Y-6B, $R^2$ is c-$C_3H_5$, $R^9$ is $CH_3$ and $R^{10}$ is $CH_3$.

Table 589. Compounds of formula I.7 wherein $R^1$ is Y-7A, $R^2$ is c-$C_3H_5$, $R^9$ is H and $R^{10}$ is H.

Table 590. Compounds of formula I.7 wherein $R^1$ is Y-7A, $R^2$ is c-$C_3H_5$, $R^9$ is $CH_3$ and $R^{10}$ is H.

Table 591. Compounds of formula I.7 wherein $R^1$ is Y-7A, $R^2$ is c-$C_3H_5$, $R^9$ is $CH_3$ and $R^{10}$ is $CH_3$.

Table 592. Compounds of formula I.7 wherein $R^1$ is Y-7B, $R^2$ is c-$C_3H_5$, $R^9$ is H and $R^{10}$ is H.

Table 593. Compounds of formula I.7 wherein $R^1$ is Y-7B, $R^2$ is c-$C_3H_5$, $R^9$ is $CH_3$ and $R^{10}$ is H.

Table 594. Compounds of formula I.7 wherein $R^1$ is Y-7B, $R^2$ is c-$C_3H_5$, $R^9$ is $CH_3$ and $R^{10}$ is $CH_3$.

Table 595. Compounds of formula I.7 wherein $R^1$ is Y-8A, $R^2$ is c-$C_3H_5$, $R^9$ is H and $R^{10}$ is H.

Table 596. Compounds of formula I.7 wherein $R^1$ is Y-8A, $R^2$ is c-$C_3H_5$, $R^9$ is $CH_3$ and $R^{10}$ is H.

Table 597. Compounds of formula I.7 wherein $R^1$ is Y-8A, $R^2$ is c-$C_3H_5$, $R^9$ is $CH_3$ and $R^{10}$ is $CH_3$.

Table 598. Compounds of formula I.7 wherein $R^1$ is Y-8B, $R^2$ is c-$C_3H_5$, $R^9$ is H and $R^{10}$ is H.

Table 599. Compounds of formula I.7 wherein $R^1$ is Y-8B, $R^2$ is c-$C_3H_5$, $R^9$ is $CH_3$ and $R^{10}$ is H.

Table 600. Compounds of formula I.7 wherein $R^1$ is Y-8B, $R^2$ is c-$C_3H_5$, $R^9$ is $CH_3$ and $R^{10}$ is $CH_3$.

Table 601. Compounds of formula I.8 wherein $R^1$ is Y-1A, $R^2$ is H, $R^9$ is H and $R^{10}$ is H.

Table 602. Compounds of formula I.8 wherein $R^1$ is Y-1A, $R^2$ is H, $R^9$ is $CH_3$ and, $R^{10}$ is H.

Table 603. Compounds of formula I.8 wherein $R^1$ is Y-1A, $R^2$ is H, $R^9$ is $CH_3$ and $R^{10}$ is $CH_3$.

Table 604. Compounds of formula I.8 wherein $R^1$ is Y-1B, $R^2$ is H, $R^9$ is H and $R^{10}$ is H.

Table 605. Compounds of formula I.8 wherein $R^1$ is Y-1B, $R^2$ is H, $R^9$ is $CH_3$ and $R^{10}$ is H.

Table 606. Compounds of formula I.8 wherein $R^1$ is Y-1B, $R^2$ is H, $R^9$ is $CH_3$ and $R^{10}$ is $CH_3$.

Table 607. Compounds of formula I.8 wherein $R^1$ is Y-2A, $R^2$ is H, $R^9$ is H and $R^{10}$ is H.

Table 608. Compounds of formula I.8 wherein $R^1$ is Y-2A, $R^2$ is H, $R^9$ is $CH_3$ and $R^{10}$ is H.

Table 609. Compounds of formula I.8 wherein $R^1$ is Y-2A, $R^2$ is H, $R^9$ is $CH_3$ and $R^{10}$ is $CH_3$.

Table 610. Compounds of formula I.8 wherein $R^1$ is Y-2B, $R^2$ is H, $R^9$ is H and $R^{10}$ is H.

Table 611. Compounds of formula I.8 wherein $R^1$ is Y-2B, $R^2$ is H, $R^9$ is $CH_3$ and $R^{10}$ is H.

Table 612. Compounds of formula I.8 wherein $R^1$ is Y-2B, $R^2$ is H, $R^9$ is $CH_3$ and $R^{10}$ is $CH_3$.

Table 613. Compounds of formula I.8 wherein $R^1$ is Y-3A, $R^2$ is H, $R^9$ is H and $R^{10}$ is H.

Table 614. Compounds of formula I.8 wherein $R^1$ is Y-3A, $R^2$ is H, $R^9$ is $CH_3$ and $R^{10}$ is H.

Table 615. Compounds of formula I.8 wherein $R^1$ is Y-3A, $R^2$ is H, $R^9$ is $CH_3$ and $R^{10}$ is $CH_3$.

Table 616. Compounds of formula I.8 wherein $R^1$ is Y-3B, $R^2$ is H, $R^9$ is H and $R^{10}$ is H.

Table 617. Compounds of formula I.8 wherein $R^1$ is Y-3B, $R^2$ is H, $R^9$ is $CH_3$ and $R^{10}$ is H.

Table 618. Compounds of formula I.8 wherein $R^1$ is Y-3B, $R^2$ is H, $R^9$ is $CH_3$ and $R^{10}$ is $CH_3$.

Table 619. Compounds of formula I.8 wherein $R^1$ is Y-3C, $R^2$ is H, $R^9$ is H and $R^{10}$ is H.

Table 620. Compounds of formula I.8 wherein $R^1$ is Y-3C, $R^2$ is H, $R^9$ is $CH_3$ and $R^{10}$ is H.

Table 621. Compounds of formula I.8 wherein $R^1$ is Y-3C, $R^2$ is H, $R^9$ is $CH_3$ and $R^{10}$ is $CH_3$.

Table 622. Compounds of formula I.8 wherein $R^1$ is Y-3D, $R^2$ is H, $R^9$ is H and $R^{10}$ is H.

Table 623. Compounds of formula I.8 wherein $R^1$ is Y-3D, $R^2$ is H, $R^9$ is $CH_3$ and $R^{10}$ is H.

Table 624. Compounds of formula I.8 wherein $R^1$ is Y-3D, $R^2$ is H, $R^9$ is $CH_3$ and $R^{10}$ is $CH_3$.

Table 625. Compounds of formula I.8 wherein $R^1$ is Y-4A, $R^2$ is H, $R^9$ is H and $R^{10}$ is H.

Table 626. Compounds of formula I.8 wherein $R^1$ is Y-4A, $R^2$ is H, $R^9$ is $CH_3$ and $R^{10}$ is H.

Table 627. Compounds of formula I.8 wherein $R^1$ is Y-4A, $R^2$ is H, $R^9$ is $CH_3$ and $R^{10}$ is $CH_3$.

Table 628. Compounds of formula I.8 wherein $R^1$ is Y-4B, $R^2$ is H, $R^9$ is H and $R^{10}$ is H.

Table 629. Compounds of formula I.8 wherein $R^1$ is Y-4B, $R^2$ is H, $R^9$ is $CH_3$ and $R^{10}$ is H.

Table 630. Compounds of formula I.8 wherein $R^1$ is Y-4B, $R^2$ is H, $R^9$ is $CH_3$ and $R^{10}$ is $CH_3$.

Table 631. Compounds of formula I.8 wherein $R^1$ is Y-4C, $R^2$ is H, $R^9$ is H and $R^{10}$ is H.

Table 632. Compounds of formula I.8 wherein $R^1$ is Y-4C, $R^2$ is H, $R^9$ is $CH_3$ and $R^{10}$ is H.

Table 633. Compounds of formula I.8 wherein $R^1$ is Y-4C, $R^2$ is H, $R^9$ is $CH_3$ and $R^{10}$ is $CH_3$.

Table 634. Compounds of formula I.8 wherein $R^1$ is Y-4D, $R^2$ is H, $R^9$ is H and $R^{10}$ is H.

Table 635. Compounds of formula I.8 wherein $R^1$ is Y-4D, $R^2$ is H, $R^9$ is $CH_3$ and $R^{10}$ is H.

Table 636. Compounds of formula I.8 wherein $R^1$ is Y-4D, $R^2$ is H, $R^9$ is $CH_3$ and $R^{10}$ is $CH_3$.

Table 637. Compounds of formula I.8 wherein $R^1$ is Y-5A, $R^2$ is H, $R^9$ is H and $R^{10}$ is H.

Table 638. Compounds of formula I.8 wherein $R^1$ is Y-5A, $R^2$ is H, $R^9$ is $CH_3$ and $R^{10}$ is H.

Table 639. Compounds of formula I.8 wherein $R^1$ is Y-5A, $R^2$ is H, $R^9$ is $CH_3$ and $R^{10}$ is $CH_3$.

Table 640. Compounds of formula I.8 wherein $R^1$ is Y-5B, $R^2$ is H, $R^9$ is H and $R^{10}$ is H.

Table 641. Compounds of formula I.8 wherein $R^1$ is Y-5B, $R^2$ is H, $R^9$ is $CH_3$ and $R^{10}$ is H.

Table 642. Compounds of formula I.8 wherein $R^1$ is Y-5B, $R^2$ is H, $R^9$ is $CH_3$ and $R^{10}$ is $CH_3$.

Table 643. Compounds of formula I.8 wherein $R^1$ is Y-6A, $R^2$ is H, $R^9$ is H and $R^{10}$ is H.

Table 644. Compounds of formula I.8 wherein $R^1$ is Y-6A, $R^2$ is H, $R^9$ is $CH_3$ and $R^{10}$ is H.

Table 645. Compounds of formula I.8 wherein $R^1$ is Y-6A, $R^2$ is H, $R^9$ is $CH_3$ and $R^{10}$ is $CH_3$.

Table 646. Compounds of formula I.8 wherein $R^1$ is Y-6B, $R^2$ is H, $R^9$ is H and $R^{10}$ is H.

Table 647. Compounds of formula I.8 wherein $R^1$ is Y-6B, $R^2$ is H, $R^9$ is $CH_3$ and $R^{10}$ is H.

Table 648. Compounds of formula I.8 wherein $R^1$ is Y-6B, $R^2$ is H, $R^9$ is $CH_3$ and $R^{10}$ is $CH_3$.

Table 649. Compounds of formula I.8 wherein $R^1$ is Y-7A, $R^2$ is H, $R^9$ is H and $R^{10}$ is H.

Table 650. Compounds of formula I.8 wherein $R^1$ is Y-7A, $R^2$ is H, $R^9$ is $CH_3$ and $R^{10}$ is H.

Table 651. Compounds of formula I.8 wherein $R^1$ is Y-7A, $R^2$ is H, $R^9$ is $CH_3$ and $R^{10}$ is $CH_3$.

Table 652. Compounds of formula I.8 wherein $R^1$ is Y-7B, $R^2$ is H, $R^9$ is H and $R^{10}$ is H.

Table 653. Compounds of formula I.8 wherein $R^1$ is Y-7B, $R^2$ is H, $R^9$ is $CH_3$ and $R^{10}$ is H.

Table 654. Compounds of formula I.8 wherein $R^1$ is Y-7B, $R^2$ is H, $R^9$ is $CH_3$ and $R^{10}$ is $CH_3$.

Table 655. Compounds of formula I.8 wherein $R^1$ is Y-8A, $R^2$ is H, $R^9$ is H and $R^{10}$ is H.

Table 656. Compounds of formula I.8 wherein $R^1$ is Y-8A, $R^2$ is H, $R^9$ is $CH_3$ and $R^{10}$ is H.

Table 657. Compounds of formula I.8 wherein $R^1$ is Y-8A, $R^2$ is H, $R^9$ is $CH_3$ and $R^{10}$ is $CH_3$.

Table 658. Compounds of formula I.8 wherein $R^1$ is Y-8B, $R^2$ is H, $R^9$ is H and $R^{10}$ is H.

Table 659. Compounds of formula I.8 wherein $R^1$ is Y-8B, $R^2$ is H, $R^9$ is $CH_3$ and $R^{10}$ is H.

Table 660. Compounds of formula I.8 wherein $R^1$ is Y-8B, $R^2$ is H, $R^9$ is $CH_3$ and $R^{10}$ is $CH_3$.

Table 661. Compounds of formula I.8 wherein $R^1$ is Y-1A, $R^2$ is $CH_3$, $R^9$ is H and $R^{10}$ is H.

Table 662. Compounds of formula I.8 wherein $R^1$ is Y-1A, $R^2$ is $CH_3$, $R^9$ is $CH_3$ and $R^{10}$ is H.

Table 663. Compounds of formula I.8 wherein $R^1$ is Y-1A, $R^2$ is $CH_3$, $R^9$ is $CH_3$ and $R^{10}$ is $CH_3$.

Table 664. Compounds of formula I.8 wherein $R^1$ is Y-1B, $R^2$ is $CH_3$, $R^9$ is H and $R^{10}$ is H.

Table 665. Compounds of formula I.8 wherein $R^1$ is Y-1B, $R^2$ is $CH_3$, $R^9$ is $CH_3$ and $R^{10}$ is H.

Table 666. Compounds of formula I.8 wherein $R^1$ is Y-1B, $R^2$ is $CH_3$, $R^9$ is $CH_3$ and $R^{10}$ is $CH_3$.

Table 667. Compounds of formula I.8 wherein $R^1$ is Y-2A, $R^2$ is $CH_3$, $R^9$ is H and $R^{10}$ is H.

Table 668. Compounds of formula I.8 wherein $R^1$ is Y-2A, $R^2$ is $CH_3$, $R^9$ is $CH_3$ and $R^{10}$ is H.

Table 669. Compounds of formula I.8 wherein $R^1$ is Y-2A, $R^2$ is $CH_3$, $R^9$ is $CH_3$ and $R^{10}$ is $CH_3$.

Table 670. Compounds of formula I.8 wherein $R^1$ is Y-2B, $R^2$ is $CH_3$, $R^9$ is H and $R^{10}$ is H.

Table 671. Compounds of formula I.8 wherein $R^1$ is Y-2B, $R^2$ is $CH_3$, $R^9$ is $CH_3$ and $R^{10}$ is H.

Table 672. Compounds of formula I.8 wherein $R^1$ is Y-2B, $R^2$ is $CH_3$, $R^9$ is $CH_3$ and $R^{10}$ is $CH_3$.

Table 673. Compounds of formula I.8 wherein $R^1$ is Y-3A, $R^2$ is $CH_3$, $R^9$ is H and $R^{10}$ is H.

Table 674. Compounds of formula I.8 wherein $R^1$ is Y-3A, $R^2$ is $CH_3$, $R^9$ is $CH_3$ and $R^{10}$ is H.

Table 675. Compounds of formula I.8 wherein $R^1$ is Y-3A, $R^2$ is $CH_3$, $R^9$ is $CH_3$ and $R^{10}$ is $CH_3$.

Table 676. Compounds of formula I.8 wherein $R^1$ is Y-3B, $R^2$ is $CH_3$, $R^9$ is H and $R^{10}$ is H.

Table 677. Compounds of formula I.8 wherein $R^1$ is Y-3B, $R^2$ is $CH_3$, $R^9$ is $CH_3$ and $R^{10}$ is H.

Table 678. Compounds of formula I.8 wherein $R^1$ is Y-3B, $R^2$ is $CH_3$, $R^9$ is $CH_3$ and $R^{10}$ is $CH_3$.

Table 679. Compounds of formula I.8 wherein $R^1$ is Y-3C, $R^2$ is $CH_3$, $R^9$ is H and $R^{10}$ is H.

Table 680. Compounds of formula I.8 wherein $R^1$ is Y-3C, $R^2$ is $CH_3$, $R^9$ is $CH_3$ and $R^{10}$ is H.

Table 681. Compounds of formula I.8 wherein $R^1$ is Y-3C, $R^2$ is $CH_3$, $R^9$ is $CH_3$ and $R^{10}$ is $CH_3$.

Table 682. Compounds of formula I.8 wherein $R^1$ is Y-3D, $R^2$ is $CH_3$, $R^9$ is H and $R^{10}$ is H.

Table 683. Compounds of formula I.8 wherein $R^1$ is Y-3D, $R^2$ is $CH_3$, $R^9$ is $CH_3$ and $R^{10}$ is H.

Table 684. Compounds of formula I.8 wherein $R^1$ is Y-3D, $R^2$ is $CH_3$, $R^9$ is $CH_3$ and $R^{10}$ is $CH_3$.

Table 685. Compounds of formula I.8 wherein $R^1$ is Y-4A, $R^2$ is $CH_3$, $R^9$ is H and $R^{10}$ is H.

Table 686. Compounds of formula I.8 wherein $R^1$ is Y-4A, $R^2$ is $CH_3$, $R^9$ is $CH_3$ and $R^{10}$ is H.

Table 687. Compounds of formula I.8 wherein $R^1$ is Y-4A, $R^2$ is $CH_3$, $R^9$ is $CH_3$ and $R^{10}$ is $CH_3$.

Table 688. Compounds of formula I.8 wherein $R^1$ is Y-4B, $R^2$ is $CH_3$, $R^9$ is H and $R^{10}$ is H.

Table 689. Compounds of formula I.8 wherein $R^1$ is Y-4B, $R^2$ is $CH_3$, $R^9$ is $CH_3$ and $R^{10}$ is H.

Table 690. Compounds of formula I.8 wherein $R^1$ is Y-4B, $R^2$ is $CH_3$, $R^9$ is $CH_3$ and $R^{10}$ is $CH_3$.

Table 691. Compounds of formula I.8 wherein $R^1$ is Y-4C, $R^2$ is $CH_3$, $R^9$ is H and $R^{10}$ is H.

Table 692. Compounds of formula I.8 wherein $R^1$ is Y-4C, $R^2$ is $CH_3$, $R^9$ is $CH_3$ and $R^{10}$ is H.

Table 693. Compounds of formula I.8 wherein $R^1$ is Y-40, $R^2$ is $CH_3$, $R^9$ is $CH_3$ and $R^{10}$ is $CH_3$.

Table 694. Compounds of formula I.8 wherein $R^1$ is Y-4D, $R^2$ is $CH_3$, $R^9$ is H and $R^{10}$ is H.

Table 695. Compounds of formula I.8 wherein $R^1$ is Y-4D, $R^2$ is $CH_3$, $R^9$ is $CH_3$ and $R^{10}$ is H.

Table 696. Compounds of formula I.8 wherein $R^1$ is Y-4D, $R^2$ is $CH_3$, $R^9$ is $CH_3$ and $R^{10}$ is $CH_3$.

Table 697. Compounds of formula I.8 wherein $R^1$ is Y-5A, $R^2$ is $CH_3$, $R^9$ is H and $R^{10}$ is H.

Table 698. Compounds of formula I.8 wherein $R^1$ is Y-5A, $R^2$ is $CH_3$, $R^9$ is $CH_3$ and $R^{10}$ is H.

Table 699. Compounds of formula I.8 wherein $R^1$ is Y-5A, $R^2$ is $CH_3$, $R^9$ is $CH_3$ and $R^{10}$ is $CH_3$.

Table 700. Compounds of formula I.8 wherein $R^1$ is Y-5B, $R^2$ is $CH_3$, $R^9$ is H and $R^{10}$ is H.

Table 701. Compounds of formula I.8 wherein $R^1$ is Y-5B, $R^2$ is $CH_3$, $R^9$ is $CH_3$ and $R^{10}$ is H.

Table 702. Compounds of formula I.8 wherein $R^1$ is Y-5B, $R^2$ is $CH_3$, $R^9$ is $CH_3$ and $R^{10}$ is $CH_3$.

Table 703. Compounds of formula I.8 wherein $R^1$ is Y-6A, $R^2$ is $CH_3$, $R^9$ is H and $R^{10}$ is H.

Table 704. Compounds of formula I.8 wherein $R^1$ is Y-6A, $R^2$ is $CH_3$, $R^9$ is $CH_3$ and $R^{10}$ is H.

Table 705. Compounds of formula I.8 wherein $R^1$ is Y-6A, $R^2$ is $CH_3$, $R^9$ is $CH_3$ and $R^{10}$ is $CH_3$.

Table 706. Compounds of formula I.8 wherein $R^1$ is Y-6B, $R^2$ is $CH_3$, $R^9$ is H and $R^{10}$ is H.

Table 707. Compounds of formula I.8 wherein $R^1$ is Y-6B, $R^2$ is $CH_3$, $R^9$ is $CH_3$ and $R^{10}$ is H.

Table 708. Compounds of formula I.8 wherein $R^1$ is Y-6B, $R^2$ is $CH_3$, $R^9$ is $CH_3$ and $R^{10}$ is $CH_3$.

Table 709. Compounds of formula I.8 wherein $R^1$ is Y-7A, $R^2$ is $CH_3$, $R^9$ is H and $R^{10}$ is H.

Table 710. Compounds of formula I.8 wherein $R^1$ is Y-7A, $R^2$ is $CH_3$, $R^9$ is $CH_3$ and $R^{10}$ is H.

Table 711. Compounds of formula I.8 wherein $R^1$ is Y-7A, $R^2$ is $CH_3$, $R^9$ is $CH_3$ and $R^{10}$ is $CH_3$.

Table 712. Compounds of formula I.8 wherein $R^1$ is Y-7B, $R^2$ is $CH_3$, $R^9$ is H and $R^{10}$ is H.

Table 713. Compounds of formula I.8 wherein $R^1$ is Y-7B, $R^2$ is $CH_3$, $R^9$ is $CH_3$ and $R^{10}$ is H.

Table 714. Compounds of formula I.8 wherein $R^1$ is Y-7B, $R^2$ is $CH_3$, $R^9$ is $CH_3$ and $R^{10}$ is $CH_3$.

Table 715. Compounds of formula I.8 wherein $R^1$ is Y-8A, $R^2$ is $CH_3$, $R^9$ is H and $R^{10}$ is H.

Table 716. Compounds of formula I.8 wherein $R^1$ is Y-8A, $R^2$ is $CH_3$, $R^9$ is $CH_3$ and $R^{10}$ is H.

Table 717. Compounds of formula I.8 wherein $R^1$ is Y-8A, $R^2$ is $CH_3$, $R^9$ is $CH_3$ and $R^{10}$ is $CH_3$.

Table 718. Compounds of formula I.8 wherein $R^1$ is Y-8B, $R^2$ is $CH_3$, $R^9$ is H and $R^{10}$ is H.

Table 719. Compounds of formula I.8 wherein $R^1$ is Y-8B, $R^2$ is $CH_3$, $R^9$ is $CH_3$ and $R^{10}$ is H.

Table 720. Compounds of formula I.8 wherein $R^1$ is Y-8B, $R^2$ is $CH_3$, $R^9$ is $CH_3$ and $R^{10}$ is $CH_3$.

Table 721. Compounds of formula I.8 wherein $R^1$ is Y-1A, $R^2$ is $C_2H_5$, $R^9$ is H and $R^{10}$ is H.

Table 722. Compounds of formula I.8 wherein $R^1$ is Y-1A, $R^2$ is $C_2H_5$, $R^9$ is $CH_3$ and $R^{10}$ is H.

Table 723. Compounds of formula I.8 wherein $R^1$ is Y-1A, $R^2$ is $C_2H_5$, $R^9$ is $CH_3$ and $R^{10}$ is $CH_3$.

Table 724. Compounds of formula I.8 wherein $R^1$ is Y-1B, $R^2$ is $C_2H_5$, $R^9$ is H and $R^{10}$ is H.

Table 725. Compounds of formula I.8 wherein $R^1$ is Y-1B, $R^2$ is $C_2H_5$, $R^9$ is $CH_3$ and $R^{10}$ is H.

Table 726. Compounds of formula I.8 wherein $R^1$ is Y-1B, $R^2$ is $C_2H_5$, $R^9$ is $CH_3$ and $R^{10}$ is $CH_3$.

Table 727. Compounds of formula I.8 wherein $R^1$ is Y-2A, $R^2$ is $C_2H_5$, $R^9$ is H and $R^{10}$ is H.

Table 728. Compounds of formula I.8 wherein $R^1$ is Y-2A, $R^2$ is $C_2H_5$, $R^9$ is $CH_3$ and $R^{10}$ is H.

Table 729. Compounds of formula I.8 wherein $R^1$ is Y-2A, $R^2$ is $C_2H_5$, $R^9$ is $CH_3$ and $R^{10}$ is $CH_3$.

Table 730. Compounds of formula I.8 wherein $R^1$ is Y-2B, $R^2$ is $C_2H_5$, $R^9$ is H and $R^{10}$ is H.

Table 731. Compounds of formula I.8 wherein $R^1$ is Y-2B, $R^2$ is $C_2H_5$, $R^9$ is $CH_3$ and $R^{10}$ is H.

Table 732. Compounds of formula I.8 wherein $R^1$ is Y-2B, $R^2$ is $C_2H_5$, $R^9$ is $CH_3$ and $R^{10}$ is $CH_3$.

Table 733. Compounds of formula I.8 wherein $R^1$ is Y-3A, $R^2$ is $C_2H_5$, $R^9$ is H and $R^{10}$ is H.

Table 734. Compounds of formula I.8 wherein $R^1$ is Y-3A, $R^2$ is $C_2H_5$, $R^9$ is $CH_3$ and $R^{10}$ is H.

Table 735. Compounds of formula I.8 wherein $R^1$ is Y-3A, $R^2$ is $C_2H_5$, $R^9$ is $CH_3$ and $R^{10}$ is $CH_3$.

Table 736. Compounds of formula I.8 wherein $R^1$ is Y-3B, $R^2$ is $C_2H_5$, $R^9$ is H and $R^{10}$ is H.

Table 737. Compounds of formula I.8 wherein $R^1$ is Y-3B, $R^2$ is $C_2H_5$, $R^9$ is $CH_3$ and $R^{10}$ is H.

Table 738. Compounds of formula I.8 wherein $R^1$ is Y-3B, $R^2$ is $C_2H_5$, $R^9$ is $CH_3$ and $R^{10}$ is $CH_3$.

Table 739. Compounds of formula I.8 wherein $R^1$ is Y-3C, $R^2$ is $C_2H_5$, $R^9$ is H and $R^{10}$ is H.

Table 740. Compounds of formula I.8 wherein $R^1$ is Y-3C, $R^2$ is $C_2H_5$, $R^9$ is $CH_3$ and $R^{10}$ is H.

Table 741. Compounds of formula I.8 wherein $R^1$ is Y-3C, $R^2$ is $C_2H_5$, $R^9$ is $CH_3$ and $R^{10}$ is $CH_3$.

Table 742. Compounds of formula I.8 wherein $R^1$ is Y-3D, $R^2$ is $C_2H_5$, $R^9$ is H and $R^{10}$ is H.

Table 743. Compounds of formula I.8 wherein $R^1$ is Y-3D, $R^2$ is $C_2H_5$, $R^9$ is $CH_3$ and $R^{10}$ is H.

Table 744. Compounds of formula I.8 wherein $R^1$ is Y-3D, $R^2$ is $C_2H_5$, $R^9$ is $CH_3$ and $R^{10}$ is $CH_3$.

Table 745. Compounds of formula I.8 wherein $R^1$ is Y-4A, $R^2$ is $C_2H_5$, $R^9$ is H and $R^{10}$ is H.

Table 746. Compounds of formula I.8 wherein $R^1$ is Y-4A, $R^2$ is $C_2H_5$, $R^9$ is $CH_3$ and $R^{10}$ is H.

Table 747. Compounds of formula I.8 wherein $R^1$ is Y-4A, $R^2$ is $C_2H_5$, $R^9$ is $CH_3$ and $R^{10}$ is $CH_3$.

Table 748. Compounds of formula I.8 wherein $R^1$ is Y-4B, $R^2$ is $C_2H_5$, $R^9$ is H and $R^{10}$ is H.

Table 749. Compounds of formula I.8 wherein $R^1$ is Y-4B, $R^2$ is $C_2H_5$, $R^9$ is $CH_3$ and $R^{10}$ is H.

Table 750. Compounds of formula I.8 wherein $R^1$ is Y-4B, $R^2$ is $C_2H_5$, $R^9$ is $CH_3$ and $R^{10}$ is $CH_3$.

Table 751. Compounds of formula I.8 wherein $R^1$ is Y-4C, $R^2$ is $C_2H_5$, $R^9$ is H and $R^{10}$ is H.

Table 752. Compounds of formula I.8 wherein $R^1$ is Y-4C, $R^2$ is $C_2H_5$, $R^9$ is $CH_3$ and $R^{10}$ is H.

Table 753. Compounds of formula I.8 wherein $R^1$ is Y-4C, $R^2$ is $C_2H_5$, $R^9$ is $CH_3$ and $R^{10}$ is $CH_3$.

Table 754. Compounds of formula I.8 wherein $R^1$ is Y-4D, $R^2$ is $C_2H_5$, $R^9$ is H and $R^{10}$ is H.

Table 755. Compounds of formula I.8 wherein $R^1$ is Y-4D, $R^2$ is $C_2H_5$, $R^9$ is $CH_3$ and $R^{10}$ is H.

Table 756. Compounds of formula I.8 wherein $R^1$ is Y-4D, $R^2$ is $C_2H_5$, $R^9$ is $CH_3$ and $R^{10}$ is $CH_3$.

Table 757. Compounds of formula I.8 wherein $R^1$ is Y-5A, $R^2$ is $C_2H_5$, $R^9$ is H and $R^{10}$ is H.

Table 758. Compounds of formula I.8 wherein $R^1$ is Y-5A, $R^2$ is $C_2H_5$, $R^9$ is $CH_3$ and $R^{10}$ is H.

Table 759. Compounds of formula I.8 wherein $R^1$ is Y-5A, $R^2$ is $C_2H_5$, $R^9$ is $CH_3$ and $R^{10}$ is $CH_3$.

Table 760. Compounds of formula I.8 wherein $R^1$ is Y-5B, $R^2$ is $C_2H_5$, $R^9$ is H and $R^{10}$ is H.

Table 761. Compounds of formula I.8 wherein $R^1$ is Y-5B, $R^2$ is $C_2H_5$, $R^9$ is $CH_3$ and $R^{10}$ is H.

Table 762. Compounds of formula I.8 wherein $R^1$ is Y-5B, $R^2$ is $C_2H_5$, $R^9$ is $CH_3$ and $R^{10}$ is $CH_3$.

Table 763. Compounds of formula I.8 wherein $R^1$ is Y-6A, $R^2$ is $C_2H_5$, $R^9$ is H and $R^{10}$ is H.

Table 764. Compounds of formula I.8 wherein $R^1$ is Y-6A, $R^2$ is $C_2H_5$, $R^9$ is $CH_3$ and $R^{10}$ is H.

Table 765. Compounds of formula I.8 wherein $R^1$ is Y-6A, $R^2$ is $C_2H_5$, $R^9$ is $CH_3$ and $R^{10}$ is $CH_3$.

Table 766. Compounds of formula I.8 wherein $R^1$ is Y-6B, $R^2$ is $C_2H_5$, $R^9$ is H and $R^{10}$ is H.

Table 767. Compounds of formula I.8 wherein $R^1$ is Y-6B, $R^2$ is $C_2H_5$, $R^9$ is $CH_3$ and $R^{10}$ is H.

Table 768. Compounds of formula I.8 wherein $R^1$ is Y-6B, $R^2$ is $C_2H_5$, $R^9$ is $CH_3$ and $R^{10}$ is $CH_3$.

Table 769. Compounds of formula I.8 wherein $R^1$ is Y-7A, $R^2$ is $C_2H_5$, $R^9$ is H and $R^{10}$ is H.

Table 770. Compounds of formula I.8 wherein $R^1$ is Y-7A, $R^2$ is $C_2H_5$, $R^9$ is $CH_3$ and $R^{10}$ is H.

Table 771. Compounds of formula I.8 wherein $R^1$ is Y-7A, $R^2$ is $C_2H_5$, $R^9$ is $CH_3$ and $R^{10}$ is $CH_3$.

Table 772. Compounds of formula I.8 wherein $R^1$ is Y-7B, $R^2$ is $C_2H_5$, $R^9$ is H and $R^{10}$ is H.

Table 773. Compounds of formula I.8 wherein $R^1$ is Y-7B, $R^2$ is $C_2H_5$, $R^9$ is $CH_3$ and $R^{10}$ is H.

Table 774. Compounds of formula I.8 wherein $R^1$ is Y-7B, $R^2$ is $C_2H_5$, $R^9$ is $CH_3$ and $R^{10}$ is $CH_3$.

Table 775. Compounds of formula I.8 wherein $R^1$ is Y-8A, $R^2$ is $C_2H_5$, $R^9$ is H and $R^{10}$ is H.

Table 776. Compounds of formula I.8 wherein $R^1$ is Y-8A, $R^2$ is $C_2H_5$, $R^9$ is $CH_3$ and $R^{10}$ is H.

Table 777. Compounds of formula I.8 wherein $R^1$ is Y-8A, $R^2$ is $C_2H_5$, $R^9$ is $CH_3$ and $R^{10}$ is $CH_3$.

Table 778. Compounds of formula I.8 wherein $R^1$ is Y-8B, $R^2$ is $C_2H_5$, $R^9$ is H and $R^{10}$ is H.

Table 779. Compounds of formula I.8 wherein $R^1$ is Y-8B, $R^2$ is $C_2H_5$, $R^9$ is $CH_3$ and $R^{10}$ is H.

Table 780. Compounds of formula I.8 wherein $R^1$ is Y-8B, $R^2$ is $C_2H_5$, $R^9$ is $CH_3$ and $R^{10}$ is $CH_3$.

Table 781. Compounds of formula I.8 wherein $R^1$ is Y-1A, $R^2$ is c-$C_3H_5$, $R^9$ is H and $R^{10}$ is H.

Table 782. Compounds of formula I.8 wherein $R^1$ is Y-1A, $R^2$ is c-$C_3H_5$, $R^9$ is $CH_3$ and $R^{10}$ is H.

Table 783. Compounds of formula I.8 wherein $R^1$ is Y-1A, $R^2$ is c-$C_3H_5$, $R^9$ is $CH_3$ and $R^{10}$ is $CH_3$.

Table 784. Compounds of formula I.8 wherein $R^1$ is Y-1B, $R^2$ is c-$C_3H_5$, $R^9$ is H and $R^{10}$ is H.

Table 785. Compounds of formula I.8 wherein $R^1$ is Y-1B, $R^2$ is c-$C_3H_5$, $R^9$ is $CH_3$, $R^{10}$ is H.

Table 786. Compounds of formula I.8 wherein $R^1$ is Y-1B, $R^2$ is c-$C_3H_5$, $R^9$ is $CH_3$ and $R^{10}$ is $CH_3$.

Table 787. Compounds of formula I.8 wherein $R^1$ is Y-2A, $R^2$ is c-$C_3H_5$, $R^9$ is H and $R^{10}$ is H.

Table 788. Compounds of formula I.8 wherein $R^1$ is Y-2A, $R^2$ is c-$C_3H_5$, $R^9$ is $CH_3$ and $R^{10}$ is H.

Table 789. Compounds of formula I.8 wherein $R^1$ is Y-2A, $R^2$ is c-$C_3H_5$, $R^9$ is $CH_3$ and $R^{10}$ is $CH_3$.

Table 790. Compounds of formula I.8 wherein $R^1$ is Y-2B, $R^2$ is c-$C_3H_5$, $R^9$ is H and $R^{10}$ is H.

Table 791. Compounds of formula I.8 wherein $R^1$ is Y-2B, $R^2$ is c-$C_3H_5$, $R^9$ is $CH_3$ and $R^{10}$ is H.

Table 792. Compounds of formula I.8 wherein $R^1$ is Y-2B, $R^2$ is c-$C_3H_5$, $R^9$ is $CH_3$ and $R^{10}$ is $CH_3$.

Table 793. Compounds of formula I.8 wherein $R^1$ is Y-3A, $R^2$ is c-$C_3H_5$, $R^9$ is H and $R^{10}$ is H.

Table 794. Compounds of formula I.8 wherein $R^1$ is Y-3A, $R^2$ is c-$C_3H_5$, $R^9$ is $CH_3$ and $R^{10}$ is H.

Table 795. Compounds of formula I.8 wherein $R^1$ is Y-3A, $R^2$ is c-$C_3H_5$, $R^9$ is $CH_3$ and $R^{10}$ is $CH_3$.

Table 796. Compounds of formula I.8 wherein $R^1$ is Y-3B, $R^2$ is c-$C_3H_5$, $R^9$ is H and $R^{10}$ is H.

Table 797. Compounds of formula I.8 wherein $R^1$ is Y-3B, $R^2$ is c-$C_3H_5$, $R^9$ is $CH_3$ and $R^{10}$ is H.

Table 798. Compounds of formula I.8 wherein $R^1$ is Y-3B, $R^2$ is c-$C_3H_5$, $R^9$ is $CH_3$ and $R^{10}$ is $CH_3$.

Table 799. Compounds of formula I.8 wherein $R^1$ is Y-3C, $R^2$ is c-$C_3H_5$, $R^9$ is H and $R^{10}$ is H.

Table 800. Compounds of formula I.8 wherein $R^1$ is Y-3C, $R^2$ is c-$C_3H_5$, $R^9$ is $CH_3$ and $R^{10}$ is H.

Table 801. Compounds of formula I.8 wherein $R^1$ is Y-3C, $R^2$ is c-$C_3H_5$, $R^9$ is $CH_3$ and $R^{10}$ is $CH_3$.

Table 802. Compounds of formula I.8 wherein $R^1$ is Y-3D, $R^2$ is c-$C_3H_5$, $R^9$ is H and $R^{10}$ is H.

Table 803. Compounds of formula I.8 wherein $R^1$ is Y-3D, $R^2$ is c-$C_3H_5$, $R^9$ is $CH_3$ and $R^{10}$ is H.

Table 804. Compounds of formula I.8 wherein $R^1$ is Y-3D, $R^2$ is c-$C_3H_5$, $R^9$ is $CH_3$ and $R^{10}$ is $CH_3$.

Table 805. Compounds of formula I.8 wherein $R^1$ is Y-4A, $R^2$ is c-$C_3H_5$, $R^9$ is H and $R^{10}$ is H.

Table 806. Compounds of formula I.8 wherein $R^1$ is Y-4A, $R^2$ is c-$C_3H_5$, $R^9$ is $CH_3$ and $R^{10}$ is H.

Table 807. Compounds of formula I.8 wherein $R^1$ is Y-4A, $R^2$ is c-$C_3H_5$, $R^9$ is $CH_3$ and $R^{10}$ is $CH_3$.

Table 808. Compounds of formula I.8 wherein $R^1$ is Y-4B, $R^2$ is c-$C_3H_5$, $R^9$ is H and $R^{10}$ is H.

Table 809. Compounds of formula I.8 wherein $R^1$ is Y-4B, $R^2$ is c-$C_3H_5$, $R^9$ is $CH_3$ and $R^{10}$ is H.

Table 810. Compounds of formula I.8 wherein $R^1$ is Y-4B, $R^2$ is c-$C_3H_5$, $R^9$ is $CH_3$ and $R^{10}$ is $CH_3$.

Table 811. Compounds of formula I.8 wherein $R^1$ is Y-40, $R^2$ is c-$C_3H_5$, $R^9$ is H and $R^{10}$ is H.

Table 812. Compounds of formula I.8 wherein $R^1$ is Y-40, $R^2$ is c-$C_3H_5$, $R^9$ is $CH_3$ and $R^{10}$ is H.

Table 813. Compounds of formula I.8 wherein $R^1$ is Y-40, $R^2$ is c-$C_3H_5$, $R^9$ is $CH_3$ and $R^{10}$ is $CH_3$.

Table 814. Compounds of formula I.8 wherein $R^1$ is Y-4D, $R^2$ is c-$C_3H_5$, $R^9$ is H and $R^{10}$ is H.

Table 815. Compounds of formula I.8 wherein $R^1$ is Y-4D, $R^2$ is c-$C_3H_5$, $R^9$ is $CH_3$ and $R^{10}$ is H.

Table 816. Compounds of formula I.8 wherein $R^1$ is Y-4D, $R^2$ is c-$C_3H_5$, $R^9$ is $CH_3$ and $R^{10}$ is $CH_3$.

Table 817. Compounds of formula I.8 wherein $R^1$ is Y-5A, $R^2$ is c-$C_3H_5$, $R^9$ is H and $R^{10}$ is H.

Table 818. Compounds of formula I.8 wherein $R^1$ is Y-5A, $R^2$ is c-$C_3H_5$, $R^9$ is $CH_3$ and $R^{10}$ is H.

Table 819. Compounds of formula I.8 wherein $R^1$ is Y-5A, $R^2$ is c-$C_3H_5$, $R^9$ is $CH_3$ and $R^{10}$ is $CH_3$.

Table 820. Compounds of formula I.8 wherein $R^1$ is Y-5B, $R^2$ is c-$C_3H_5$, $R^9$ is H and $R^{10}$ is H.

Table 821. Compounds of formula I.8 wherein $R^1$ is Y-5B, $R^2$ is c-$C_3H_5$, $R^9$ is $CH_3$ and $R^{10}$ is H.

Table 822. Compounds of formula I.8 wherein $R^1$ is Y-5B, $R^2$ is c-$C_3H_5$, $R^9$ is $CH_3$ and $R^{10}$ is $CH_3$.

Table 823. Compounds of formula I.8 wherein $R^1$ is Y-6A, $R^2$ is c-$C_3H_5$, $R^9$ is H and $R^{10}$ is H.

Table 824. Compounds of formula I.8 wherein $R^1$ is Y-6A, $R^2$ is c-$C_3H_5$, $R^9$ is $CH_3$ and $R^{10}$ is H.

Table 825. Compounds of formula I.8 wherein $R^1$ is Y-6A, $R^2$ is c-$C_3H_5$, $R^9$ is $CH_3$ and $R^{10}$ is $CH_3$.

Table 826. Compounds of formula I.8 wherein $R^1$ is Y-6B, $R^2$ is c-$C_3H_5$, $R^9$ is H and $R^{10}$ is H.

Table 827. Compounds of formula I.8 wherein $R^1$ is Y-6B, $R^2$ is c-$C_3H_5$, $R^9$ is $CH_3$ and $R^{10}$ is H.

Table 828. Compounds of formula I.8 wherein $R^1$ is Y-6B, $R^2$ is c-$C_3H_5$, $R^9$ is $CH_3$ and $R^{10}$ is $CH_3$.

Table 829. Compounds of formula I.8 wherein $R^1$ is Y-7A, $R^2$ is c-$C_3H_5$, $R^9$ is H and $R^{10}$ is H.

Table 830. Compounds of formula I.8 wherein $R^1$ is Y-7A, $R^2$ is c-$C_3H_5$, $R^9$ is $CH_3$ and $R^{10}$ is H.

Table 831. Compounds of formula I.8 wherein $R^1$ is Y-7A, $R^2$ is c-$C_3H_5$, $R^9$ is $CH_3$ and $R^{10}$ is $CH_3$.

Table 832. Compounds of formula I.8 wherein $R^1$ is Y-7B, $R^2$ is c-$C_3H_5$, $R^9$ is H and $R^{10}$ is H.

Table 833. Compounds of formula I.8 wherein $R^1$ is Y-7B, $R^2$ is c-$C_3H_5$, $R^9$ is $CH_3$ and $R^{10}$ is H.

Table 834. Compounds of formula I.8 wherein $R^1$ is Y-7B, $R^2$ is c-$C_3H_5$, $R^9$ is $CH_3$ and $R^{10}$ is $CH_3$.

Table 835. Compounds of formula I.8 wherein $R^1$ is Y-8A, $R^2$ is c-$C_3H_5$, $R^9$ is H and $R^{10}$ is H.

Table 836. Compounds of formula I.8 wherein $R^1$ is Y-8A, $R^2$ is c-$C_3H_5$, $R^9$ is $CH_3$ and $R^{10}$ is H.

Table 837. Compounds of formula I.8 wherein $R^1$ is Y-8A, $R^2$ is c-$C_3H_5$, $R^9$ is $CH_3$ and $R^{10}$ is $CH_3$.

Table 838. Compounds of formula I.8 wherein $R^1$ is Y-8B, $R^2$ is c-$C_3H_5$, $R^9$ is H and $R^{10}$ is H.

Table 839. Compounds of formula I.8 wherein $R^1$ is Y-8B, $R^2$ is c-$C_3H_5$, $R^9$ is $CH_3$ and $R^{10}$ is H.

Table 840. Compounds of formula I.8 wherein $R^1$ is Y-8B, $R^2$ is c-$C_3H_5$, $R^9$ is $CH_3$ and $R^{10}$ is $CH_3$.

Table 841. Compounds of formula I.9 wherein $R^1$ is Y-1A, $R^2$ is H, $R^9$ is H and $R^{10}$ is H.

Table 842. Compounds of formula I.9 wherein $R^1$ is Y-1A, $R^2$ is H, $R^9$ is $CH_3$ and, $R^{10}$ is H.

Table 843. Compounds of formula I.9 wherein $R^1$ is Y-1A, $R^2$ is H, $R^9$ is $CH_3$ and $R^{10}$ is $CH_3$.

Table 844. Compounds of formula I.9 wherein $R^1$ is Y-1B, $R^2$ is H, $R^9$ is H and $R^{10}$ is H.

Table 845. Compounds of formula I.9 wherein $R^1$ is Y-1B, $R^2$ is H, $R^9$ is $CH_3$ and $R^{10}$ is H.

Table 846. Compounds of formula I.9 wherein $R^1$ is Y-1B, $R^2$ is H, $R^9$ is $CH_3$ and $R^{10}$ is $CH_3$.

Table 847. Compounds of formula I.9 wherein $R^1$ is Y-2A, $R^2$ is H, $R^9$ is H and $R^{10}$ is H.

Table 848. Compounds of formula I.9 wherein $R^1$ is Y-2A, $R^2$ is H, $R^9$ is $CH_3$ and $R^{10}$ is H.

Table 849. Compounds of formula I.9 wherein $R^1$ is Y-2A, $R^2$ is H, $R^9$ is $CH_3$ and $R^{10}$ is $CH_3$.

Table 850. Compounds of formula I.9 wherein $R^1$ is Y-2B, $R^2$ is H, $R^9$ is H and $R^{10}$ is H.

Table 851. Compounds of formula I.9 wherein $R^1$ is Y-2B, $R^2$ is H, $R^9$ is $CH_3$ and $R^{10}$ is H.

Table 852. Compounds of formula I.9 wherein $R^1$ is Y-2B, $R^2$ is H, $R^9$ is $CH_3$ and $R^{10}$ is $CH_3$.

Table 853. Compounds of formula I.9 wherein $R^1$ is Y-3A, $R^2$ is H, $R^9$ is H and $R^{10}$ is H.

Table 854. Compounds of formula I.9 wherein $R^1$ is Y-3A, $R^2$ is H, $R^9$ is $CH_3$ and $R^{10}$ is H.

Table 855. Compounds of formula I.9 wherein $R^1$ is Y-3A, $R^2$ is H, $R^9$ is $CH_3$ and $R^{10}$ is $CH_3$.

Table 856. Compounds of formula I.9 wherein $R^1$ is Y-3B, $R^2$ is H, $R^9$ is H and $R^{10}$ is H.

Table 857. Compounds of formula I.9 wherein $R^1$ is Y-3B, $R^2$ is H, $R^9$ is $CH_3$ and $R^{10}$ is H.

Table 858. Compounds of formula I.9 wherein $R^1$ is Y-3B, $R^2$ is H, $R^9$ is $CH_3$ and $R^{10}$ is $CH_3$.

Table 859. Compounds of formula I.9 wherein $R^1$ is Y-3C, $R^2$ is H, $R^9$ is H and $R^{10}$ is H.

Table 860. Compounds of formula I.9 wherein $R^1$ is Y-3C, $R^2$ is H, $R^9$ is $CH_3$ and $R^{10}$ is H.

Table 861. Compounds of formula I.9 wherein $R^1$ is Y-3C, $R^2$ is H, $R^9$ is $CH_3$ and $R^{10}$ is $CH_3$.

Table 862. Compounds of formula I.9 wherein $R^1$ is Y-3D, $R^2$ is H, $R^9$ is H and $R^{10}$ is H.

Table 863. Compounds of formula I.9 wherein $R^1$ is Y-3D, $R^2$ is H, $R^9$ is $CH_3$ and $R^{10}$ is H.

Table 864. Compounds of formula I.9 wherein $R^1$ is Y-3D, $R^2$ is H, $R^9$ is $CH_3$ and $R^{10}$ is $CH_3$.

Table 865. Compounds of formula I.9 wherein $R^1$ is Y-4A, $R^2$ is H, $R^9$ is H and $R^{10}$ is H.

Table 866. Compounds of formula I.9 wherein $R^1$ is Y-4A, $R^2$ is H, $R^9$ is $CH_3$ and $R^{10}$ is H.

Table 867. Compounds of formula I.9 wherein $R^1$ is Y-4A, $R^2$ is H, $R^9$ is $CH_3$ and $R^{10}$ is $CH_3$.

Table 868. Compounds of formula I.9 wherein $R^1$ is Y-4B, $R^2$ is H, $R^9$ is H and $R^{10}$ is H.

Table 869. Compounds of formula I.9 wherein $R^1$ is Y-4B, $R^2$ is H, $R^9$ is $CH_3$ and $R^{10}$ is H.

Table 870. Compounds of formula I.9 wherein $R^1$ is Y-4B, $R^2$ is H, $R^9$ is $CH_3$ and $R^{10}$ is $CH_3$.

Table 871. Compounds of formula I.9 wherein $R^1$ is Y-4C, $R^2$ is H, $R^9$ is H and $R^{10}$ is H.

Table 872. Compounds of formula I.9 wherein $R^1$ is Y-4C, $R^2$ is H, $R^9$ is $CH_3$ and $R^{10}$ is H.

Table 873. Compounds of formula I.9 wherein $R^1$ is Y-4C, $R^2$ is H, $R^9$ is $CH_3$ and $R^{10}$ is $CH_3$.

Table 874. Compounds of formula I.9 wherein $R^1$ is Y-4D, $R^2$ is H, $R^9$ is H and $R^{10}$ is H.

Table 875. Compounds of formula I.9 wherein $R^1$ is Y-4D, $R^2$ is H, $R^9$ is $CH_3$ and $R^{10}$ is H.

Table 876. Compounds of formula I.9 wherein $R^1$ is Y-4D, $R^2$ is H, $R^9$ is $CH_3$ and $R^{10}$ is $CH_3$.

Table 877. Compounds of formula I.9 wherein $R^1$ is Y-5A, $R^2$ is H, $R^9$ is H and $R^{10}$ is H.

Table 878. Compounds of formula I.9 wherein $R^1$ is Y-5A, $R^2$ is H, $R^9$ is $CH_3$ and $R^{10}$ is H.

Table 879. Compounds of formula I.9 wherein $R^1$ is Y-5A, $R^2$ is H, $R^9$ is $CH_3$ and $R^{10}$ is $CH_3$.

Table 880. Compounds of formula I.9 wherein $R^1$ is Y-5B, $R^2$ is H, $R^9$ is H and $R^{10}$ is H.

Table 881. Compounds of formula I.9 wherein $R^1$ is Y-5B, $R^2$ is H, $R^9$ is $CH_3$ and $R^{10}$ is H.

Table 882. Compounds of formula I.9 wherein $R^1$ is Y-5B, $R^2$ is H, $R^9$ is $CH_3$ and $R^{10}$ is $CH_3$.

Table 883. Compounds of formula I.9 wherein $R^1$ is Y-6A, $R^2$ is H, $R^9$ is H and $R^{10}$ is H.

Table 884. Compounds of formula I.9 wherein $R^1$ is Y-6A, $R^2$ is H, $R^9$ is $CH_3$ and $R^{10}$ is H.

Table 885. Compounds of formula I.9 wherein $R^1$ is Y-6A, $R^2$ is H, $R^9$ is $CH_3$ and $R^{10}$ is $CH_3$.

Table 886. Compounds of formula I.9 wherein $R^1$ is Y-6B, $R^2$ is H, $R^9$ is H and $R^{10}$ is H.

Table 887. Compounds of formula I.9 wherein $R^1$ is Y-6B, $R^2$ is H, $R^9$ is $CH_3$ and $R^{10}$ is H.

Table 888. Compounds of formula I.9 wherein $R^1$ is Y-6B, $R^2$ is H, $R^9$ is $CH_3$ and $R^{10}$ is $CH_3$.

Table 889. Compounds of formula I.9 wherein $R^1$ is Y-7A, $R^2$ is H, $R^9$ is H and $R^{10}$ is H.

Table 890. Compounds of formula I.9 wherein $R^1$ is Y-7A, $R^2$ is H, $R^9$ is $CH_3$ and $R^{10}$ is H.

Table 891. Compounds of formula I.9 wherein $R^1$ is Y-7A, $R^2$ is H, $R^9$ is $CH_3$ and $R^{10}$ is $CH_3$.

Table 892. Compounds of formula I.9 wherein $R^1$ is Y-7B, $R^2$ is H, $R^9$ is H and $R^{10}$ is H.

Table 893. Compounds of formula I.9 wherein $R^1$ is Y-7B, $R^2$ is H, $R^9$ is $CH_3$ and $R^{10}$ is H.

Table 894. Compounds of formula I.9 wherein $R^1$ is Y-7B, $R^2$ is H, $R^9$ is $CH_3$ and $R^{10}$ is $CH_3$.

Table 895. Compounds of formula I.9 wherein $R^1$ is Y-8A, $R^2$ is H, $R^9$ is H and $R^{10}$ is H.

Table 896. Compounds of formula I.9 wherein $R^1$ is Y-8A, $R^2$ is H, $R^9$ is $CH_3$ and $R^{10}$ is H.

Table 897. Compounds of formula I.9 wherein $R^1$ is Y-8A, $R^2$ is H, $R^9$ is $CH_3$ and $R^{10}$ is $CH_3$.

Table 898. Compounds of formula I.9 wherein $R^1$ is Y-8B, $R^2$ is H, $R^9$ is H and $R^{10}$ is H.

Table 899. Compounds of formula I.9 wherein $R^1$ is Y-8B, $R^2$ is H, $R^9$ is $CH_3$ and $R^{10}$ is H.

Table 900. Compounds of formula I.9 wherein $R^1$ is Y-8B, $R^2$ is H, $R^9$ is $CH_3$ and $R^{10}$ is $CH_3$.

Table 901. Compounds of formula I.9 wherein $R^1$ is Y-1A, $R^2$ is $CH_3$, $R^9$ is H and $R^{10}$ is H.

Table 902. Compounds of formula I.9 wherein $R^1$ is Y-1A, $R^2$ is $CH_3$, $R^9$ is $CH_3$ and $R^{10}$ is H.

Table 903. Compounds of formula I.9 wherein $R^1$ is Y-1A, $R^2$ is $CH_3$, $R^9$ is $CH_3$ and $R^{10}$ is $CH_3$.

Table 904. Compounds of formula I.9 wherein $R^1$ is Y-1B, $R^2$ is $CH_3$, $R^9$ is H and $R^{10}$ is H.

Table 905. Compounds of formula I.9 wherein $R^1$ is Y-1B, $R^2$ is $CH_3$, $R^9$ is $CH_3$ and $R^{10}$ is H.

Table 906. Compounds of formula I.9 wherein $R^1$ is Y-1B, $R^2$ is $CH_3$, $R^9$ is $CH_3$ and $R^{10}$ is $CH_3$.

Table 907. Compounds of formula I.9 wherein $R^1$ is Y-2A, $R^2$ is $CH_3$, $R^9$ is H and $R^{10}$ is H.

Table 908. Compounds of formula I.9 wherein $R^1$ is Y-2A, $R^2$ is $CH_3$, $R^9$ is $CH_3$ and $R^{10}$ is H.

Table 909. Compounds of formula I.9 wherein $R^1$ is Y-2A, $R^2$ is $CH_3$, $R^9$ is $CH_3$ and $R^{10}$ is $CH_3$.

Table 910. Compounds of formula I.9 wherein $R^1$ is Y-2B, $R^2$ is $CH_3$, $R^9$ is H and $R^{10}$ is H.

Table 911. Compounds of formula I.9 wherein $R^1$ is Y-2B, $R^2$ is $CH_3$, $R^9$ is $CH_3$ and $R^{10}$ is H.

Table 912. Compounds of formula I.9 wherein $R^1$ is Y-2B, $R^2$ is $CH_3$, $R^9$ is $CH_3$ and $R^{10}$ is $CH_3$.

Table 913. Compounds of formula I.9 wherein $R^1$ is Y-3A, $R^2$ is $CH_3$, $R^9$ is H and $R^{10}$ is H.

Table 914. Compounds of formula I.9 wherein $R^1$ is Y-3A, $R^2$ is $CH_3$, $R^9$ is $CH_3$ and $R^{10}$ is H.

Table 915. Compounds of formula I.9 wherein $R^1$ is Y-3A, $R^2$ is $CH_3$, $R^9$ is $CH_3$ and $R^{10}$ is $CH_3$.

Table 916. Compounds of formula I.9 wherein $R^1$ is Y-3B, $R^2$ is $CH_3$, $R^9$ is H and $R^{10}$ is H.

Table 917. Compounds of formula I.9 wherein $R^1$ is Y-3B, $R^2$ is $CH_3$, $R^9$ is $CH_3$ and $R^{10}$ is H.

Table 918. Compounds of formula I.9 wherein $R^1$ is Y-3B, $R^2$ is $CH_3$, $R^9$ is $CH_3$ and $R^{10}$ is $CH_3$.

Table 919. Compounds of formula I.9 wherein $R^1$ is Y-3C, $R^2$ is $CH_3$, $R^9$ is H and $R^{10}$ is H.

Table 920. Compounds of formula I.9 wherein $R^1$ is Y-3C, $R^2$ is $CH_3$, $R^9$ is $CH_3$ and $R^{10}$ is H.

Table 921. Compounds of formula I.9 wherein $R^1$ is Y-3C, $R^2$ is $CH_3$, $R^9$ is $CH_3$ and $R^{10}$ is $CH_3$.

Table 922. Compounds of formula I.9 wherein $R^1$ is Y-3D, $R^2$ is $CH_3$, $R^9$ is H and $R^{10}$ is H.

Table 923. Compounds of formula I.9 wherein $R^1$ is Y-3D, $R^2$ is $CH_3$, $R^9$ is $CH_3$ and $R^{10}$ is H.

Table 924. Compounds of formula I.9 wherein $R^1$ is Y-3D, $R^2$ is $CH_3$, $R^9$ is $CH_3$ and $R^{10}$ is $CH_3$.

Table 925. Compounds of formula I.9 wherein $R^1$ is Y-4A, $R^2$ is $CH_3$, $R^9$ is H and $R^{10}$ is H.

Table 926. Compounds of formula I.9 wherein $R^1$ is Y-4A, $R^2$ is $CH_3$, $R^9$ is $CH_3$ and $R^{10}$ is H.

Table 927. Compounds of formula I.9 wherein $R^1$ is Y-4A, $R^2$ is $CH_3$, $R^9$ is $CH_3$ and $R^{10}$ is $CH_3$.

Table 928. Compounds of formula I.9 wherein $R^1$ is Y-4B, $R^2$ is $CH_3$, $R^9$ is H and $R^{10}$ is H.

Table 929. Compounds of formula I.9 wherein $R^1$ is Y-4B, $R^2$ is $CH_3$, $R^9$ is $CH_3$ and $R^{10}$ is H.

Table 930. Compounds of formula I.9 wherein $R^1$ is Y-4B, $R^2$ is $CH_3$, $R^9$ is $CH_3$ and $R^{10}$ is $CH_3$.

Table 931. Compounds of formula I.9 wherein $R^1$ is Y-4C, $R^2$ is $CH_3$, $R^9$ is H and $R^{10}$ is H.

Table 932. Compounds of formula I.9 wherein $R^1$ is Y-4C, $R^2$ is $CH_3$, $R^9$ is $CH_3$ and $R^{10}$ is H.

Table 933. Compounds of formula I.9 wherein $R^1$ is Y-4C, $R^2$ is $CH_3$, $R^9$ is $CH_3$ and $R^{10}$ is $CH_3$.

Table 934. Compounds of formula I.9 wherein $R^1$ is Y-4D, $R^2$ is $CH_3$, $R^9$ is H and $R^{10}$ is H.

Table 935. Compounds of formula I.9 wherein $R^1$ is Y-4D, $R^2$ is $CH_3$, $R^9$ is $CH_3$ and $R^{10}$ is H.

Table 936. Compounds of formula I.9 wherein $R^1$ is Y-4D, $R^2$ is $CH_3$, $R^9$ is $CH_3$ and $R^{10}$ is $CH_3$.

Table 937. Compounds of formula I.9 wherein $R^1$ is Y-5A, $R^2$ is $CH_3$, $R^9$ is H and $R^{10}$ is H.

Table 938. Compounds of formula I.9 wherein $R^1$ is Y-5A, $R^2$ is $CH_3$, $R^9$ is $CH_3$ and $R^{10}$ is H.

Table 939. Compounds of formula I.9 wherein $R^1$ is Y-5A, $R^2$ is $CH_3$, $R^9$ is $CH_3$ and $R^{10}$ is $CH_3$.

Table 940. Compounds of formula I.9 wherein $R^1$ is Y-5B, $R^2$ is $CH_3$, $R^9$ is H and $R^{10}$ is H.

Table 941. Compounds of formula I.9 wherein $R^1$ is Y-5B, $R^2$ is $CH_3$, $R^9$ is $CH_3$ and $R^{10}$ is H.

Table 942. Compounds of formula I.9 wherein $R^1$ is Y-5B, $R^2$ is $CH_3$, $R^9$ is $CH_3$ and $R^{10}$ is $CH_3$.

Table 943. Compounds of formula I.9 wherein $R^1$ is Y-6A, $R^2$ is $CH_3$, $R^9$ is H and $R^{10}$ is H.

Table 944. Compounds of formula I.9 wherein $R^1$ is Y-6A, $R^2$ is $CH_3$, $R^9$ is $CH_3$ and $R^{10}$ is H.

Table 945. Compounds of formula I.9 wherein $R^1$ is Y-6A, $R^2$ is $CH_3$, $R^9$ is $CH_3$ and $R^{10}$ is $CH_3$.

Table 946. Compounds of formula I.9 wherein $R^1$ is Y-6B, $R^2$ is $CH_3$, $R^9$ is H and $R^{10}$ is H.

Table 947. Compounds of formula I.9 wherein $R^1$ is Y-6B, $R^2$ is $CH_3$, $R^9$ is $CH_3$ and $R^{10}$ is H.

Table 948. Compounds of formula I.9 wherein $R^1$ is Y-6B, $R^2$ is $CH_3$, $R^9$ is $CH_3$ and $R^{10}$ is $CH_3$.

Table 949. Compounds of formula I.9 wherein $R^1$ is Y-7A, $R^2$ is $CH_3$, $R^9$ is H and $R^{10}$ is H.

Table 950. Compounds of formula I.9 wherein $R^1$ is Y-7A, $R^2$ is $CH_3$, $R^9$ is $CH_3$ and $R^{10}$ is H.

Table 951. Compounds of formula I.9 wherein $R^1$ is Y-7A, $R^2$ is $CH_3$, $R^9$ is $CH_3$ and $R^{10}$ is $CH_3$.

Table 952. Compounds of formula I.9 wherein $R^1$ is Y-7B, $R^2$ is $CH_3$, $R^9$ is H and $R^{10}$ is H.

Table 953. Compounds of formula I.9 wherein $R^1$ is Y-7B, $R^2$ is $CH_3$, $R^9$ is $CH_3$ and $R^{10}$ is H.

Table 954. Compounds of formula I.9 wherein $R^1$ is Y-7B, $R^2$ is $CH_3$, $R^9$ is $CH_3$ and $R^{10}$ is $CH_3$.

Table 955. Compounds of formula I.9 wherein $R^1$ is Y-8A, $R^2$ is $CH_3$, $R^9$ is H and $R^{10}$ is H.

Table 956. Compounds of formula I.9 wherein $R^1$ is Y-8A, $R^2$ is $CH_3$, $R^9$ is $CH_3$ and $R^{10}$ is H.

Table 957. Compounds of formula I.9 wherein $R^1$ is Y-8A, $R^2$ is $CH_3$, $R^9$ is $CH_3$ and $R^{10}$ is $CH_3$.

Table 958. Compounds of formula I.9 wherein $R^1$ is Y-8B, $R^2$ is $CH_3$, $R^9$ is H and $R^{10}$ is H.

Table 959. Compounds of formula I.9 wherein $R^1$ is Y-8B, $R^2$ is $CH_3$, $R^9$ is $CH_3$ and $R^{10}$ is H.

Table 960. Compounds of formula I.9 wherein $R^1$ is Y-8B, $R^2$ is $CH_3$, $R^9$ is $CH_3$ and $R^{10}$ is $CH_3$.

Table 961. Compounds of formula I.9 wherein $R^1$ is Y-1A, $R^2$ is $C_2H_5$, $R^9$ is H and $R^{10}$ is H.

Table 962. Compounds of formula I.9 wherein $R^1$ is Y-1A, $R^2$ is $C_2H_5$, $R^9$ is $CH_3$ and $R^{10}$ is H.

Table 963. Compounds of formula I.9 wherein $R^1$ is Y-1A, $R^2$ is $C_2H_5$, $R^9$ is $CH_3$ and $R^{10}$ is $CH_3$.

Table 964. Compounds of formula I.9 wherein $R^1$ is Y-1B, $R^2$ is $C_2H_5$, $R^9$ is H and $R^{10}$ is H.

Table 965. Compounds of formula I.9 wherein $R^1$ is Y-1B, $R^2$ is $C_2H_5$, $R^9$ is $CH_3$ and $R^{10}$ is H.

Table 966. Compounds of formula I.9 wherein $R^1$ is Y-1B, $R^2$ is $C_2H_5$, $R^9$ is $CH_3$ and $R^{10}$ is $CH_3$.

Table 967. Compounds of formula I.9 wherein $R^1$ is Y-2A, $R^2$ is $C_2H_5$, $R^9$ is H and $R^{10}$ is H.

Table 968. Compounds of formula I.9 wherein $R^1$ is Y-2A, $R^2$ is $C_2H_5$, $R^9$ is $CH_3$ and $R^{10}$ is H.

Table 969. Compounds of formula I.9 wherein $R^1$ is Y-2A, $R^2$ is $C_2H_5$, $R^9$ is $CH_3$ and $R^{10}$ is $CH_3$.

Table 970. Compounds of formula I.9 wherein $R^1$ is Y-2B, $R^2$ is $C_2H_5$, $R^9$ is H and $R^{10}$ is H.

Table 971. Compounds of formula I.9 wherein $R^1$ is Y-2B, $R^2$ is $C_2H_5$, $R^9$ is $CH_3$ and $R^{10}$ is H.

Table 972. Compounds of formula I.9 wherein $R^1$ is Y-2B, $R^2$ is $C_2H_5$, $R^9$ is $CH_3$ and $R^{10}$ is $CH_3$.

Table 973. Compounds of formula I.9 wherein $R^1$ is Y-3A, $R^2$ is $C_2H_5$, $R^9$ is H and $R^{10}$ is H.

Table 974. Compounds of formula I.9 wherein $R^1$ is Y-3A, $R^2$ is $C_2H_5$, $R^9$ is $CH_3$ and $R^{10}$ is H.

Table 975. Compounds of formula I.9 wherein $R^1$ is Y-3A, $R^2$ is $C_2H_5$, $R^9$ is $CH_3$ and $R^{10}$ is $CH_3$.

Table 976. Compounds of formula I.9 wherein $R^1$ is Y-3B, $R^2$ is $C_2H_5$, $R^9$ is H and $R^{10}$ is H.

Table 977. Compounds of formula I.9 wherein $R^1$ is Y-3B, $R^2$ is $C_2H_5$, $R^9$ is $CH_3$ and $R^{10}$ is H.

Table 978. Compounds of formula I.9 wherein $R^1$ is Y-3B, $R^2$ is $C_2H_5$, $R^9$ is $CH_3$ and $R^{10}$ is $CH_3$.

Table 979. Compounds of formula I.9 wherein $R^1$ is Y-3C, $R^2$ is $C_2H_5$, $R^9$ is H and $R^{10}$ is H.

Table 980. Compounds of formula I.9 wherein $R^1$ is Y-3C, $R^2$ is $C_2H_5$, $R^9$ is $CH_3$ and $R^{10}$ is H.

Table 981. Compounds of formula I.9 wherein $R^1$ is Y-3C, $R^2$ is $C_2H_5$, $R^9$ is $CH_3$ and $R^{10}$ is $CH_3$.

Table 982. Compounds of formula I.9 wherein $R^1$ is Y-3D, $R^2$ is $C_2H_5$, $R^9$ is H and $R^{10}$ is H.

Table 983. Compounds of formula I.9 wherein $R^1$ is Y-3D, $R^2$ is $C_2H_5$, $R^9$ is $CH_3$ and $R^{10}$ is H.

Table 984. Compounds of formula I.9 wherein $R^1$ is Y-3D, $R^2$ is $C_2H_5$, $R^9$ is $CH_3$ and $R^{10}$ is $CH_3$.

Table 985. Compounds of formula I.9 wherein $R^1$ is Y-4A, $R^2$ is $C_2H_5$, $R^9$ is H and $R^{10}$ is H.

Table 986. Compounds of formula I.9 wherein $R^1$ is Y-4A, $R^2$ is $C_2H_5$, $R^9$ is $CH_3$ and $R^{10}$ is H.

Table 987. Compounds of formula I.9 wherein $R^1$ is Y-4A, $R^2$ is $C_2H_5$, $R^9$ is $CH_3$ and $R^{10}$ is $CH_3$.

Table 988. Compounds of formula I.9 wherein $R^1$ is Y-4B, $R^2$ is $C_2H_5$, $R^9$ is H and $R^{10}$ is H.

Table 989. Compounds of formula I.9 wherein $R^1$ is Y-4B, $R^2$ is $C_2H_5$, $R^9$ is $CH_3$ and $R^{10}$ is H.

Table 990. Compounds of formula I.9 wherein $R^1$ is Y-4B, $R^2$ is $C_2H_5$, $R^9$ is $CH_3$ and $R^{10}$ is $CH_3$.

Table 991. Compounds of formula I.9 wherein $R^1$ is Y-4C, $R^2$ is $C_2H_5$, $R^9$ is H and $R^{10}$ is H.

Table 992. Compounds of formula I.9 wherein $R^1$ is Y-4C, $R^2$ is $C_2H_5$, $R^9$ is $CH_3$ and $R^{10}$ is H.

Table 993. Compounds of formula I.9 wherein $R^1$ is Y-4C, $R^2$ is $C_2H_5$, $R^9$ is $CH_3$ and $R^{10}$ is $CH_3$.

Table 994. Compounds of formula I.9 wherein $R^1$ is Y-4D, $R^2$ is $C_2H_5$, $R^9$ is H and $R^{10}$ is H.

Table 995. Compounds of formula I.9 wherein $R^1$ is Y-4D, $R^2$ is $C_2H_5$, $R^9$ is $CH_3$ and $R^{10}$ is H.

Table 996. Compounds of formula I.9 wherein $R^1$ is Y-4D, $R^2$ is $C_2H_5$, $R^9$ is $CH_3$ and $R^{10}$ is $CH_3$.

Table 997. Compounds of formula I.9 wherein $R^1$ is Y-5A, $R^2$ is $C_2H_5$, $R^9$ is H and $R^{10}$ is H.

Table 998. Compounds of formula I.9 wherein $R^1$ is Y-5A, $R^2$ is $C_2H_5$, $R^9$ is $CH_3$ and $R^{10}$ is H.

Table 999. Compounds of formula I.9 wherein $R^1$ is Y-5A, $R^2$ is $C_2H_5$, $R^9$ is $CH_3$ and $R^{10}$ is $CH_3$.

Table 1000. Compounds of formula I.9 wherein $R^1$ is Y-5B, $R^2$ is $C_2H_5$, $R^9$ is H and $R^{10}$ is H.

Table 1001. Compounds of formula I.9 wherein $R^1$ is Y-5B, $R^2$ is $C_2H_5$, $R^9$ is $CH_3$ and $R^{10}$ is H.

Table 1002. Compounds of formula I.9 wherein $R^1$ is Y-5B, $R^2$ is $C_2H_5$, $R^9$ is $CH_3$ and $R^{10}$ is $CH_3$.

Table 1003. Compounds of formula I.9 wherein $R^1$ is Y-6A, $R^2$ is $C_2H_5$, $R^9$ is H and $R^{10}$ is H.

Table 1004. Compounds of formula I.9 wherein $R^1$ is Y-6A, $R^2$ is $C_2H_5$, $R^9$ is $CH_3$ and $R^{10}$ is H.

Table 1005. Compounds of formula I.9 wherein $R^1$ is Y-6A, $R^2$ is $C_2H_5$, $R^9$ is $CH_3$ and $R^{10}$ is $CH_3$.

Table 1006. Compounds of formula I.9 wherein $R^1$ is Y-6B, $R^2$ is $C_2H_5$, $R^9$ is H and $R^{10}$ is H.

Table 1007. Compounds of formula I.9 wherein $R^1$ is Y-6B, $R^2$ is $C_2H_5$, $R^9$ is $CH_3$ and $R^{10}$ is H.

Table 1008. Compounds of formula I.9 wherein $R^1$ is Y-6B, $R^2$ is $C_2H_5$, $R^9$ is $CH_3$ and $R^{10}$ is $CH_3$.

Table 1009. Compounds of formula I.9 wherein $R^1$ is Y-7A, $R^2$ is $C_2H_5$, $R^9$ is H and $R^{10}$ is H.

Table 1010. Compounds of formula I.9 wherein $R^1$ is Y-7A, $R^2$ is $C_2H_5$, $R^9$ is $CH_3$ and $R^{10}$ is H.

Table 1011. Compounds of formula I.9 wherein $R^1$ is Y-7A, $R^2$ is $C_2H_5$, $R^9$ is $CH_3$ and $R^{10}$ is $CH_3$.

Table 1012. Compounds of formula I.9 wherein $R^1$ is Y-7B, $R^2$ is $C_2H_5$, $R^9$ is H and $R^{10}$ is H.

Table 1013. Compounds of formula I.9 wherein $R^1$ is Y-7B, $R^2$ is $C_2H_5$, $R^9$ is $CH_3$ and $R^{10}$ is H.

Table 1014. Compounds of formula I.9 wherein $R^1$ is Y-7B, $R^2$ is $C_2H_5$, $R^9$ is $CH_3$ and $R^{10}$ is $CH_3$.

Table 1015. Compounds of formula I.9 wherein $R^1$ is Y-8A, $R^2$ is $C_2H_5$, $R^9$ is H and $R^{10}$ is H.

Table 1016. Compounds of formula I.9 wherein $R^1$ is Y-8A, $R^2$ is $C_2H_5$, $R^9$ is $CH_3$ and $R^{10}$ is H.

Table 1017. Compounds of formula I.9 wherein $R^1$ is Y-8A, $R^2$ is $C_2H_5$, $R^9$ is $CH_3$ and $R^{10}$ is $CH_3$.

Table 1018. Compounds of formula I.9 wherein $R^1$ is Y-8B, $R^2$ is $C_2H_5$, $R^9$ is H and $R^{10}$ is H.

Table 1019. Compounds of formula I.9 wherein $R^1$ is Y-8B, $R^2$ is $C_2H_5$, $R^9$ is $CH_3$ and $R^{10}$ is H.

Table 1020. Compounds of formula I.9 wherein $R^1$ is Y-8B, $R^2$ is $C_2H_5$, $R^9$ is $CH_3$ and $R^{10}$ is $CH_3$.

Table 1021. Compounds of formula I.9 wherein $R^1$ is Y-1A, $R^2$ is c-$C_3H_5$, $R^9$ is H and $R^{10}$ is H.

Table 1022. Compounds of formula I.9 wherein $R^1$ is Y-1A, $R^2$ is c-$C_3H_5$, $R^9$ is $CH_3$ and $R^{10}$ is H.

Table 1023. Compounds of formula I.9 wherein $R^1$ is Y-1A, $R^2$ is c-$C_3H_5$, $R^9$ is $CH_3$ and $R^{10}$ is $CH_3$.

Table 1024. Compounds of formula I.9 wherein $R^1$ is Y-1B, $R^2$ is c-$C_3H_5$, $R^9$ is H and $R^{10}$ is H.

Table 1025. Compounds of formula I.9 wherein $R^1$ is Y-1B, $R^2$ is c-$C_3H_5$, $R^9$ is $CH_3$, $R^{10}$ is H.

Table 1026. Compounds of formula I.9 wherein $R^1$ is Y-1B, $R^2$ is c-$C_3H_5$, $R^9$ is $CH_3$ and $R^{10}$ is $CH_3$.

Table 1027. Compounds of formula I.9 wherein $R^1$ is Y-2A, $R^2$ is c-$C_3H_5$, $R^9$ is H and $R^{10}$ is H.

Table 1028. Compounds of formula I.9 wherein $R^1$ is Y-2A, $R^2$ is c-$C_3H_5$, $R^9$ is $CH_3$ and $R^{10}$ is H.

Table 1029. Compounds of formula I.9 wherein $R^1$ is Y-2A, $R^2$ is c-$C_3H_5$, $R^9$ is $CH_3$ and $R^{10}$ is $CH_3$.

Table 1030. Compounds of formula I.9 wherein $R^1$ is Y-2B, $R^2$ is c-$C_3H_5$, $R^9$ is H and $R^{10}$ is H.

Table 1031. Compounds of formula I.9 wherein $R^1$ is Y-2B, $R^2$ is c-$C_3H_5$, $R^9$ is $CH_3$ and $R^{10}$ is H.

Table 1032. Compounds of formula I.9 wherein $R^1$ is Y-2B, $R^2$ is c-$C_3H_5$, $R^9$ is $CH_3$ and $R^{10}$ is $CH_3$.

Table 1033. Compounds of formula I.9 wherein $R^1$ is Y-3A, $R^2$ is c-$C_3H_5$, $R^9$ is H and $R^{10}$ is H.

Table 1034. Compounds of formula I.9 wherein $R^1$ is Y-3A, $R^2$ is c-$C_3H_5$, $R^9$ is $CH_3$ and $R^{10}$ is H.

Table 1035. Compounds of formula I.9 wherein $R^1$ is Y-3A, $R^2$ is c-$C_3H_5$, $R^9$ is $CH_3$ and $R^{10}$ is $CH_3$.

Table 1036. Compounds of formula I.9 wherein $R^1$ is Y-3B, $R^2$ is c-$C_3H_5$, $R^9$ is H and $R^{10}$ is H.

Table 1037. Compounds of formula I.9 wherein $R^1$ is Y-3B, $R^2$ is c-$C_3H_5$, $R^9$ is $CH_3$ and $R^{10}$ is H.

Table 1038. Compounds of formula I.9 wherein $R^1$ is Y-3B, $R^2$ is c-$C_3H_5$, $R^9$ is $CH_3$ and $R^{10}$ is $CH_3$.

Table 1039. Compounds of formula I.9 wherein $R^1$ is Y-3C, $R^2$ is c-$C_3H_5$, $R^9$ is H and $R^{10}$ is H.

Table 1040. Compounds of formula I.9 wherein $R^1$ is Y-3C, $R^2$ is c-$C_3H_5$, $R^9$ is $CH_3$ and $R^{10}$ is H.

Table 1041. Compounds of formula I.9 wherein $R^1$ is Y-3C, $R^2$ is c-$C_3H_5$, $R^9$ is $CH_3$ and $R^{10}$ is $CH_3$.

Table 1042. Compounds of formula I.9 wherein $R^1$ is Y-3D, $R^2$ is c-$C_3H_5$, $R^9$ is H and $R^{10}$ is H.

Table 1043. Compounds of formula I.9 wherein $R^1$ is Y-3D, $R^2$ is c-$C_3H_5$, $R^9$ is $CH_3$ and $R^{10}$ is H.

Table 1044. Compounds of formula I.9 wherein $R^1$ is Y-3D, $R^2$ is c-$C_3H_5$, $R^9$ is $CH_3$ and $R^{10}$ is $CH_3$.

Table 1045. Compounds of formula I.9 wherein $R^1$ is Y-4A, $R^2$ is c-$C_3H_5$, $R^9$ is H and $R^{10}$ is H.

Table 1046. Compounds of formula I.9 wherein $R^1$ is Y-4A, $R^2$ is c-$C_3H_5$, $R^9$ is $CH_3$ and $R^{10}$ is H.

Table 1047. Compounds of formula I.9 wherein $R^1$ is Y-4A, $R^2$ is c-$C_3H_5$, $R^9$ is $CH_3$ and $R^{10}$ is $CH_3$.

Table 1048. Compounds of formula I.9 wherein $R^1$ is Y-4B, $R^2$ is c-$C_3H_5$, $R^9$ is H and $R^{10}$ is H.

Table 1049. Compounds of formula I.9 wherein $R^1$ is Y-4B, $R^2$ is c-$C_3H_5$, $R^9$ is $CH_3$ and $R^{10}$ is H.

Table 1050. Compounds of formula I.9 wherein $R^1$ is Y-4B, $R^2$ is c-$C_3H_5$, $R^9$ is $CH_3$ and $R^{10}$ is $CH_3$.

Table 1051. Compounds of formula I.9 wherein $R^1$ is Y-4C, $R^2$ is c-$C_3H_5$, $R^9$ is H and $R^{10}$ is H.

Table 1052. Compounds of formula I.9 wherein $R^1$ is Y-4C, $R^2$ is c-$C_3H_5$, $R^9$ is $CH_3$ and $R^{10}$ is H.

Table 1053. Compounds of formula I.9 wherein $R^1$ is Y-4C, $R^2$ is c-$C_3H_5$, $R^9$ is $CH_3$ and $R^{10}$ is $CH_3$.

Table 1054. Compounds of formula I.9 wherein $R^1$ is Y-4D, $R^2$ is c-$C_3H_5$, $R^9$ is H and $R^{10}$ is H.

Table 1055. Compounds of formula I.9 wherein $R^1$ is Y-4D, $R^2$ is c-$C_3H_5$, $R^9$ is $CH_3$ and $R^{10}$ is H.

Table 1056. Compounds of formula I.9 wherein $R^1$ is Y-4D, $R^2$ is c-$C_3H_5$, $R^9$ is $CH_3$ and $R^{10}$ is $CH_3$.

Table 1057. Compounds of formula I.9 wherein $R^1$ is Y-5A, $R^2$ is c-$C_3H_5$, $R^9$ is H and $R^{10}$ is H.

Table 1058. Compounds of formula I.9 wherein $R^1$ is Y-5A, $R^2$ is c-$C_3H_5$, $R^9$ is $CH_3$ and $R^{10}$ is H.

Table 1059. Compounds of formula I.9 wherein $R^1$ is Y-5A, $R^2$ is c-$C_3H_5$, $R^9$ is $CH_3$ and $R^{10}$ is $CH_3$.

Table 1060. Compounds of formula I.9 wherein $R^1$ is Y-5B, $R^2$ is c-$C_3H_5$, $R^9$ is H and $R^{10}$ is H.

Table 1061. Compounds of formula I.9 wherein $R^1$ is Y-5B, $R^2$ is c-$C_3H_5$, $R^9$ is $CH_3$ and $R^{10}$ is H.

Table 1062. Compounds of formula I.9 wherein $R^1$ is Y-5B, $R^2$ is c-$C_3H_5$, $R^9$ is $CH_3$ and $R^{10}$ is $CH_3$.

Table 1063. Compounds of formula I.9 wherein $R^1$ is Y-6A, $R^2$ is c-$C_3H_5$, $R^9$ is H and $R^{10}$ is H.

Table 1064. Compounds of formula I.9 wherein $R^1$ is Y-6A, $R^2$ is c-$C_3H_5$, $R^9$ is $CH_3$ and $R^{10}$ is H.

Table 1065. Compounds of formula I.9 wherein $R^1$ is Y-6A, $R^2$ is c-$C_3H_5$, $R^9$ is $CH_3$ and $R^{10}$ is $CH_3$.

Table 1066. Compounds of formula I.9 wherein $R^1$ is Y-6B, $R^2$ is c-$C_3H_5$, $R^9$ is H and $R^{10}$ is H.

Table 1067. Compounds of formula I.9 wherein $R^1$ is Y-6B, $R^2$ is c-$C_3H_5$, $R^9$ is $CH_3$ and $R^{10}$ is H.

Table 1068. Compounds of formula I.9 wherein $R^1$ is Y-6B, $R^2$ is c-$C_3H_5$, $R^9$ is $CH_3$ and $R^{10}$ is $CH_3$.

Table 1069. Compounds of formula I.9 wherein $R^1$ is Y-7A, $R^2$ is c-$C_3H_5$, $R^9$ is H and $R^{10}$ is H.

Table 1070. Compounds of formula I.9 wherein $R^1$ is Y-7A, $R^2$ is c-$C_3H_5$, $R^9$ is $CH_3$ and $R^{10}$ is H.

Table 1071. Compounds of formula I.9 wherein $R^1$ is Y-7A, $R^2$ is c-$C_3H_5$, $R^9$ is $CH_3$ and $R^{10}$ is $CH_3$.

Table 1072. Compounds of formula I.9 wherein $R^1$ is Y-7B, $R^2$ is c-$C_3H_5$, $R^9$ is H and $R^{10}$ is H.

Table 1073. Compounds of formula I.9 wherein $R^1$ is Y-7B, $R^2$ is c-$C_3H_5$, $R^9$ is $CH_3$ and $R^{10}$ is H.

Table 1074. Compounds of formula I.9 wherein $R^1$ is Y-7B, $R^2$ is c-$C_3H_5$, $R^9$ is $CH_3$ and $R^{10}$ is $CH_3$.

Table 1075. Compounds of formula I.9 wherein $R^1$ is Y-8A, $R^2$ is c-$C_3H_5$, $R^9$ is H and $R^{10}$ is H.

Table 1076. Compounds of formula I.9 wherein $R^1$ is Y-8A, $R^2$ is c-$C_3H_5$, $R^9$ is $CH_3$ and $R^{10}$ is H.

Table 1077. Compounds of formula I.9 wherein $R^1$ is Y-8A, $R^2$ is c-$C_3H_5$, $R^9$ is $CH_3$ and $R^{10}$ is $CH_3$.

Table 1078. Compounds of formula I.9 wherein $R^1$ is Y-8B, $R^2$ is c-$C_3H_5$, $R^9$ is H and $R^{10}$ is H.

Table 1079. Compounds of formula I.9 wherein $R^1$ is Y-8B, $R^2$ is c-$C_3H_5$, $R^9$ is $CH_3$ and $R^{10}$ is H.

Table 1080. Compounds of formula I.9 wherein $R^1$ is Y-8B, $R^2$ is c-$C_3H_5$, $R^9$ is $CH_3$ and $R^{10}$ is $CH_3$.

Table 1081. Compounds of formula I.13 wherein $R^1$ is Y-1A and $R^2$ is H.

Table 1082. Compounds of formula I.13 wherein $R^1$ is Y-1B and $R^2$ is H.

Table 1083. Compounds of formula I.13 wherein $R^1$ is Y-2A and $R^2$ is H.

Table 1084. Compounds of formula I.13 wherein $R^1$ is Y-2B and $R^2$ is H.

Table 1085. Compounds of formula I.13 wherein $R^1$ is Y-3A and $R^2$ is H.

Table 1086. Compounds of formula I.13 wherein $R^1$ is Y-3B and $R^2$ is H.

Table 1087. Compounds of formula I.13 wherein $R^1$ is Y-3C and $R^2$ is H.

Table 1088. Compounds of formula I.13 wherein $R^1$ is Y-3D and $R^2$ is H.

Table 1089. Compounds of formula I.13 wherein $R^1$ is Y-4A and $R^2$ is H.

Table 1090. Compounds of formula I.13 wherein $R^1$ is Y-4B and $R^2$ is H.

Table 1091. Compounds of formula I.13 wherein $R^1$ is Y-4C and $R^2$ is H.

Table 1092. Compounds of formula I.13 wherein $R^1$ is Y-4D and $R^2$ is H.

Table 1093. Compounds of formula I.13 wherein $R^1$ is Y-5A and $R^2$ is H.

Table 1094. Compounds of formula I.13 wherein $R^1$ is Y-5B and $R^2$ is H.

Table 1095. Compounds of formula I.13 wherein $R^1$ is Y-6A and $R^2$ is H.

Table 1096. Compounds of formula I.13 wherein $R^1$ is Y-6B and $R^2$ is H.

Table 1097. Compounds of formula I.13 wherein $R^1$ is Y-7A and $R^2$ is H.

Table 1098. Compounds of formula I.13 wherein $R^1$ is Y-7B and $R^2$ is H.

Table 1099. Compounds of formula I.13 wherein $R^1$ is Y-8A and $R^2$ is H.

Table 1100. Compounds of formula I.13 wherein $R^1$ is Y-8B and $R^2$ is H.

Table 1101. Compounds of formula I.13 wherein $R^1$ is Y-1A and $R^2$ is $CH_3$.

Table 1102. Compounds of formula I.13 wherein $R^1$ is Y-1B and $R^2$ is $CH_3$.

Table 1103. Compounds of formula I.13 wherein $R^1$ is Y-2A and $R^2$ is $CH_3$.

Table 1104. Compounds of formula I.13 wherein $R^1$ is Y-2B and $R^2$ is $CH_3$.

Table 1105. Compounds of formula I.13 wherein $R^1$ is Y-3A and $R^2$ is $CH_3$.

Table 1106. Compounds of formula I.13 wherein $R^1$ is Y-3B and $R^2$ is $CH_3$.

Table 1107. Compounds of formula I.13 wherein $R^1$ is Y-3C and $R^2$ is $CH_3$.

Table 1108. Compounds of formula I.13 wherein $R^1$ is Y-3D and $R^2$ is $CH_3$.

Table 1109. Compounds of formula I.13 wherein $R^1$ is Y-4A and $R^2$ is $CH_3$.

Table 1110. Compounds of formula I.13 wherein $R^1$ is Y-4B and $R^2$ is $CH_3$.

Table 1111. Compounds of formula I.13 wherein $R^1$ is Y-4C and $R^2$ is $CH_3$.

Table 1112. Compounds of formula I.13 wherein $R^1$ is Y-4D and $R^2$ is $CH_3$.

Table 1113. Compounds of formula I.13 wherein $R^1$ is Y-5A and $R^2$ is $CH_3$.

Table 1114. Compounds of formula I.13 wherein $R^1$ is Y-5B and $R^2$ is $CH_3$.

Table 1115. Compounds of formula I.13 wherein $R^1$ is Y-6A and $R^2$ is $CH_3$.

Table 1116. Compounds of formula I.13 wherein $R^1$ is Y-6B and $R^2$ is $CH_3$.

Table 1117. Compounds of formula I.13 wherein $R^1$ is Y-7A and $R^2$ is $CH_3$.

Table 1118. Compounds of formula I.13 wherein $R^1$ is Y-7B and $R^2$ is $CH_3$.

Table 1119. Compounds of formula I.13 wherein $R^1$ is Y-8A and $R^2$ is $CH_3$.

Table 1120. Compounds of formula I.13 wherein $R^1$ is Y-8B and $R^2$ is $CH_3$.

Table 1121. Compounds of formula I.13 wherein $R^1$ is Y-1A and $R^2$ is c-$C_3H_5$.

Table 1122. Compounds of formula I.13 wherein $R^1$ is Y-1B and $R^2$ is c-$C_3H_5$.

Table 1123. Compounds of formula I.13 wherein $R^1$ is Y-2A and $R^2$ is c-$C_3H_5$.

Table 1124. Compounds of formula I.13 wherein $R^1$ is Y-2B and $R^2$ is c-$C_3H_5$.

Table 1125. Compounds of formula I.13 wherein $R^1$ is Y-3A and $R^2$ is c-$C_3H_5$.

Table 1126. Compounds of formula I.13 wherein $R^1$ is Y-3B and $R^2$ is c-$C_3H_5$.

Table 1127. Compounds of formula I.13 wherein $R^1$ is Y-3C and $R^2$ is c-$C_3H_5$.

Table 1128. Compounds of formula I.13 wherein $R^1$ is Y-3D and $R^2$ is c-$C_3H_5$.

Table 1129. Compounds of formula I.13 wherein $R^1$ is Y-4A and $R^2$ is c-$C_3H_5$.

Table 1130. Compounds of formula I.13 wherein $R^1$ is Y-4B and $R^2$ is c-$C_3H_5$.

Table 1131. Compounds of formula I.13 wherein $R^1$ is Y-4C and $R^2$ is c-$C_3H_5$.

Table 1132. Compounds of formula I.13 wherein $R^1$ is Y-4D and $R^2$ is c-$C_3H_5$.

Table 1133. Compounds of formula I.13 wherein $R^1$ is Y-5A and $R^2$ is c-$C_3H_5$.

Table 1134. Compounds of formula I.13 wherein $R^1$ is Y-5B and $R^2$ is c-$C_3H_5$.

Table 1135. Compounds of formula I.13 wherein $R^1$ is Y-6A and $R^2$ is c-$C_3H_5$.

Table 1136. Compounds of formula I.13 wherein $R^1$ is Y-6B and $R^2$ is c-$C_3H_5$.

Table 1137. Compounds of formula I.13 wherein $R^1$ is Y-7A and $R^2$ is c-$C_3H_5$.

Table 1138. Compounds of formula I.13 wherein $R^1$ is Y-7B and $R^2$ is c-$C_3H_5$.

Table 1139. Compounds of formula I.13 wherein $R^1$ is Y-8A and $R^2$ is c-$C_3H_5$.

Table 1140. Compounds of formula I.13 wherein $R^1$ is Y-8B and $R^2$ is c-$C_3H_5$.

Table 1141. Compounds of formula I.14 wherein $R^1$ is Y-1A and $R^2$ is H.

Table 1142. Compounds of formula I.14 wherein $R^1$ is Y-1B and $R^2$ is H.

Table 1143. Compounds of formula I.14 wherein $R^1$ is Y-2A and $R^2$ is H.

Table 1144. Compounds of formula I.14 wherein $R^1$ is Y-2B and $R^2$ is H.

Table 1145. Compounds of formula I.14 wherein $R^1$ is Y-3A and $R^2$ is H.

Table 1146. Compounds of formula I.14 wherein $R^1$ is Y-3B and $R^2$ is H.

Table 1147. Compounds of formula I.14 wherein $R^1$ is Y-3C and $R^2$ is H.

Table 1148. Compounds of formula I.14 wherein $R^1$ is Y-3D and $R^2$ is H.

Table 1149. Compounds of formula I.14 wherein $R^1$ is Y-4A and $R^2$ is H.

Table 1150. Compounds of formula I.14 wherein $R^1$ is Y-4B and $R^2$ is H.

Table 1151. Compounds of formula I.14 wherein $R^1$ is Y-4C and $R^2$ is H.

Table 1152. Compounds of formula I.14 wherein $R^1$ is Y-4D and $R^2$ is H.

Table 1153. Compounds of formula I.14 wherein $R^1$ is Y-5A and $R^2$ is H.

Table 1154. Compounds of formula I.14 wherein $R^1$ is Y-5B and $R^2$ is H.

Table 1155. Compounds of formula I.14 wherein $R^1$ is Y-6A and $R^2$ is H.

Table 1156. Compounds of formula I.14 wherein $R^1$ is Y-6B and $R^2$ is H.

Table 1157. Compounds of formula I.14 wherein $R^1$ is Y-7A and $R^2$ is H.

Table 1158. Compounds of formula I.14 wherein $R^1$ is Y-7B and $R^2$ is H.

Table 1159. Compounds of formula I.14 wherein $R^1$ is Y-8A and $R^2$ is H.

Table 1160. Compounds of formula I.14 wherein $R^1$ is Y-8B and $R^2$ is H.

Table 1161. Compounds of formula I.14 wherein $R^1$ is Y-1A and $R^2$ is $CH_3$.

Table 1162. Compounds of formula I.14 wherein $R^1$ is Y-1B and $R^2$ is $CH_3$.

Table 1163. Compounds of formula I.14 wherein $R^1$ is Y-2A and $R^2$ is $CH_3$.

Table 1164. Compounds of formula I.14 wherein $R^1$ is Y-2B and $R^2$ is $CH_3$.

Table 1165. Compounds of formula I.14 wherein $R^1$ is Y-3A and $R^2$ is $CH_3$.

Table 1166. Compounds of formula I.14 wherein $R^1$ is Y-3B and $R^2$ is $CH_3$.

Table 1167. Compounds of formula I.14 wherein $R^1$ is Y-3C and $R^2$ is $CH_3$.

Table 1168. Compounds of formula I.14 wherein $R^1$ is Y-3D and $R^2$ is $CH_3$.

Table 1169. Compounds of formula I.14 wherein $R^1$ is Y-4A and $R^2$ is $CH_3$.

Table 1170. Compounds of formula I.14 wherein $R^1$ is Y-4B and $R^2$ is $CH_3$.

Table 1171. Compounds of formula I.14 wherein $R^1$ is Y-4C and $R^2$ is $CH_3$.

Table 1172. Compounds of formula I.14 wherein $R^1$ is Y-4D and $R^2$ is $CH_3$.

Table 1173. Compounds of formula I.14 wherein $R^1$ is Y-5A and $R^2$ is $CH_3$.

Table 1174. Compounds of formula I.14 wherein $R^1$ is Y-5B and $R^2$ is $CH_3$.

Table 1175. Compounds of formula I.14 wherein $R^1$ is Y-6A and $R^2$ is $CH_3$.

Table 1176. Compounds of formula I.14 wherein $R^1$ is Y-6B and $R^2$ is $CH_3$.

Table 1177. Compounds of formula I.14 wherein $R^1$ is Y-7A and $R^2$ is $CH_3$.

Table 1178. Compounds of formula I.14 wherein $R^1$ is Y-7B and $R^2$ is $CH_3$.

Table 1179. Compounds of formula I.14 wherein $R^1$ is Y-8A and $R^2$ is $CH_3$.

Table 1180. Compounds of formula I.14 wherein $R^1$ is Y-8B and $R^2$ is $CH_3$.

Table 1181. Compounds of formula I.14 wherein $R^1$ is Y-1A and $R^2$ is c-$C_3H_5$.

Table 1182. Compounds of formula I.14 wherein $R^1$ is Y-1B and $R^2$ is c-$C_3H_5$.

Table 1183. Compounds of formula I.14 wherein $R^1$ is Y-2A and $R^2$ is c-$C_3H_5$.

Table 1184. Compounds of formula I.14 wherein $R^1$ is Y-2B and $R^2$ is c-$C_3H_5$.

Table 1185. Compounds of formula I.14 wherein $R^1$ is Y-3A and $R^2$ is c-$C_3H_5$.

Table 1186. Compounds of formula I.14 wherein $R^1$ is Y-3B and $R^2$ is c-$C_3H_5$.

Table 1187. Compounds of formula I.14 wherein $R^1$ is Y-3C and $R^2$ is c-$C_3H_5$.

Table 1188. Compounds of formula I.14 wherein $R^1$ is Y-3D and $R^2$ is c-$C_3H_5$.

Table 1189. Compounds of formula I.14 wherein $R^1$ is Y-4A and $R^2$ is c-$C_3H_5$.

Table 1190. Compounds of formula I.14 wherein $R^1$ is Y-4B and $R^2$ is c-$C_3H_5$.

Table 1191. Compounds of formula I.14 wherein $R^1$ is Y-4C and $R^2$ is c-$C_3H_5$.

Table 1192. Compounds of formula I.14 wherein $R^1$ is Y-4D and $R^2$ is c-$C_3H_5$.

Table 1193. Compounds of formula I.14 wherein $R^1$ is Y-5A and $R^2$ is c-$C_3H_5$.

Table 1194. Compounds of formula I.14 wherein $R^1$ is Y-5B and $R^2$ is c-$C_3H_5$.

Table 1195. Compounds of formula I.14 wherein $R^1$ is Y-6A and $R^2$ is c-$C_3H_5$.

Table 1196. Compounds of formula I.14 wherein $R^1$ is Y-6B and $R^2$ is c-$C_3H_5$.

Table 1197. Compounds of formula I.14 wherein $R^1$ is Y-7A and $R^2$ is c-$C_3H_5$.

Table 1198. Compounds of formula I.14 wherein $R^1$ is Y-7B and $R^2$ is c-$C_3H_5$.

Table 1199. Compounds of formula I.14 wherein $R^1$ is Y-8A and $R^2$ is c-$C_3H_5$.

Table 1200. Compounds of formula I.14 wherein $R^1$ is Y-8B and $R^2$ is c-$C_3H_5$.

Table 1201. Compounds of formula I.15 wherein $R^1$ is Y-1A and $R^2$ is H.

Table 1202. Compounds of formula I.15 wherein $R^1$ is Y-1B and $R^2$ is H.

Table 1203. Compounds of formula I.15 wherein $R^1$ is Y-2A and $R^2$ is H.

Table 1204. Compounds of formula I.15 wherein $R^1$ is Y-2B and $R^2$ is H.

Table 1205. Compounds of formula I.15 wherein $R^1$ is Y-3A and $R^2$ is H.

Table 1206. Compounds of formula I.15 wherein $R^1$ is Y-3B and $R^2$ is H.

Table 1207. Compounds of formula I.15 wherein $R^1$ is Y-3C and $R^2$ is H.

Table 1208. Compounds of formula I.15 wherein $R^1$ is Y-3D and $R^2$ is H.

Table 1209. Compounds of formula I.15 wherein $R^1$ is Y-4A and $R^2$ is H.

Table 1210. Compounds of formula I.15 wherein $R^1$ is Y-4B and $R^2$ is H.

Table 1211. Compounds of formula I.15 wherein $R^1$ is Y-4C and $R^2$ is H.

Table 1212. Compounds of formula I.15 wherein $R^1$ is Y-4D and $R^2$ is H.

Table 1213. Compounds of formula I.15 wherein $R^1$ is Y-5A and $R^2$ is H.

Table 1214. Compounds of formula I.15 wherein $R^1$ is Y-5B and $R^2$ is H.

Table 1215. Compounds of formula I.15 wherein $R^1$ is Y-6A and $R^2$ is H.

Table 1216. Compounds of formula I.15 wherein $R^1$ is Y-6B and $R^2$ is H.

Table 1217. Compounds of formula I.15 wherein $R^1$ is Y-7A and $R^2$ is H.

Table 1218. Compounds of formula I.15 wherein $R^1$ is Y-7B and $R^2$ is H.

Table 1219. Compounds of formula I.15 wherein $R^1$ is Y-8A and $R^2$ is H.

Table 1220. Compounds of formula I.15 wherein $R^1$ is Y-8B and $R^2$ is H.

Table 1221. Compounds of formula I.15 wherein $R^1$ is Y-1A and $R^2$ is $CH_3$.

Table 1222. Compounds of formula I.15 wherein $R^1$ is Y-1B and $R^2$ is $CH_3$.

Table 1223. Compounds of formula I.15 wherein $R^1$ is Y-2A and $R^2$ is $CH_3$.

Table 1224. Compounds of formula I.15 wherein $R^1$ is Y-2B and $R^2$ is $CH_3$.

Table 1225. Compounds of formula I.15 wherein $R^1$ is Y-3A and $R^2$ is $CH_3$.

Table 1226. Compounds of formula I.15 wherein $R^1$ is Y-3B and $R^2$ is $CH_3$.

Table 1227. Compounds of formula I.15 wherein $R^1$ is Y-3C and $R^2$ is $CH_3$.

Table 1228. Compounds of formula I.15 wherein $R^1$ is Y-3D and $R^2$ is $CH_3$.

Table 1229. Compounds of formula I.15 wherein $R^1$ is Y-4A and $R^2$ is $CH_3$.

Table 1230. Compounds of formula I.15 wherein $R^1$ is Y-4B and $R^2$ is $CH_3$.

Table 1231. Compounds of formula I.15 wherein $R^1$ is Y-4C and $R^2$ is $CH_3$.

Table 1232. Compounds of formula I.15 wherein $R^1$ is Y-4D and $R^2$ is $CH_3$.

Table 1233. Compounds of formula I.15 wherein $R^1$ is Y-5A and $R^2$ is $CH_3$.

Table 1234. Compounds of formula I.15 wherein $R^1$ is Y-5B and $R^2$ is $CH_3$.

Table 1235. Compounds of formula I.15 wherein $R^1$ is Y-6A and $R^2$ is $CH_3$.

Table 1236. Compounds of formula I.15 wherein $R^1$ is Y-6B and $R^2$ is $CH_3$.

Table 1237. Compounds of formula I.15 wherein $R^1$ is Y-7A and $R^2$ is $CH_3$.

Table 1238. Compounds of formula I.15 wherein $R^1$ is Y-7B and $R^2$ is $CH_3$.

Table 1239. Compounds of formula I.15 wherein $R^1$ is Y-8A and $R^2$ is $CH_3$.

Table 1240. Compounds of formula I.15 wherein $R^1$ is Y-8B and $R^2$ is $CH_3$.

Table 1241. Compounds of formula I.15 wherein $R^1$ is Y-1A and $R^2$ is c-$C_3H_5$.

Table 1242. Compounds of formula I.15 wherein $R^1$ is Y-1B and $R^2$ is c-$C_3H_5$.

Table 1243. Compounds of formula I.15 wherein $R^1$ is Y-2A and $R^2$ is c-$C_3H_5$.

Table 1244. Compounds of formula I.15 wherein $R^1$ is Y-2B and $R^2$ is c-$C_3H_5$.

Table 1245. Compounds of formula I.15 wherein $R^1$ is Y-3A and $R^2$ is c-$C_3H_5$.

Table 1246. Compounds of formula I.15 wherein $R^1$ is Y-3B and $R^2$ is c-$C_3H_5$.

Table 1247. Compounds of formula I.15 wherein $R^1$ is Y-3C and $R^2$ is c-$C_3H_5$.

Table 1248. Compounds of formula I.15 wherein $R^1$ is Y-3D and $R^2$ is c-$C_3H_5$.

Table 1249. Compounds of formula I.15 wherein $R^1$ is Y-4A and $R^2$ is c-$C_3H_5$.

Table 1250. Compounds of formula I.15 wherein $R^1$ is Y-4B and $R^2$ is c-$C_3H_5$.

Table 1251. Compounds of formula I.15 wherein $R^1$ is Y-4C and $R^2$ is c-$C_3H_5$.

Table 1252. Compounds of formula I.15 wherein $R^1$ is Y-4D and $R^2$ is c-$C_3H_5$.

Table 1253. Compounds of formula I.15 wherein $R^1$ is Y-5A and $R^2$ is c-$C_3H_5$.

Table 1254. Compounds of formula I.15 wherein $R^1$ is Y-5B and $R^2$ is c-$C_3H_5$.

Table 1255. Compounds of formula I.15 wherein $R^1$ is Y-6A and $R^2$ is c-$C_3H_5$.

Table 1256. Compounds of formula I.15 wherein $R^1$ is Y-6B and $R^2$ is c-$C_3H_5$.

Table 1257. Compounds of formula I.15 wherein $R^1$ is Y-7A and $R^2$ is c-$C_3H_5$.

Table 1258. Compounds of formula I.15 wherein $R^1$ is Y-7B and $R^2$ is c-$C_3H_5$.

Table 1259. Compounds of formula I.15 wherein $R^1$ is Y-8A and $R^2$ is c-$C_3H_5$.

Table 1260. Compounds of formula I.15 wherein $R^1$ is Y-8B and $R^2$ is c-$C_3H_5$.

Table 1261. Compounds of formula I.16 wherein $R^1$ is Y-1A and $R^2$ is H.

Table 1262. Compounds of formula I.16 wherein $R^1$ is Y-1B and $R^2$ is H.

Table 1263. Compounds of formula I.16 wherein $R^1$ is Y-2A and $R^2$ is H.

Table 1264. Compounds of formula I.16 wherein $R^1$ is Y-2B and $R^2$ is H.

Table 1265. Compounds of formula I.16 wherein $R^1$ is Y-3A and $R^2$ is H.

Table 1266. Compounds of formula I.16 wherein $R^1$ is Y-3B and $R^2$ is H.

Table 1267. Compounds of formula I.16 wherein $R^1$ is Y-3C and $R^2$ is H.

Table 1268. Compounds of formula I.16 wherein $R^1$ is Y-3D and $R^2$ is H.

Table 1269. Compounds of formula I.16 wherein $R^1$ is Y-4A and $R^2$ is H.

Table 1270. Compounds of formula I.16 wherein $R^1$ is Y-4B and $R^2$ is H.

Table 1271. Compounds of formula I.16 wherein $R^1$ is Y-4C and $R^2$ is H.

Table 1272. Compounds of formula I.16 wherein $R^1$ is Y-4D and $R^2$ is H.

Table 1273. Compounds of formula I.16 wherein $R^1$ is Y-5A and $R^2$ is H.

Table 1274. Compounds of formula I.16 wherein $R^1$ is Y-5B and $R^2$ is H.

Table 1275. Compounds of formula I.16 wherein $R^1$ is Y-6A and $R^2$ is H.

Table 1276. Compounds of formula I.16 wherein $R^1$ is Y-6B and $R^2$ is H.

Table 1277. Compounds of formula I.16 wherein $R^1$ is Y-7A and $R^2$ is H.

Table 1278. Compounds of formula I.16 wherein $R^1$ is Y-7B and $R^2$ is H.

Table 1279. Compounds of formula I.16 wherein $R^1$ is Y-8A and $R^2$ is H.

Table 1280. Compounds of formula I.16 wherein $R^1$ is Y-8B and $R^2$ is H.

Table 1281. Compounds of formula I.16 wherein $R^1$ is Y-1A and $R^2$ is $CH_3$.

Table 1282. Compounds of formula I.16 wherein $R^1$ is Y-1B and $R^2$ is $CH_3$.

Table 1283. Compounds of formula I.16 wherein $R^1$ is Y-2A and $R^2$ is $CH_3$.

Table 1284. Compounds of formula I.16 wherein $R^1$ is Y-2B and $R^2$ is $CH_3$.

Table 1285. Compounds of formula I.16 wherein $R^1$ is Y-3A and $R^2$ is $CH_3$.

Table 1286. Compounds of formula I.16 wherein $R^1$ is Y-3B and $R^2$ is $CH_3$.

Table 1287. Compounds of formula I.16 wherein $R^1$ is Y-3C and $R^2$ is $CH_3$.

Table 1288. Compounds of formula I.16 wherein $R^1$ is Y-3D and $R^2$ is $CH_3$.

Table 1289. Compounds of formula I.16 wherein $R^1$ is Y-4A and $R^2$ is $CH_3$.

Table 1290. Compounds of formula I.16 wherein $R^1$ is Y-4B and $R^2$ is $CH_3$.

Table 1291. Compounds of formula I.16 wherein $R^1$ is Y-4C and $R^2$ is $CH_3$.

Table 1292. Compounds of formula I.16 wherein $R^1$ is Y-4D and $R^2$ is $CH_3$.

Table 1293. Compounds of formula I.16 wherein $R^1$ is Y-5A and $R^2$ is $CH_3$.

Table 1294. Compounds of formula I.16 wherein $R^1$ is Y-5B and $R^2$ is $CH_3$.

Table 1295. Compounds of formula I.16 wherein $R^1$ is Y-6A and $R^2$ is $CH_3$.

Table 1296. Compounds of formula I.16 wherein $R^1$ is Y-6B and $R^2$ is $CH_3$.

Table 1297. Compounds of formula I.16 wherein $R^1$ is Y-7A and $R^2$ is $CH_3$.

Table 1298. Compounds of formula I.16 wherein $R^1$ is Y-7B and $R^2$ is $CH_3$.

Table 1299. Compounds of formula I.16 wherein $R^1$ is Y-8A and $R^2$ is $CH_3$.

Table 1300. Compounds of formula I.16 wherein $R^1$ is Y-8B and $R^2$ is $CH_3$.

Table 1301. Compounds of formula I.16 wherein $R^1$ is Y-1A and $R^2$ is c-$C_3H_5$.

Table 1302. Compounds of formula I.16 wherein $R^1$ is Y-1B and $R^2$ is c-$C_3H_5$.

Table 1303. Compounds of formula I.16 wherein $R^1$ is Y-2A and $R^2$ is c-$C_3H_5$.

Table 1304. Compounds of formula I.16 wherein $R^1$ is Y-2B and $R^2$ is c-$C_3H_5$.

Table 1305. Compounds of formula I.16 wherein $R^1$ is Y-3A and $R^2$ is c-$C_3H_5$.

Table 1306. Compounds of formula I.16 wherein $R^1$ is Y-3B and $R^2$ is c-$C_3H_5$.

Table 1307. Compounds of formula I.16 wherein $R^1$ is Y-3C and $R^2$ is c-$C_3H_5$.

Table 1308. Compounds of formula I.16 wherein $R^1$ is Y-3D and $R^2$ is c-$C_3H_5$.

Table 1309. Compounds of formula I.16 wherein $R^1$ is Y-4A and $R^2$ is c-$C_3H_5$.

Table 1310. Compounds of formula I.16 wherein $R^1$ is Y-4B and $R^2$ is c-$C_3H_5$.

Table 1311. Compounds of formula I.16 wherein $R^1$ is Y-4C and $R^2$ is c-$C_3H_5$.

Table 1312. Compounds of formula I.16 wherein $R^1$ is Y-4D and $R^2$ is c-$C_3H_5$.

Table 1313. Compounds of formula I.16 wherein $R^1$ is Y-5A and $R^2$ is c-$C_3H_5$.

Table 1314. Compounds of formula I.16 wherein $R^1$ is Y-5B and $R^2$ is c-$C_3H_5$.

Table 1315. Compounds of formula I.16 wherein $R^1$ is Y-6A and $R^2$ is c-$C_3H_5$.

Table 1316. Compounds of formula I.16 wherein $R^1$ is Y-6B and $R^2$ is c-$C_3H_5$.

Table 1317. Compounds of formula I.16 wherein $R^1$ is Y-7A and $R^2$ is c-$C_3H_5$.

Table 1318. Compounds of formula I.16 wherein $R^1$ is Y-7B and $R^2$ is c-$C_3H_5$.

Table 1319. Compounds of formula I.16 wherein $R^1$ is Y-8A and $R^2$ is c-$C_3H_5$.

Table 1320. Compounds of formula I.16 wherein $R^1$ is Y-8B and $R^2$ is c-$C_3H_5$.

Table 1321. Compounds of formula I.17 wherein $R^1$ is Y-1A and $R^2$ is H.

Table 1322. Compounds of formula I.17 wherein $R^1$ is Y-1B and $R^2$ is H.

Table 1323. Compounds of formula I.17 wherein $R^1$ is Y-2A and $R^2$ is H.

Table 1324. Compounds of formula I.17 wherein $R^1$ is Y-2B and $R^2$ is H.

Table 1325. Compounds of formula I.17 wherein $R^1$ is Y-3A and $R^2$ is H.

Table 1326. Compounds of formula I.17 wherein $R^1$ is Y-3B and $R^2$ is H.

Table 1327. Compounds of formula I.17 wherein $R^1$ is Y-3C and $R^2$ is H.

Table 1328. Compounds of formula I.17 wherein $R^1$ is Y-3D and $R^2$ is H.

Table 1329. Compounds of formula I.17 wherein $R^1$ is Y-4A and $R^2$ is H.

Table 1330. Compounds of formula I.17 wherein $R^1$ is Y-4B and $R^2$ is H.

Table 1331. Compounds of formula I.17 wherein $R^1$ is Y-4C and $R^2$ is H.

Table 1332. Compounds of formula I.17 wherein $R^1$ is Y-4D and $R^2$ is H.

Table 1333. Compounds of formula I.17 wherein $R^1$ is Y-5A and $R^2$ is H.

Table 1334. Compounds of formula I.17 wherein $R^1$ is Y-5B and $R^2$ is H.

Table 1335. Compounds of formula I.17 wherein $R^1$ is Y-6A and $R^2$ is H.

Table 1336. Compounds of formula I.17 wherein $R^1$ is Y-6B and $R^2$ is H.

Table 1337. Compounds of formula I.17 wherein $R^1$ is Y-7A and $R^2$ is H.

Table 1338. Compounds of formula I.17 wherein $R^1$ is Y-7B and $R^2$ is H.

Table 1339. Compounds of formula I.17 wherein $R^1$ is Y-8A and $R^2$ is H.

Table 1340. Compounds of formula I.17 wherein $R^1$ is Y-8B and $R^2$ is H.

Table 1341. Compounds of formula I.17 wherein $R^1$ is Y-1A and $R^2$ is $CH_3$.

Table 1342. Compounds of formula I.17 wherein $R^1$ is Y-1B and $R^2$ is $CH_3$.

Table 1343. Compounds of formula I.17 wherein $R^1$ is Y-2A and $R^2$ is $CH_3$.

Table 1344. Compounds of formula I.17 wherein $R^1$ is Y-2B and $R^2$ is $CH_3$.

Table 1345. Compounds of formula I.17 wherein $R^1$ is Y-3A and $R^2$ is $CH_3$.

Table 1346. Compounds of formula I.17 wherein $R^1$ is Y-3B and $R^2$ is $CH_3$.

Table 1347. Compounds of formula I.17 wherein $R^1$ is Y-3C and $R^2$ is $CH_3$.

Table 1348. Compounds of formula I.17 wherein $R^1$ is Y-3D and $R^2$ is $CH_3$.

Table 1349. Compounds of formula I.17 wherein $R^1$ is Y-4A and $R^2$ is $CH_3$.

Table 1350. Compounds of formula I.17 wherein $R^1$ is Y-4B and $R^2$ is $CH_3$.

Table 1351. Compounds of formula I.17 wherein $R^1$ is Y-4C and $R^2$ is $CH_3$.

Table 1352. Compounds of formula I.17 wherein $R^1$ is Y-4D and $R^2$ is $CH_3$.

Table 1353. Compounds of formula I.17 wherein $R^1$ is Y-5A and $R^2$ is $CH_3$.

Table 1354. Compounds of formula I.17 wherein $R^1$ is Y-5B and $R^2$ is $CH_3$.

Table 1355. Compounds of formula I.17 wherein $R^1$ is Y-6A and $R^2$ is $CH_3$.

Table 1356. Compounds of formula I.17 wherein $R^1$ is Y-6B and $R^2$ is $CH_3$.

Table 1357. Compounds of formula I.17 wherein $R^1$ is Y-7A and $R^2$ is $CH_3$.

Table 1358. Compounds of formula I.17 wherein $R^1$ is Y-7B and $R^2$ is $CH_3$.

Table 1359. Compounds of formula I.17 wherein $R^1$ is Y-8A and $R^2$ is $CH_3$.

Table 1360. Compounds of formula I.17 wherein $R^1$ is Y-8B and $R^2$ is $CH_3$.

Table 1361. Compounds of formula I.17 wherein $R^1$ is Y-1A and $R^2$ is c-$C_3H_5$.

Table 1362. Compounds of formula I.17 wherein $R^1$ is Y-1B and $R^2$ is c-$C_3H_5$.

Table 1363. Compounds of formula I.17 wherein $R^1$ is Y-2A and $R^2$ is c-$C_3H_5$.

Table 1364. Compounds of formula I.17 wherein $R^1$ is Y-2B and $R^2$ is c-$C_3H_5$.

Table 1365. Compounds of formula I.17 wherein $R^1$ is Y-3A and $R^2$ is c-$C_3H_5$.

Table 1366. Compounds of formula I.17 wherein $R^1$ is Y-3B and $R^2$ is c-$C_3H_5$.

Table 1367. Compounds of formula I.17 wherein $R^1$ is Y-3C and $R^2$ is c-$C_3H_5$.

Table 1368. Compounds of formula I.17 wherein $R^1$ is Y-3D and $R^2$ is c-$C_3H_5$.

Table 1369. Compounds of formula I.17 wherein $R^1$ is Y-4A and $R^2$ is c-$C_3H_5$.

Table 1370. Compounds of formula I.17 wherein $R^1$ is Y-4B and $R^2$ is c-$C_3H_5$.

Table 1371. Compounds of formula I.17 wherein $R^1$ is Y-4C and $R^2$ is c-$C_3H_5$.

Table 1372. Compounds of formula I.17 wherein $R^1$ is Y-4D and $R^2$ is c-$C_3H_5$.

Table 1373. Compounds of formula I.17 wherein $R^1$ is Y-5A and $R^2$ is c-$C_3H_5$.

Table 1374. Compounds of formula I.17 wherein $R^1$ is Y-5B and $R^2$ is c-$C_3H_5$.

Table 1375. Compounds of formula I.17 wherein $R^1$ is Y-6A and $R^2$ is c-$C_3H_5$.

Table 1376. Compounds of formula I.17 wherein $R^1$ is Y-6B and $R^2$ is c-$C_3H_5$.

Table 1377. Compounds of formula I.17 wherein $R^1$ is Y-7A and $R^2$ is c-$C_3H_5$.

Table 1378. Compounds of formula I.17 wherein $R^1$ is Y-7B and $R^2$ is c-$C_3H_5$.

Table 1379. Compounds of formula I.17 wherein $R^1$ is Y-8A and $R^2$ is c-$C_3H_5$.

Table 1380. Compounds of formula I.17 wherein $R^1$ is Y-8B and $R^2$ is c-$C_3H_5$.

Table 1381. Compounds of formula I.18 wherein $R^1$ is Y-1A and $R^2$ is H.

Table 1382. Compounds of formula I.18 wherein $R^1$ is Y-1B and $R^2$ is H.

Table 1383. Compounds of formula I.18 wherein $R^1$ is Y-2A and $R^2$ is H.

Table 1384. Compounds of formula I.18 wherein $R^1$ is Y-2B and $R^2$ is H.

Table 1385. Compounds of formula I.18 wherein $R^1$ is Y-3A and $R^2$ is H.

Table 1386. Compounds of formula I.18 wherein $R^1$ is Y-3B and $R^2$ is H.

Table 1387. Compounds of formula I.18 wherein $R^1$ is Y-3C and $R^2$ is H.

Table 1388. Compounds of formula I.18 wherein $R^1$ is Y-3D and $R^2$ is H.

Table 1389. Compounds of formula I.18 wherein $R^1$ is Y-4A and $R^2$ is H.

Table 1390. Compounds of formula I.18 wherein $R^1$ is Y-4B and $R^2$ is H.

Table 1391. Compounds of formula I.18 wherein $R^1$ is Y-4C and $R^2$ is H.

Table 1392. Compounds of formula I.18 wherein $R^1$ is Y-4D and $R^2$ is H.

Table 1393. Compounds of formula I.18 wherein $R^1$ is Y-5A and $R^2$ is H.

Table 1394. Compounds of formula I.18 wherein $R^1$ is Y-5B and $R^2$ is H.

Table 1395. Compounds of formula I.18 wherein $R^1$ is Y-6A and $R^2$ is H.

Table 1396. Compounds of formula I.18 wherein $R^1$ is Y-6B and $R^2$ is H.

Table 1397. Compounds of formula I.18 wherein $R^1$ is Y-7A and $R^2$ is H.

Table 1398. Compounds of formula I.18 wherein $R^1$ is Y-7B and $R^2$ is H.

Table 1399. Compounds of formula I.18 wherein $R^1$ is Y-8A and $R^2$ is H.

Table 1400. Compounds of formula I.18 wherein $R^1$ is Y-8B and $R^2$ is H.

Table 1401. Compounds of formula I.18 wherein $R^1$ is Y-1A and $R^2$ is $CH_3$.

Table 1402. Compounds of formula I.18 wherein $R^1$ is Y-1B and $R^2$ is $CH_3$.

Table 1403. Compounds of formula I.18 wherein $R^1$ is Y-2A and $R^2$ is $CH_3$.

Table 1404. Compounds of formula I.18 wherein $R^1$ is Y-2B and $R^2$ is $CH_3$.

Table 1405. Compounds of formula I.18 wherein $R^1$ is Y-3A and $R^2$ is $CH_3$.

Table 1406. Compounds of formula I.18 wherein $R^1$ is Y-3B and $R^2$ is $CH_3$.

Table 1407. Compounds of formula I.18 wherein $R^1$ is Y-3C and $R^2$ is $CH_3$.

Table 1408. Compounds of formula I.18 wherein $R^1$ is Y-3D and $R^2$ is $CH_3$.

Table 1409. Compounds of formula I.18 wherein $R^1$ is Y-4A and $R^2$ is $CH_3$.

Table 1410. Compounds of formula I.18 wherein $R^1$ is Y-4B and $R^2$ is $CH_3$.

Table 1411. Compounds of formula I.18 wherein $R^1$ is Y-4C and $R^2$ is $CH_3$.

Table 1412. Compounds of formula I.18 wherein $R^1$ is Y-4D and $R^2$ is $CH_3$.

Table 1413. Compounds of formula I.18 wherein $R^1$ is Y-5A and $R^2$ is $CH_3$.

Table 1414. Compounds of formula I.18 wherein $R^1$ is Y-5B and $R^2$ is $CH_3$.

Table 1415. Compounds of formula I.18 wherein $R^1$ is Y-6A and $R^2$ is $CH_3$.

Table 1416. Compounds of formula I.18 wherein $R^1$ is Y-6B and $R^2$ is $CH_3$.

Table 1417. Compounds of formula I.18 wherein $R^1$ is Y-7A and $R^2$ is $CH_3$.

Table 1418. Compounds of formula I.18 wherein $R^1$ is Y-7B and $R^2$ is $CH_3$.

Table 1419. Compounds of formula I.18 wherein $R^1$ is Y-8A and $R^2$ is $CH_3$.

Table 1420. Compounds of formula I.18 wherein $R^1$ is Y-8B and $R^2$ is $CH_3$.

Table 1421. Compounds of formula I.18 wherein $R^1$ is Y-1A and $R^2$ is c-$C_3H_5$.

Table 1422. Compounds of formula I.18 wherein $R^1$ is Y-1B and $R^2$ is c-$C_3H_5$.

Table 1423. Compounds of formula I.18 wherein $R^1$ is Y-2A and $R^2$ is c-$C_3H_5$.

Table 1424. Compounds of formula I.18 wherein $R^1$ is Y-2B and $R^2$ is c-$C_3H_5$.

Table 1425. Compounds of formula I.18 wherein $R^1$ is Y-3A and $R^2$ is c-$C_3H_5$.

Table 1426. Compounds of formula I.18 wherein $R^1$ is Y-3B and $R^2$ is c-$C_3H_5$.

Table 1427. Compounds of formula I.18 wherein $R^1$ is Y-3C and $R^2$ is c-$C_3H_5$.

Table 1428. Compounds of formula I.18 wherein $R^1$ is Y-3D and $R^2$ is c-$C_3H_5$.

Table 1429. Compounds of formula I.18 wherein $R^1$ is Y-4A and $R^2$ is c-$C_3H_5$.

Table 1430. Compounds of formula I.18 wherein $R^1$ is Y-4B and $R^2$ is c-$C_3H_5$.

Table 1431. Compounds of formula I.18 wherein $R^1$ is Y-4C and $R^2$ is c-$C_3H_5$.

Table 1432. Compounds of formula I.18 wherein $R^1$ is Y-4D and $R^2$ is c-$C_3H_5$.

Table 1433. Compounds of formula I.18 wherein $R^1$ is Y-5A and $R^2$ is c-$C_3H_5$.

Table 1434. Compounds of formula I.18 wherein $R^1$ is Y-5B and $R^2$ is c-$C_3H_5$.

Table 1435. Compounds of formula I.18 wherein $R^1$ is Y-6A and $R^2$ is c-$C_3H_5$.

Table 1436. Compounds of formula I.18 wherein $R^1$ is Y-6B and $R^2$ is c-$C_3H_5$.

Table 1437. Compounds of formula I.18 wherein $R^1$ is Y-7A and $R^2$ is c-$C_3H_5$.

Table 1438. Compounds of formula I.18 wherein $R^1$ is Y-7B and $R^2$ is c-$C_3H_5$.

Table 1439. Compounds of formula I.18 wherein $R^1$ is Y-8A and $R^2$ is c-$C_3H_5$.

Table 1440. Compounds of formula I.18 wherein $R^1$ is Y-8B and $R^2$ is c-$C_3H_5$.

TABLE B

| Line | W | $B^1$ | $B^2$ | $B^3$ | Ar | D |
|---|---|---|---|---|---|---|
| 1 | N1 | CH | CH | CH | $Ar^1$ | $R^{11}$-1 |
| 2 | N1 | CH | CH | CH | $Ar^1$ | $R^{11}$-2 |
| 3 | N1 | CH | CH | CH | $Ar^1$ | $R^{11}$-3 |
| 4 | N1 | CH | CH | CH | $Ar^1$ | $R^{11}$-5 |
| 5 | N1 | CH | CH | CH | $Ar^1$ | $R^{11}$-6 |
| 6 | N1 | CH | CH | CH | $Ar^1$ | $R^{11}$-7 |
| 7 | N1 | CH | CH | CH | $Ar^1$ | $R^{11}$-8 |
| 8 | N1 | CH | CH | CH | $Ar^1$ | $R^{11}$-9 |
| 9 | N1 | CH | CH | CH | $Ar^1$ | $R^{11}$-10 |
| 10 | N1 | CH | CH | CH | $Ar^1$ | $R^{11}$-11 |
| 11 | N1 | CH | CH | CH | $Ar^1$ | $R^{11}$-12 |
| 12 | N1 | CH | CH | CH | $Ar^1$ | $R^{11}$-13 |
| 13 | N1 | CH | CH | CH | $Ar^1$ | $R^{11}$-14 |
| 14 | N1 | CH | CH | CH | $Ar^1$ | $R^{11}$-15 |
| 15 | N1 | CH | CH | CH | $Ar^1$ | $R^{11}$-16 |
| 16 | N1 | CH | CH | CH | $Ar^1$ | $R^{11}$-17 |
| 17 | N1 | CH | CH | CH | $Ar^1$ | $R^{11}$-18 |
| 18 | N1 | CH | CH | CH | $Ar^1$ | $R^{11}$-19 |
| 19 | N1 | CH | CH | CH | $Ar^1$ | $R^{11}$-20 |
| 20 | N1 | CH | CH | CH | $Ar^1$ | $R^{11}$-21 |
| 21 | N1 | CH | CH | CH | $Ar^1$ | $R^{11}$-22 |
| 22 | N1 | CH | CH | CH | $Ar^1$ | $R^{11}$-23 |
| 23 | N1 | CH | CH | CH | $Ar^1$ | $R^{11}$-25 |
| 24 | N1 | CH | CH | CH | $Ar^1$ | $R^{11}$-26 |
| 25 | N1 | CH | CH | CH | $Ar^1$ | $R^{11}$-27 |
| 26 | N1 | CH | CH | CH | $Ar^1$ | $R^{11}$-28 |
| 27 | N1 | CH | CH | CH | $Ar^1$ | $R^{11}$-29 |
| 28 | N1 | CH | CH | CH | $Ar^1$ | $A^{11}$-1 |
| 29 | N1 | CH | CH | CH | $Ar^1$ | $A^{11}$-2 |
| 30 | N1 | CH | CH | CH | $Ar^1$ | $A^{11}$-3 |
| 31 | N1 | CH | CH | CH | $Ar^2$ | $R^{11}$-1 |
| 32 | N1 | CH | CH | CH | $Ar^2$ | $R^{11}$-2 |
| 33 | N1 | CH | CH | CH | $Ar^2$ | $R^{11}$-3 |
| 34 | N1 | CH | CH | CH | $Ar^2$ | $R^{11}$-5 |
| 35 | N1 | CH | CH | CH | $Ar^2$ | $R^{11}$-6 |
| 36 | N1 | CH | CH | CH | $Ar^2$ | $R^{11}$-7 |
| 37 | N1 | CH | CH | CH | $Ar^2$ | $R^{11}$-8 |
| 38 | N1 | CH | CH | CH | $Ar^2$ | $R^{11}$-9 |
| 39 | N1 | CH | CH | CH | $Ar^2$ | $R^{11}$-10 |
| 40 | N1 | CH | CH | CH | $Ar^2$ | $R^{11}$-11 |
| 41 | N1 | CH | CH | CH | $Ar^2$ | $R^{11}$-12 |
| 42 | N1 | CH | CH | CH | $Ar^2$ | $R^{11}$-13 |
| 43 | N1 | CH | CH | CH | $Ar^2$ | $R^{11}$-14 |
| 44 | N1 | CH | CH | CH | $Ar^2$ | $R^{11}$-15 |
| 45 | N1 | CH | CH | CH | $Ar^2$ | $R^{11}$-16 |
| 46 | N1 | CH | CH | CH | $Ar^2$ | $R^{11}$-17 |
| 47 | N1 | CH | CH | CH | $Ar^2$ | $R^{11}$-18 |
| 48 | N1 | CH | CH | CH | $Ar^2$ | $R^{11}$-19 |
| 49 | N1 | CH | CH | CH | $Ar^2$ | $R^{11}$-20 |
| 50 | N1 | CH | CH | CH | $Ar^2$ | $R^{11}$-21 |
| 51 | N1 | CH | CH | CH | $Ar^2$ | $R^{11}$-22 |
| 52 | N1 | CH | CH | CH | $Ar^2$ | $R^{11}$-23 |
| 53 | N1 | CH | CH | CH | $Ar^2$ | $R^{11}$-25 |
| 54 | N1 | CH | CH | CH | $Ar^2$ | $R^{11}$-26 |
| 55 | N1 | CH | CH | CH | $Ar^2$ | $R^{11}$-27 |
| 56 | N1 | CH | CH | CH | $Ar^2$ | $R^{11}$-28 |
| 57 | N1 | CH | CH | CH | $Ar^2$ | $R^{11}$-29 |
| 58 | N1 | CH | CH | CH | $Ar^2$ | $A^{11}$-1 |
| 59 | N1 | CH | CH | CH | $Ar^2$ | $A^{11}$-2 |
| 60 | N1 | CH | CH | CH | $Ar^2$ | $A^{11}$-3 |
| 61 | N1 | CH | CH | CH | $Ar^3$ | $R^{11}$-1 |
| 62 | N1 | CH | CH | CH | $Ar^3$ | $R^{11}$-2 |
| 63 | N1 | CH | CH | CH | $Ar^3$ | $R^{11}$-3 |
| 64 | N1 | CH | CH | CH | $Ar^3$ | $R^{11}$-5 |
| 65 | N1 | CH | CH | CH | $Ar^3$ | $R^{11}$-6 |
| 66 | N1 | CH | CH | CH | $Ar^3$ | $R^{11}$-7 |
| 67 | N1 | CH | CH | CH | $Ar^3$ | $R^{11}$-8 |
| 68 | N1 | CH | CH | CH | $Ar^3$ | $R^{11}$-9 |
| 69 | N1 | CH | CH | CH | $Ar^3$ | $R^{11}$-10 |
| 70 | N1 | CH | CH | CH | $Ar^3$ | $R^{11}$-11 |
| 71 | N1 | CH | CH | CH | $Ar^3$ | $R^{11}$-12 |
| 72 | N1 | CH | CH | CH | $Ar^3$ | $R^{11}$-13 |
| 73 | N1 | CH | CH | CH | $Ar^3$ | $R^{11}$-14 |
| 74 | N1 | CH | CH | CH | $Ar^3$ | $R^{11}$-15 |
| 75 | N1 | CH | CH | CH | $Ar^3$ | $R^{11}$-16 |
| 76 | N1 | CH | CH | CH | $Ar^3$ | $R^{11}$-17 |
| 77 | N1 | CH | CH | CH | $Ar^3$ | $R^{11}$-18 |
| 78 | N1 | CH | CH | CH | $Ar^3$ | $R^{11}$-19 |
| 79 | N1 | CH | CH | CH | $Ar^3$ | $R^{11}$-20 |
| 80 | N1 | CH | CH | CH | $Ar^3$ | $R^{11}$-21 |
| 81 | N1 | CH | CH | CH | $Ar^3$ | $R^{11}$-22 |
| 82 | N1 | CH | CH | CH | $Ar^3$ | $R^{11}$-23 |
| 83 | N1 | CH | CH | CH | $Ar^3$ | $R^{11}$-25 |
| 84 | N1 | CH | CH | CH | $Ar^3$ | $R^{11}$-26 |
| 85 | N1 | CH | CH | CH | $Ar^3$ | $R^{11}$-27 |
| 86 | N1 | CH | CH | CH | $Ar^3$ | $R^{11}$-28 |
| 87 | N1 | CH | CH | CH | $Ar^3$ | $R^{11}$-29 |
| 88 | N1 | CH | CH | CH | $Ar^3$ | $A^{11}$-1 |
| 89 | N1 | CH | CH | CH | $Ar^3$ | $A^{11}$-2 |
| 90 | N1 | CH | CH | CH | $Ar^3$ | $A^{11}$-3 |
| 91 | N1 | CH | CH | CH | $Ar^4$ | $R^{11}$-1 |
| 92 | N1 | CH | CH | CH | $Ar^4$ | $R^{11}$-2 |
| 93 | N1 | CH | CH | CH | $Ar^4$ | $R^{11}$-3 |
| 94 | N1 | CH | CH | CH | $Ar^4$ | $R^{11}$-5 |
| 95 | N1 | CH | CH | CH | $Ar^4$ | $R^{11}$-6 |
| 96 | N1 | CH | CH | CH | $Ar^4$ | $R^{11}$-7 |
| 97 | N1 | CH | CH | CH | $Ar^4$ | $R^{11}$-8 |
| 98 | N1 | CH | CH | CH | $Ar^4$ | $R^{11}$-9 |
| 99 | N1 | CH | CH | CH | $Ar^4$ | $R^{11}$-10 |
| 100 | N1 | CH | CH | CH | $Ar^4$ | $R^{11}$-11 |
| 101 | N1 | CH | CH | CH | $Ar^4$ | $R^{11}$-12 |
| 102 | N1 | CH | CH | CH | $Ar^4$ | $R^{11}$-13 |
| 103 | N1 | CH | CH | CH | $Ar^4$ | $R^{11}$-14 |
| 104 | N1 | CH | CH | CH | $Ar^4$ | $R^{11}$-15 |
| 105 | N1 | CH | CH | CH | $Ar^4$ | $R^{11}$-16 |
| 106 | N1 | CH | CH | CH | $Ar^4$ | $R^{11}$-17 |
| 107 | N1 | CH | CH | CH | $Ar^4$ | $R^{11}$-18 |
| 108 | N1 | CH | CH | CH | $Ar^4$ | $R^{11}$-19 |
| 109 | N1 | CH | CH | CH | $Ar^4$ | $R^{11}$-20 |
| 110 | N1 | CH | CH | CH | $Ar^4$ | $R^{11}$-21 |
| 111 | N1 | CH | CH | CH | $Ar^4$ | $R^{11}$-22 |
| 112 | N1 | CH | CH | CH | $Ar^4$ | $R^{11}$-23 |
| 113 | N1 | CH | CH | CH | $Ar^4$ | $R^{11}$-25 |
| 114 | N1 | CH | CH | CH | $Ar^4$ | $R^{11}$-26 |
| 115 | N1 | CH | CH | CH | $Ar^4$ | $R^{11}$-27 |
| 116 | N1 | CH | CH | CH | $Ar^4$ | $R^{11}$-28 |
| 117 | N1 | CH | CH | CH | $Ar^4$ | $R^{11}$-29 |
| 118 | N1 | CH | CH | CH | $Ar^4$ | $A^{11}$-1 |
| 119 | N1 | CH | CH | CH | $Ar^4$ | $A^{11}$-2 |
| 120 | N1 | CH | CH | CH | $Ar^4$ | $A^{11}$-3 |
| 121 | N1 | CH | CH | CH | $Ar^{10}$ | $R^{11}$-1 |
| 122 | N1 | CH | CH | CH | $Ar^{10}$ | $R^{11}$-2 |
| 123 | N1 | CH | CH | CH | $Ar^{10}$ | $R^{11}$-3 |
| 124 | N1 | CH | CH | CH | $Ar^{10}$ | $R^{11}$-5 |
| 125 | N1 | CH | CH | CH | $Ar^{10}$ | $R^{11}$-6 |
| 126 | N1 | CH | CH | CH | $Ar^{10}$ | $R^{11}$-7 |
| 127 | N1 | CH | CH | CH | $Ar^{10}$ | $R^{11}$-8 |
| 128 | N1 | CH | CH | CH | $Ar^{10}$ | $R^{11}$-9 |
| 129 | N1 | CH | CH | CH | $Ar^{10}$ | $R^{11}$-10 |
| 130 | N1 | CH | CH | CH | $Ar^{10}$ | $R^{11}$-11 |
| 131 | N1 | CH | CH | CH | $Ar^{10}$ | $R^{11}$-12 |
| 132 | N1 | CH | CH | CH | $Ar^{10}$ | $R^{11}$-13 |
| 133 | N1 | CH | CH | CH | $Ar^{10}$ | $R^{11}$-14 |
| 134 | N1 | CH | CH | CH | $Ar^{10}$ | $R^{11}$-15 |
| 135 | N1 | CH | CH | CH | $Ar^{10}$ | $R^{11}$-16 |
| 136 | N1 | CH | CH | CH | $Ar^{10}$ | $R^{11}$-17 |
| 137 | N1 | CH | CH | CH | $Ar^{10}$ | $R^{11}$-18 |
| 138 | N1 | CH | CH | CH | $Ar^{10}$ | $R^{11}$-19 |
| 139 | N1 | CH | CH | CH | $Ar^{10}$ | $R^{11}$-20 |
| 140 | N1 | CH | CH | CH | $Ar^{10}$ | $R^{11}$-21 |
| 141 | N1 | CH | CH | CH | $Ar^{10}$ | $R^{11}$-22 |
| 142 | N1 | CH | CH | CH | $Ar^{10}$ | $R^{11}$-23 |
| 143 | N1 | CH | CH | CH | $Ar^{10}$ | $R^{11}$-25 |
| 144 | N1 | CH | CH | CH | $Ar^{10}$ | $R^{11}$-26 |
| 145 | N1 | CH | CH | CH | $Ar^{10}$ | $R^{11}$-27 |

TABLE B-continued

| Line | W | $B^1$ | $B^2$ | $B^3$ | Ar | D |
|---|---|---|---|---|---|---|
| 146 | N1 | CH | CH | CH | $Ar^{10}$ | $R^{11}$-28 |
| 147 | N1 | CH | CH | CH | $Ar^{10}$ | $R^{11}$-29 |
| 148 | N1 | CH | CH | CH | $Ar^{10}$ | $A^{11}$-1 |
| 149 | N1 | CH | CH | CH | $Ar^{10}$ | $A^{11}$-2 |
| 150 | N1 | CH | CH | CH | $Ar^{10}$ | $A^{11}$-3 |
| 151 | N1 | CH | CH | CH | $Ar^{17}$ | $R^{11}$-1 |
| 152 | N1 | CH | CH | CH | $Ar^{17}$ | $R^{11}$-2 |
| 153 | N1 | CH | CH | CH | $Ar^{17}$ | $R^{11}$-3 |
| 154 | N1 | CH | CH | CH | $Ar^{17}$ | $R^{11}$-5 |
| 155 | N1 | CH | CH | CH | $Ar^{17}$ | $R^{11}$-6 |
| 156 | N1 | CH | CH | CH | $Ar^{17}$ | $R^{11}$-7 |
| 157 | N1 | CH | CH | CH | $Ar^{17}$ | $R^{11}$-8 |
| 158 | N1 | CH | CH | CH | $Ar^{17}$ | $R^{11}$-9 |
| 159 | N1 | CH | CH | CH | $Ar^{17}$ | $R^{11}$-10 |
| 160 | N1 | CH | CH | CH | $Ar^{17}$ | $R^{11}$-11 |
| 161 | N1 | CH | CH | CH | $Ar^{17}$ | $R^{11}$-12 |
| 162 | N1 | CH | CH | CH | $Ar^{17}$ | $R^{11}$-13 |
| 163 | N1 | CH | CH | CH | $Ar^{17}$ | $R^{11}$-14 |
| 164 | N1 | CH | CH | CH | $Ar^{17}$ | $R^{11}$-15 |
| 165 | N1 | CH | CH | CH | $Ar^{17}$ | $R^{11}$-16 |
| 166 | N1 | CH | CH | CH | $Ar^{17}$ | $R^{11}$-17 |
| 167 | N1 | CH | CH | CH | $Ar^{17}$ | $R^{11}$-18 |
| 168 | N1 | CH | CH | CH | $Ar^{17}$ | $R^{11}$-19 |
| 169 | N1 | CH | CH | CH | $Ar^{17}$ | $R^{11}$-20 |
| 170 | N1 | CH | CH | CH | $Ar^{17}$ | $R^{11}$-21 |
| 171 | N1 | CH | CH | CH | $Ar^{17}$ | $R^{11}$-22 |
| 172 | N1 | CH | CH | CH | $Ar^{17}$ | $R^{11}$-23 |
| 173 | N1 | CH | CH | CH | $Ar^{17}$ | $R^{11}$-25 |
| 174 | N1 | CH | CH | CH | $Ar^{17}$ | $R^{11}$-26 |
| 175 | N1 | CH | CH | CH | $Ar^{17}$ | $R^{11}$-27 |
| 176 | N1 | CH | CH | CH | $Ar^{17}$ | $R^{11}$-28 |
| 177 | N1 | CH | CH | CH | $Ar^{17}$ | $R^{11}$-29 |
| 178 | N1 | CH | CH | CH | $Ar^{17}$ | $A^{11}$-1 |
| 179 | N1 | CH | CH | CH | $Ar^{17}$ | $A^{11}$-2 |
| 180 | N1 | CH | CH | CH | $Ar^{17}$ | $A^{11}$-3 |
| 181 | N1 | CH | CH | CH | $Ar^{18}$ | $R^{11}$-1 |
| 182 | N1 | CH | CH | CH | $Ar^{18}$ | $R^{11}$-2 |
| 183 | N1 | CH | CH | CH | $Ar^{18}$ | $R^{11}$-3 |
| 184 | N1 | CH | CH | CH | $Ar^{18}$ | $R^{11}$-5 |
| 185 | N1 | CH | CH | CH | $Ar^{18}$ | $R^{11}$-6 |
| 186 | N1 | CH | CH | CH | $Ar^{18}$ | $R^{11}$-7 |
| 187 | N1 | CH | CH | CH | $Ar^{18}$ | $R^{11}$-8 |
| 188 | N1 | CH | CH | CH | $Ar^{18}$ | $R^{11}$-9 |
| 189 | N1 | CH | CH | CH | $Ar^{18}$ | $R^{11}$-10 |
| 190 | N1 | CH | CH | CH | $Ar^{18}$ | $R^{11}$-11 |
| 191 | N1 | CH | CH | CH | $Ar^{18}$ | $R^{11}$-12 |
| 192 | N1 | CH | CH | CH | $Ar^{18}$ | $R^{11}$-13 |
| 193 | N1 | CH | CH | CH | $Ar^{18}$ | $R^{11}$-14 |
| 194 | N1 | CH | CH | CH | $Ar^{18}$ | $R^{11}$-15 |
| 195 | N1 | CH | CH | CH | $Ar^{18}$ | $R^{11}$-16 |
| 196 | N1 | CH | CH | CH | $Ar^{18}$ | $R^{11}$-17 |
| 197 | N1 | CH | CH | CH | $Ar^{18}$ | $R^{11}$-18 |
| 198 | N1 | CH | CH | CH | $Ar^{18}$ | $R^{11}$-19 |
| 199 | N1 | CH | CH | CH | $Ar^{18}$ | $R^{11}$-20 |
| 200 | N1 | CH | CH | CH | $Ar^{18}$ | $R^{11}$-21 |
| 201 | N1 | CH | CH | CH | $Ar^{18}$ | $R^{11}$-22 |
| 202 | N1 | CH | CH | CH | $Ar^{18}$ | $R^{11}$-23 |
| 203 | N1 | CH | CH | CH | $Ar^{18}$ | $R^{11}$-25 |
| 204 | N1 | CH | CH | CH | $Ar^{18}$ | $R^{11}$-26 |
| 205 | N1 | CH | CH | CH | $Ar^{18}$ | $R^{11}$-27 |
| 206 | N1 | CH | CH | CH | $Ar^{18}$ | $R^{11}$-28 |
| 207 | N1 | CH | CH | CH | $Ar^{18}$ | $R^{11}$-29 |
| 208 | N1 | CH | CH | CH | $Ar^{18}$ | $A^{11}$-1 |
| 209 | N1 | CH | CH | CH | $Ar^{18}$ | $A^{11}$-2 |
| 210 | N1 | CH | CH | CH | $Ar^{18}$ | $A^{11}$-3 |
| 211 | N2 | CH | CH | CH | $Ar^1$ | $R^{11}$-1 |
| 212 | N2 | CH | CH | CH | $Ar^1$ | $R^{11}$-2 |
| 213 | N2 | CH | CH | CH | $Ar^1$ | $R^{11}$-3 |
| 214 | N2 | CH | CH | CH | $Ar^1$ | $R^{11}$-5 |
| 215 | N2 | CH | CH | CH | $Ar^1$ | $R^{11}$-6 |
| 216 | N2 | CH | CH | CH | $Ar^1$ | $R^{11}$-7 |
| 217 | N2 | CH | CH | CH | $Ar^1$ | $R^{11}$-8 |
| 218 | N2 | CH | CH | CH | $Ar^1$ | $R^{11}$-9 |
| 219 | N2 | CH | CH | CH | $Ar^1$ | $R^{11}$-10 |
| 220 | N2 | CH | CH | CH | $Ar^1$ | $R^{11}$-11 |
| 221 | N2 | CH | CH | CH | $Ar^1$ | $R^{11}$-12 |
| 222 | N2 | CH | CH | CH | $Ar^1$ | $R^{11}$-13 |
| 223 | N2 | CH | CH | CH | $Ar^1$ | $R^{11}$-14 |
| 224 | N2 | CH | CH | CH | $Ar^1$ | $R^{11}$-15 |
| 225 | N2 | CH | CH | CH | $Ar^1$ | $R^{11}$-16 |
| 226 | N2 | CH | CH | CH | $Ar^1$ | $R^{11}$-17 |
| 227 | N2 | CH | CH | CH | $Ar^1$ | $R^{11}$-18 |
| 228 | N2 | CH | CH | CH | $Ar^1$ | $R^{11}$-19 |
| 229 | N2 | CH | CH | CH | $Ar^1$ | $R^{11}$-20 |
| 230 | N2 | CH | CH | CH | $Ar^1$ | $R^{11}$-21 |
| 231 | N2 | CH | CH | CH | $Ar^1$ | $R^{11}$-22 |
| 232 | N2 | CH | CH | CH | $Ar^1$ | $R^{11}$-23 |
| 233 | N2 | CH | CH | CH | $Ar^1$ | $R^{11}$-25 |
| 234 | N2 | CH | CH | CH | $Ar^1$ | $R^{11}$-26 |
| 235 | N2 | CH | CH | CH | $Ar^1$ | $R^{11}$-27 |
| 236 | N2 | CH | CH | CH | $Ar^1$ | $R^{11}$-28 |
| 237 | N2 | CH | CH | CH | $Ar^1$ | $R^{11}$-29 |
| 238 | N2 | CH | CH | CH | $Ar^1$ | $A^{11}$-1 |
| 239 | N2 | CH | CH | CH | $Ar^1$ | $A^{11}$-2 |
| 240 | N2 | CH | CH | CH | $Ar^1$ | $A^{11}$-3 |
| 241 | N2 | CH | CH | CH | $Ar^2$ | $R^{11}$-1 |
| 242 | N2 | CH | CH | CH | $Ar^2$ | $R^{11}$-2 |
| 243 | N2 | CH | CH | CH | $Ar^2$ | $R^{11}$-3 |
| 244 | N2 | CH | CH | CH | $Ar^2$ | $R^{11}$-5 |
| 245 | N2 | CH | CH | CH | $Ar^2$ | $R^{11}$-6 |
| 246 | N2 | CH | CH | CH | $Ar^2$ | $R^{11}$-7 |
| 247 | N2 | CH | CH | CH | $Ar^2$ | $R^{11}$-8 |
| 248 | N2 | CH | CH | CH | $Ar^2$ | $R^{11}$-9 |
| 249 | N2 | CH | CH | CH | $Ar^2$ | $R^{11}$-10 |
| 250 | N2 | CH | CH | CH | $Ar^2$ | $R^{11}$-11 |
| 251 | N2 | CH | CH | CH | $Ar^2$ | $R^{11}$-12 |
| 252 | N2 | CH | CH | CH | $Ar^2$ | $R^{11}$-13 |
| 253 | N2 | CH | CH | CH | $Ar^2$ | $R^{11}$-14 |
| 254 | N2 | CH | CH | CH | $Ar^2$ | $R^{11}$-15 |
| 255 | N2 | CH | CH | CH | $Ar^2$ | $R^{11}$-16 |
| 256 | N2 | CH | CH | CH | $Ar^2$ | $R^{11}$-17 |
| 257 | N2 | CH | CH | CH | $Ar^2$ | $R^{11}$-18 |
| 258 | N2 | CH | CH | CH | $Ar^2$ | $R^{11}$-19 |
| 259 | N2 | CH | CH | CH | $Ar^2$ | $R^{11}$-20 |
| 260 | N2 | CH | CH | CH | $Ar^2$ | $R^{11}$-21 |
| 261 | N2 | CH | CH | CH | $Ar^2$ | $R^{11}$-22 |
| 262 | N2 | CH | CH | CH | $Ar^2$ | $R^{11}$-23 |
| 263 | N2 | CH | CH | CH | $Ar^2$ | $R^{11}$-25 |
| 264 | N2 | CH | CH | CH | $Ar^2$ | $R^{11}$-26 |
| 265 | N2 | CH | CH | CH | $Ar^2$ | $R^{11}$-27 |
| 266 | N2 | CH | CH | CH | $Ar^2$ | $R^{11}$-28 |
| 267 | N2 | CH | CH | CH | $Ar^2$ | $R^{11}$-29 |
| 268 | N2 | CH | CH | CH | $Ar^2$ | $A^{11}$-1 |
| 269 | N2 | CH | CH | CH | $Ar^2$ | $A^{11}$-2 |
| 270 | N2 | CH | CH | CH | $Ar^2$ | $A^{11}$-3 |
| 271 | N2 | CH | CH | CH | $Ar^3$ | $R^{11}$-1 |
| 272 | N2 | CH | CH | CH | $Ar^3$ | $R^{11}$-2 |
| 273 | N2 | CH | CH | CH | $Ar^3$ | $R^{11}$-3 |
| 274 | N2 | CH | CH | CH | $Ar^3$ | $R^{11}$-5 |
| 275 | N2 | CH | CH | CH | $Ar^3$ | $R^{11}$-6 |
| 276 | N2 | CH | CH | CH | $Ar^3$ | $R^{11}$-7 |
| 277 | N2 | CH | CH | CH | $Ar^3$ | $R^{11}$-8 |
| 278 | N2 | CH | CH | CH | $Ar^3$ | $R^{11}$-9 |
| 279 | N2 | CH | CH | CH | $Ar^3$ | $R^{11}$-10 |
| 280 | N2 | CH | CH | CH | $Ar^3$ | $R^{11}$-11 |
| 281 | N2 | CH | CH | CH | $Ar^3$ | $R^{11}$-12 |
| 282 | N2 | CH | CH | CH | $Ar^3$ | $R^{11}$-13 |
| 283 | N2 | CH | CH | CH | $Ar^3$ | $R^{11}$-14 |
| 284 | N2 | CH | CH | CH | $Ar^3$ | $R^{11}$-15 |
| 285 | N2 | CH | CH | CH | $Ar^3$ | $R^{11}$-16 |
| 286 | N2 | CH | CH | CH | $Ar^3$ | $R^{11}$-17 |
| 287 | N2 | CH | CH | CH | $Ar^3$ | $R^{11}$-18 |
| 288 | N2 | CH | CH | CH | $Ar^3$ | $R^{11}$-19 |
| 289 | N2 | CH | CH | CH | $Ar^3$ | $R^{11}$-20 |
| 290 | N2 | CH | CH | CH | $Ar^3$ | $R^{11}$-21 |
| 291 | N2 | CH | CH | CH | $Ar^3$ | $R^{11}$-22 |
| 292 | N2 | CH | CH | CH | $Ar^3$ | $R^{11}$-23 |
| 293 | N2 | CH | CH | CH | $Ar^3$ | $R^{11}$-25 |
| 294 | N2 | CH | CH | CH | $Ar^3$ | $R^{11}$-26 |
| 295 | N2 | CH | CH | CH | $Ar^3$ | $R^{11}$-27 |
| 296 | N2 | CH | CH | CH | $Ar^3$ | $R^{11}$-28 |
| 297 | N2 | CH | CH | CH | $Ar^3$ | $R^{11}$-29 |
| 298 | N2 | CH | CH | CH | $Ar^3$ | $A^{11}$-1 |
| 299 | N2 | CH | CH | CH | $Ar^3$ | $A^{11}$-2 |
| 300 | N2 | CH | CH | CH | $Ar^3$ | $A^{11}$-3 |
| 301 | N2 | CH | CH | CH | $Ar^4$ | $R^{11}$-1 |

TABLE B-continued

| Line | W | $B^1$ | $B^2$ | $B^3$ | Ar | D |
|---|---|---|---|---|---|---|
| 302 | N2 | CH | CH | CH | $Ar^4$ | $R^{11}$-2 |
| 303 | N2 | CH | CH | CH | $Ar^4$ | $R^{11}$-3 |
| 304 | N2 | CH | CH | CH | $Ar^4$ | $R^{11}$-5 |
| 305 | N2 | CH | CH | CH | $Ar^4$ | $R^{11}$-6 |
| 306 | N2 | CH | CH | CH | $Ar^4$ | $R^{11}$-7 |
| 307 | N2 | CH | CH | CH | $Ar^4$ | $R^{11}$-8 |
| 308 | N2 | CH | CH | CH | $Ar^4$ | $R^{11}$-9 |
| 309 | N2 | CH | CH | CH | $Ar^4$ | $R^{11}$-10 |
| 310 | N2 | CH | CH | CH | $Ar^4$ | $R^{11}$-11 |
| 311 | N2 | CH | CH | CH | $Ar^4$ | $R^{11}$-12 |
| 312 | N2 | CH | CH | CH | $Ar^4$ | $R^{11}$-13 |
| 313 | N2 | CH | CH | CH | $Ar^4$ | $R^{11}$-14 |
| 314 | N2 | CH | CH | CH | $Ar^4$ | $R^{11}$-15 |
| 315 | N2 | CH | CH | CH | $Ar^4$ | $R^{11}$-16 |
| 316 | N2 | CH | CH | CH | $Ar^4$ | $R^{11}$-17 |
| 317 | N2 | CH | CH | CH | $Ar^4$ | $R^{11}$-18 |
| 318 | N2 | CH | CH | CH | $Ar^4$ | $R^{11}$-19 |
| 319 | N2 | CH | CH | CH | $Ar^4$ | $R^{11}$-20 |
| 320 | N2 | CH | CH | CH | $Ar^4$ | $R^{11}$-21 |
| 321 | N2 | CH | CH | CH | $Ar^4$ | $R^{11}$-22 |
| 322 | N2 | CH | CH | CH | $Ar^4$ | $R^{11}$-23 |
| 323 | N2 | CH | CH | CH | $Ar^4$ | $R^{11}$-25 |
| 324 | N2 | CH | CH | CH | $Ar^4$ | $R^{11}$-26 |
| 325 | N2 | CH | CH | CH | $Ar^4$ | $R^{11}$-27 |
| 326 | N2 | CH | CH | CH | $Ar^4$ | $R^{11}$-28 |
| 327 | N2 | CH | CH | CH | $Ar^4$ | $R^{11}$-29 |
| 328 | N2 | CH | CH | CH | $Ar^4$ | $A^{11}$-1 |
| 329 | N2 | CH | CH | CH | $Ar^4$ | $A^{11}$-2 |
| 330 | N2 | CH | CH | CH | $Ar^4$ | $A^{11}$-3 |
| 331 | N2 | CH | CH | CH | $Ar^{10}$ | $R^{11}$-1 |
| 332 | N2 | CH | CH | CH | $Ar^{10}$ | $R^{11}$-2 |
| 333 | N2 | CH | CH | CH | $Ar^{10}$ | $R^{11}$-3 |
| 334 | N2 | CH | CH | CH | $Ar^{10}$ | $R^{11}$-5 |
| 335 | N2 | CH | CH | CH | $Ar^{10}$ | $R^{11}$-6 |
| 336 | N2 | CH | CH | CH | $Ar^{10}$ | $R^{11}$-7 |
| 337 | N2 | CH | CH | CH | $Ar^{10}$ | $R^{11}$-8 |
| 338 | N2 | CH | CH | CH | $Ar^{10}$ | $R^{11}$-9 |
| 339 | N2 | CH | CH | CH | $Ar^{10}$ | $R^{11}$-10 |
| 340 | N2 | CH | CH | CH | $Ar^{10}$ | $R^{11}$-11 |
| 341 | N2 | CH | CH | CH | $Ar^{10}$ | $R^{11}$-12 |
| 342 | N2 | CH | CH | CH | $Ar^{10}$ | $R^{11}$-13 |
| 343 | N2 | CH | CH | CH | $Ar^{10}$ | $R^{11}$-14 |
| 344 | N2 | CH | CH | CH | $Ar^{10}$ | $R^{11}$-15 |
| 345 | N2 | CH | CH | CH | $Ar^{10}$ | $R^{11}$-16 |
| 346 | N2 | CH | CH | CH | $Ar^{10}$ | $R^{11}$-17 |
| 347 | N2 | CH | CH | CH | $Ar^{10}$ | $R^{11}$-18 |
| 348 | N2 | CH | CH | CH | $Ar^{10}$ | $R^{11}$-19 |
| 349 | N2 | CH | CH | CH | $Ar^{10}$ | $R^{11}$-20 |
| 350 | N2 | CH | CH | CH | $Ar^{10}$ | $R^{11}$-21 |
| 351 | N2 | CH | CH | CH | $Ar^{10}$ | $R^{11}$-22 |
| 352 | N2 | CH | CH | CH | $Ar^{10}$ | $R^{11}$-23 |
| 353 | N2 | CH | CH | CH | $Ar^{10}$ | $R^{11}$-25 |
| 354 | N2 | CH | CH | CH | $Ar^{10}$ | $R^{11}$-26 |
| 355 | N2 | CH | CH | CH | $Ar^{10}$ | $R^{11}$-27 |
| 356 | N2 | CH | CH | CH | $Ar^{10}$ | $R^{11}$-28 |
| 357 | N2 | CH | CH | CH | $Ar^{10}$ | $R^{11}$-29 |
| 358 | N2 | CH | CH | CH | $Ar^{10}$ | $A^{11}$-1 |
| 359 | N2 | CH | CH | CH | $Ar^{10}$ | $A^{11}$-2 |
| 360 | N2 | CH | CH | CH | $Ar^{10}$ | $A^{11}$-3 |
| 361 | N2 | CH | CH | CH | $Ar^{17}$ | $R^{11}$-1 |
| 362 | N2 | CH | CH | CH | $Ar^{17}$ | $R^{11}$-2 |
| 363 | N2 | CH | CH | CH | $Ar^{17}$ | $R^{11}$-3 |
| 364 | N2 | CH | CH | CH | $Ar^{17}$ | $R^{11}$-5 |
| 365 | N2 | CH | CH | CH | $Ar^{17}$ | $R^{11}$-6 |
| 366 | N2 | CH | CH | CH | $Ar^{17}$ | $R^{11}$-7 |
| 367 | N2 | CH | CH | CH | $Ar^{17}$ | $R^{11}$-8 |
| 368 | N2 | CH | CH | CH | $Ar^{17}$ | $R^{11}$-9 |
| 369 | N2 | CH | CH | CH | $Ar^{17}$ | $R^{11}$-10 |
| 370 | N2 | CH | CH | CH | $Ar^{17}$ | $R^{11}$-11 |
| 371 | N2 | CH | CH | CH | $Ar^{17}$ | $R^{11}$-12 |
| 372 | N2 | CH | CH | CH | $Ar^{17}$ | $R^{11}$-13 |
| 373 | N2 | CH | CH | CH | $Ar^{17}$ | $R^{11}$-14 |
| 374 | N2 | CH | CH | CH | $Ar^{17}$ | $R^{11}$-15 |
| 375 | N2 | CH | CH | CH | $Ar^{17}$ | $R^{11}$-16 |
| 376 | N2 | CH | CH | CH | $Ar^{17}$ | $R^{11}$-17 |
| 377 | N2 | CH | CH | CH | $Ar^{17}$ | $R^{11}$-18 |
| 378 | N2 | CH | CH | CH | $Ar^{17}$ | $R^{11}$-19 |
| 379 | N2 | CH | CH | CH | $Ar^{17}$ | $R^{11}$-20 |

TABLE B-continued

| Line | W | $B^1$ | $B^2$ | $B^3$ | Ar | D |
|---|---|---|---|---|---|---|
| 380 | N2 | CH | CH | CH | $Ar^{17}$ | $R^{11}$-21 |
| 381 | N2 | CH | CH | CH | $Ar^{17}$ | $R^{11}$-22 |
| 382 | N2 | CH | CH | CH | $Ar^{17}$ | $R^{11}$-23 |
| 383 | N2 | CH | CH | CH | $Ar^{17}$ | $R^{11}$-25 |
| 384 | N2 | CH | CH | CH | $Ar^{17}$ | $R^{11}$-26 |
| 385 | N2 | CH | CH | CH | $Ar^{17}$ | $R^{11}$-27 |
| 386 | N2 | CH | CH | CH | $Ar^{17}$ | $R^{11}$-28 |
| 387 | N2 | CH | CH | CH | $Ar^{17}$ | $R^{11}$-29 |
| 388 | N2 | CH | CH | CH | $Ar^{17}$ | $A^{11}$-1 |
| 389 | N2 | CH | CH | CH | $Ar^{17}$ | $A^{11}$-2 |
| 390 | N2 | CH | CH | CH | $Ar^{17}$ | $A^{11}$-3 |
| 391 | N2 | CH | CH | CH | $Ar^{18}$ | $R^{11}$-1 |
| 392 | N2 | CH | CH | CH | $Ar^{18}$ | $R^{11}$-2 |
| 393 | N2 | CH | CH | CH | $Ar^{18}$ | $R^{11}$-3 |
| 394 | N2 | CH | CH | CH | $Ar^{18}$ | $R^{11}$-5 |
| 395 | N2 | CH | CH | CH | $Ar^{18}$ | $R^{11}$-6 |
| 396 | N2 | CH | CH | CH | $Ar^{18}$ | $R^{11}$-7 |
| 397 | N2 | CH | CH | CH | $Ar^{18}$ | $R^{11}$-8 |
| 398 | N2 | CH | CH | CH | $Ar^{18}$ | $R^{11}$-9 |
| 399 | N2 | CH | CH | CH | $Ar^{18}$ | $R^{11}$-10 |
| 400 | N2 | CH | CH | CH | $Ar^{18}$ | $R^{11}$-11 |
| 401 | N2 | CH | CH | CH | $Ar^{18}$ | $R^{11}$-12 |
| 402 | N2 | CH | CH | CH | $Ar^{18}$ | $R^{11}$-13 |
| 403 | N2 | CH | CH | CH | $Ar^{18}$ | $R^{11}$-14 |
| 404 | N2 | CH | CH | CH | $Ar^{18}$ | $R^{11}$-15 |
| 405 | N2 | CH | CH | CH | $Ar^{18}$ | $R^{11}$-16 |
| 406 | N2 | CH | CH | CH | $Ar^{18}$ | $R^{11}$-17 |
| 407 | N2 | CH | CH | CH | $Ar^{18}$ | $R^{11}$-18 |
| 408 | N2 | CH | CH | CH | $Ar^{18}$ | $R^{11}$-19 |
| 409 | N2 | CH | CH | CH | $Ar^{18}$ | $R^{11}$-20 |
| 410 | N2 | CH | CH | CH | $Ar^{18}$ | $R^{11}$-21 |
| 411 | N2 | CH | CH | CH | $Ar^{18}$ | $R^{11}$-22 |
| 412 | N2 | CH | CH | CH | $Ar^{18}$ | $R^{11}$-23 |
| 413 | N2 | CH | CH | CH | $Ar^{18}$ | $R^{11}$-25 |
| 414 | N2 | CH | CH | CH | $Ar^{18}$ | $R^{11}$-26 |
| 415 | N2 | CH | CH | CH | $Ar^{18}$ | $R^{11}$-27 |
| 416 | N2 | CH | CH | CH | $Ar^{18}$ | $R^{11}$-28 |
| 417 | N2 | CH | CH | CH | $Ar^{18}$ | $R^{11}$-29 |
| 418 | N2 | CH | CH | CH | $Ar^{18}$ | $A^{11}$-1 |
| 419 | N2 | CH | CH | CH | $Ar^{18}$ | $A^{11}$-2 |
| 420 | N2 | CH | CH | CH | $Ar^{18}$ | $A^{11}$-3 |
| 421 | N3 | CH | CH | CH | $Ar^1$ | $R^{11}$-1 |
| 422 | N3 | CH | CH | CH | $Ar^1$ | $R^{11}$-2 |
| 423 | N3 | CH | CH | CH | $Ar^1$ | $R^{11}$-3 |
| 424 | N3 | CH | CH | CH | $Ar^1$ | $R^{11}$-5 |
| 425 | N3 | CH | CH | CH | $Ar^1$ | $R^{11}$-6 |
| 426 | N3 | CH | CH | CH | $Ar^1$ | $R^{11}$-7 |
| 427 | N3 | CH | CH | CH | $Ar^1$ | $R^{11}$-8 |
| 428 | N3 | CH | CH | CH | $Ar^1$ | $R^{11}$-9 |
| 429 | N3 | CH | CH | CH | $Ar^1$ | $R^{11}$-10 |
| 430 | N3 | CH | CH | CH | $Ar^1$ | $R^{11}$-11 |
| 431 | N3 | CH | CH | CH | $Ar^1$ | $R^{11}$-12 |
| 432 | N3 | CH | CH | CH | $Ar^1$ | $R^{11}$-13 |
| 433 | N3 | CH | CH | CH | $Ar^1$ | $R^{11}$-14 |
| 434 | N3 | CH | CH | CH | $Ar^1$ | $R^{11}$-15 |
| 435 | N3 | CH | CH | CH | $Ar^1$ | $R^{11}$-16 |
| 436 | N3 | CH | CH | CH | $Ar^1$ | $R^{11}$-17 |
| 437 | N3 | CH | CH | CH | $Ar^1$ | $R^{11}$-18 |
| 438 | N3 | CH | CH | CH | $Ar^1$ | $R^{11}$-19 |
| 439 | N3 | CH | CH | CH | $Ar^1$ | $R^{11}$-20 |
| 440 | N3 | CH | CH | CH | $Ar^1$ | $R^{11}$-21 |
| 441 | N3 | CH | CH | CH | $Ar^1$ | $R^{11}$-22 |
| 442 | N3 | CH | CH | CH | $Ar^1$ | $R^{11}$-23 |
| 443 | N3 | CH | CH | CH | $Ar^1$ | $R^{11}$-25 |
| 444 | N3 | CH | CH | CH | $Ar^1$ | $R^{11}$-26 |
| 445 | N3 | CH | CH | CH | $Ar^1$ | $R^{11}$-27 |
| 446 | N3 | CH | CH | CH | $Ar^1$ | $R^{11}$-28 |
| 447 | N3 | CH | CH | CH | $Ar^1$ | $R^{11}$-29 |
| 448 | N3 | CH | CH | CH | $Ar^1$ | $A^{11}$-1 |
| 449 | N3 | CH | CH | CH | $Ar^1$ | $A^{11}$-2 |
| 450 | N3 | CH | CH | CH | $Ar^1$ | $A^{11}$-3 |
| 451 | N3 | CH | CH | CH | $Ar^2$ | $R^{11}$-1 |
| 452 | N3 | CH | CH | CH | $Ar^2$ | $R^{11}$-2 |
| 453 | N3 | CH | CH | CH | $Ar^2$ | $R^{11}$-3 |
| 454 | N3 | CH | CH | CH | $Ar^2$ | $R^{11}$-5 |
| 455 | N3 | CH | CH | CH | $Ar^2$ | $R^{11}$-6 |
| 456 | N3 | CH | CH | CH | $Ar^2$ | $R^{11}$-7 |
| 457 | N3 | CH | CH | CH | $Ar^2$ | $R^{11}$-8 |

TABLE B-continued

| Line | W | $B^1$ | $B^2$ | $B^3$ | Ar | D |
|---|---|---|---|---|---|---|
| 458 | N3 | CH | CH | CH | $Ar^2$ | $R^{11}$-9 |
| 459 | N3 | CH | CH | CH | $Ar^2$ | $R^{11}$-10 |
| 460 | N3 | CH | CH | CH | $Ar^2$ | $R^{11}$-11 |
| 461 | N3 | CH | CH | CH | $Ar^2$ | $R^{11}$-12 |
| 462 | N3 | CH | CH | CH | $Ar^2$ | $R^{11}$-13 |
| 463 | N3 | CH | CH | CH | $Ar^2$ | $R^{11}$-14 |
| 464 | N3 | CH | CH | CH | $Ar^2$ | $R^{11}$-15 |
| 465 | N3 | CH | CH | CH | $Ar^2$ | $R^{11}$-16 |
| 466 | N3 | CH | CH | CH | $Ar^2$ | $R^{11}$-17 |
| 467 | N3 | CH | CH | CH | $Ar^2$ | $R^{11}$-18 |
| 468 | N3 | CH | CH | CH | $Ar^2$ | $R^{11}$-19 |
| 469 | N3 | CH | CH | CH | $Ar^2$ | $R^{11}$-20 |
| 470 | N3 | CH | CH | CH | $Ar^2$ | $R^{11}$-21 |
| 471 | N3 | CH | CH | CH | $Ar^2$ | $R^{11}$-22 |
| 472 | N3 | CH | CH | CH | $Ar^2$ | $R^{11}$-23 |
| 473 | N3 | CH | CH | CH | $Ar^2$ | $R^{11}$-25 |
| 474 | N3 | CH | CH | CH | $Ar^2$ | $R^{11}$-26 |
| 475 | N3 | CH | CH | CH | $Ar^2$ | $R^{11}$-27 |
| 476 | N3 | CH | CH | CH | $Ar^2$ | $R^{11}$-28 |
| 477 | N3 | CH | CH | CH | $Ar^2$ | $R^{11}$-29 |
| 478 | N3 | CH | CH | CH | $Ar^2$ | $A^{11}$-1 |
| 479 | N3 | CH | CH | CH | $Ar^2$ | $A^{11}$-2 |
| 480 | N3 | CH | CH | CH | $Ar^2$ | $A^{11}$-3 |
| 481 | N3 | CH | CH | CH | $Ar^3$ | $R^{11}$-1 |
| 482 | N3 | CH | CH | CH | $Ar^3$ | $R^{11}$-2 |
| 483 | N3 | CH | CH | CH | $Ar^3$ | $R^{11}$-3 |
| 484 | N3 | CH | CH | CH | $Ar^3$ | $R^{11}$-5 |
| 485 | N3 | CH | CH | CH | $Ar^3$ | $R^{11}$-6 |
| 486 | N3 | CH | CH | CH | $Ar^3$ | $R^{11}$-7 |
| 487 | N3 | CH | CH | CH | $Ar^3$ | $R^{11}$-8 |
| 488 | N3 | CH | CH | CH | $Ar^3$ | $R^{11}$-9 |
| 489 | N3 | CH | CH | CH | $Ar^3$ | $R^{11}$-10 |
| 490 | N3 | CH | CH | CH | $Ar^3$ | $R^{11}$-11 |
| 491 | N3 | CH | CH | CH | $Ar^3$ | $R^{11}$-12 |
| 492 | N3 | CH | CH | CH | $Ar^3$ | $R^{11}$-13 |
| 493 | N3 | CH | CH | CH | $Ar^3$ | $R^{11}$-14 |
| 494 | N3 | CH | CH | CH | $Ar^3$ | $R^{11}$-15 |
| 495 | N3 | CH | CH | CH | $Ar^3$ | $R^{11}$-16 |
| 496 | N3 | CH | CH | CH | $Ar^3$ | $R^{11}$-17 |
| 497 | N3 | CH | CH | CH | $Ar^3$ | $R^{11}$-18 |
| 498 | N3 | CH | CH | CH | $Ar^3$ | $R^{11}$-19 |
| 499 | N3 | CH | CH | CH | $Ar^3$ | $R^{11}$-20 |
| 500 | N3 | CH | CH | CH | $Ar^3$ | $R^{11}$-21 |
| 501 | N3 | CH | CH | CH | $Ar^3$ | $R^{11}$-22 |
| 502 | N3 | CH | CH | CH | $Ar^3$ | $R^{11}$-23 |
| 503 | N3 | CH | CH | CH | $Ar^3$ | $R^{11}$-25 |
| 504 | N3 | CH | CH | CH | $Ar^3$ | $R^{11}$-26 |
| 505 | N3 | CH | CH | CH | $Ar^3$ | $R^{11}$-27 |
| 506 | N3 | CH | CH | CH | $Ar^3$ | $R^{11}$-28 |
| 507 | N3 | CH | CH | CH | $Ar^3$ | $R^{11}$-29 |
| 508 | N3 | CH | CH | CH | $Ar^3$ | $A^{11}$-1 |
| 509 | N3 | CH | CH | CH | $Ar^3$ | $A^{11}$-2 |
| 510 | N3 | CH | CH | CH | $Ar^3$ | $A^{11}$-3 |
| 511 | N3 | CH | CH | CH | $Ar^4$ | $R^{11}$-1 |
| 512 | N3 | CH | CH | CH | $Ar^4$ | $R^{11}$-2 |
| 513 | N3 | CH | CH | CH | $Ar^4$ | $R^{11}$-3 |
| 514 | N3 | CH | CH | CH | $Ar^4$ | $R^{11}$-5 |
| 515 | N3 | CH | CH | CH | $Ar^4$ | $R^{11}$-6 |
| 516 | N3 | CH | CH | CH | $Ar^4$ | $R^{11}$-7 |
| 517 | N3 | CH | CH | CH | $Ar^4$ | $R^{11}$-8 |
| 518 | N3 | CH | CH | CH | $Ar^4$ | $R^{11}$-9 |
| 519 | N3 | CH | CH | CH | $Ar^4$ | $R^{11}$-10 |
| 520 | N3 | CH | CH | CH | $Ar^4$ | $R^{11}$-11 |
| 521 | N3 | CH | CH | CH | $Ar^4$ | $R^{11}$-12 |
| 522 | N3 | CH | CH | CH | $Ar^4$ | $R^{11}$-13 |
| 523 | N3 | CH | CH | CH | $Ar^4$ | $R^{11}$-14 |
| 524 | N3 | CH | CH | CH | $Ar^4$ | $R^{11}$-15 |
| 525 | N3 | CH | CH | CH | $Ar^4$ | $R^{11}$-16 |
| 526 | N3 | CH | CH | CH | $Ar^4$ | $R^{11}$-17 |
| 527 | N3 | CH | CH | CH | $Ar^4$ | $R^{11}$-18 |
| 528 | N3 | CH | CH | CH | $Ar^4$ | $R^{11}$-19 |
| 529 | N3 | CH | CH | CH | $Ar^4$ | $R^{11}$-20 |
| 530 | N3 | CH | CH | CH | $Ar^4$ | $R^{11}$-21 |
| 531 | N3 | CH | CH | CH | $Ar^4$ | $R^{11}$-22 |
| 532 | N3 | CH | CH | CH | $Ar^4$ | $R^{11}$-23 |
| 533 | N3 | CH | CH | CH | $Ar^4$ | $R^{11}$-25 |
| 534 | N3 | CH | CH | CH | $Ar^4$ | $R^{11}$-26 |
| 535 | N3 | CH | CH | CH | $Ar^4$ | $R^{11}$-27 |

TABLE B-continued

| Line | W | $B^1$ | $B^2$ | $B^3$ | Ar | D |
|---|---|---|---|---|---|---|
| 536 | N3 | CH | CH | CH | $Ar^4$ | $R^{11}$-28 |
| 537 | N3 | CH | CH | CH | $Ar^4$ | $R^{11}$-29 |
| 538 | N3 | CH | CH | CH | $Ar^4$ | $A^{11}$-1 |
| 539 | N3 | CH | CH | CH | $Ar^4$ | $A^{11}$-2 |
| 540 | N3 | CH | CH | CH | $Ar^4$ | $A^{11}$-3 |
| 541 | N3 | CH | CH | CH | $Ar^{10}$ | $R^{11}$-1 |
| 542 | N3 | CH | CH | CH | $Ar^{10}$ | $R^{11}$-2 |
| 543 | N3 | CH | CH | CH | $Ar^{10}$ | $R^{11}$-3 |
| 544 | N3 | CH | CH | CH | $Ar^{10}$ | $R^{11}$-5 |
| 545 | N3 | CH | CH | CH | $Ar^{10}$ | $R^{11}$-6 |
| 546 | N3 | CH | CH | CH | $Ar^{10}$ | $R^{11}$-7 |
| 547 | N3 | CH | CH | CH | $Ar^{10}$ | $R^{11}$-8 |
| 548 | N3 | CH | CH | CH | $Ar^{10}$ | $R^{11}$-9 |
| 549 | N3 | CH | CH | CH | $Ar^{10}$ | $R^{11}$-10 |
| 550 | N3 | CH | CH | CH | $Ar^{10}$ | $R^{11}$-11 |
| 551 | N3 | CH | CH | CH | $Ar^{10}$ | $R^{11}$-12 |
| 552 | N3 | CH | CH | CH | $Ar^{10}$ | $R^{11}$-13 |
| 553 | N3 | CH | CH | CH | $Ar^{10}$ | $R^{11}$-14 |
| 554 | N3 | CH | CH | CH | $Ar^{10}$ | $R^{11}$-15 |
| 555 | N3 | CH | CH | CH | $Ar^{10}$ | $R^{11}$-16 |
| 556 | N3 | CH | CH | CH | $Ar^{10}$ | $R^{11}$-17 |
| 557 | N3 | CH | CH | CH | $Ar^{10}$ | $R^{11}$-18 |
| 558 | N3 | CH | CH | CH | $Ar^{10}$ | $R^{11}$-19 |
| 559 | N3 | CH | CH | CH | $Ar^{10}$ | $R^{11}$-20 |
| 560 | N3 | CH | CH | CH | $Ar^{10}$ | $R^{11}$-21 |
| 561 | N3 | CH | CH | CH | $Ar^{10}$ | $R^{11}$-22 |
| 562 | N3 | CH | CH | CH | $Ar^{10}$ | $R^{11}$-23 |
| 563 | N3 | CH | CH | CH | $Ar^{10}$ | $R^{11}$-25 |
| 564 | N3 | CH | CH | CH | $Ar^{10}$ | $R^{11}$-26 |
| 565 | N3 | CH | CH | CH | $Ar^{10}$ | $R^{11}$-27 |
| 566 | N3 | CH | CH | CH | $Ar^{10}$ | $R^{11}$-28 |
| 567 | N3 | CH | CH | CH | $Ar^{10}$ | $R^{11}$-29 |
| 568 | N3 | CH | CH | CH | $Ar^{10}$ | $A^{11}$-1 |
| 569 | N3 | CH | CH | CH | $Ar^{10}$ | $A^{11}$-2 |
| 570 | N3 | CH | CH | CH | $Ar^{10}$ | $A^{11}$-3 |
| 571 | N3 | CH | CH | CH | $Ar^{17}$ | $R^{11}$-1 |
| 572 | N3 | CH | CH | CH | $Ar^{17}$ | $R^{11}$-2 |
| 573 | N3 | CH | CH | CH | $Ar^{17}$ | $R^{11}$-3 |
| 574 | N3 | CH | CH | CH | $Ar^{17}$ | $R^{11}$-5 |
| 575 | N3 | CH | CH | CH | $Ar^{17}$ | $R^{11}$-6 |
| 576 | N3 | CH | CH | CH | $Ar^{17}$ | $R^{11}$-7 |
| 577 | N3 | CH | CH | CH | $Ar^{17}$ | $R^{11}$-8 |
| 578 | N3 | CH | CH | CH | $Ar^{17}$ | $R^{11}$-9 |
| 579 | N3 | CH | CH | CH | $Ar^{17}$ | $R^{11}$-10 |
| 580 | N3 | CH | CH | CH | $Ar^{17}$ | $R^{11}$-11 |
| 581 | N3 | CH | CH | CH | $Ar^{17}$ | $R^{11}$-12 |
| 582 | N3 | CH | CH | CH | $Ar^{17}$ | $R^{11}$-13 |
| 583 | N3 | CH | CH | CH | $Ar^{17}$ | $R^{11}$-14 |
| 584 | N3 | CH | CH | CH | $Ar^{17}$ | $R^{11}$-15 |
| 585 | N3 | CH | CH | CH | $Ar^{17}$ | $R^{11}$-16 |
| 586 | N3 | CH | CH | CH | $Ar^{17}$ | $R^{11}$-17 |
| 587 | N3 | CH | CH | CH | $Ar^{17}$ | $R^{11}$-18 |
| 588 | N3 | CH | CH | CH | $Ar^{17}$ | $R^{11}$-19 |
| 589 | N3 | CH | CH | CH | $Ar^{17}$ | $R^{11}$-20 |
| 590 | N3 | CH | CH | CH | $Ar^{17}$ | $R^{11}$-21 |
| 591 | N3 | CH | CH | CH | $Ar^{17}$ | $R^{11}$-22 |
| 592 | N3 | CH | CH | CH | $Ar^{17}$ | $R^{11}$-23 |
| 593 | N3 | CH | CH | CH | $Ar^{17}$ | $R^{11}$-25 |
| 594 | N3 | CH | CH | CH | $Ar^{17}$ | $R^{11}$-26 |
| 595 | N3 | CH | CH | CH | $Ar^{17}$ | $R^{11}$-27 |
| 596 | N3 | CH | CH | CH | $Ar^{17}$ | $R^{11}$-28 |
| 597 | N3 | CH | CH | CH | $Ar^{17}$ | $R^{11}$-29 |
| 598 | N3 | CH | CH | CH | $Ar^{17}$ | $A^{11}$-1 |
| 599 | N3 | CH | CH | CH | $Ar^{17}$ | $A^{11}$-2 |
| 600 | N3 | CH | CH | CH | $Ar^{17}$ | $A^{11}$-3 |
| 601 | N3 | CH | CH | CH | $Ar^{18}$ | $R^{11}$-1 |
| 602 | N3 | CH | CH | CH | $Ar^{18}$ | $R^{11}$-2 |
| 603 | N3 | CH | CH | CH | $Ar^{18}$ | $R^{11}$-3 |
| 604 | N3 | CH | CH | CH | $Ar^{18}$ | $R^{11}$-5 |
| 605 | N3 | CH | CH | CH | $Ar^{18}$ | $R^{11}$-6 |
| 606 | N3 | CH | CH | CH | $Ar^{18}$ | $R^{11}$-7 |
| 607 | N3 | CH | CH | CH | $Ar^{18}$ | $R^{11}$-8 |
| 608 | N3 | CH | CH | CH | $Ar^{18}$ | $R^{11}$-9 |
| 609 | N3 | CH | CH | CH | $Ar^{18}$ | $R^{11}$-10 |
| 610 | N3 | CH | CH | CH | $Ar^{18}$ | $R^{11}$-11 |
| 611 | N3 | CH | CH | CH | $Ar^{18}$ | $R^{11}$-12 |
| 612 | N3 | CH | CH | CH | $Ar^{18}$ | $R^{11}$-13 |
| 613 | N3 | CH | CH | CH | $Ar^{18}$ | $R^{11}$-14 |

TABLE B-continued

| Line | W | $B^1$ | $B^2$ | $B^3$ | Ar | D |
|---|---|---|---|---|---|---|
| 614 | N3 | CH | CH | CH | $Ar^{18}$ | $R^{11}$-15 |
| 615 | N3 | CH | CH | CH | $Ar^{18}$ | $R^{11}$-16 |
| 616 | N3 | CH | CH | CH | $Ar^{18}$ | $R^{11}$-17 |
| 617 | N3 | CH | CH | CH | $Ar^{18}$ | $R^{11}$-18 |
| 618 | N3 | CH | CH | CH | $Ar^{18}$ | $R^{11}$-19 |
| 619 | N3 | CH | CH | CH | $Ar^{18}$ | $R^{11}$-20 |
| 620 | N3 | CH | CH | CH | $Ar^{18}$ | $R^{11}$-21 |
| 621 | N3 | CH | CH | CH | $Ar^{18}$ | $R^{11}$-22 |
| 622 | N3 | CH | CH | CH | $Ar^{18}$ | $R^{11}$-23 |
| 623 | N3 | CH | CH | CH | $Ar^{18}$ | $R^{11}$-25 |
| 624 | N3 | CH | CH | CH | $Ar^{18}$ | $R^{11}$-26 |
| 625 | N3 | CH | CH | CH | $Ar^{18}$ | $R^{11}$-27 |
| 626 | N3 | CH | CH | CH | $Ar^{18}$ | $R^{11}$-28 |
| 627 | N3 | CH | CH | CH | $Ar^{18}$ | $R^{11}$-29 |
| 628 | N3 | CH | CH | CH | $Ar^{18}$ | $A^{11}$-1 |
| 629 | N3 | CH | CH | CH | $Ar^{18}$ | $A^{11}$-2 |
| 630 | N3 | CH | CH | CH | $Ar^{18}$ | $A^{11}$-3 |
| 631 | O | CH | CH | CH | $Ar^1$ | $R^{11}$-1 |
| 632 | O | CH | CH | CH | $Ar^1$ | $R^{11}$-2 |
| 633 | O | CH | CH | CH | $Ar^1$ | $R^{11}$-3 |
| 634 | O | CH | CH | CH | $Ar^1$ | $R^{11}$-5 |
| 635 | O | CH | CH | CH | $Ar^1$ | $R^{11}$-6 |
| 636 | O | CH | CH | CH | $Ar^1$ | $R^{11}$-7 |
| 637 | O | CH | CH | CH | $Ar^1$ | $R^{11}$-8 |
| 638 | O | CH | CH | CH | $Ar^1$ | $R^{11}$-9 |
| 639 | O | CH | CH | CH | $Ar^1$ | $R^{11}$-10 |
| 640 | O | CH | CH | CH | $Ar^1$ | $R^{11}$-11 |
| 641 | O | CH | CH | CH | $Ar^1$ | $R^{11}$-12 |
| 642 | O | CH | CH | CH | $Ar^1$ | $R^{11}$-13 |
| 643 | O | CH | CH | CH | $Ar^1$ | $R^{11}$-14 |
| 644 | O | CH | CH | CH | $Ar^1$ | $R^{11}$-15 |
| 645 | O | CH | CH | CH | $Ar^1$ | $R^{11}$-16 |
| 646 | O | CH | CH | CH | $Ar^1$ | $R^{11}$-17 |
| 647 | O | CH | CH | CH | $Ar^1$ | $R^{11}$-18 |
| 648 | O | CH | CH | CH | $Ar^1$ | $R^{11}$-19 |
| 649 | O | CH | CH | CH | $Ar^1$ | $R^{11}$-20 |
| 650 | O | CH | CH | CH | $Ar^1$ | $R^{11}$-21 |
| 651 | O | CH | CH | CH | $Ar^1$ | $R^{11}$-22 |
| 652 | O | CH | CH | CH | $Ar^1$ | $R^{11}$-23 |
| 653 | O | CH | CH | CH | $Ar^1$ | $R^{11}$-25 |
| 654 | O | CH | CH | CH | $Ar^1$ | $R^{11}$-26 |
| 655 | O | CH | CH | CH | $Ar^1$ | $R^{11}$-27 |
| 656 | O | CH | CH | CH | $Ar^1$ | $R^{11}$-28 |
| 657 | O | CH | CH | CH | $Ar^1$ | $R^{11}$-29 |
| 658 | O | CH | CH | CH | $Ar^1$ | $A^{11}$-1 |
| 659 | O | CH | CH | CH | $Ar^1$ | $A^{11}$-2 |
| 660 | O | CH | CH | CH | $Ar^1$ | $A^{11}$-3 |
| 661 | O | CH | CH | CH | $Ar^2$ | $R^{11}$-1 |
| 662 | O | CH | CH | CH | $Ar^2$ | $R^{11}$-2 |
| 663 | O | CH | CH | CH | $Ar^2$ | $R^{11}$-3 |
| 664 | O | CH | CH | CH | $Ar^2$ | $R^{11}$-5 |
| 665 | O | CH | CH | CH | $Ar^2$ | $R^{11}$-6 |
| 666 | O | CH | CH | CH | $Ar^2$ | $R^{11}$-7 |
| 667 | O | CH | CH | CH | $Ar^2$ | $R^{11}$-8 |
| 668 | O | CH | CH | CH | $Ar^2$ | $R^{11}$-9 |
| 669 | O | CH | CH | CH | $Ar^2$ | $R^{11}$-10 |
| 670 | O | CH | CH | CH | $Ar^2$ | $R^{11}$-11 |
| 671 | O | CH | CH | CH | $Ar^2$ | $R^{11}$-12 |
| 672 | O | CH | CH | CH | $Ar^2$ | $R^{11}$-13 |
| 673 | O | CH | CH | CH | $Ar^2$ | $R^{11}$-14 |
| 674 | O | CH | CH | CH | $Ar^2$ | $R^{11}$-15 |
| 675 | O | CH | CH | CH | $Ar^2$ | $R^{11}$-16 |
| 676 | O | CH | CH | CH | $Ar^2$ | $R^{11}$-17 |
| 677 | O | CH | CH | CH | $Ar^2$ | $R^{11}$-18 |
| 678 | O | CH | CH | CH | $Ar^2$ | $R^{11}$-19 |
| 679 | O | CH | CH | CH | $Ar^2$ | $R^{11}$-20 |
| 680 | O | CH | CH | CH | $Ar^2$ | $R^{11}$-21 |
| 681 | O | CH | CH | CH | $Ar^2$ | $R^{11}$-22 |
| 682 | O | CH | CH | CH | $Ar^2$ | $R^{11}$-23 |
| 683 | O | CH | CH | CH | $Ar^2$ | $R^{11}$-25 |
| 684 | O | CH | CH | CH | $Ar^2$ | $R^{11}$-26 |
| 685 | O | CH | CH | CH | $Ar^2$ | $R^{11}$-27 |
| 686 | O | CH | CH | CH | $Ar^2$ | $R^{11}$-28 |
| 687 | O | CH | CH | CH | $Ar^2$ | $R^{11}$-29 |
| 688 | O | CH | CH | CH | $Ar^2$ | $A^{11}$-1 |
| 689 | O | CH | CH | CH | $Ar^2$ | $A^{11}$-2 |
| 690 | O | CH | CH | CH | $Ar^2$ | $A^{11}$-3 |
| 691 | O | CH | CH | CH | $Ar^3$ | $R^{11}$-1 |

TABLE B-continued

| Line | W | $B^1$ | $B^2$ | $B^3$ | Ar | D |
|---|---|---|---|---|---|---|
| 692 | O | CH | CH | CH | $Ar^3$ | $R^{11}$-2 |
| 693 | O | CH | CH | CH | $Ar^3$ | $R^{11}$-3 |
| 694 | O | CH | CH | CH | $Ar^3$ | $R^{11}$-5 |
| 695 | O | CH | CH | CH | $Ar^3$ | $R^{11}$-6 |
| 696 | O | CH | CH | CH | $Ar^3$ | $R^{11}$-7 |
| 697 | O | CH | CH | CH | $Ar^3$ | $R^{11}$-8 |
| 698 | O | CH | CH | CH | $Ar^3$ | $R^{11}$-9 |
| 699 | O | CH | CH | CH | $Ar^3$ | $R^{11}$-10 |
| 700 | O | CH | CH | CH | $Ar^3$ | $R^{11}$-11 |
| 701 | O | CH | CH | CH | $Ar^3$ | $R^{11}$-12 |
| 702 | O | CH | CH | CH | $Ar^3$ | $R^{11}$-13 |
| 703 | O | CH | CH | CH | $Ar^3$ | $R^{11}$-14 |
| 704 | O | CH | CH | CH | $Ar^3$ | $R^{11}$-15 |
| 705 | O | CH | CH | CH | $Ar^3$ | $R^{11}$-16 |
| 706 | O | CH | CH | CH | $Ar^3$ | $R^{11}$-17 |
| 707 | O | CH | CH | CH | $Ar^3$ | $R^{11}$-18 |
| 708 | O | CH | CH | CH | $Ar^3$ | $R^{11}$-19 |
| 709 | O | CH | CH | CH | $Ar^3$ | $R^{11}$-20 |
| 710 | O | CH | CH | CH | $Ar^3$ | $R^{11}$-21 |
| 711 | O | CH | CH | CH | $Ar^3$ | $R^{11}$-22 |
| 712 | O | CH | CH | CH | $Ar^3$ | $R^{11}$-23 |
| 713 | O | CH | CH | CH | $Ar^3$ | $R^{11}$-25 |
| 714 | O | CH | CH | CH | $Ar^3$ | $R^{11}$-26 |
| 715 | O | CH | CH | CH | $Ar^3$ | $R^{11}$-27 |
| 716 | O | CH | CH | CH | $Ar^3$ | $R^{11}$-28 |
| 717 | O | CH | CH | CH | $Ar^3$ | $R^{11}$-29 |
| 718 | O | CH | CH | CH | $Ar^3$ | $A^{11}$-1 |
| 719 | O | CH | CH | CH | $Ar^3$ | $A^{11}$-2 |
| 720 | O | CH | CH | CH | $Ar^3$ | $A^{11}$-3 |
| 721 | O | CH | CH | CH | $Ar^4$ | $R^{11}$-1 |
| 722 | O | CH | CH | CH | $Ar^4$ | $R^{11}$-2 |
| 723 | O | CH | CH | CH | $Ar^4$ | $R^{11}$-3 |
| 724 | O | CH | CH | CH | $Ar^4$ | $R^{11}$-5 |
| 725 | O | CH | CH | CH | $Ar^4$ | $R^{11}$-6 |
| 726 | O | CH | CH | CH | $Ar^4$ | $R^{11}$-7 |
| 727 | O | CH | CH | CH | $Ar^4$ | $R^{11}$-8 |
| 728 | O | CH | CH | CH | $Ar^4$ | $R^{11}$-9 |
| 729 | O | CH | CH | CH | $Ar^4$ | $R^{11}$-10 |
| 730 | O | CH | CH | CH | $Ar^4$ | $R^{11}$-11 |
| 731 | O | CH | CH | CH | $Ar^4$ | $R^{11}$-12 |
| 732 | O | CH | CH | CH | $Ar^4$ | $R^{11}$-13 |
| 733 | O | CH | CH | CH | $Ar^4$ | $R^{11}$-14 |
| 734 | O | CH | CH | CH | $Ar^4$ | $R^{11}$-15 |
| 735 | O | CH | CH | CH | $Ar^4$ | $R^{11}$-16 |
| 736 | O | CH | CH | CH | $Ar^4$ | $R^{11}$-17 |
| 737 | O | CH | CH | CH | $Ar^4$ | $R^{11}$-18 |
| 738 | O | CH | CH | CH | $Ar^4$ | $R^{11}$-19 |
| 739 | O | CH | CH | CH | $Ar^4$ | $R^{11}$-20 |
| 740 | O | CH | CH | CH | $Ar^4$ | $R^{11}$-21 |
| 741 | O | CH | CH | CH | $Ar^4$ | $R^{11}$-22 |
| 742 | O | CH | CH | CH | $Ar^4$ | $R^{11}$-23 |
| 743 | O | CH | CH | CH | $Ar^4$ | $R^{11}$-25 |
| 744 | O | CH | CH | CH | $Ar^4$ | $R^{11}$-26 |
| 745 | O | CH | CH | CH | $Ar^4$ | $R^{11}$-27 |
| 746 | O | CH | CH | CH | $Ar^4$ | $R^{11}$-28 |
| 747 | O | CH | CH | CH | $Ar^4$ | $R^{11}$-29 |
| 748 | O | CH | CH | CH | $Ar^4$ | $A^{11}$-1 |
| 749 | O | CH | CH | CH | $Ar^4$ | $A^{11}$-2 |
| 750 | O | CH | CH | CH | $Ar^4$ | $A^{11}$-3 |
| 751 | O | CH | CH | CH | $Ar^{10}$ | $R^{11}$-1 |
| 752 | O | CH | CH | CH | $Ar^{10}$ | $R^{11}$-2 |
| 753 | O | CH | CH | CH | $Ar^{10}$ | $R^{11}$-3 |
| 754 | O | CH | CH | CH | $Ar^{10}$ | $R^{11}$-5 |
| 755 | O | CH | CH | CH | $Ar^{10}$ | $R^{11}$-6 |
| 756 | O | CH | CH | CH | $Ar^{10}$ | $R^{11}$-7 |
| 757 | O | CH | CH | CH | $Ar^{10}$ | $R^{11}$-8 |
| 758 | O | CH | CH | CH | $Ar^{10}$ | $R^{11}$-9 |
| 759 | O | CH | CH | CH | $Ar^{10}$ | $R^{11}$-10 |
| 760 | O | CH | CH | CH | $Ar^{10}$ | $R^{11}$-11 |
| 761 | O | CH | CH | CH | $Ar^{10}$ | $R^{11}$-12 |
| 762 | O | CH | CH | CH | $Ar^{10}$ | $R^{11}$-13 |
| 763 | O | CH | CH | CH | $Ar^{10}$ | $R^{11}$-14 |
| 764 | O | CH | CH | CH | $Ar^{10}$ | $R^{11}$-15 |
| 765 | O | CH | CH | CH | $Ar^{10}$ | $R^{11}$-16 |
| 766 | O | CH | CH | CH | $Ar^{10}$ | $R^{11}$-17 |
| 767 | O | CH | CH | CH | $Ar^{10}$ | $R^{11}$-18 |
| 768 | O | CH | CH | CH | $Ar^{10}$ | $R^{11}$-19 |
| 769 | O | CH | CH | CH | $Ar^{10}$ | $R^{11}$-20 |

TABLE B-continued

| Line | W | $B^1$ | $B^2$ | $B^3$ | Ar | D |
|---|---|---|---|---|---|---|
| 770 | O | CH | CH | CH | $Ar^{10}$ | $R^{11}$-21 |
| 771 | O | CH | CH | CH | $Ar^{10}$ | $R^{11}$-22 |
| 772 | O | CH | CH | CH | $Ar^{10}$ | $R^{11}$-23 |
| 773 | O | CH | CH | CH | $Ar^{10}$ | $R^{11}$-25 |
| 774 | O | CH | CH | CH | $Ar^{10}$ | $R^{11}$-26 |
| 775 | O | CH | CH | CH | $Ar^{10}$ | $R^{11}$-27 |
| 776 | O | CH | CH | CH | $Ar^{10}$ | $R^{11}$-28 |
| 777 | O | CH | CH | CH | $Ar^{10}$ | $R^{11}$-29 |
| 778 | O | CH | CH | CH | $Ar^{10}$ | $A^{11}$-1 |
| 779 | O | CH | CH | CH | $Ar^{10}$ | $A^{11}$-2 |
| 780 | O | CH | CH | CH | $Ar^{10}$ | $A^{11}$-3 |
| 781 | O | CH | CH | CH | $Ar^{17}$ | $R^{11}$-1 |
| 782 | O | CH | CH | CH | $Ar^{17}$ | $R^{11}$-2 |
| 783 | O | CH | CH | CH | $Ar^{17}$ | $R^{11}$-3 |
| 784 | O | CH | CH | CH | $Ar^{17}$ | $R^{11}$-5 |
| 785 | O | CH | CH | CH | $Ar^{17}$ | $R^{11}$-6 |
| 786 | O | CH | CH | CH | $Ar^{17}$ | $R^{11}$-7 |
| 787 | O | CH | CH | CH | $Ar^{17}$ | $R^{11}$-8 |
| 788 | O | CH | CH | CH | $Ar^{17}$ | $R^{11}$-9 |
| 789 | O | CH | CH | CH | $Ar^{17}$ | $R^{11}$-10 |
| 790 | O | CH | CH | CH | $Ar^{17}$ | $R^{11}$-11 |
| 791 | O | CH | CH | CH | $Ar^{17}$ | $R^{11}$-12 |
| 792 | O | CH | CH | CH | $Ar^{17}$ | $R^{11}$-13 |
| 793 | O | CH | CH | CH | $Ar^{17}$ | $R^{11}$-14 |
| 794 | O | CH | CH | CH | $Ar^{17}$ | $R^{11}$-15 |
| 795 | O | CH | CH | CH | $Ar^{17}$ | $R^{11}$-16 |
| 796 | O | CH | CH | CH | $Ar^{17}$ | $R^{11}$-17 |
| 797 | O | CH | CH | CH | $Ar^{17}$ | $R^{11}$-18 |
| 798 | O | CH | CH | CH | $Ar^{17}$ | $R^{11}$-19 |
| 799 | O | CH | CH | CH | $Ar^{17}$ | $R^{11}$-20 |
| 800 | O | CH | CH | CH | $Ar^{17}$ | $R^{11}$-21 |
| 801 | O | CH | CH | CH | $Ar^{17}$ | $R^{11}$-22 |
| 802 | O | CH | CH | CH | $Ar^{17}$ | $R^{11}$-23 |
| 803 | O | CH | CH | CH | $Ar^{17}$ | $R^{11}$-25 |
| 804 | O | CH | CH | CH | $Ar^{17}$ | $R^{11}$-26 |
| 805 | O | CH | CH | CH | $Ar^{17}$ | $R^{11}$-27 |
| 806 | O | CH | CH | CH | $Ar^{17}$ | $R^{11}$-28 |
| 807 | O | CH | CH | CH | $Ar^{17}$ | $R^{11}$-29 |
| 808 | O | CH | CH | CH | $Ar^{17}$ | $A^{11}$-1 |
| 809 | O | CH | CH | CH | $Ar^{17}$ | $A^{11}$-2 |
| 810 | O | CH | CH | CH | $Ar^{17}$ | $A^{11}$-3 |
| 811 | O | CH | CH | CH | $Ar^{18}$ | $R^{11}$-1 |
| 812 | O | CH | CH | CH | $Ar^{18}$ | $R^{11}$-2 |
| 813 | O | CH | CH | CH | $Ar^{18}$ | $R^{11}$-3 |
| 814 | O | CH | CH | CH | $Ar^{18}$ | $R^{11}$-5 |
| 815 | O | CH | CH | CH | $Ar^{18}$ | $R^{11}$-6 |
| 816 | O | CH | CH | CH | $Ar^{18}$ | $R^{11}$-7 |
| 817 | O | CH | CH | CH | $Ar^{18}$ | $R^{11}$-8 |
| 818 | O | CH | CH | CH | $Ar^{18}$ | $R^{11}$-9 |
| 819 | O | CH | CH | CH | $Ar^{18}$ | $R^{11}$-10 |
| 820 | O | CH | CH | CH | $Ar^{18}$ | $R^{11}$-11 |
| 821 | O | CH | CH | CH | $Ar^{18}$ | $R^{11}$-12 |
| 822 | O | CH | CH | CH | $Ar^{18}$ | $R^{11}$-13 |
| 823 | O | CH | CH | CH | $Ar^{18}$ | $R^{11}$-14 |
| 824 | O | CH | CH | CH | $Ar^{18}$ | $R^{11}$-15 |
| 825 | O | CH | CH | CH | $Ar^{18}$ | $R^{11}$-16 |
| 826 | O | CH | CH | CH | $Ar^{18}$ | $R^{11}$-17 |
| 827 | O | CH | CH | CH | $Ar^{18}$ | $R^{11}$-18 |
| 828 | O | CH | CH | CH | $Ar^{18}$ | $R^{11}$-19 |
| 829 | O | CH | CH | CH | $Ar^{18}$ | $R^{11}$-20 |
| 830 | O | CH | CH | CH | $Ar^{18}$ | $R^{11}$-21 |
| 831 | O | CH | CH | CH | $Ar^{18}$ | $R^{11}$-22 |
| 832 | O | CH | CH | CH | $Ar^{18}$ | $R^{11}$-23 |
| 833 | O | CH | CH | CH | $Ar^{18}$ | $R^{11}$-25 |
| 834 | O | CH | CH | CH | $Ar^{18}$ | $R^{11}$-26 |
| 835 | O | CH | CH | CH | $Ar^{18}$ | $R^{11}$-27 |
| 836 | O | CH | CH | CH | $Ar^{18}$ | $R^{11}$-28 |
| 837 | O | CH | CH | CH | $Ar^{18}$ | $R^{11}$-29 |
| 838 | O | CH | CH | CH | $Ar^{18}$ | $A^{11}$-1 |
| 839 | O | CH | CH | CH | $Ar^{18}$ | $A^{11}$-2 |
| 840 | O | CH | CH | CH | $Ar^{18}$ | $A^{11}$-3 |
| 841 | S | CH | CH | CH | $Ar^1$ | $R^{11}$-1 |
| 842 | S | CH | CH | CH | $Ar^1$ | $R^{11}$-2 |
| 843 | S | CH | CH | CH | $Ar^1$ | $R^{11}$-3 |
| 844 | S | CH | CH | CH | $Ar^1$ | $R^{11}$-5 |
| 845 | S | CH | CH | CH | $Ar^1$ | $R^{11}$-6 |
| 846 | S | CH | CH | CH | $Ar^1$ | $R^{11}$-7 |
| 847 | S | CH | CH | CH | $Ar^1$ | $R^{11}$-8 |

TABLE B-continued

| Line | W | $B^1$ | $B^2$ | $B^3$ | Ar | D |
|---|---|---|---|---|---|---|
| 848 | S | CH | CH | CH | $Ar^1$ | $R^{11}$-9 |
| 849 | S | CH | CH | CH | $Ar^1$ | $R^{11}$-10 |
| 850 | S | CH | CH | CH | $Ar^1$ | $R^{11}$-11 |
| 851 | S | CH | CH | CH | $Ar^1$ | $R^{11}$-12 |
| 852 | S | CH | CH | CH | $Ar^1$ | $R^{11}$-13 |
| 853 | S | CH | CH | CH | $Ar^1$ | $R^{11}$-14 |
| 854 | S | CH | CH | CH | $Ar^1$ | $R^{11}$-15 |
| 855 | S | CH | CH | CH | $Ar^1$ | $R^{11}$-16 |
| 856 | S | CH | CH | CH | $Ar^1$ | $R^{11}$-17 |
| 857 | S | CH | CH | CH | $Ar^1$ | $R^{11}$-18 |
| 858 | S | CH | CH | CH | $Ar^1$ | $R^{11}$-19 |
| 859 | S | CH | CH | CH | $Ar^1$ | $R^{11}$-20 |
| 860 | S | CH | CH | CH | $Ar^1$ | $R^{11}$-21 |
| 861 | S | CH | CH | CH | $Ar^1$ | $R^{11}$-22 |
| 862 | S | CH | CH | CH | $Ar^1$ | $R^{11}$-23 |
| 863 | S | CH | CH | CH | $Ar^1$ | $R^{11}$-25 |
| 864 | S | CH | CH | CH | $Ar^1$ | $R^{11}$-26 |
| 865 | S | CH | CH | CH | $Ar^1$ | $R^{11}$-27 |
| 866 | S | CH | CH | CH | $Ar^1$ | $R^{11}$-28 |
| 867 | S | CH | CH | CH | $Ar^1$ | $R^{11}$-29 |
| 868 | S | CH | CH | CH | $Ar^1$ | $A^{11}$-1 |
| 869 | S | CH | CH | CH | $Ar^1$ | $A^{11}$-2 |
| 870 | S | CH | CH | CH | $Ar^1$ | $A^{11}$-3 |
| 871 | S | CH | CH | CH | $Ar^2$ | $R^{11}$-1 |
| 872 | S | CH | CH | CH | $Ar^2$ | $R^{11}$-2 |
| 873 | S | CH | CH | CH | $Ar^2$ | $R^{11}$-3 |
| 874 | S | CH | CH | CH | $Ar^2$ | $R^{11}$-5 |
| 875 | S | CH | CH | CH | $Ar^2$ | $R^{11}$-6 |
| 876 | S | CH | CH | CH | $Ar^2$ | $R^{11}$-7 |
| 877 | S | CH | CH | CH | $Ar^2$ | $R^{11}$-8 |
| 878 | S | CH | CH | CH | $Ar^2$ | $R^{11}$-9 |
| 879 | S | CH | CH | CH | $Ar^2$ | $R^{11}$-10 |
| 880 | S | CH | CH | CH | $Ar^2$ | $R^{11}$-11 |
| 881 | S | CH | CH | CH | $Ar^2$ | $R^{11}$-12 |
| 882 | S | CH | CH | CH | $Ar^2$ | $R^{11}$-13 |
| 883 | S | CH | CH | CH | $Ar^2$ | $R^{11}$-14 |
| 884 | S | CH | CH | CH | $Ar^2$ | $R^{11}$-15 |
| 885 | S | CH | CH | CH | $Ar^2$ | $R^{11}$-16 |
| 886 | S | CH | CH | CH | $Ar^2$ | $R^{11}$-17 |
| 887 | S | CH | CH | CH | $Ar^2$ | $R^{11}$-18 |
| 888 | S | CH | CH | CH | $Ar^2$ | $R^{11}$-19 |
| 889 | S | CH | CH | CH | $Ar^2$ | $R^{11}$-20 |
| 890 | S | CH | CH | CH | $Ar^2$ | $R^{11}$-21 |
| 891 | S | CH | CH | CH | $Ar^2$ | $R^{11}$-22 |
| 892 | S | CH | CH | CH | $Ar^2$ | $R^{11}$-23 |
| 893 | S | CH | CH | CH | $Ar^2$ | $R^{11}$-25 |
| 894 | S | CH | CH | CH | $Ar^2$ | $R^{11}$-26 |
| 895 | S | CH | CH | CH | $Ar^2$ | $R^{11}$-27 |
| 896 | S | CH | CH | CH | $Ar^2$ | $R^{11}$-28 |
| 897 | S | CH | CH | CH | $Ar^2$ | $R^{11}$-29 |
| 898 | S | CH | CH | CH | $Ar^2$ | $A^{11}$-1 |
| 899 | S | CH | CH | CH | $Ar^2$ | $A^{11}$-2 |
| 900 | S | CH | CH | CH | $Ar^2$ | $A^{11}$-3 |
| 901 | S | CH | CH | CH | $Ar^3$ | $R^{11}$-1 |
| 902 | S | CH | CH | CH | $Ar^3$ | $R^{11}$-2 |
| 903 | S | CH | CH | CH | $Ar^3$ | $R^{11}$-3 |
| 904 | S | CH | CH | CH | $Ar^3$ | $R^{11}$-5 |
| 905 | S | CH | CH | CH | $Ar^3$ | $R^{11}$-6 |
| 906 | S | CH | CH | CH | $Ar^3$ | $R^{11}$-7 |
| 907 | S | CH | CH | CH | $Ar^3$ | $R^{11}$-8 |
| 908 | S | CH | CH | CH | $Ar^3$ | $R^{11}$-9 |
| 909 | S | CH | CH | CH | $Ar^3$ | $R^{11}$-10 |
| 910 | S | CH | CH | CH | $Ar^3$ | $R^{11}$-11 |
| 911 | S | CH | CH | CH | $Ar^3$ | $R^{11}$-12 |
| 912 | S | CH | CH | CH | $Ar^3$ | $R^{11}$-13 |
| 913 | S | CH | CH | CH | $Ar^3$ | $R^{11}$-14 |
| 914 | S | CH | CH | CH | $Ar^3$ | $R^{11}$-15 |
| 915 | S | CH | CH | CH | $Ar^3$ | $R^{11}$-16 |
| 916 | S | CH | CH | CH | $Ar^3$ | $R^{11}$-17 |
| 917 | S | CH | CH | CH | $Ar^3$ | $R^{11}$-18 |
| 918 | S | CH | CH | CH | $Ar^3$ | $R^{11}$-19 |
| 919 | S | CH | CH | CH | $Ar^3$ | $R^{11}$-20 |
| 920 | S | CH | CH | CH | $Ar^3$ | $R^{11}$-21 |
| 921 | S | CH | CH | CH | $Ar^3$ | $R^{11}$-22 |
| 922 | S | CH | CH | CH | $Ar^3$ | $R^{11}$-23 |
| 923 | S | CH | CH | CH | $Ar^3$ | $R^{11}$-25 |
| 924 | S | CH | CH | CH | $Ar^3$ | $R^{11}$-26 |
| 925 | S | CH | CH | CH | $Ar^3$ | $R^{11}$-27 |

TABLE B-continued

| Line | W | $B^1$ | $B^2$ | $B^3$ | Ar | D |
|---|---|---|---|---|---|---|
| 926 | S | CH | CH | CH | $Ar^3$ | $R^{11}$-28 |
| 927 | S | CH | CH | CH | $Ar^3$ | $R^{11}$-29 |
| 928 | S | CH | CH | CH | $Ar^3$ | $A^{11}$-1 |
| 929 | S | CH | CH | CH | $Ar^3$ | $A^{11}$-2 |
| 930 | S | CH | CH | CH | $Ar^3$ | $A^{11}$-3 |
| 931 | S | CH | CH | CH | $Ar^4$ | $R^{11}$-1 |
| 932 | S | CH | CH | CH | $Ar^4$ | $R^{11}$-2 |
| 933 | S | CH | CH | CH | $Ar^4$ | $R^{11}$-3 |
| 934 | S | CH | CH | CH | $Ar^4$ | $R^{11}$-5 |
| 935 | S | CH | CH | CH | $Ar^4$ | $R^{11}$-6 |
| 936 | S | CH | CH | CH | $Ar^4$ | $R^{11}$-7 |
| 937 | S | CH | CH | CH | $Ar^4$ | $R^{11}$-8 |
| 938 | S | CH | CH | CH | $Ar^4$ | $R^{11}$-9 |
| 939 | S | CH | CH | CH | $Ar^4$ | $R^{11}$-10 |
| 940 | S | CH | CH | CH | $Ar^4$ | $R^{11}$-11 |
| 941 | S | CH | CH | CH | $Ar^4$ | $R^{11}$-12 |
| 942 | S | CH | CH | CH | $Ar^4$ | $R^{11}$-13 |
| 943 | S | CH | CH | CH | $Ar^4$ | $R^{11}$-14 |
| 944 | S | CH | CH | CH | $Ar^4$ | $R^{11}$-15 |
| 945 | S | CH | CH | CH | $Ar^4$ | $R^{11}$-16 |
| 946 | S | CH | CH | CH | $Ar^4$ | $R^{11}$-17 |
| 947 | S | CH | CH | CH | $Ar^4$ | $R^{11}$-18 |
| 948 | S | CH | CH | CH | $Ar^4$ | $R^{11}$-19 |
| 949 | S | CH | CH | CH | $Ar^4$ | $R^{11}$-20 |
| 950 | S | CH | CH | CH | $Ar^4$ | $R^{11}$-21 |
| 951 | S | CH | CH | CH | $Ar^4$ | $R^{11}$-22 |
| 952 | S | CH | CH | CH | $Ar^4$ | $R^{11}$-23 |
| 953 | S | CH | CH | CH | $Ar^4$ | $R^{11}$-25 |
| 954 | S | CH | CH | CH | $Ar^4$ | $R^{11}$-26 |
| 955 | S | CH | CH | CH | $Ar^4$ | $R^{11}$-27 |
| 956 | S | CH | CH | CH | $Ar^4$ | $R^{11}$-28 |
| 957 | S | CH | CH | CH | $Ar^4$ | $R^{11}$-29 |
| 958 | S | CH | CH | CH | $Ar^4$ | $A^{11}$-1 |
| 959 | S | CH | CH | CH | $Ar^4$ | $A^{11}$-2 |
| 960 | S | CH | CH | CH | $Ar^4$ | $A^{11}$-3 |
| 961 | S | CH | CH | CH | $Ar^{10}$ | $R^{11}$-1 |
| 962 | S | CH | CH | CH | $Ar^{10}$ | $R^{11}$-2 |
| 963 | S | CH | CH | CH | $Ar^{10}$ | $R^{11}$-3 |
| 964 | S | CH | CH | CH | $Ar^{10}$ | $R^{11}$-5 |
| 965 | S | CH | CH | CH | $Ar^{10}$ | $R^{11}$-6 |
| 966 | S | CH | CH | CH | $Ar^{10}$ | $R^{11}$-7 |
| 967 | S | CH | CH | CH | $Ar^{10}$ | $R^{11}$-8 |
| 968 | S | CH | CH | CH | $Ar^{10}$ | $R^{11}$-9 |
| 969 | S | CH | CH | CH | $Ar^{10}$ | $R^{11}$-10 |
| 970 | S | CH | CH | CH | $Ar^{10}$ | $R^{11}$-11 |
| 971 | S | CH | CH | CH | $Ar^{10}$ | $R^{11}$-12 |
| 972 | S | CH | CH | CH | $Ar^{10}$ | $R^{11}$-13 |
| 973 | S | CH | CH | CH | $Ar^{10}$ | $R^{11}$-14 |
| 974 | S | CH | CH | CH | $Ar^{10}$ | $R^{11}$-15 |
| 975 | S | CH | CH | CH | $Ar^{10}$ | $R^{11}$-16 |
| 976 | S | CH | CH | CH | $Ar^{10}$ | $R^{11}$-17 |
| 977 | S | CH | CH | CH | $Ar^{10}$ | $R^{11}$-18 |
| 978 | S | CH | CH | CH | $Ar^{10}$ | $R^{11}$-19 |
| 979 | S | CH | CH | CH | $Ar^{10}$ | $R^{11}$-20 |
| 980 | S | CH | CH | CH | $Ar^{10}$ | $R^{11}$-21 |
| 981 | S | CH | CH | CH | $Ar^{10}$ | $R^{11}$-22 |
| 982 | S | CH | CH | CH | $Ar^{10}$ | $R^{11}$-23 |
| 983 | S | CH | CH | CH | $Ar^{10}$ | $R^{11}$-25 |
| 984 | S | CH | CH | CH | $Ar^{10}$ | $R^{11}$-26 |
| 985 | S | CH | CH | CH | $Ar^{10}$ | $R^{11}$-27 |
| 986 | S | CH | CH | CH | $Ar^{10}$ | $R^{11}$-28 |
| 987 | S | CH | CH | CH | $Ar^{10}$ | $R^{11}$-29 |
| 988 | S | CH | CH | CH | $Ar^{10}$ | $A^{11}$-1 |
| 989 | S | CH | CH | CH | $Ar^{10}$ | $A^{11}$-2 |
| 990 | S | CH | CH | CH | $Ar^{10}$ | $A^{11}$-3 |
| 991 | S | CH | CH | CH | $Ar^{17}$ | $R^{11}$-1 |
| 992 | S | CH | CH | CH | $Ar^{17}$ | $R^{11}$-2 |
| 993 | S | CH | CH | CH | $Ar^{17}$ | $R^{11}$-3 |
| 994 | S | CH | CH | CH | $Ar^{17}$ | $R^{11}$-5 |
| 995 | S | CH | CH | CH | $Ar^{17}$ | $R^{11}$-6 |
| 996 | S | CH | CH | CH | $Ar^{17}$ | $R^{11}$-7 |
| 997 | S | CH | CH | CH | $Ar^{17}$ | $R^{11}$-8 |
| 998 | S | CH | CH | CH | $Ar^{17}$ | $R^{11}$-9 |
| 999 | S | CH | CH | CH | $Ar^{17}$ | $R^{11}$-10 |
| 1000 | S | CH | CH | CH | $Ar^{17}$ | $R^{11}$-11 |
| 1001 | S | CH | CH | CH | $Ar^{17}$ | $R^{11}$-12 |
| 1002 | S | CH | CH | CH | $Ar^{17}$ | $R^{11}$-13 |
| 1003 | S | CH | CH | CH | $Ar^{17}$ | $R^{11}$-14 |
| 1004 | S | CH | CH | CH | $Ar^{17}$ | $R^{11}$-15 |
| 1005 | S | CH | CH | CH | $Ar^{17}$ | $R^{11}$-16 |
| 1006 | S | CH | CH | CH | $Ar^{17}$ | $R^{11}$-17 |
| 1007 | S | CH | CH | CH | $Ar^{17}$ | $R^{11}$-18 |
| 1008 | S | CH | CH | CH | $Ar^{17}$ | $R^{11}$-19 |
| 1009 | S | CH | CH | CH | $Ar^{17}$ | $R^{11}$-20 |
| 1010 | S | CH | CH | CH | $Ar^{17}$ | $R^{11}$-21 |
| 1011 | S | CH | CH | CH | $Ar^{17}$ | $R^{11}$-22 |
| 1012 | S | CH | CH | CH | $Ar^{17}$ | $R^{11}$-23 |
| 1013 | S | CH | CH | CH | $Ar^{17}$ | $R^{11}$-25 |
| 1014 | S | CH | CH | CH | $Ar^{17}$ | $R^{11}$-26 |
| 1015 | S | CH | CH | CH | $Ar^{17}$ | $R^{11}$-27 |
| 1016 | S | CH | CH | CH | $Ar^{17}$ | $R^{11}$-28 |
| 1017 | S | CH | CH | CH | $Ar^{17}$ | $R^{11}$-29 |
| 1018 | S | CH | CH | CH | $Ar^{17}$ | $A^{11}$-1 |
| 1019 | S | CH | CH | CH | $Ar^{17}$ | $A^{11}$-2 |
| 1020 | S | CH | CH | CH | $Ar^{17}$ | $A^{11}$-3 |
| 1021 | S | CH | CH | CH | $Ar^{18}$ | $R^{11}$-1 |
| 1022 | S | CH | CH | CH | $Ar^{18}$ | $R^{11}$-2 |
| 1023 | S | CH | CH | CH | $Ar^{18}$ | $R^{11}$-3 |
| 1024 | S | CH | CH | CH | $Ar^{18}$ | $R^{11}$-5 |
| 1025 | S | CH | CH | CH | $Ar^{18}$ | $R^{11}$-6 |
| 1026 | S | CH | CH | CH | $Ar^{18}$ | $R^{11}$-7 |
| 1027 | S | CH | CH | CH | $Ar^{18}$ | $R^{11}$-8 |
| 1028 | S | CH | CH | CH | $Ar^{18}$ | $R^{11}$-9 |
| 1029 | S | CH | CH | CH | $Ar^{18}$ | $R^{11}$-10 |
| 1030 | S | CH | CH | CH | $Ar^{18}$ | $R^{11}$-11 |
| 1031 | S | CH | CH | CH | $Ar^{18}$ | $R^{11}$-12 |
| 1032 | S | CH | CH | CH | $Ar^{18}$ | $R^{11}$-13 |
| 1033 | S | CH | CH | CH | $Ar^{18}$ | $R^{11}$-14 |
| 1034 | S | CH | CH | CH | $Ar^{18}$ | $R^{11}$-15 |
| 1035 | S | CH | CH | CH | $Ar^{18}$ | $R^{11}$-16 |
| 1036 | S | CH | CH | CH | $Ar^{18}$ | $R^{11}$-17 |
| 1037 | S | CH | CH | CH | $Ar^{18}$ | $R^{11}$-18 |
| 1038 | S | CH | CH | CH | $Ar^{18}$ | $R^{11}$-19 |
| 1039 | S | CH | CH | CH | $Ar^{18}$ | $R^{11}$-20 |
| 1040 | S | CH | CH | CH | $Ar^{18}$ | $R^{11}$-21 |
| 1041 | S | CH | CH | CH | $Ar^{18}$ | $R^{11}$-22 |
| 1042 | S | CH | CH | CH | $Ar^{18}$ | $R^{11}$-23 |
| 1043 | S | CH | CH | CH | $Ar^{18}$ | $R^{11}$-25 |
| 1044 | S | CH | CH | CH | $Ar^{18}$ | $R^{11}$-26 |
| 1045 | S | CH | CH | CH | $Ar^{18}$ | $R^{11}$-27 |
| 1046 | S | CH | CH | CH | $Ar^{18}$ | $R^{11}$-28 |
| 1047 | S | CH | CH | CH | $Ar^{18}$ | $R^{11}$-29 |
| 1048 | S | CH | CH | CH | $Ar^{18}$ | $A^{11}$-1 |
| 1049 | S | CH | CH | CH | $Ar^{18}$ | $A^{11}$-2 |
| 1050 | S | CH | CH | CH | $Ar^{18}$ | $A^{11}$-3 |

Abbreviations used in Table B are NH = N1, $NCH_3$ = N2, and $NC_2H_5$ = N3

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes their salts, tautomers, stereoisomers, and N-oxides.

The present invention also relates to a mixture of at least one compound of the invention with at least one mixing partner as defined herein. Preferred are binary mixtures of one compound of the invention as component I with one mixing partner as defined herein as component II. Preferred weight ratios for such binary mixtures are from 5000:1 to 1:5000, preferably from 1000:1 to 1:1000, more preferably from 100:1 to 1:100, particularly from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers. Preferred mixing partners are insecticides, nematicides and fungicides.

The following list M of pesticides, grouped and numbered according the Mode of Action Classification of the Insecticide Resistance Action Committee (IRAC), together with which the compounds of the invention can be used and with which potential synergistic effects might be produced, is intended to illustrate the possible combinations, but not to impose any limitation:

- M.1 Acetylcholine esterase (AChE) inhibitors: M.1A carbamates, e.g. aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or M.1B organophosphates, e.g. acephate, azamethiphos, azinphos-ethyl, azinphosm-ethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathionmethyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, and vamidothion;
- M.2. GABA-gated chloride channel antagonists: M.2A cyclodiene organochlorine compounds, e.g. endosulfan or chlordane; or M.2B fiproles (phenylpyrazoles), e.g. ethiprole, fipronil, flufiprole, pyrafluprole, and pyriprole;
- M.3 Sodium channel modulators from the class of M.3A pyrethroids, e.g. acrinathrin, allethrin, d-cis-trans allethrin, d-trans allethrin, bifenthrin, kappa-bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin,metofluthrin, momfluorothrin, epsilon-momfluorothrin, permethrin, phenothrin, prallethrin, profluthrin, pyrethrin (pyrethrum), resmethrin, silafluofen, tefluthrin, kappa-tefluthrin, tetramethylfluthrin, tetramethrin, tralomethrin, and transfluthrin; or M.3B sodium channel modulators such as DDT or methoxychlor;
- M.4 Nicotinic acetylcholine receptor agonists (nAChR): M.4A neonicotinoids, e.g. acetamiprid, clothianidin, cycloxaprid, dinotefuran, imidacloprid, nitenpyram, thiacloprid and thiamethoxam; or the compounds M.4A.1 4,5-Dihydro-N-nitro-1-(2-oxiranylmethyl)-1H-imidazol-2-amine, M.4A.2: (2E-)-1-[(6-Chloropyridin-3-yl)methyl]-N'-nitro-2-pentylidenehydrazinecarboximidamide; or M4. A.3: 1-[(6-Chloropyridin-3-yl)methyl]-7-methyl-8-nitro-5-propoxy-1,2,3,5,6,7-hexahydroimidazo[1,2-a]pyridine; or M.4B nicotine; M.4C sulfoxaflor; M.4D flupyradifurone; M.4E triflumezopyrim;
- M.5 Nicotinic acetylcholine receptor allosteric activators: spinosyns, e.g. spinosad or spinetoram;
- M.6 Chloride channel activators from the class of avermectins and milbemycins, e.g. abamectin, emamectin benzoate, ivermectin, lepimectin, or milbemectin;
- M.7 Juvenile hormone mimics, such as M.7A juvenile hormone analogues hydroprene, kinoprene, and methoprene; or M.76 fenoxycarb, or M.7C pyriproxyfen;
- M.8 miscellaneous non-specific (multi-site) inhibitors, e.g. M.8A alkyl halides as methyl bromide and other alkyl halides, M.86 chloropicrin, M.8C sulfuryl fluoride, M.8D borax, or M.8E tartar emetic;
- M.9 Chordotonal organ TRPV channel modulators, e.g. M.96 pymetrozine; pyrifluquinazon;
- M.10 Mite growth inhibitors, e.g. M.10A clofentezine, hexythiazox, and diflovidazin, or M.10B etoxazole;
- M.11 Microbial disruptors of insect midgut membranes, e.g. *Bacillus thuringiensis* or *Bacillus sphaericus* and the insecticdal proteins they produce such as *Bacillus thuringiensis* subsp. *israelensis, Bacillus sphaericus, Bacillus thuringiensis* subsp. *aizawai Bacillus thuringiensis* subsp. *kurstakiand Bacillus thuringiensis* subsp. *tenebrionis*, or the Bt crop proteins: Cry1Ab, Cry1Ac, Cry1Fa, Cry2Ab, mCry3A, Cry3Ab, Cry3Bb, and Cry34/35Ab1;
- M.12 Inhibitors of mitochondrial ATP synthase, e.g. M.12A diafenthiuron, or M.12B organotin miticides such as azocyclotin, cyhexatin, or fenbutatin oxide, M.12C propargite, or M.12D tetradifon;
- M.13 Uncouplers of oxidative phosphorylation via disruption of the proton gradient, e.g. chlorfenapyr, DNOC, or sulfluramid;
- M.14 Nicotinic acetylcholine receptor (nAChR) channel blockers, e.g. nereistoxin analogues bensultap, cartap hydrochloride, thiocyclam, or thiosultap sodium;
- M.15 Inhibitors of the chitin biosynthesis type 0, such as benzoylureas e.g. bistrifluron, chlorfluazuron, diflubenzuron, flucycloxuron, flufenoxuron, hexaflumuron, lufenuron, novaluron, noviflumuron, teflubenzuron, or triflumuron;
- M.16 Inhibitors of the chitin biosynthesis type 1, e.g. buprofezin;
- M.17 Moulting disruptors, Dipteran, e.g. cyromazine;
- M.18 Ecdyson receptor agonists such as diacylhydrazines, e.g. methoxyfenozide, tebufenozide, halofenozide, fufenozide, or chromafenozide;
- M.19 Octopamin receptor agonists, e.g. amitraz;
- M.20 Mitochondrial complex III electron transport inhibitors, e.g. M.20A hydramethylnon,
- M.20B acequinocyl, M.20C fluacrypyrim; or M.20D bifenazate;
- M.21 Mitochondrial complex I electron transport inhibitors, e.g. M.21A METI acaricides and insecticides such as fenazaquin, fenpyroximate, pyrimidifen, pyridaben, tebufenpyrad or tolfenpyrad, or M.21B rotenone;
- M.22 Voltage-dependent sodium channel blockers, e.g. M.22A indoxacarb, M.22B metaflumizone, or M.22B.1: 2-[2-(4-Cyanophenyl)-1-[3-(trifluoromethyl) phenyl]ethylidene]-N-[4-(difluoromethoxy)phenyl]-hydrazinecarboxamide or M.22B.2: N-(3-Chloro-2-methylphenyl)-2-[(4-chloro-phenyl)[4-[methyl (methylsulfonyl)amino]phenyl]methylene]-hydrazinecarboxamide;
- M.23 Inhibitors of the of acetyl CoA carboxylase, such as Tetronic and Tetramic acid derivatives, e.g. spirodiclofen, spiromesifen, or spirotetramat; M.23.1 spiropidion;

M.24 Mitochondrial complex IV electron transport inhibitors, e.g. M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, e.g. cyenopyrafen or cyflumetofen;

M.28 Ryanodine receptor-modulators from the class of diamides, e.g. flubendiamide, chlorantraniliprole, cyantraniliprole, tetraniliprole, M.28.1: (R)-3-Chlor-N1-{2-methyl-4-[1,2,2,2-tetra-fluoro-1-(trifluoromethyl) ethyl]phenyl}-N2-(1-methyl-2-methylsulfonylethyl) phthalamid, M.28.2: (S)-3-Chloro-N1-{2-methyl-4-[1,2,2,2-tetrafluoro-1-(trifluoromethyl)ethyl]phenyl}-N2-(1-methyl-2-methylsulfonylethyl)phthalamid, M.28.3: cyclaniliprole, or M.28.4: methyl-2-[3,5-dibromo-2-({[3-bromo-1-(3-chlorpyridin-2-yl)-1H-pyrazol-5-yl] carbonyl}amino)benzoyl]-1,2-dimethylhydrazine-carboxylate; or M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl) pyrazole-3-carboxamide; M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene) carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethypamino]carbonyl]phenyl]-1H-pyrazole-5-carboxamide; M.28.5k) 3-Bromo-N-[2,4-dichloro-6-(methylcarbamoyl)phenyl]-1-(3,5-dichloro-2-pyridyl)-1H-pyrazole-5-carboxamide; M.28.5l) N-[4-Chloro-2-[[(1,1-dimethylethyl)amino]carbonyl]-6-methyl-phenyl]-1-(3-chloro-2-pyridinyl)-3-(fluoromethoxy)-1H-pyrazole-5-carboxamide; or M.28.6: cyhalodiamide; or M.29: Chordotonal organ Modulators—undefined target site, e.g. flonicamid;

M.UN. insecticidal active compounds of unknown or uncertain mode of action, e.g. afidopyropen, afoxolaner, azadirachtin, amidoflumet, benzoximate, broflanilide, bromopropylate, chinomethionat, cryolite, dicloromezotiaz, dicofol, flufenerim, flometoquin, fluensulfone, fluhexafon, fluopyram, fluralaner, metaldehyde, metoxadiazone, piperonyl butoxide, pyflubumide, pyridalyl, tioxazafen, M.UN.3: 11-(4-chloro-2,6-dimethylphenyl)-12-hydroxy-1,4-dioxa-9-aza-dispiro [4.2.4.2]-tetradec-11-en-10-one, M.UN.4: 3-(4'-fluoro-2,4-dimethylbiphenyl-3-yl)-4-hydroxy-8-oxa-1-azaspiro[4.5]dec-3-en-2-one, M.UN.5: 1-[2-fluoro-4-methyl-5-[(2,2,2-trifluoroethyl) sulfinyl]phenyl]-3-(trifluoromethyl)-1H-1,2,4-triazole-5-amine, or actives on basis of *Bacillus firmus* (Votivo, I-1582);

M.UN.6: flupyrimin;

M.UN.8: fluazaindolizine; M.UN.9. a): 4-[5-(3,5-dichlorophenyl)-5-(trifluoromethyl)-4H-isoxazol-3-yl]-2-methyl-N-(1-oxothietan-3-yl)benzamide; M.UN.9. b): fluxametamide; M.UN.10: 5-[3-[2,6-dichloro-4-(3,3-dichloroallyloxy)phenoxy]propoxy]-1H-pyrazole;

M.UN.11. i) 4-cyano-N-[2-cyano-5-[[2,6-dibromo-4-[1,2,2,3,3,3-hexafluoro-1-(trifluoromethyl)-propyl]phenyl]carbamoyl]phenyl]-2-methyl-benzamide; M.UN.11. j) 4-cyano-3-[(4-cyano-2-methyl-benzoyl) amino]-N-[2,6-dichloro-4-[1,2,2,3,3,3-hexafluoro-1-(trifluoromethyl)propyl]phenyl]-2-fluoro-benzamide; M.UN.11. k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; M.UN.11. l) N-[5-[[2-bromo-6-chloro-4-[2,2,2-trifluoro-1-hydroxy-1-(trifluoromethypethyl]phenyl]carbamoyl]-2-cyano-phenyl]-4-cyano-2-methyl-benzamide; M.UN.11. m) N-[5-[[2-bromo-6-chloro-4-[1,2,2,3,3,3-hexafluoro-1-(trifluoromethyl)propyl]phenyl] carbamoyl]-2-cyano-phenyl]-4-cyano-2-methyl-benzamide; M.UN.11. n) 4-cyano-N-[2-cyano-5-[[2,6-dichloro-4-[1,2,2,3,3,3-hexafluoro-1-(trifluoromethyl) propyl]phenyl]carbamoyl]phenyl]-2-methyl-benzamide; M.UN.11. o) 4-cyano-N-[2-cyano-5-[[2,6-dichloro-4-[1,2,2,2-tetrafluoro-1-(trifluoromethypethyl]phenyl]carbamoyl]phenyl]-2-methyl-benzamide; M.UN.11. p) N-[5-[[2-bromo-6-chloro-4-[1,2,2,2-tetrafluoro-1-(trifluorome-thyl)ethyl] phenyl]carbamoyl]-2-cyano-phenyl]-4-cyano-2-methyl-benzamide; or M.UN.12. a) 2-(1,3-Dioxan-2-yl)-6-[2-(3-pyridinyl)-5-thiazolyl]-pyridine; M.UN.12. b) 2-[6-[2-(5-Fluoro-3-pyridinyl)-5-thiazolyl]-2-pyridinyl]-pyrimidine; M.UN.12. c) 2-[6-[2-(3-Pyridinyl)-5-thia-zolyl]-2-pyridinyl]-pyrimidine; M.UN.12. d) N-Methylsulfonyl-6-[2-(3-pyridyl)thiazol-5-yl]pyridine-2-carboxamide; M.UN.12. e) N-Methylsulfonyl-6-[2-(3-pyridyl) thiazol-5-yl]pyridine-2-carboxamide;

M.UN.14a) 1-[(6-Chloro-3-pyridinyl)methyl]-1,2,3,5,6,7-hexahydro-5-methoxy-7-methyl-8-nitro-imidazo[1,2-a]pyridine; or M.UN.14b) 1-[(6-Chloropyridin-3-yl) methyl]-7-methyl-8-nitro-1,2,3,5,6,7-hexahydroimidazo[1,2-a]pyridin-5-ol;

M.UN.16a) 1-isopropyl-N,5-dimethyl-N-pyridazin-4-yl-pyrazole-4-carboxamide; or M.UN.16b) 1-(1,2-dimethylpropyl)-N-ethyl-5-methyl-N-pyridazin-4-yl-pyrazole-4-carboxamide; M.UN.16c) N,5-dimethyl-N-pyridazin-4-yl-1-(2,2,2-trifluoro-1-methyl-ethyl) pyrazole-4-carboxamide; M.UN.16d) 1-[1-(1-cyanocyclopropypethyl]-N-ethyl-5-methyl-N-pyridazin-4-yl-pyrazole-4-carboxamide; M.UN.16e) N-ethyl-1-(2-fluoro-1-methyl-propyl)-5-methyl-N-pyridazin-4-yl-pyrazole-4-carboxamide; M.UN.16f) 1-(1,2-dimethylpropyl)-N,5-dimethyl-N-pyridazin-4-yl-pyrazole-4-carboxamide; M.UN.16g) 1-[1-(1-cyanocyclopropypethyl]-N,5-dimethyl-N-pyridazin-4-yl-pyrazole-4-carboxamide; M.UN.16h) N-methyl-1-(2-fluoro-1-methyl-propyl]-5-methyl-N-pyridazin-4-yl-pyrazole-4-carboxamide; M.UN.16i) 1-(4,4-difluorocyclohexyl)-N-ethyl-5-methyl-N-pyridazin-4-yl-pyrazole-4-carboxamide; or M.UN.16j) 1-(4,4-difluorocyclohexyl)-N,5-dimethyl-N-pyridazin-4-yl-pyrazole-4-carboxamide, M.UN.17a) N-(1-methylethyl)-2-(3-pyridinyl)-2H-indazole-4-carboxamide; M.UN.17b) N-cyclo-propyl-2-(3-pyridinyl)-2H-indazole-4-carboxamide; M.UN.17c) N-cyclohexyl-2-(3-pyridinyl)-2H-indazole-4-carboxamide; M.UN.17d) 2-(3-pyridinyl)-N-(2,2,2-trifluoroethyl)-2H-indazole-4-carboxamide; M.UN.17e) 2-(3-pyridinyl)-N-[(tetrahydro-2-furanyl)methyl]-2H-indazole-5-carboxamide; M.UN.17f) methyl 2-[[2-(3-pyridinyl)-2H-indazol-5-yl]carbonyl] hydrazinecarboxylate; M.UN.17g) N-[(2,2-difluorocyclopropyl)methyl]-2-(3-pyridinyl)-2H-indazole-5-carboxamide; M.UN.17h) N-(2,2-difluoropropyl)-2-(3-pyridinyl)-2H-indazole-5-carboxamide; M.UN.171) 2-(3-pyridinyl)-N-(2-pyrimidinylmethyl)-2H-indazole-5-carboxamide; M.UN.17j) N-[(5-methyl-2-pyra-zinyl)methyl]-2-(3-pyridinyl)-2H-indazole-5-carboxamide, M.UN.18. tyclopyrazoflor;

M.UN.19 sarolaner, M.UN.20 lotilaner;

M.U N.21 N-[4-Chloro-3-[[(phenylmethyl)amino]carbonyl]phenyl]-1-methyl-3-(1,1,2,2,2-pentafluoroethyl)-4-(trifluoromethyl)-1H-pyrazole-5-carboxamide; M.UN.22a 2-(3-ethylsulfonyl-2-pyridyl)-3-methyl-6-(trifluoromethypimidazo[4,5-b]pyridine, or M.UN.22b 2-[3-ethylsulfonyl-5-(trifluoromethyl)-2-pyridyl]-3-methyl-6-(trifluoromethypimidazo[4,5-b]pyridine;

M.UN.23a) 4-[5-(3,5-dichlorophenyl)-5-(trifluoromethyl)-4H-isoxazol-3-yl]-N-[(4R)-2-ethyl-3-oxo-isoxazolidin-4-yl]-2-methyl-benzamide, or M.UN.23b) 4-[5-(3,5-dichloro-4-fluoro-phenyl)-5-(trifluoromethyl)-4H-isoxazol-3-yl]-N-[(4R)-2-ethyl-3-oxo-isoxazolidin-4-yl]-2-methyl-benzamide;

M.UN.24a) N-[4-chloro-3-(cyclopropylcarbamoyl)phenyl]-2-methyl-5-(1,1,2,2,2-pentafluoroethyl)-4-(trifluoromethyl)pyrazole-3-carboxamide or M.UN.24b) N-[4-chloro-3-[(1-cyanocyclopropyl)carbamoyl]phenyl]-2-methyl-5-(1,1,2,2,2-pentafluoroethyl)-4-(trifluoromethyl)pyrazole-3-carboxamide; M.UN.25 acynonapyr; M.UN.26 benzpyrimoxan; M.UN.27 2-chloro-N-(1-cyanocyclopropyl)-5-[1-[2-methyl-5-(1,1,2,2,2-pentafluoroethyl)-4-(trifluoromethyl)pyrazol-3-yl] pyrazol-4-yl]benzamide; M.UN.28 Oxazosulfyl;

M.UN.29a) [(2S,3R,4R,5S,6S)-3,5-dimethoxy-6-methyl-4-propoxy-tetrahydropyran-2-yl]N-[4-[1-[4-(trifluoromethoxy)phenyl]-1,2,4-triazol-3-yl]phenyl]carbamate; M.UN.29b) [(2S,3R,4R,5S,6S)-3,4,5-trimethoxy-6-methyl-tetrahydropyran-2-yl] N-[4-[1-[4-(trifluoromethoxy)phenyl]-1,2,4-triazol-3-yl]phenyl] carbamate; M.UN.29c) [(2S,3R,4R,5S,6S)-3,5-dimethoxy-6-methyl-4-propoxy-tetrahydropyran-2-yl] N-[4-[1-[4-(1,1,2,2,2-pentafluoroethoxy)phenyl]-1,2,4-triazol-3-yl]phenyl]carbamate; M.UN.29d) [(2S,3R,4R,5S,6S)-3,4,5-trimethoxy-6-methyl-tetrahydropyran-2-yl] N-[4-[1-[4-(1,1,2,2,2-pentafluoroethoxy) phenyl]-1,2,4-triazol-3-yl]phenyl]carbamate; M.UN.29. e) (2Z)-3-(2-isopropylphenyl)-2-[(E)-[4-[1-[4-(trifluoromethoxy)phenyl]-1,2,4-triazol-3-yl]phenyl]methylenehydrazono]thiazolidin-4-one or M.UN.29f) (2Z)-3-(2-isopropylphenyl)-2-[(E)-[4-[1-[4-(1,1,2,2,2-pentafluoroethoxy)phenyl]-1,2,4-triazol-3-yl]phenyl]methylenehydrazono]thiazolidin-4-one.

The commercially available compounds of the group M listed above may be found in The Pesticide Manual, 17th Edition, C. MacBean, British Crop Protection Council (2015) among other publications. The online Pesticide Manual is updated regularly.

The M.4 cycloxaprid is known from WO2010/069266 and WO2011/069456. M.4A.1 is known from CN 103814937; CN105367557, CN 105481839. M.4A.2, guadipyr, is known from WO 2013/003977, and M.4A.3 (approved as paichongding in China) is known from WO 2007/101369. M.22B.1 is described in CN10171577 and M.22B.2 in CN102126994. Spiropidion M.23.1 is known from WO 2014/191271. M.28.1 and M.28.2 are known from WO2007/101540. M.28.3 is described in WO2005/077934. M.28.4 is described in WO2007/043677. M.28.5a) to M.28.5d) and M.28.5h) are described in WO 2007/006670, WO2013/024009 and WO 2013/024010, M.28.5i) is described in WO2011/085575, M.28.5j) in WO2008/134969, M.28.5k) in US2011/046186 and M.28.51) in WO2012/034403. M.28.6 can be found in WO2012/034472. M.UN.3 is known from WO2006/089633 and M.UN.4 from WO2008/067911. M.UN.5 is described in WO2006/043635, and biological control agents on the basis of *Bacillus firmus* are described in WO2009/124707. Flupyrimin is described in WO2012/029672. M.UN.8 is known from WO2013/055584. M.UN.9. a) is described in WO2013/050317. M.UN.9. b) is described in WO2014/126208. M.UN.10 is known from WO2010/060379. Broflanilide and M.UN.11. b) to M.UN.11. h) are described in WO2010/018714, and M.UN.11i) to M.UN.11. p) in WO 2010/127926. M.UN.12. a) to M.UN.12. c) are known from WO2010/006713, M.UN.12. d) and M.UN.12. e) are known from WO2012/000896. M.UN.14a) and M.UN.14b) are known from WO2007/101369. M.UN.16. a) to M.UN.16h) are described in WO2010/034737, WO2012/084670, and WO2012/143317, resp., and M.UN.16i) and M.UN.16j) are described in WO2015/055497. M.UN.17a) to M.UN.17. j) are described in WO2015/038503. M.UN.18 Tyclo-prazoflor is described in US2014/0213448. M.UN.19 is described in WO2014/036056. M.UN.20 is known from WO2014/090918. M.UN.21 is known from EP2910126. M.UN.22a and M.UN.22b are known from WO2015/059039 and WO2015/190316. M.UN.23a and M.UN.23b are known from WO2013/050302. M.UN.24a) and M.UN.24b) are known from WO2012/126766. Acynonapyr M.UN.25 is known from WO 2011/105506. Benzpyrimoxan M.UN.26 is known from WO2016/104516. M.UN.27 is known from WO2016/174049. M.UN.28 Oxazosulfyl is known from WO2017/104592. M.UN.29a) to M.UN.29f) are known from WO2009/102736 or WO2013116053.

The following list of fungicides, in conjunction with which the compounds of the present invention can be used, is intended to illustrate the possible combinations but does not limit them:

A) Respiration Inhibitors

Inhibitors of complex III at $Q_o$ site: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phe-nyl]-N-methoxy-carbamate (A.1.22), 1-[2-[[1-(4-chlorophenyl)pyrazol-3-yl]oxymethyl]-3-methylphenyl]-4-methyl-tetrazol-5-one (A.1.25), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2,5-dimethylphenyl-oxymethylen)phenyl)-3-methoxy-acrylic acid methylester (A.1.38);

inhibitors of complex III at $Q_i$ site: cyazofamid (A.2.1), amisulbrom (A.2.2), [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A.2.3), fenpicoxamid (A.2.4);

inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), pydiflumetofen (A.3.17), pyraziflumid (A.3.18), sedaxane (A.3.19), tecloftalam (A.3.20), thifluzamide (A.3.21), inpyrfluxam (A.3.22), pyrapropoyne (A.3.23), fluindapyr (A.3.28), methyl (E)-2-[2-[(5-cyano-2-methylphenoxy)methyl]phenyl]-3-methoxy-prop-2-enoate (A.3.30), isoflucypram (A.3.31), 2-(difluoromethyl)-N-(1,1,3-trimethyl-indan-4-Apyridine-3-carboxamide (A.3.32), 2-(difluoromethyl)-N-[(3R)-1,1,3-trimethyl-indan-4-yl]pyridine-3-carboxamide (A.3.33), 2-(difluoromethyl)-N-(3-ethyl-1,1-dimethyl-indan-4-yl) pyridine-3-carboxamide (A.3.34), 2-(difluoromethyl)-N-[(3R)-3-ethyl-1,1-dimethyl-indan-4-yl]pyridine-3-carboxamide (A.3.35), 2-(difluoromethyl)-N-(1,1-dimethyl-3-propyl-indan-4-yl)pyridine-3-carboxamide (A.3.36), 2-(difluoromethyl)-N-[(3R)-1,1-dimethyl-3-propyl-indan-4-yl]pyridine-3-carboxamide (A.3.37), 2-(difluoromethyl)-N-(3-isobutyl-1,1-dimethyl-indan-4-yl)pyridine-3-carboxamide (A.3.38), 2-(difluoromethyl)-N-[(3R)-3-isobutyl-1,1-dimethyl-indan-4-yl] pyridine-3-carboxamide (A.3.39);

other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e.g. fentin-acetate (A.4.8), fentin chloride (A.4.9) or fentin hydroxide (A.4.10); ametoctradin (A.4.11); silthiofam (A.4.12);

B) Sterol Biosynthesis Inhibitors (SBI Fungicides)

C14 demethylase inhibitors: triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 2-(2,4-difluorophenyl)-1,1-difluoro-3-(tetrazol-1-yl)-1-[5-[4-(2,2,2-trifluoroethoxy)phenyl]-2-pyridyl]propan-2-ol (B.1.31), 2-(2,4-difluorophenyl)-1,1-difluoro-3-(tetrazol-1-yl)-1-[5-[4-(trifluoromethoxy)phenyl]-2-pyridyl] propan-2-ol (B.1.32), ipfentrifluconazole (B.1.37), mefentrifluconazole (B.1.38), 2-(chloromethyl)-2-methyl-5-(p-tolylmethyl)-1-(1,2,4-triazol-1-ylmethyl) cyclopentanol (B.1.43); imidazoles: imazalil (B.1.44), pefurazoate (B.1.45), prochloraz (B.1.46), triflumizol (B.1.47); pyrimidines, pyridines, piperazines: fenarimol (B.1.49), pyrifenox (B.1.50), triforine (B.1.51), [3-(4-chloro-2-fluoro-phenyl)-5-(2,4-difluorophenyl) isoxazol-4-yl]-(3-pyridyl)methanol (B.1.52);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

Other Sterol biosynthesis inhibitors: chlorphenomizole (B.4.1);

C) Nucleic Acid Synthesis Inhibitors phenylamides or acyl amino acid fungicides: benalaxyl (C.1.1), benalaxyl-M (C.1.2), kiral-axyl (C.1.3), metalaxyl (C.1.4), metalaxyl-M (C.1.5), ofurace (C.1.6), oxadixyl (C.1.7);

other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7), 5-fluoro-2-(4-chlorophenylmethoxy)pyrimidin-4 amine (C.2.8);

D) Inhibitors of Cell Division and Cytoskeleton tubulin inhibitors: benomyl (D.1.1), carbendazim (D.1.2), fuberidazole (D1.3), thiabendazole (D.1.4), thiophanate-methyl (D.1.5), 3-chloro-4-(2,6-difluorophenyl)-6-methyl-5-phenyl-pyridazine (D.1.6), 3-chloro-6-methyl-5-phenyl-4-(2,4,6-trifluorophenyl)pyridazine (D.1.7), N-ethyl-2-[(3-ethynyl-8-methyl-6-quinolyl) oxy]butanamide (D.1.8), N-ethyl-2-[(3-ethynyl-8-methyl-6-quinolyl)oxy]-2-methylsulfanyl-acetamide (D.1.9), 2-[(3-ethynyl-8-methyl-6-quinolyl)oxy]-N-(2-fluoroethyl)butanamide (D.1.10), 2-[(3-ethynyl-8-methyl-6-quinolyl)oxy]-N-(2-fluoroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2-[(3-ethynyl-8-methyl-6-quinolyl)oxy]-N-(2-fluoroethyl)-2-methylsulfanyl-acetamide (D.1.15), 4-(2-bromo-4-fluoro-phenyl)-N-(2-chloro-6-fluoro-phenyl)-2,5-dimethyl-pyrazol-3-amine (D.1.16);

other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7);

E) Inhibitors of Amino Acid and Protein Synthesis methionine synthesis inhibitors: cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6);

F) Signal Transduction Inhibitors

MAP/histidine kinase inhibitors: fluoroimid (F.1.1), iprodione (F.1.2), procymidone (F.1.3), vinclozolin (F.1.4), fludioxonil (F.1.5);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7);

compounds affecting cell membrane permeability and fatty acides: propamocarb (G.4.1);

inhibitors of oxysterol binding protein: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazol-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl)pyrazol-1-yl]acetyl]-4-piperidyl]-N-tetralin-1-yl-pyridine-2-carboxamide (G.5.9), 4-[1-[2-[3,5-bis(trifluoromethyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl]acetyl]-4-piperidyl]-N-tetralin-1-yl-pyridine-2-carboxamide (G.5.11);

H) Inhibitors with Multi Site Action inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), calcium phosphonate (J.1.11), potassium phosphonate (J.1.12), potassium or sodium bicarbonate (J.1.9), 4-cyclopropyl-N-(2,4-dimethoxyphenyl)thiadiazole-5-carboxamide (J 1.10);

K) Unknown Mode of Action bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), difenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), methasulfocarb (K.1.18), nitrapyrin (K.1.19), nitrothal-isopropyl (K.1.20), tolprocarb (K.1.21), oxin-copper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N-methyl formamidine (K.1.27), N'-(4-(4-fluoro-3-trifluoromethyl-phenoxy)-2,5-dimethyl-phenyl)-N-ethyl-N-methyl formamidine (K.1.28), N'-[4-[[3-[(4-chlorophenyl)methyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenyl)ethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N'-[5-bromo-2-methyl-6-(1-phenylethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2-methyl-4-(3-trimethylsilanyl-propoxy)-phenyl)-N-ethyl-N-methyl formamidine (K.1.35), 2-(4-chloro-phenyl)-N-[4-(3,4-dimethoxy-phenyl)-isoxazol-5-yl]-2-prop-2-ynyloxy-acetamide (K.1.36), 3-[5-(4-chloro-phenyl)-2,3-dimethyl-isoxazolidin-3-yl]-pyridine (pyrisoxazole) (K.1.37), 3-[5-(4-methylphenyl)-2,3-dimethyl-isoxazolidin-3 yl]-pyridine (K.1.38), 5-chloro-1-(4,6-di-methoxy-pyrimidin-2-yl)-2-methyl-1H-benzoimidazole (K.1.39), ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynyl N-[6-[[(Z)-[(1-methyltetrazol-5-yl)-phenyl-methylene]amino]oxymethyl]-2-pyridyl]carbamate (K.1.43), 2-[2-[(7,8-difluoro-2-methyl-3-quinolyl)oxy]-6-fluoro-phenyl]propan-2-ol (K.1.44), 2-[2-fluoro-6-[(8-fluoro-2-methyl-3-quinolyl)oxy]phen-yl]propan-2-ol (K.1.45), quinofumelin (K.1.47), 9-fluoro-2,2-dimethyl-5-(3-quinolyl)-3H-1,4-benzoxazepine (K.1.49), 2-(6-benzyl-2-pyridyl)quinazoline (K.1.50), 2-[6-(3-fluoro-4-methoxy-phenyl)-5-methyl-2-pyridyl]quinazoline (K.1.51), dichlobentiazox (K.1.52), N'-(2,5-dimethyl-4-phenoxy-phenyl)-N-ethyl-N-methyl-formamidine (K.1.53), pyrifenamine (K.1.54).

The fungicides described by common names, their preparation and their activity e.g. against harmful fungi is known; these substances are commercially available.

The active substances mentioned above, their preparation and their activity e. g. against harmful fungi is known; these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941;

EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441). Some compounds are identified by their CAS Registry Number which is separated by hyphens into three parts, the first consisting from two up to seven digits, the second consisting of two digits, and the third consisting of a single digit.

Suitable mixing partners for the compounds of the present invention also include biopesticides.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multicellular.

(2) Biochemical pesticides are naturally occurring substances or or structurally-similar and functionally identical to a naturally-occurring substance and extracts from biological sources that control pests or provide other crop protection uses as defined below, but have non-toxic mode of actions (such as growth or developmental regulation, attractents, repellents or defence activators (e.g. induced resistance) and are relatively non-toxic to mammals.

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

A major growth area for biopesticides is in the area of seed treatments and soil amendments. Biopesticidal seed treatments are e.g. used to control soil borne fungal pathogens that cause seed rots, damping-off, root rot and seedling blights. They can also be used to control internal seed borne fungal pathogens as well as fungal pathogens that are on the surface of the seed. Many biopesticidal products also show capacities to stimulate plant host defenses and other physiological processes that can make treated crops more resistant to a variety of biotic and abiotic stresses or can regulate plant growth. Many biopesticidal products also show capacities to stimulate plant health, plant growth and/or yield enhancing activity.

The following list of biopesticides, in conjunction with which the compounds of the present invention can be used, is intended to illustrate the possible combinations but does not limit them:

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibaclllus alvei, Paenibaclllus epiphyticus, P. polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperelloides, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia*, zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartll, Burkholderia* spp., *Chromobacterium subtsugae, Cydia pomonella* granulovirus (CpGV), *Cryptophlebia leucotreta* granulovirus (CrleGV), *Flavobacterium* spp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecanicillium longisporum, L. muscarium, Metarhizium anisopliae, M. anisopliae* var. *anisopliae, M. anisopliae* var. *acridum, Nomuraea rileyi, Paecilomyces fumosoroseus, P. lilacinus, Paenibacillus popillae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus, S. microflavus;*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cisjasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, (R)-1-octen-3-ol, pentatermanone, (E,Z,Z)-3,8,11-tetradecatrienyl acetate, (Z,E)-9,12-tetradecadien-1-yl acetate, (Z)-7-tetradecen-2-one, (Z)-9-tetradecen-1-yl acetate, (2)-11-tetradecenal, (Z)-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* spp., *B. elkanii, B. japonicum, B. liaoningense, B. lupini, Delftia acidovorans, Glomus intraradices, Mesorhizobium* spp., *Rhizobium leguminosarum* bv. *phaseoli, R. I.* bv. *trifolii, R. I.* bv. viciae, R. tropici, Sinorhizobium meliloti.

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices such as ATCC or DSM refer to the acronym of the respective culture collection, are referred to in literature registered and/or are commercially available: mixtures of *Aureobasidium pullulans* DSM 14940 and DSM 14941 isolated in 1989 in Konstanz, Germany (e.g. blastospores in BlossomProtect® from bio-ferm GmbH, Austria), *Azospirillum brasilense* Sp245 originally isolated in wheat reagion of South Brazil (Passo Fundo) at least prior to 1980 (BR 11005; e.g. GELFIX® Gramineas from BASF Agricultural Specialties Ltd., Brazil), *A. brasilense* strains Ab-V5 and Ab-V6 (e.g. in AzoMax from Novozymes BioAg Produtos papra Agricultura Ltda., Quattro Barras, Brazil or Simbiose-Maiz® from Simbiose-Agro, Brazil; Plant Soil 331, 413-425, 2010), *Bacillus amyloliquefaciens* strain AP-188 (NRRL B-50615 and B-50331; U.S. Pat. No. 8,445,255); *B. amyloliquefaciens* spp. *plantarum* D747 isolated from air in Kikugawa-shi, Japan (US 20130236522 A1; FERM BP-8234; e.g. Double Nickel™ 55 WDG from Certis LLC, USA), *B. amyloliquefaciens* spp. *plantarum* FZB24 isolated from soil in Brandenburg, Germany (also called SB3615; DSM 96-2; J. Plant Dis. Prot. 105, 181-197, 1998; e.g. Taegro® from Novozyme Biologicals, Inc., USA), *B. amyloliquefaciens* ssp. *plantarum* FZB42 isolated from soil in Brandenburg, Germany (DSM 23117; J. Plant Dis. Prot. 105, 181-197, 1998; e.g. RhizoVital® 42 from AbiTEP GmbH, Germany), *B. amyloliquefaciens* ssp. *plantarum* MBI600 isolated from faba bean in Sutton Bonington, Nottinghamshire, U.K. at least before 1988 (also called 1430; NRRL B-50595; US 2012/0149571 A1; e.g. Integral® from BASF Corp., USA), *B. amyloliquefaciens* spp. *plantarum* QST-713 isolated from peach orchard in 1995 in California, U.S.A. (NRRL B-21661; e.g. Serenade® MAX from Bayer Crop Science LP, USA), *B. amyloliquefaciens* spp. *plantarum* TJ1000 isolated in 1992 in South Dakota, U.S.A. (also called 1BE; ATCC BAA-390; CA 2471555 A1; e.g. QuickRoots™ from TJ Technologies, Watertown, SD, USA), *B. firmus* CNCM I-1582, a variant of parental strain EIP-N1 (CNCM I-1556) isolated from soil of central plain area of Israel (WO 2009/126473, U.S. Pat. No. 6,406,690; e.g. Votivo® from Bayer CropScience LP, USA), *B. pumilus* GHA 180 isolated from apple tree rhizosphere in Mexico (IDAC 260707-01; e.g. PROMIX® BX from Premier Horticulture, Quebec, Canada), *B. pumilus* INR-7 otherwise referred to as BU—F22 and BU—F33 isolated at least before 1993 from cucumber infested by *Erwinia tracheiphila* (NRRL B-50185, NRRL B-50153; U.S. Pat. No. 8,445,255), *B. pumilus* KFP9F isolated from the rhizosphere of grasses in South Africa at least before 2008 (NRRL B-50754; WO 2014/029697; e.g. BAC-UP or FUSION-P from BASF Agricultural Specialities (Pty) Ltd., South Africa), *B. pumilus* QST 2808 was isolated from soil collected in Pohnpei, Federated States of Micronesia, in 1998 (NRRL B-30087; e.g. Sonata® or Ballad® Plus from Bayer Crop Science LP, USA), *B. simplex* ABU 288 (NRRL B-50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* ssp. *aizawai* ABTS-1857 isolated from soil taken from a lawn in Ephraim, Wisconsin, U.S.A., in 1987 (also called ABG-6346; ATCC SD-1372; e.g. XenTari® from BioFa AG, Münsingen, Germany), *B. t.* ssp. *kurstaki* ABTS-351 identical to HD-1 isolated in 1967 from diseased Pink Bollworm black larvae in Brownsville, Texas, U.S.A. (ATCC SD-1275; e.g. Dipel® DF from Valent BioSciences, IL, USA), *B. t.* ssp. *kurstaki* SB4 isolated from *E. saccharina* larval cadavers (NRRL B-50753; e.g. Beta Pro® from BASF Agricultural Specialities (Pty) Ltd., South Africa), *B. t.* ssp. *tenebrionis* NB-176-1, a mutant of strain NB-125, a wild type strain isolated in 1982 from a dead pupa of the beetle *Tenebrio molitor* (DSM 5480; EP 585 215B1; e.g. Novodor® from Valent BioSciences, Switzerland), *Beauveria bassiana* GHA (ATCC 74250; e.g. BotaniGard® 22WGP from Laverlam Int. Corp., USA), *B. bassiana* JW-1 (ATCC 74040; e.g. Naturalis® from CBC (Europe) S.r.l., Italy), *B. bassiana* PPRI 5339 isolated from the larva of the tortoise beetle *Conchyloctenia punctata* (NRRL 50757; e.g. Broad Band® from BASF Agricultural Specialities (Pty) Ltd., South Africa), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbiol. 73(8), 2635, 2007; e.g. GELFIX 5 from BASF Agricultural Specialties Ltd., Brazil), *B. japonicum* 532c isolated from Wisconsin field in U.S.A. (Nitragin 61A152; Can. J. Plant. Sci. 70, 661-666, 1990; e.g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e.g. GELFIX 5 or ADHERE 60 from BASF Agricultural Specialties Ltd., Brazil), *B. japonicum* SEMIA 5080 obtained under lab conditions by Embrapa-Cerrados in Brazil and used in commercial inoculants since 1992, being a natural variant of SEMIA 586 (CB1809) originally isolated in U.S.A. (CPAC 7; e.g. GELFIX 5 or ADHERE 60 from BASF Agricultural Specialties Ltd., Brazil); *Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e.g. Contans® WG, Intercept® WG from Bayer CropScience AG, Germany), harpin (alpha-beta) protein (Science 257, 85-88, 1992; e.g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e.g. Helicovex® from Adermatt Biocontrol, Switzerland; Diplomata® from Koppert, Brazil; Vivus® Max from AgBiTech Pty Ltd., Queensland, Australia), *Helicoverpa zea* single capsid nucleopolyhedrovirus (HzSNPV) (e.g. Gemstar® from Certis LLC, USA), *Helicoverpa zea* nucleopolyhedrovirus ABA-NPV—U (e.g. Heligen® from AgBiTech Pty Ltd., Queensland, Australia), *Heterorhabditis bacteriophora* (e.g. Nemasys® G from BASF Agricultural Specialities Limited, UK), *Isaria fumosorosea* Apopka-97 isolated from mealy bug on gynura in Apopka, Florida, U.S.A. (ATCC 20874; Biocontrol Science Technol. 22(7), 747-761, 2012; e.g. PFR-97™ or PreFeRal® from Certis LLC, USA), *Metarhizium anisopliae* var. *anisopliae* F52 also called 275 or V275 isolated from codling moth in Austria (DSM 3884, ATCC 90448; e.g. Met52® Novozymes Biologicals BioAg Group, Canada), *Metschnikowia fructicola* 277 isolated from grapes in the central part of Israel (U.S. Pat. No. 6,994,849; NRRL Y-30752; e.g. formerly Shemer® from Agrogreen, Israel), *Paecilomyces ilacinus* 251 isolated from infected nematode eggs in the Philippines (AGAL 89/030550; WO1991/02051; Crop Protection 27, 352-361, 2008; e.g. BioAct®from Bayer CropScience AG, Germany and MeloCon® from Certis, USA), *Paenibacillus alvei* NAS6G6 isolated from the rhizosphere of grasses in South Africa at least before 2008 (WO 2014/029697; NRRL B-50755; e.g. BAC-UP from BASF Agricultural Specialties (Pty) Ltd., South Africa), *Paenibacillus* strains isolated from soil samples from a variety of European locations including Germany: *P. epiphyticus* Lu17015 (WO 2016/020371; DSM 26971), *P. polymyxa* ssp. *plantarum* Lu16774 (WO 2016/020371; DSM 26969), *P. p.* ssp. *plantarum* strain Lu17007 (WO 2016/020371; DSM 26970); *Pasteuria nishizawae* Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilail*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e.g. Jump Start®, Provide® from Novozymes Biologicals BioAg Group, Canada), *Reynoutria sachalinensis* extract (EP 0307510B1; e.g. Regalia® SC from Marrone BioInovations, Davis, CA, USA or Milsana® from BioFa AG, Germany), *Steinernema carpocapsae* (e.g. Millenium® from BASF Agricultural Specialities Limited, UK), *S. feltiae* (e.g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *Trichoderma asperelloides* JM41R isolated in South Africa (NRRL 50759; also referred to as *T. fertile*; e.g. Trichoplus® from BASF Agricultural Specialities (Pty) Ltd., South Africa), *T. harzianum* T-22 also called KRL-AG2 (ATCC 20847; BioControl 57, 687-696, 2012; e.g. Plantshield® from BioWorks Inc., USA or SabrEx™ from Advanced Biological Marketing Inc., Van Wert, OH, USA).

According to the invention, the solid material (dry matter) of the biopesticides (with the exception of oils such as Neem oil) are considered as active components (e.g. to be obtained after drying or evaporation of the extraction or suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

When mixtures comprising microbial pesticides are employed in crop protection, the application rates preferably range from about $1\times10^{6}$ to $5\times10^{15}$ (or more) CFU/ha, preferably from about $1\times10^{8}$ to about $1\times10^{13}$ CFU/ha, and even more preferably from about $1\times10^{9}$ to about $1\times10^{12}$ CFU/ha. In the case of (entomopathogenic) nematodes as microbial pesticides (e.g. *Steinernema feltiae*), the application rates preferably range inform about $1\times10^{5}$ to $1\times10^{12}$ (or more), more preferably from $1\times10^{8}$ to $1\times10^{11}$, even more preferably from $5\times10^{8}$ to $1\times10^{10}$ individuals (e.g. in the form of eggs, juvenile or any other live stages, preferably in an infetive juvenile stage) per ha.

When mixtures comprising microbial pesticides are employed in seed treatment, the application rates with respect to plant propagation material preferably range from about $1\times10^{6}$ to $1\times10^{12}$ (or more) CFU/seed. Preferably, the concentration is about $1\times10^{6}$ to about $1\times10^{9}$ CFU/seed. In the case of the microbial pesticides II, the application rates with respect to plant propagation material also preferably range from about $1\times10^{7}$ to $1\times10^{14}$ (or more) CFU per 100 kg of seed, preferably from $1\times10^{9}$ to about $1\times10^{12}$ CFU per 100 kg of seed.

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.)

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsititued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanofer-rate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-soluble concentrates (SL, LS)

10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible concentrates (DC)

5-25 wt % of a compound I according to the invention and 1-10 wt % dispersant (e.g. polyvinylpyrrolidone) are dissolved in up to 100 wt % organic solvent (e.g. cyclohexanone). Dilution with water gives a dispersion.

iii) Emulsifiable concentrates (EC)

15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0, 1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable micro-emulsion.

x) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insolu-ble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the for-mation of a polyurea microcapsule. The monomers amount to 1-10 wt %. The wt % relate to the total CS composition.

xi) Dustable powders (DP, DS)

1-10 wt % of a compound I according to the invention are ground finely and mixed intimately with up to 100 wt % solid carrier, e.g. finely divided kaolin.

xii) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xiii) Ultra-low volume liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e.g. components comprising compounds of the present invention and/or mixing partners as defined above, can be applied jointly (e.g. after tank mix) or consecutively.

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called Stevie); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers; eucalyptus; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "cultivated plants" is to be understood as including plants which have been modified by mutagenesis or genetic engineering in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include in particular herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by conventional methods of mutagenesis and breeding comprise plant varieties commercially available under the name Clearfield®. However, most of the herbicide tolerance traits have been created via the use of transgenes.

Herbicide tolerance has been created to glyphosate, glufosinate, 2,4-D, dicamba, oxynil herbicides, like bromoxynil and ioxynil, sulfonylurea herbicides, ALS inhibitor herbicides and 4-hydroxyphenylpyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621 and goxv247, for tolerance to glufosinate: pat and bar, for tolerance to 2,4-D: aad-1 and aad-12, for tolerance to dicamba: dmo, for tolerance to oxynil herbicies: bxn, for tolerance to sulfonylurea herbicides: zm-hra, csr1-2, gm-hra, S4-HrA, for tolerance to ALS inhibitor herbicides: csr1-2, for tolerance to HPPD inhibitor herbicides: hppdPF, W336 and avhppd-03.

Transgenic corn events comprising herbicide tolerance genes are for example, but not excluding others, DAS40278, MON801, MON802, MON809, MON810, MON832, MON87411, MON87419, MON87427, MON88017, MON89034, NK603, GA21, MZHGOJG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes are for example, but not excluding others, GTS 40-3-2, MON87705, MON87708, MON87712, MON87769, MON89788, A2704-12, A2704-21, A5547-127, A5547-35, DP356043, DAS44406-6, DAS68416-4, DAS-81419-2, GU262, SYHTØH2, W62, W98, FG72 and CV127.

Transgenic cotton events comprising herbicide tolerance genes are for example, but not excluding others, 19-51a, 31707, 42317, 81910, 281-24-236, 3006-210-23, BXN10211, BXN10215, BXN10222, BXN10224, MON1445, MON1698, MON88701, MON88913, GHB119, GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants. Transgenes which have most frequently been used are toxin genes of *Bacillus spec*. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin have been transferred to other plants. In particular genes coding for protease inhibitors, like CpTI and pinII. A further approach uses transgenes in order to produce double stranded RNA in plants to target and downregulate insect genes. An example for such a transgene is dvsnf7.

Transgenic corn events comprising genes for insecticidal proteins or double stranded RNA are for example, but not excluding others, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098.

Transgenic soybean events comprising genes for insecticidal proteins are for example, but not excluding others, MON87701, MON87751 and DAS-81419.

Transgenic cotton events comprising genes for insecticidal proteins are for example, but not excluding others, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by increasing ear biomass using the transgene athb17, being present in corn event MON87403, or by enhancing photosynthesis using the transgene bbx32, being present in the soybean event MON87712.

Cultivated plants comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, in particular to tolerance to drought, has been created by using the transgene cspB, comprised by the corn event MON87460 and by using the transgene Hahb-4, comprised by soybean event IND-ØØ41Ø-5.

Traits are frequently combined by combining genes in a transformation event or by combining different events during the breeding process. Preferred combination of traits are herbicide tolerance to different groups of herbicides, insect tolerance to different kind of insects, in particular tolerance to lepidopteran and coleopteran insects, herbicide tolerance with one or several types of insect resistance, herbicide tolerance with increased yield as well as a combination of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agri-biotech Applications (ISAAA)" and the "Center for Environmental Risk Assessment (CERA)", Further information on specific events and methods to detect them can be found for canola events MS1, MS8, RF3, GT73, MON88302, KK179 in WO01/031042, WO01/041558, WO01/041558, WO02/036831, WO11/153186, WO13/003558, for cotton events MON1445, MON15985, MON531(MON15985), LLCotton25, MON88913, COT102, 281-24-236, 3006-210-23, COT67B, GHB614, T304-40, GHB119, MON88701, 81910 in WO02/034946, WO02/100163, WO02/100163, WO03/013224, WO04/072235, WO04/039986, WO05/103266, WO05/103266, WO06/128573, WO07/017186, WO08/122406, WO08/151780, WO12/134808, WO13/112527, for corn events GA21, MON810, DLL25, TC1507, MON863, MIR604, LY038, MON88017, 3272, 59122, NK603, MIR162, MON89034, 98140, 32138, MON87460, 5307, 4114, MON87427, DAS40278, MON87411, 33121, MON87403, MON87419 in WO98/044140, US02/102582, US03/126634, WO04/099447, WO04/011601, WO05/103301, WO05/061720, WO05/059103, WO06/098952, WO06/039376, US2007/292854, WO07/142840, WO07/140256, WO08/112019, WO09/103049, WO09/111263, WO10/077816, WO11/084621, WO11/062904, WO11/022469, WO13/169923, WO14/116854, WO15/053998, WO15/142571, for potato events E12, F10, J3, J55, V11, X17, Y9 in WO14/178910, WO14/178913, WO14/178941, WO14/179276, WO16/183445, WO17/062831, WO17/062825, for rice events LLRICE06, LLRICE601, LLRICE62 in WO00/026345, WO00/026356, WO00/026345 for soybean events H7-1, MON89788, A2704-12, A5547-127, DP305423, DP356043, MON87701, MON87769, CV127, MON87705, DAS68416-4, MON87708, MON87712, SYHT0H2, DAS81419, DAS81419×DA544406-6, MON87751 in WO04/074492, WO06/130436, WO06/108674, WO06/108675, WO08/054747, WO08/002872, WO09/064652, WO09/102873, WO10/080829, WO10/037016, WO11/066384, WO11/034704, WO12/051199, WO12/082548, WO13/016527, WO13/016516, WO14/201235.

The use of compositions according to the invention on cultivated plants may result in effects which are specific to a cultivated plant comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, mycoplasma, viral or viroid pathogens as well as early vigour, early or delayed ripening, cold or heat tolerance as well as changed amino acid or fatty acid spectrum or content.

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 $m^2$, preferably from 0.001 to 20 g per 100 $m^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the invention are particularly suitable for use in the treatment of seeds in order to protect the seeds from insect pests, in particular from soil-living insect pests, and the resulting seedling's roots and shoots against soil pests and foliar insects. The invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which have been modified by mutagenisis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the invention, or an agriculturally useful salt thereof, as defined herein. The amount of the compound of the invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the invention may also be used for improving the health of a plant. Therefore, the invention also relates to a method for improving plant health by treating a plant, plant propagation material and/or the locus where the plant is growing or is to grow with an effective and non-phytotoxic amount of a compound of the invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound. Formulations of the compounds of the invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

The compounds of the the invention are especially suitable for efficiently combating animal pests such as arthropods, gastropods and nematodes including but not limited to:

insects from the order of Lepidoptera, for example *Achroia grisella, Acleris* spp. such as *A. fimbriana, A.*

*gloverana, A. variana; Acrolepiopsis assectella, Acronicta major, Adoxophyes* spp. such as *A. cyrtosema, A. orana; Aedia leucomelas, Agrotis* spp. such as *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia* (=*Thermesia*) spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Caloptilis theivora, Capua reticulana, Carposina* spp. such as *C. niponensis, C. sasakii; Cephus* spp., *Chaetocnema aridula, Cheimatobia brumata, Chilo* spp. such as *C. Indicus, C. sup pressalis, C. partellus; Choreutis pariana, Choristoneura* spp. such as *C. conflictana, C. fumiferana, C. longicellana, C. murinana, C. occidentalis, C. rosaceana; Chrysodeixis* (=*Pseudoplusia*) spp. such as *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema* (=*Epinotia*) *aporema, Cydalima* (=*Diaphania*) *perspectalis, Cydia* (=*Carpocapsa*) spp. such as *C. pomonella, C. latiferreana; Dalaca noctuides, Datana integerrima, Dasychira pinicola, Dendrolimus* spp. such as *D. pini, D. spectabilis, D. sibiricus; Desmia funeralis, Diaphania* spp. such as *D. nitidalis, D. hyalinata; Diatraea grandiosella, Diatraea saccharalis, Dipthera festiva, Earias* spp. such as *E. insulana, E. vittella; Ecdytolopha aurantianu, Egira* (=*Xylomyges*) *curialis, Elasmopalpus lignosellus, Eldana saccharina, Endopiza viteana, Ennomos subsignaria, Eoreuma loftini, Ephestia* spp. such as *E. cautella, E. elutella, E. kuehniella; Epinotia aporema, Epiphyas postvittana, Erannis tiliana, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedylepta* spp., *Helicoverpa* spp. such as *H. armigera* (=*Heliothis armigera*), *H. zea* (=*Heliothis zea*); *Heliothis* spp. such as *H. assulta, H. subflexa, H. virescens; Hellula* spp. such as *H. undalis, H. rogatalis; Helocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantna cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma salicis, Leucoptera* spp. such as *L. coffeella, L. scitella; Leuminivora lycinivorella, Lithocolletis blancardella, Lithophane antennata, Llattia octo* (=*Amyna axis*), *Lobesia botrana, Lophocampa* spp., *Loxagrotis albicosta, Loxostege* spp. such as *L. sticticalis, L. cereralis; Lymantria* spp. such as *L. dispar, L. monacha; Lyonetia clerkella, Lyonetia prunifoliella, Malacosoma* spp. such as *M. americanum, M. californicum, M. constrictum, M. neustria; Mamestra* spp. such as *M. brassicae, M. configurata; Mamstra brassicae, Manduca* spp. such as *M. quinquemaculata, M. sexta; Marasmia* spp, *Marmara* spp., *Maruca testulalis, Megalopyge lanata, Melanchra picta, Melanitis leda, Mocis* spp. such as *M. lapites, M. repanda; Mocis latipes, Monochroa fragariae, Mythimna separata, Nemapogon cloacella, Neoleucinodes elegantalis, Nepytia* spp., *Nymphula* spp., *Oiketicus* spp., *Omiodes indicata, Omphisa anastomosalis, Operophtera brumata, Orgyia pseudotsugata, Oria* spp., *Orthaga thyrisalis, Ostrinia* spp. such as *O. nubilalis; Oulema oryzae, Paleacrita vernata, Panolis flammea, Parnara* spp., *Papaipema nebris, Papilio cresphontes, Paramyelois transitella, Paranthrene regalis, Paysandisia archon, Pectinophora* spp. such as *P. gossypiella; Peridroma saucia, Perileucoptera* spp., such as *P. coffeella; Phalera bucephala, Phryganidia californica, Phthorimaea* spp. such as *P. operculella; Phyllocnistis citrella, Phyllonorycter* spp. such as *P. blancardella, P. crataegella, P. issikii, P. ringoniella; Pieris* spp. such as *P. brassicae, P. rapae, P. napi; Pilocrocis tripunctata, Plathypena scabra, Platynota* spp. such as *P. flavedana, P. idaeusalis, P. stultana; Platyptilia carduidactyla, Plebejus argus, Plodia interpunctella, Plusia* spp, *Plutella maculipennis, Plutella xylostella, Pontia protodica, Prays* spp., *Prodenia* spp., *Proxenus lepigone, Pseudaletia* spp. such as *P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius* spp., *Schreckensteinia festaliella, Scirpophaga* spp. such as *S. incertulas, S. innotata; Scotia segetum, Sesamia* spp. such as *S. inferens, Seudyra subflava, Sitotroga ce realella, Sparganothis pilleriana, Spilonota lechnaspis, S. ocellana, Spodoptera* (=*Lamphygma*) spp. such as *S. cosmoides, S. eridania, S. exigua, S. frugiperda, S. latisfascia, S. littoralis, S. litura, S. omithogalli; Stigmella* spp., *Stomopteryx subsecivella, Strymon bazochii, Sylepta derogata, Synanthedon* spp. such as *S. exitiosa, Tecia solanivora, Telehin licus, Thaumatopoea pityocampa, Thaumatotibia* (=*Cryptophlebia*) *leucotreta, Thaumetopoea pityocampa, Thecla* spp., *Theresimima ampelophaga, Thyrinteina* spp, *Tildenia inconspicuella, Tinea* spp. such as *T. cloacella, T. pellionella; Tineola bisselliella, Tortrix* spp. such as *T. viridana; Trichophaga tapetzella, Trichoplusia* spp. such as *T. ni; Tuta* (=*Scrobipalpula*) *absoluta, Udea* spp. such as *U. rubigalis, U. rubigalis; Virachola* spp., *Yponomeuta padella*, and *Zeiraphera canadensis;* insects from the order of Coleoptera, for example *Acalymma vittatum, Acanthoscehdes obtectus, Adoretus* spp., *Agelastica alni, Agrilus* spp. such as *A. anxius, A. planipennis, A. sinuatus; Agriotes* spp. such as *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora* spp. such as *A. glabripennis; Anthonomus* spp. such as *A. eugenii, A. grandis, A. pomorum; Anthrenus* spp., *Aphthona euphoridae, Apion* spp., *Apogonia* spp., *Athous haemorrhoidalis, Atomaria* spp. such as *A. linearis; Attagenus* spp., *Aulacophora femoralis, Blastophagus piniperda, Blitophaga undata, Bruchidius obtectus, Bruchus* spp. such as *B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. such as *C. assimilis, C. napi; Chaetocnema tibialis, Cleonus mendicus, Conoderus* spp. such as *C. vespertinus; Conotrachelus nenuphar, Cosmopolites* spp., *Costelytra zealandica, Crioceris asparagi, Cryptolestes fer-*

*rugineus, Cryptorhynchus lapathi, Ctenicera* spp. such as *C. destructor; Curculio* spp., *Cylindrocopturus* spp., *Cyclocephala* spp., *Dactylispa balyi, Dectes texanus, Dermestes* spp., *Diabrotica* spp. such as *D. un decimpunctata, D. speciosa, D. longicornis, D. semipunctata, D. virgifera; Diaprepes abbreviates, Dichocrocis* spp., *Dicladispa armigera, Diloboderus abderus, Diocalandra frumenti* (*Diocalandra stigmaticollis*), *Enaphalodes rufulus, Epilachna* spp. such as *E. varivestis, E. vigintioctomaculata; Epitrix* spp. such as *E. hirtipennis, E. similaris; Eutheola humilis, Eutinobothrus brasiliensis, Faustinus cubae, Gibbium psylloides, Gnathocerus cornutus, Hellula undaks, Heteronychus arator, Hylamorpha elegans, Hylobius abietis, Hylotrupes bajulus, Hypera* spp. such as *H. brunneipennis, H. postica; Hypomeces squamosus, Hypothenemus* spp., *Ips typographus, Lachnosterna consanguinea, Lasioderma serricorne, Latheticus oryzae, Lathridius* spp., *Lema* spp. such as *L. bilineata, L. melanopus; Leptinotarsa* spp. such as *L. decemlineata; Leptispa pygmaea, Limonius californicus, Lissorhoptrus oryzophilus, Lixus* spp., *Luperodes* spp., *Lyctus* spp. such as *L. bruneus; Liogenys fuscus, Macrodactylus* spp. such as *M. subspinosus; Maladera matrida, Megaplatypus mutates, Megascelis* spp., *Melanotus communis, Meligethes* spp. such as *M. aeneus; Melolontha* spp. such as *M. hippocastani, M. melolontha; Metamasius hemipterus, Microtheca* spp., *Migdolus* spp. such as *M. fryanus, Monochamus* spp. such as *M. alternatus; Naupactus xanthographus, Niptus hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetoni a jucunda, Phaedon* spp. such as *P. brassicae, P. cochleariae; Phoracantha recurva, Phyllobius pyri, Phyllopertha horticola, Phyllophaga* spp. such as *P. helleri; Phyllotreta* spp. such as *P. chrysocephala, P. nemorum, P. striolata, P. vittula; Phyllopertha horticola, Popillia japonica, Premnotrypes* spp., *Psacothea hilaris, Psylliodes chrysocephala, Prostephanus truncates, Psylliodes* spp., *Ptinus* spp., *Pulga saltona, Rhizopertha dominica, Rhynchophorus* spp. such as *R. billineatus, R. ferrugineus, R. palmarum, R. phoenicis, R. vulneratus; Saperda candida, Scolytus schevyrewi, Scyphophorus acupunctatus, Sitona lineatus, Sitophilus* spp. such as *S. granaria, S. oryzae, S. zeamais; Sphenophorus* spp. such as *S. levis; Stegobium paniceum, Sternechus* spp. such as *S. subsignatus; Strophomorphus ctenotus, Symphyletes* spp., *Tanymecus* spp., *Tenebrio molitor, Tenebrioides mauretanicus, Tribolium* spp. such as *T. castaneum; Trogoderma* spp., *Tychius* spp., *Xylotrechus* spp. such as *X. pyrrhoderus*; and, *Zabrus* spp. such as *Z. tenebrioides;* insects from the order of Diptera e.g. *Aedes* spp. such as *A. aegypti, A. albopictus, A. vexans; Anastrepha ludens, Anopheles* spp. such as *A. albimanus, A. crucians, A. freeborni, A. gambiae, A. leucosphyrus, A. maculopennis, A. minimus, A. quadrimaculatus, A. sinensis; Bactrocera invadens, Bibio hortulanus, Calliphora erythrocephala, Calliphora vicina, Ceratitis capitata, Chrysomyia* spp. such as *C. bezziana, C. hominivorax, C. macellaria; Chrysops atlanticus, Chrysops discalis, Chrysops silacea, Cochliomyia* spp. such as *C. hominivorax; Contarinia* spp. such as *C. sorghicola; Cordylobia anthropophaga, Culex* spp. such as *C. nigripalpus, C. pipiens, C. quinquefasciatus, C. tarsalis, C. tritaeniorhynchus; Culicoides furens, Culiseta inornata, Culiseta melanura, Cuterebra* spp., *Dacus cucurbitae, Dacus oleae, Dasineura brassicae, Dasineura oxycoccana, Delia* spp. such as *D. antique, D. coarctata, D. platura, D. radicum; Dermatobia hominis, Drosophila* spp. such as *D. suzukii, Fannia* spp. such as *F. canicularis; Gastraphilus* spp. such as *G. intestinalis; Geomyza tipunctata, Glossina* spp. such as *G. fuscipes, G. morsitans, G. palpalis, G. tachinoides; Haematobia irritans, Haplodiplosis equestris, Hippelates* spp., *Hylemyia* spp. such as *H. platura; Hypoderma* spp. such as *H. lineata; Hyppobosca* spp., *Hydrellia philippina, Leptoconops torrens, Liriomyza* spp. such as *L. sativae, L. trifolii; Lucilia* spp. such as *L. caprin, L. cuprina, L. sericata; Lycoria pectoralis, Mansonia titillanus, Mayetiola* spp. such as *M. destructor; Musca* spp. such as *M. autumnalis, M. domestica; Muscina stabulans, Oestrus* spp. such as *O. ovis; Opomyza florum, Oscinella* spp. such as *O. frit; Orseolia oryzae, Pegomya hysocyami, Phlebotomus argentipes, Phorbia* spp. such as *P. antiqua, P. brassicae, P. coarctata; Phytomyza gymnostoma, Prosimulium mixtum, Psila rosae, Psorophora columbiae, Psorophora discolor, Rhagoletis* spp. such as *R. cerasi, R. cingulate, R. indifferens, R. mendax, R. pomonella; Rivellia quadrifasciata, Sarcophaga* spp. such as *S. haemorrhoidalis; Simulium vittatum, Sitodiplosis mosellana, Stomoxys* spp. such as *S. calcitrans; Tabanus* spp. such as *T. atratus, T. bovinus, T. lineola, T. similis; Tannia* spp., *Thecodiplosis japonensis, Tipula oleracea, Tipula paludosa*, and *Wohlfahrtia* spp;

insects from the order of Thysanoptera for example, *Baliothrips biformis, Dichromothrips corbetti, Dichromothrips* ssp., *Echinothrips americanus, Enneothrips flavens, Frankliniella* spp. such as *F. fusca, F. occidentalis, F. tritici; Heliothrips* spp., *Hercinothrips femoralis, Kakothrips* spp., *Microcephalothrips abdominalis, Neohydatothrips samayunkur, Pezothrips kellyanus, Rhipiphorothrips cruentatus, Scirtothrips* spp. such as *S. citri, S. dorsalis, S. perseae; Stenchaetothrips* spp, *Taeniothrips cardamoni, Taeniothrips inconsequens, Thrips* spp. such as *T. imagines, T. hawaiiensis, T. oryzae, T. palmi, T. parvispinus, T. tabaci;* insects from the order of Hemiptera for example, *Acizzia jamatonica, Acrosternum* spp. such as *A. hilare; Acyrthosipon* spp. such as *A. onobrychis, A. pisum; Adelges laricis, Adelges tsugae, Adelphocoris* spp., such as *A. rapidus, A. superbus; Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii; Aphis* spp. such as *A. craccivora, A. fabae, A. forbesi, A. gossypii, A. grossulariae, A. maidiradicis, A. pomi, A. sambuci, A. schneideri, A. spiraecola; Arboridia apicalis, Arilus critatus, Aspidiella* spp., *Aspidiotus* spp., *Atanus* spp., *Aulacaspis yasumatsui, Aulacorthum solani, Bactericera cockerelli* (*Paratrioza cockerelli*), *Bemisia* spp. such as *B. argentifolii, B. tabaci* (*Aleurodes tabaci*); *Blissus* spp. such as *B. leucopterus; Brachycaudus* spp. such as *B. cardui, B. helichrysi, B. persicae, B. prunicola; Brachycolus* spp., *Brachycorynella asparagi, Brevicoryne brassicae, Cacopsylla* spp. such as *C. fulguralis, C. pyricola* (*Psylla piri*); *Calligypona marginata, Calocoris* spp., *Campylomma livida, Capitophorus horni, Carneocephala fulgida, Cavelerius* spp., *Ceraplastes* spp., *Ceratovacuna lanigera, Ceroplastes ceriferus, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *C. hemibterus, C. lectularius; Coccomytilus halli, Coccus* spp. such as *C. hesperidum, C. pseudomagnoliarum, Corythucha arcuata, Creontiades dilutus, Cryptomyzus ribis, Chrysomphalus aonidum, Cryptomyzus ribis, Ctenarytaina spatulata, Cyrtopeltis notatus, Dalbulus* spp., *Dasynus piperis, Dialeurodes* spp. such as *D. citrifoli; Dalbulus maidis, Diaphorina* spp. such as *D. citri; Diaspis* spp. such as *D. bromeliae; Dichelops furcatus, Diconocoris hewetti, Doralis* spp., *Dreyfusia nordmannianae, Dreyfusia piceae, Drosicha* spp., *Dysaphis* spp. such as *D. plantaginea, D. pyri, D. radicola; Dysaulacorthum pseudosolani, Dysdercus* spp. such as *D. cingulatus, D. intermedius; Dysmicoccus* spp., *Edessa* spp., *Geocoris* spp., *Empoasca* spp. such as *E. fabae, E. solana; Epidiaspis leperii, Eriosoma* spp. such as *E. lanigerum, E. pyricola; Erythroneura* spp., *Eurygaster* spp. such as *E. integriceps; Euscelis bilobatus, Euschistus* spp. such as *E. heros, E. impictiventris, E. servus; Fiorinia theae, Geococcus coffeae, Glycaspis brimblecombei, Halyomorpha* spp. such as *H. halys; Heliopeltis* spp., *Homalodisca vitripennis* (=*H. coagulata*), *Horcias nobilellus, Hyalopterus pruni, Hyperomyzus lactucae, Icerya* spp. such as *I. purchase; Idiocerus* spp., *Idioscopus* spp., *Laodelphax striatellus, Lecanium* spp., *Lecanoideus floccissimus, Lepidosaphes* spp. such as *L. ulmi; Leptocorisa* spp., *Leptoglossus phyllopus, Lipaphis erysimi, Lygus* spp. such as *L. hesperus, L. lineolaris, L. pratensis; Maconellicoccus hirsutus, Marchalina hellenica, Macropes excavatus, Macrosiphum* spp. such as *M. rosae, M. avenae, M. euphorbiae; Macrosteles quadrilineatus, Mahanarva fimbriolata, Megacopta cribraria, Megoura viciae, Melanaphis pyrarius, Melanaphis sacchari, Melanocallis* (=*Tinocallis*) *caryaefoliae, Metcafiella* spp., *Metopolophium dirhodum, Monellia costalis, Monelliopsis pecanis, Myzocallis coryli, Murgantia* spp., *Myzus* spp. such as *M. ascalonicus, M. cerasi, M. nicotianae, M. persicae, M. varians; Nasonovia ribis-nigri, Neotoxoptera formosana, Neomegalotomus* spp, *Nephotettix* spp. such as *N. malayanus, N. nigropictus, N. parvus, N. virescens; Nezara* spp. such as *N. viridula; Nilaparvata lugens, Nysius huttoni, Oebalus* spp. such as *O. pugnax; Oncometopia* spp., *Orthezia praelonga, Oxycaraenus hyalinipennis, Parabemisia myricae, Parlatoria* spp., *Parthenolecanium* spp. such as *P. corni, P. persicae; Pemphigus* spp. such as *P. bursarius, P. populivenae; Peregrinus maidis, Perkinsiella saccharicida, Phenacoccus* spp. such as *P. aceris, P. gossypii; Phloeomyzus passerinii, Phorodon humuli, Phylloxera* spp. such as *P. devastatrix, Piesma quadrata, Piezodorus* spp. such as *P. guildinii; Pinnaspis aspidistrae, Planococcus* spp. such as *P. citri, P. ficus; Prosapia bicincta, Protopulvinaria pyriformis, Psallus seriatus, Pseudacysta persea, Pseudaulacaspis pentagon, Pseudococcus* spp. such as *P. comstocki; Psylla* spp. such as *P. mali; Pteromalus* spp., *Pulvinaria amygdali, Pyrilla* spp., *Quadraspidiotus* spp., such as *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. such as *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Spissistilus festinus* (=*Stictocephala festina*), *Stephanitis nashi, Stephanitis pyrioides, Stephanitis takeyai, Tenalaphara malayensis, Tetraleurodes perseae, Therioaphis maculate, Thyanta* spp. such as *T. accerra, T. perditor, Tibraca* spp., *Tomaspis* spp., *Toxoptera* spp. such as *T. aurantii; Trialeurodes* spp. such as *T. abutilonea, T. ricini, T. vaporariorum; Triatoma* spp., *Trioza* spp., *Typhlocyba* spp., *Unaspis* spp. such as *U. citri, U. yanonensis*; and Viteus vitifolii, Insects from the order Hymenoptera for example *Acanthomyops interjectus, Athalia rosae, Atta* spp. such as *A. capiguara, A. cephalotes, A. cephalotes, A. laevigata, A. robusta, A. sexdens, A. texana, Bombus* spp., *Brachymyrmex* spp., *Camponotus* spp. such as *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus kuriphilus, Formica* spp., *Hoplocampa* spp. such as *H. minuta, H. testudinea; Iridomyrmex humilis, Lasius* spp. such as *L. niger, Linepithema humile, Liometopum* spp., *Leptocybe invasa, Monomorium* spp. such as *M. pharaonis, Monomorium, Nylandria fulva, Pachycondyla chinensis, Paratrechina longicornis, Paravespula* spp., such as *P. germanica, P. pennsylvanica, P. vulgaris; Pheidole* spp. such as *P. megacephala; Pogonomyrmex* spp. such as *P. barbatus, P. californicus, Polistes rubiginosa, Prenolepsis impairs, Pseudomyrmex gracilis, Schelipron* spp., *Sirex cyaneus, Solenopsis* spp. such as *S. geminata, S. invicta, S. molesta, S. richten, S. xyloni, Sphecius speciosus, Sphex* spp., *Tapinoma* spp. such as *T. melanocephalum, T. sessile; Tetramorium* spp. such as *T. caespitum, T. bicarinatum, Vespa* spp. such as *V. crabro; Vespula* spp. such as *V. squamosal; Wasmannia auropunctata, Xylocopa* sp;

Insects from the order Orthoptera for example *Acheta domesticus, Calliptamus italicus, Chortoicetes terminifera, Ceuthophilus* spp., *Diastrammena asynamora, Dociostaurus maroccanus, Gryllotalpa* spp. such as *G. africana, G. gryllotalpa; Gryllus* spp., *Hieroglyphus daganensis, Kraussaria angulifera, Locusta* spp. such as *L. migratoria, L. pardalina; Melanoplus* spp. such as *M. bivittatus, M. femurrubrum, M. mexicanus, M. sanguinipes, M. spretus; Nomadacris septemfasciata, Oedaleus senegalensis, Scapteriscus* spp., *Schistocerca* spp. such as *S. americana, S. gregaria, Stemopelmatus* spp., *Tachycines asynamorus*, and *Zonozerus variegatus;*

Pests from the Class Arachnida for example Acari, e.g. of the families Argasidae, Ixodidae and Sarcoptidae, such as *Amblyomma* spp. (e.g. *A. americanum, A. variegatum, A. maculatum*), *Argas* spp. such as *A. persicu*), *Boophilus* spp. such as *B. annulatus, B. decoloratus, B. microplus, Dermacentor* spp. such as *D. silvarum, D. andersoni, D. variabilis, Hyalomma* spp. such as *H. truncatum, Ixodes* spp. such as *I. ricinus, I. rubicundus, I. scapularis, I. holocyclus, I. pacificus, Rhipicephalus sanguineus, Ornithodorus* spp. such as *O. moubata, O. hermsi, O. turicata, Ornithonyssus bacoti, Otobius megnini, Dermanyssus gallinae, Psoroptes* spp. such as *P. ovis, Rhipicephalus* spp. such as *R. sanguineus, R. appendiculatus, Rhipicephalus evertsi, Rhizoglyphus* spp., *Sarcoptes* spp. such as *S. Scabiei*; and Family Eriophyidae including *Aceria* spp. such as *A. sheldoni, A. anthocoptes, Acallitus* spp., *Aculops* spp. such as *A. lycopersici, A. pelekassi; Aculus* spp. such as *A. schlechtendali; Colomerus vitis, Epitrimerus pyri, Phyllocoptruta oleivora; Eriophytes ribis and Eriophyes* spp. such as *Eriophyes sheldoni*, Family Tarsonemidae including *Hemitarsonemus* spp., *Phytonemus pallidus* and *Polyphagotarsonemus latus, Stenotarsonemus* spp. *Steneotarsonemus spinki*; Family Tenuipalpidae including *Brevipalpus* spp. such as *B. phoenicis*; Family Tetranychidae including *Eotetranychus* spp., *Eutetranychus* spp., *Oligonychus* spp., *Petrobia latens, Tetranychus* spp. such as *T. cinnabarinus, T. evansi, T. kanzawai, T. pacificus, T. phaseulus, T. telarius* and *T. urticae; Bryobia praetiosa; Panonychus* spp. such as *P. ulmi, P. citri; Metatetranychus* spp. and *Oligonychus* spp. such as *O. pratensis, O. perseae, Vasates lycopersici; Raoiella indica*, Family Carpoglyphidae including *Carpoglyphus* spp.; *Penthaleidae* spp. such as *Halotydeus destructor*, Family Demodicidae with species such as *Dermodex* spp.; Family Trombicidea including *Trombicula* spp.; Family Macronyssidae including *Ornothonyssus* spp.; Family Pyemotidae including *Pyemotes tritici;*

*Tyrophagus putrescentiae*; Family Acaridae including *Acarus siro*; Family Araneida including *Latrodectus mactans, Tegenaria agrestis, Chiracanthium* sp, *Lycosa* sp *Achaearanea tepidariorum* and *Loxosceles reclusa;*

Pests from the Phylum Nematoda, for example, plant parasitic nematodes such as root-knot nematodes, *Meloidogyne* spp. such as *M. hapla, M. incognita, M. javanica*; cyst-forming nematodes, *Globodera* spp. such as *G. rostochiensis; Heterodera* spp. such as *H. avenae, H. glycines, H. schachtii, H. trifolii*; Seed gall nematodes, *Anguina* spp.; Stem and foliar nematodes, *Aphelenchoides* spp. such as *A. besseyi*; Sting nematodes, *Belonolaimus* spp. such as *B. longicaudatus*; Pine nematodes, *Bursaphelenchus* spp. such as *B. lignicolus, B. xylophllus*; Ring nematodes, *Criconema* spp., *Criconemella* spp. such as *C. xenoplax* and *C. ornata*; and, *Criconemoides* spp. such as *Criconemoides informis; Mesocriconema* spp.; Stem and bulb nematodes, *Ditylenchus* spp. such as *D. destructor, D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus*; Lesion nematodes, *Pratylenchus* spp. such as *P. brachyurus, P. neglectus, P. penetrans, P. curvitatus, P. goodeyi*; Burrowing nematodes, *Radopholus* spp. such as *R. similis; Rhadopholus* spp.; *Rhodopholus* spp.; Reniform nematodes, *Rotylenchus* spp. such as *R. robustus, R. reniformis; Scutellonema* spp.; Stubby-root nematode, *Trichodorus* spp. such as *T. obtusus, T. primitivus; Paratrichodorus* spp. such as *P. minor*; Stunt nematodes, *Tylenchorhynchus* spp. such as *T. claytoni, T. dubius*; Citrus nematodes, *Tylenchulus* spp. such as *T. semipenetrans*; Dagger nematodes, *Xiphinema* spp.; and other plant parasitic nematode species;

Insects from the order Isoptera for example *Calotermes flavicollis, Coptotermes* spp. such as *C. formosanus, C. gestroi, C. acinaciformis; Cornitermes cumulans, Cryptotermes* spp. such as *C. brevis, C. cavifrons; Globitermes sulfureus, Heterotermes* spp. such as *H. aureus, H. longiceps, H. tenuis; Leucotermes flavipes, Odontotermes* spp., *Incisitermes* spp. such as *I. minor, I. Snyder, Marginitermes hubbardi, Mastotermes* spp. such as *M. darwiniensis Neocapritermes* spp. such as *N. opacus, N. parvus; Neotermes* spp., *Procornitermes* spp., *Zootermopsis* spp. such as *Z. angusticollis, Z. nevadensis, Reticulitermes* spp. such as *R. hesperus, R. tibialis, R. speratus, R. flavipes, R. grassei, R. lucifugus, R. santonensis, R. virginicus; Termes natalensis,*

Insects from the order Blattaria for example *Blatta* spp. such as *B. orientails, B. lateralis; Blattella* spp. such as *B. asahinae, B. germanica; Leucophaea maderae, Panchlora nivea, Periplaneta* spp. such as *P. americana, P. australasiae, P. brunnea, P. fuligginosa, P. japonica; Supella longipalpa, Parcoblatta pennsylvanica, Eurycotis floridana, Pycnoscelus surinamensis,*

Insects from the order Siphonoptera for example *Cediopsylla simples, Ceratophyllus* spp., *Ctenocephalides* spp. such as *C. felis, C. canis, Xenopsylla cheopis, Pulex irritans, Trichodectes canis, Tunga penetrans*, and *Nosopsyllus fasciatus,*

Insects from the order Thysanura for example *Lepisma saccharin, Ctenolepisma urbana*, and *Thermobia domestica,*

Pests from the class Chilopoda for example *Geophilus* spp., *Scutigera* spp. such as *Scutigera coleoptrata;*

Pests from the class Diplopoda for example *Blaniulus guttulatus, Julus* spp., *Narceus* spp., Pests from the class Symphyla for example *Scutigerella immaculata,*

Insects from the order Dermaptera, for example *Forficula auricularia,*

Insects from the order Collembola, for example *Onychiurus* spp., such as *Onychiurus armatus,*

Pests from the order Isopoda for example, *Armadillidium vulgare, Oniscus asellus, Porcellio scaber,*

Insects from the order Phthiraptera, for example *Damalinia* spp., *Pediculus* spp. such as *Pediculus humanus capitis, Pediculus humanus corporis, Pediculus humanus humanus; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., Examples of further pest species which may be controlled by compounds of fomula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *OpSthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

The compounds of the invention are suitable for use in treating or protecting animals against infestation or infection by parasites. Therefore, the invention also relates to the use of a compound of the invention for the manufacture of a medicament for the treatment or protection of animals against infestation or infection by parasites. Furthermore, the invention relates to a method of treating or protecting animals against infestation and infection by parasites, which comprises orally, topically or parenterally administering or applying to the animals a parasiticidally effective amount of a compound of the invention.

The present invention also relates to the non-therapeutic use of compounds of the invention for treating or protecting animals against infestation and infection by parasites. Moreover, the invention relates to a non-therapeutic method of treating or protecting animals against infestation and infection by parasites, which comprises applying to a locus a parasiticidally effective amount of a compound of the invention.

The compounds of the invention are further suitable for use in combating or controlling parasites in and on animals. Furthermore, the invention relates to a method of combating or controlling parasites in and on animals, which comprises contacting the parasites with a parasitically effective amount of a compound of the invention.

The invention also relates to the non-therapeutic use of compounds of the invention for controlling or combating parasites. Moreover, the invention relates to a non-therapeutic method of combating or controlling parasites, which comprises applying to a locus a parasiticidally effective amount of a compound of the invention.

The compounds of the invention can be effective through both contact (via soil, glass, wall, bed net, carpet, blankets or animal parts) and ingestion (e.g. baits). Furthermore, the compounds of the invention can be applied to any and all developmental stages.

The compounds of the invention can be applied as such or in form of compositions comprising the compounds of the invention.

The compounds of the invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the invention and compositions comprising them can be applied orally, parenterally or topically, e.g. dermally. The compounds of the invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the invention.

The term "locus" means the habitat, food supply, breeding ground, area, material or environment in which a parasite is growing or may grow outside of the animal.

As used herein, the term "parasites" includes endo- and ectoparasites. In some embodiments of the invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*; cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*; flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and Tabanus similIs; lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*; ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*; Actinedida (Prostigmata) und Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularius, Cimex hemipterus, Reduvius senilis, Triatoma* spp., *Rhodnius* ssp., *Panstrongylus* ssp., and *Arilus critatus; Anoplurida*, e.g. *Haematopinus* spp., *Linognathus* spp., *Pediculus* spp., *Phtirus* spp., and *Solenopotes* spp.; *Mallophagida* (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. Trichinellidae (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*; Camallanida, e.g. *Dracunculus medinensis* (guinea worm); Spirurida, e.g. *Thelazia* spp., *Wuchereria* spp., *Brugia* spp., *Onchocerca* spp., *Dirofflari* spp.a, *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and

*Nanocyetes* spp.; Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenoleps* spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservetives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the invention in total amounts of 10 mg/kg to 300 mg/kg, preferably 20 mg/kg to 200 mg/kg, most preferably 25 mg/kg to 160 mg/kg body weight of the treated animal in the course of three weeks.

EXAMPLES

Preparation Examples

With appropriate modification of the starting materials, the procedures as described in the preparation examples below were used to obtain further compounds of formula I. The compounds obtained in this manner are listed in the table that follows, together with physical data.

Compounds can be characterized e.g. by coupled High Performance Liquid Chromatography/mass spectrometry (HPLC/MS), by 1H-NMR and/or by their melting points.

Analytical HPLC—Method 1: Agilent Eclipse Plus C18, 50×4.6 mm, ID 5 μm; Elution: A=10 mM Amm. Formate (0.1% Formic Acid), B=Acetonitrile (0.1% Formic Acid), Flow=1.2 ml/min. at 30° C.; Gradient: 10% B to 100% B-3 min, hold for 1 min, 1 min-10% B. Run Time=5.01 min.

Analytical HPLC—Method 2: Kinetex XB C18 1.7μ 50×2.1 mm; A=Water+0.1% TFA, B=Acetonitrile, Flow=0.8 ml/min-1.0 ml/min in 1.5 min. at 60° C.; Gradient: 5% B to 100% B-1.5 min.

1H-NMR: The signals are characterized by chemical shift (ppm, δ [delta]) vs. tetramethylsilane respectively, CDCl3 for 13C-NMR, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: d for day(s), h for hour(s), min for minute(s), r.t./room temperature for 20-25° C., Rt for retention time; DMSO for dimethyl sulfoxide, OAc for acetate, EtOAc for ethyl acetate, THF for tetrahydrofuran, DMF for N,N-Dimethylformamide, ACN for acetonitrile, DCM for dichloromethane, TEA for triethylamine and t-BuOH for tert-butanol.

Example C-1

N-[5-[4-[(E)-[(Z)-[3-(2-isopropylphenyl)-4-oxo-thiazolidin-2-ylidene]hydrazono]methyl]phenyl]-2-methyl-pyrazol-3-yl]-4-(trifluoromethoxy)benzamide (C-1)

Step-1: Synthesis of 5-(4-bromophenyl)-2-methyl-pyrazol-3-amine

To a stirred solution of methyl 3-(4-bromophenyl)-3-oxo-propanenitrile (3.6 g) in ethanol (30 mL) was added methylhydrazine 85% in water (3.6 mL) at ambient temperature. The reaction mixture was heated at 70° C. for 16 h. After completion of the reaction ethanol was removed under reduced pressure, crude was dissloved in water (50 mL). The mixture was extracted with EtOAc and the organic extracts dried over anhydrous sodium sulphate and evaporated in vacuo and the residue obtained was subjected to silica gel flash column chromatography, eluting with a gradient of EtOAc and heptane to obtain the title compound as a solid (2.0 g). HPLC/MS (method 1): Rt: 1.58 min; m/z=254 (M+2)+.

Step-2: Synthesis of N-[5-(4-bromophenyl)-2-methyl-pyrazol-3-yl]-4-(trifluoromethoxy) benzamide To a stirred solution of 5-(4-bromophenyl)-2-methyl-pyrazol-3-amine (1.75 g) in DCM:pyridine (1:1, 20 mL) was added 4-(trifluoromethoxy)benzoyl chloride (1.871 g) at 0° C. The reaction mixture was stirred at ambient temaperature for 2 h. The reaction mixture was dissloved in water (100 mL). The mixture was extracted with EtOAc and the organic extracts dried over anhydrous Sodium sulphate and evaporated in vacuo and the residue obtained was subjected to silica gel flash column chromatography, eluting with a gradient of EtOAc and heptane to obtain the title compound as a solid (1.9 g). HPLC/MS (method 1): Rt: 2.05 min; m/z=442 (M+2)+.

Step-3: Synthesis of N-[2-methyl-5-(4-vinylphenyl)pyrazol-3-yl]-4-(trifluoromethoxy) benzamide A solution of N-[5-(4-bromophenyl)-2-methyl-pyrazol-3-yl]-4-(trifluoromethoxy)benzamide (0.5 g) in toulene (10 mL) was degassed with nitrogen gas. Tri-n-butyl vinyl tin (0.54 g) and [1,1'-bis(diphenylphosphino)ferrocene]dichloropalladium(II) (0.05 g) were subsequently added and the mixture was heated at 110° C. for 4 h. The mixture was subsequently cooled to ambient temperature, diluted with water and extracted with EtOAc. The organic extracts were dried over sodium sulfate and concentrated under reduced pressure and resultant residue subjected to silica gel flash column chromatography eluting with a gradient of EtOAc and heptane to get the title compound as a solid (0.35 g). HPLC/MS (method 1): Rt: 2.04 min; m/z=388 (M+1)+.

Step-4: Synthesis of N-[5-(4-formylphenyl)-2-methyl-pyrazol-3-yl]-4-(trifluoromethoxy) benzamide To a stirred solution of N-[2-methyl-5-(4-vinylphenyl) pyrazol-3-yl]-4-(trifluoromethoxy) benzamide (0.3 g) in 1,4-dioxane (4 mL) were added a solution of osmium tetroxide (0.004 g) in water (1 mL), sodium periodate (0.364 g). The mixture was stirred for 4 h and sodium sulfite solution (0.5% in Water) was subsequently added and the mixture was extracted with EtOAc. The organic extracts dried over sodium sulfate, and the residue obtained was subjected to silica gel flash column chromatography eluting with a gradient of EtOAc and heptane to obtain the title compound as a solid (0.15 g).

Step-5: Synthesis of N-[5-[4-[(E)-[(2-isopropylphenyl)carbamothioylhydrazono]methyl]phenyl]-2-methyl-pyrazol-3-yl]-4-(trifluoromethoxy)benzamide (C-1)

A mixture of N-[5-(4-formylphenyl)-2-methyl-pyrazol-3-yl]-4-(trifluoromethoxy)benzamide (0.9 g) and 1-amino-3-(2-isopropylphenyl)thiourea (0.532 g) in ethanol (10 mL) was heated at 85° C. for 16 h. The mixture was cooled to ambient temperature and the precipitated solids were filtered and subjected to acidic alumina column chromatography using a gradient of DCM and methanol as eluent to afford the title compound as a solid (0.8 g).

HPLC/MS (method 1): Rt: 2.04 min; m/z=579 (M−1)+; 1H NMR (500 MHz, DMSO-d6) δ 11.78 (s, 1H), 10.57 (s, 1H), 10.02 (s, 1H), 8.19-8.11 (m, 3H), 7.93 (d, J=8.3 Hz, 2H), 7.84 (d, J=8.4 Hz, 2H), 7.61-7.55 (m, 2H), 7.40-7.27 (m, 2H), 7.25-7.20 (m, 2H), 6.84 (s, 1H), 3.79 (s, 3H), 3.15 (m, J=6.9 Hz, 1H), 1.20 (d, J=6.9 Hz, 6H).

Example C-2

N-[5-[4-[(E)-[(Z)-[3-(2-isopropylphenyl)-4-oxo-thiazolidin-2-ylidene]hydrazono]methyl]phenyl]-2-methyl-pyrazol-3-yl]-4-(trifluoromethoxy) benzamide (C-2)

To a stirred mixture of N-[5-[4-[(E)-[(2-isopropylphenyl)carbamothioylhydrazono]methyl]phenyl]-2-methyl-pyrazol-3-yl]-4-(trifluoromethoxy)benzamide (0.345 g), methyl 2-bromoacetate (0.136 g) in ethanol (10 mL) was added sodium acetate (0.073 g) at 0° C. The mixture was stirred at ambient temperature for 16 h. Water (50 mL) was subsequently added. The mixture was extracted with EtOAc and the organic extracts dried over anhydrous sodium sulphate and evaporated invacuo and the residue obtained was subjected to silica gel flash column chromatography, eluting with a gradient of EtOAc and heptane to obtain the title compound as a solid (0.15 g).

HPLC/MS (method 1): Rt: 2.09 min; m/z=621 (M+1)+; 1H NMR (300 MHz, DMSO-d6) δ 10.58 (s, 1H), 8.33 (s, 1H), 8.18-8.08 (m, 2H), 7.87 (d, J=8.3 Hz, 2H), 7.76 (d, J=8.4 Hz, 2H), 7.63-7.41 (m, 4H), 7.40-7.22 (m, 2H), 6.82 (s, 1H), 4.26 (d, J=17.4 Hz, 1H), 4.13 (d, J=17.4 Hz, 1H), 3.78 (s, 3H), 2.79 (m, J=6.8 Hz, 1H), 1.15 (t, J=7.3 Hz, 6H).

Example C-3

1-(2-isopropylphenyl)-3-[(E)-[4-[1-methyl-5-[[4-(trifluoromethoxy)phenyl]methylamino]pyrazol-3-yl]phenyl]methyleneamino]thiourea (C-3)

Step-1: Synthesis of methyl 4-(5-amino-1-methyl-pyrazol-3-yl)benzoate

To a stirred solution of methyl 4-(2-cyanoacetyl)benzoate (3.5 g) in ethanol (35.0 mL) was added methylhydrazine 85% in water (3.5 mL) at ambient temperature. The reaction mixture was heated at 70° C. for 16 h. After completion of the reaction ethanol was removed under reduced pressure, crude was dissolved in water (50 mL). The mixture was extracted with EtOAc and the organic extracts dried over anhydrous sodium sulphate and evaporated in vacuo and the residue obtained was subjected to silica gel flash column chromatography, eluting with a gradient of EtOAc and heptane to obtain the title compound as a solid (3.0 g). 1H NMR (300 MHz, DMSO-d6) δ 7.99-7.86 (m, 2H), 7.79 (m, 2H), 5.79 (s, 1H), 5.35 (s, 2H), 3.84 (s, 3H), 3.59 (s, 3H).

Step-2: Synthesis of methyl 4-[1-methyl-5-[[4-(trifluoromethoxy)phenyl]methylamino]pyrazol-3-yl]benzoate To a stirred solution of methyl 4-(5-amino-1-methyl-pyrazol-3-yl)benzoate (1.75 g) in DMF (20.0 mL), was added 1-(bromomethyl)-4-(trifluoromethoxy)benzene (2.12 g) and potassium carbonate (2.08 g). The mixture was heated at 80° C. for 16 h and subsequently cooled to ambient temperature. 200 mL of water was added, and the mixture extracted with EtOAc. The organic extracts were dried over anhydrous sodium sulphate, evaporated invacuo and the resultant solid was subjected to silica gel flash column chromatography, eluting with a gradient of EtOAc and Heptane to obtain the title compound as a solid. (1.60 g). 1H NMR (300 MHz, DMSO-d6) δ 7.97-7.89 (m, 2H), 7.82-7.74 (m, 2H), 7.59-7.49 (m, 2H), 7.37-7.28 (m, 2H), 6.32 (t, J=6.0 Hz, 1H), 4.30 (d, J=5.9 Hz, 2H), 3.84 (s, 3H), 3.66 (s, 3H).

Step-3: Synthesis of [4-[1-methyl-5-[[4-(trifluoromethoxy)phenyl]methylamino]pyrazol-3-yl]phenyl]methanol A solution of methyl 4-[1-methyl-5-[[4-(trifluoromethoxy)phenyl]methylamino]pyrazol-3-yl]benzoate (1.60 g) in THF (16.0 mL) and ethanol (6.0 mL), was added 2 M solution of lithium borohydride in THF (3.94 mL) at 0° C. and the mixture was stirred at rt for 16 h. The mixture was subsequently cooled to ambient temperature, quenched with saturated ammonium chloride solution (10.0 mL) and extracted with EtOAc. The organic extracts were dried over sodium sulfate and concentrated under reduced pressure and resultant residue subjected to silica gel flash column chromatography eluting with a gradient of EtOAc and heptane to get the title compound as a solid (1.20 g). 1H NMR (300 MHz, DMSO-d6) δ 7.64-7.50 (m, 4H), 7.38-7.22 (m, 4H), 6.21 (t, J=6.0 Hz, 1H), 5.73 (s, 1H), 5.13 (t, J=5.7 Hz, 1H), 4.47 (d, J=5.7 Hz, 2H), 4.29 (d, J=5.9 Hz, 2H), 3.62 (s, 3H).

Step-4: Synthesis of 4-[1-methyl-5-[[4-(trifluoromethoxy)phenyl]methylamino]pyrazol-3-yl]benzaldehyde To a stirred solution of [4-[1-methyl-5-[[4-(trifluoromethoxy)phenyl]methylamino]pyrazol-3-yl]phenyl]methanol (0.650 g) in DMSO (6.0 mL), were added triethyl amine (0.260 g), sulfur trioxide pyridine complex (0.329 g). The mixture was stirred for 4 h and, water (20.0 mL) was subsequently added and the mixture was extracted with EtOAc. The organic extracts dried over sodium sulfate, and the residue obtained was subjected to silica gel flash column chromatography eluting with a gradient of EtOAc and heptane to obtain the title compound as a solid (0.400 g). HPLC/MS (method 1): Rt: 1.926 min; m/z=374 (M−1)+.

Step-5: Synthesis of 1-(2-isopropylphenyl)-3-[(E)-[4-[1-methyl-5-[[4-(trifluoromethoxy)phenyl]methylamino]pyrazol-3-yl]phenyl]methyleneamino]thiourea (C-3)

A mixture of 4-[1-methyl-5-[[4-(trifluoromethoxy)phenyl]methylamino]pyrazol-3-yl]benzaldehyde (0.110 g) and 1-amino-3-(2-isopropylphenyl)thiourea (0.067 g) in ethanol (10.0 mL) was heated at 85° C. for 16 h. The mixture was cooled to ambient temperature and the precipitated solids were filtered and subjected to acidic alumina column chromatography using a gradient of DCM and methanol as eluent to afford the title compound as a solid (0.125 g).

HPLC/MS (method 1): Rt: 2.115 min; m/z=567.1 (M+1)+; 1H NMR (300 MHz, DMSO-d6) δ 11.74 (s, 1H), 9.97 (s, 1H), 8.12 (s, 1H), 7.94-7.77 (m, 2H), 7.78-7.60 (m, 2H), 7.62-7.45 (m, 2H), 7.45-7.28 (m, 3H), 7.27-7.07 (m, 3H), 6.27 (t, J=6.0 Hz, 1H),), 5.84 (s,1H), 4.30 (d, J=5.8 Hz, 2H), 3.64 (s, 3H), 3.12 (p, J=6.8 Hz, 1H), 1.18 (d, J=6.9 Hz, 6H).

Example C-5

1-(2-isopropylphenyl)-3-[(E)-[4-[1-methyl-5-[[4-(trifluoromethoxy) benzenecarboximidoyl]amino]pyrazol-3-yl]phenyl]methyleneamino]thiourea (C-5)

Step-1: Synthesis of 5-(4-bromophenyl)-2-methyl-pyrazol-3-amine

To a stirred solution of methyl 3-(4-bromophenyl)-3-oxo-propanenitrile (3.6 g) in ethanol (30.0 mL) was added methylhydrazine 85% in water (3.6 mL) at ambient temperature. The reaction mixture was heated at 70° C. for 16 h. After completion of the reaction ethanol was removed under reduced pressure, crude was dissolved in water (50 mL). The mixture was extracted with EtOAc and the organic extracts dried over anhydrous Sodium sulphate and evaporated in vacuo and the residue obtained was subjected to silica gel flash column chromatography, eluting with a gradient of EtOAc and heptane to obtain the title compound as a solid (2.0 g). HPLC/MS (method 1): Rt: 1.58 min; m/z=254 (M+2)+.

Step-2: Synthesis of N-[5-(4-bromophenyl)-2-methyl-pyrazol-3-yl]-4-(trifluoromethoxy)benzamidine To a stirred solution of 5-(4-bromophenyl)-2-methyl-pyrazol-3-amine (1.20 g) in toulene was added(trifluoromethoxy)benzonitrile (1.06 g) and a 2 M solution of trimethyl aluminium in toluene (4.76 mL). The mixture was heated at 110° C. for 2 h and subsequently cooled to ambient temperature. A solution of 2.0 N HCl was added dropwise and the mixture extracted with EtOAc. The organic extracts were dried over anhydrous sodium sulphate, evaporated in vacuo and the resultant solid was subjected to silica gel flash column chromatography, eluting with a gradient of EtOAc and heptane to obtain the title compound as a solid. (1.20 g). HPLC/MS (method 1): Rt: 2.10 min; m/z=438 (M−1)+.

Step-3: Synthesis of N-[2-methyl-5-(4-vinylphenyl)pyrazol-3-yl]-4-(trifluoromethoxy) benzamidine was achieved following method similar to step 3 of C-1. HPLC/MS (method 1): Rt: 1.98 min; m/z=387 (M+1)+.

Step-4: Synthesis of N-[5-(4-formylphenyl)-2-methyl-pyrazol-3-yl]-4-(trifluoromethoxy)benzamidine was achieved following method similar to step 4 of C-1. HPLC/MS (method 1): Rt: 1.86 min; m/z=387 (M−1)+.

Step-5: Synthesis of 1-(2-isopropylphenyl)-3-[(E)-[4-[1-methyl-5-[[4-(trifluoromethoxy)benzenecarboximidoyl]amino]pyrazol-3-yl]phenyl]methyleneamino]thiourea(C-5) was achieved following method similar to step 5 of C-1.

HPLC/MS (method 1): Rt: 2.10 min; m/z=579.95 (M+1)+; 1H NMR (300 MHz, DMSO-d6) δ 11.78 (s, 1H), 10.00 (s, 1H), 8.17 (d, J=9.2 Hz, 3H), 7.92 (d, J=8.3 Hz, 2H), 7.85 (d, J=8.2 Hz, 2H), 7.48 (d, J=8.4 Hz, 2H), 7.34-7.15 (m, 7H), 6.71 (s, 1H), 3.78 (s,1H), 3.14 (p, J=6.8 Hz, 1H), 1.20 (d, J=6.9 Hz, 6H).

Example C-6

Synthesis of N-[5-[4-[(E)-[(Z)-[3-(2-isopropylphenyl)-4-oxo-thiazolidin-2-ylidene]hydrazono]methyl]phenyl]-2-methyl-pyrazol-3-yl]-4-(trifluoromethoxy) benzamidine (C-6) was achieved following method similar step of C-2.

HPLC/MS (method 1): Rt: 2.16 min; m/z=620 (M+1)+; 1H NMR (500 MHz, DMSO-d6) δ 8.31 (s, 1H), 8.18 (d, J=8.7 Hz, 2H), 7.89 (d, J=8.1 Hz, 2H), 7.76 (d, J=8.1 Hz, 2H), 7.56-7.42 (m, 4H), 7.34 (td, J=7.5, 1.7 Hz, 2H), 7.27 (dd, J=7.9, 1.4 Hz, 2H), 6.69 (s, 1H), 4.36-4.09 (m, 2H), 3.79 (s, 3H), 2.80 (p, J=6.8 Hz, 1H), 1.16 (dd, J=12.9, 6.9 Hz, 6H).

Example C-10

1-(2-isopropylphenyl)-3-[(E)-[4-[1-methyl-5-[[4-(trifluoromethoxy)phenyl]methoxy]pyrazol-3-yl]phenyl]methyleneamino]thiourea (C-10)

Step-1: Synthesis of 5-(4-bromophenyl)-2-methyl-pyrazol-3-ol

To a stirred solution of ethyl 3-(4-bromophenyl)-3-oxo-propanoate (2.0 g) in acetic acid (20.0 mL), was added methylhydrazine 85% in water (3.0 mL) at ambient temperature. The reaction mixture was heated at 70° C. for 16 h. After completion of the reaction Acetic acid was removed under reduced pressure, crude was dissolved in water (50 mL). The mixture was extracted with EtOAc and the organic extracts dried over anhydrous Sodium sulphate and evaporated in vacuo and the residue obtained was subjected to silica gel flash column chromatography, eluting with a gradient of EtOAc and heptane to obtain the title compound as a solid (0.90 g). HPLC/MS (method 1): Rt: 1.54 min; m/z=252.7 (M+1)+.

Step-2: Synthesis of 3-(4-bromophenyl)-1-methyl-5-[[4-(trifluoromethoxy) phenyl]methoxy]pyrazole.

To a stirred solution of 5-(4-bromophenyl)-2-methyl-pyrazol-3-ol (0.800 g) in DMF, was added sodium hydride (0.169 g, 60% dispersion in mineral), and a 1-(bromomethyl)-4-(trifluoromethoxy)benzene (0.887 g). The mixture was stirred at rt for 16 h. Water (50.0 mL) was subsequently added and the mixture extracted with EtOAc. The organic extracts were dried over anhydrous Sodium sulphate, evaporated in vacuo and the resultant solid was subjected to silica gel flash column chromatography, eluting with a gradient of EtOAc and heptane to obtain the title compound as a solid. (0.400 g). HPLC/MS (method 1): Rt: 2.20 min; m/z=428.9 (M+1)+.

Step-3: Synthesis of 1-methyl-5-[[4-(trifluoromethoxy)phenyl]methoxy]-3-(4-vinylphenyl)pyrazole was achieved following method similar to step 3 of C-1. H PLC/MS (method 1): Rt: 2.20 min; m/z=373 (M−1)+.

Step-4: Synthesis of 4-[1-methyl-5-[[4-(trifluoromethoxy) phenyl]methoxy]pyrazol-3-yl]benzaldehyde was achieved following method similar to step 4 of C-1. H PLC/MS (method 1): Rt: 2.06 min; m/z=375 (M−1)+.

Step-5: Synthesis of 1-(2-isopropylphenyl)-3-[(E)-[4-[1-methyl-5-[[4-(trifluoromethoxy) phenyl]methoxy]pyrazol-3-yl]phenyl]methyleneamino]thiourea (C-10) was achieved following method similar to step 5 of C-1.

HPLC/MS (method 1): Rt: 2.251 min; m/z=567.90 (M+1)+; 1H NMR (500 MHz, DMSO-d6) δ 11.78 (s, 1H), 10.00 (s, 1H), 8.15 (s, 1H), 7.91 (d, J=8.3 Hz, 2H), 7.79-7.74 (m, 2H), 7.69-7.63 (m, 2H), 7.46-7.40 (m, 2H), 7.40-7.34 (m, 1H), 7.30 (ddd, J=8.0, 5.4, 3.3 Hz, 1H), 7.26-7.19 (m, 2H), 6.37 (s, 1H), 5.27 (s, 2H), 3.64 (s, 3H), 3.13 (h, J=6.8 Hz, 1H), 1.20 (d, J=6.8 Hz, 6H).

Example C-12

(2Z)-2-(2-isopropylphenyl)imino-3-[(E)-[4-[1-methyl-5-[[4-(trifluoromethoxy)phenyl]methoxy]pyrazol-3-yl]phenyl]methyleneamino]thiazolidin-4-one (C-12)

To a stirred mixture of 4-[1-methyl-5-[[4-(trifluoromethoxy)phenyl]methoxy]pyrazol-3-yl]benzaldehyde (0.120 g), (2E)-3-amino-2-(2-isopropylphenyl)imino-thiazolidin-4-one (0.095 g) in acetic acid (3.0 mL) was stirred at ambient temperature for 4 h. Water (50.0 mL) was subsequently added. The mixture was extracted with EtOAc and the organic extracts dried over anhydrous sodium sulphate and evaporated invacuo and the residue obtained was subjected to silica gel flash column chromatography, eluting with a gradient of EtOAc and heptane to obtain the title compound as a solid (0.150 g).

HPLC/MS (method 1): Rt: 2.33 min; m/z=608 (M+1)+; 1H NMR (500 MHz, DMSO-d6) δ 9.05 (s, 1H), 7.97-7.87

(m, 4H), 7.70-7.64 (m, 2H), 7.46-7.40 (m, 2H), 7.31 (dd, J=7.7, 1.6 Hz, 1H), 7.18 (td, J=7.5, 1.6 Hz, 1H), 7.12 (td, J=7.5, 1.5 Hz, 1H), 6.86 (dd, J=7.8, 1.4 Hz, 1H), 6.42 (s, 1H), 5.29 (s, 2H), 4.15 (s, 2H), 3.66 (s, 3H), 3.00 (hept, J=6.9 Hz, 1H), 1.14 (d, J=6.9 Hz, 6H).

Example C-15

N-[5-[4-[(E)-[(2-isopropylphenyl)carbamothioylhydrazono]methyl]phenyl]-2,4-dimethyl-pyrazol-3-yl]-4-(trifluoromethyl)benzamide Step 1: Synthesis of N-(2,4-dimethylpyrazol-3-yl)-4-(trifluoromethypenzamide To a stirred solution of 4-(trifluoromethyl)benzoic acid (2.5 g) in DMF (75 mL) was added HATU (10.0 g) and DIPEA (6.771 mL) at 0° C. After stirring the reaction mixture for 1 h, 2,4-di-methylpyrazol-3-amine (1.754 g) was added at 0° C. The mixture was stirred at room temperature for 16 h. The reaction mixture was diluted with brine (NaCl aq. solution) and extracted with EtOAc. The organic phase was dried over sodium sulfate, concentrated under reduced pressure and resultant residue subjected to silica gel flash column chromatography, eluting with a gradient of MeOH and DCM to obtain the title compound as a solid (3.5 g). HPLC/MS (method 2): Rt: 0.983 min; m/z=283.9 (M+1)+.

Step 2: Synthesis of N-(5-iodo-2,4-dimethyl-pyrazol-3-yl)-4-(trifluoromethyl)benzamide To a stirred solution of N-(2,4-dimethylpyrazol-3-yl)-4-(trifluoromethyl)benzamide (1.0 g) in DMF (30.0 mL) was added N-iodosuccinimide. The mixture was stirred for 16 h at 60° C. and water (30.0 mL) was subsequently added and the mixture was extracted with EtOAc and aq. NaHCO3. The organic phase was dried over sodium sulfate, and the residue obtained was subjected to silica gel flash column chromatography eluting with a gradient of EtOAc and cyclohexane to obtain the title compound as a solid (0.5 g).

HPLC/MS (method 2): Rt: 1.118 min; m/z=409.7 (M+1)+.

Step 3: Synthesis of N-[5-(4-formylphenyl)-2,4-dimethyl-pyrazol-3-yl]-4-(trifluoromethyl)benzamide A solution of N-(5-iodo-2,4-dimethyl-pyrazol-3-yl)-4-(trifluoromethyl)benzamide (0.490 g), (4-formylphenyl)boronic acid (0.269 g), potassium carbonate (0.414 g), water (1 mL) in 1,2-di-methoxyethane (20 mL) was set under argon atmosphere. Pd(dppf)Cl2 (0.044 g) was added to the reaction mixture and stirred for 16 h at 80° C. The solvent was removed under reduced pressure and the mixture was extracted with EtOAc and water. The organic phase was dried over sodium sulfate, and the residue obtained was subjected to silica gel flash column chromatography eluting with a gradient of EtOAc and cyclohexane to obtain the title compound as a solid (0.270 g). HPLC/MS (method 2): Rt: 1.122 min; m/z=387.8 (M+1)+.

Step 4: Synthesis of N-[5-[4-[(E)-[(2-isopropylphenyl)carbamothioylhydrazono]methyl]phenyl]-2,4-dimethyl-pyrazol-3-yl]-4-(trifluoromethypenzamide was achieved following method similar to step 5 of C-1.

HPLC/MS (method 2): Rt: 1.318 min; m/z=579.0 (M+1)+. 1H NMR (400 MHz, Chloroform-d) δ 9.46 (s, 1H), 8.99 (s, 1H), 8.20 (d, J=8.0 Hz, 2H), 7.86-7.78 (m, 3H), 7.75 (d, J=8.2 Hz, 2H), 7.68 (d, J=8.1 Hz, 2H), 7.61 (d, J=7.7 Hz, 1H), 7.41-7.26 (m, 4H), 3.97 (s, 3H), 3.15 (p, J=6.9 Hz, 1H), 2.16 (s, 3H), 1.30 (s, 3H), 1.28 (s, 3H).

Example C-29

N-[2-ethyl-5-[4-[(E)-[(2-isopropylphenyl)carbamothioylhydrazono]methyl]phenyl]pyrazol-3-yl]-4-(trifluoromethoxy)benzamide (C-29)

Step-1: Synthesis of 5-(4-bromophenyl)-2-ethyl-pyrazol-3-amine

To a stirred solution of 3-(4-bromophenyl)-3-oxo-propanenitrile (6 g) in ethanol (60.0 mL) were added ethylhydrazine dihydrochloride (4.27 g) and diisopropyl ethylamine (6.92 g) at ambient temperature. The reaction mixture was heated at 85° C. for 12 h and after completion of the reaction ethanol was removed under reduced pressure, crude was dissloved in water. The mixture was extracted with EtOAc and the organic extracts dried over anhydrous Sodium sulphate and evaporated in vacuo. The residue obtained was subjected to silica gel flash column chromatography, eluting with a gradient of EtOAc and heptane to obtain the title compound as a solid (6.2 g). HPLC/MS (method 1): Rt: 1.64 min; m/z=265.50 (M+1)+.

Step-2: Synthesis of N-[5-(4-bromophenyl)-2-ethyl-pyrazol-3-yl]-4-(trifluoromethoxy) benzamide was achieved following method similar to step 2 of C-1.

HPLC/MS (method 1): Rt: 2.069 min; m/z=455.15 (M+1)+.

Step-3: Synthesis of N-[2-ethyl-5-(4-vinylphenyl)pyrazol-3-yl]-4-(trifluoromethoxy) Benzamide was achieved following method similar to step 3 of C-1.

HPLC/MS (method 1): Rt: 2.027 min; m/z=401.55 (M+1)+.

Step-4: Synthesis of N[2-ethyl-5-(4-formylphenyl)pyrazol-3-yl]-4 (trifluoromethoxy) Benzamide was achieved following method similar to step 4 of C-1.

HPLC/MS (method 1): Rt: 1.909 min; m/z=403.45 (M+1)+.

Step-5: Synthesis of N-[2-ethyl-5-[4-[(E)-[(2 isopropylphenyl)carbamothioylhydrazono]methyl]phenyl]pyrazol-3-yl]-4 (trifluoromethoxy)benzamide (C-29) was achieved following method similar to step 5 of C-1.

HPLC/MS (method 1): Rt: 2.112 min; m/z=592.70 (M−1)+.

Example C-32

Synthesis of N-[2-ethyl-5-[4-[(E)-[(2S,3R,4R,5S,6S)-3,4,5-trimethoxy-6-methyl-tetrahydropyran-2-yl]oxyiminomethyl]phenyl]pyrazol-3-yl]-4-(trifluoromethoxy)benzamide (C-32)

A mixture of N[2-ethyl-5-(4-formylphenyl)pyrazol-3-yl]-4-(trifluoromethoxy)benzamide (0.4 g) and O-[(2S,3R,4R,5S,6S)-3,4,5-trimethoxy-6-methyl-tetrahydropyran-2-yl] hydroxylamine (0.219 g) in ethanol (4.0 mL) was heated at 85° C. for 3 h. The mixture was cooled to ambient temperature and the solvent concentrated under reduced pressure and resultant residue subjected to silica gel flash column chromatography eluting with a gradient of EtOAc and heptane to obtain the title compound as a solid (0.220 g).

HPLC/MS (method 1): Rt: 2.059 min; m/z=605 (M−1)+; 1H NMR (500 MHz, DMSO-d6) δ 10.52 (s, 1H), 8.42 (s, 1H), 8.17-8.10 (m, 2H), 7.91-7.81 (m, 2H), 7.72-7.67 (m, 2H), 7.61-7.55 (m, 2H), 6.81 (s, 1H), 5.52 (d, J=2.1 Hz, 1H), 4.11 (q, J=7.2 Hz, 2H), 3.80 (dd, J=3.3, 2.1 Hz, 1H), 3.56

(dq, J=9.5, 6.3 Hz, 1H), 3.46-3.36 (m, 10H), 3.05 (t, J=9.3 Hz, 1H), 1.38 (t, J=7.2 Hz, 3H), 1.18 (d, J=6.2 Hz, 3H).

Example C-33

Synthesis of [(2S,3R,4R,5S,6S)-3,4,5-trimethoxy-6-methyl-tetrahydropyran-2-yl] N-[4-[1-ethyl-5-[[4-(trifluoromethoxy)benzoyl]amino]pyrazol-3-yl]phenyl]carbamate (C-33)

Step-1: Synthesis of 2-ethyl-5-(4-nitrophenyl)pyrazol-3-amine

To a stirred solution of 3-(4-nitrophenyl)-3-oxo-propanenitrile (1.0 g) in ethanol (10.0 mL) were added ethylhydrazine dihydrochloride (0.839 g) and diisopropyl ethylamine (1.359 g) at ambient temperature. The reaction mixture was heated at 85° C. for 12 h and after completion of the reaction ethanol was removed under reduced pressure, crude was dissloved in water. The mixture was extracted with EtOAc and the organic extracts dried over anhydrous Sodium sulphate and evaporated in vacuo. The residue obtained was subjected to silica gel flash column chromatography, eluting with a gradient of EtOAc and heptane to obtain the title compound as a solid (1.2 g). HPLC/MS (method 1): Rt: 1.557 min; m/z=231.8 (M−1)+.

Step-2: Synthesis of N-[2-ethyl-5-(4-nitrophenyl)pyrazol-3-yl]-4-(trifluoromethoxy) benzamide To a stirred solution of 2-ethyl-5-(4-nitrophenyl)pyrazol-3-amine (1.2 g) in DCM, pyridine (12:3 mL) was added 4-(trifluoromethoxy)benzoyl chloride (1.276 g) at 0° C. The reaction mixture was stirred at ambient temaperature for 12 h. The reaction mixture was dissloved in water and the mixture was extracted with EtOAc. The organic extracts dried over anhydrous Sodium sulphate and evaporated in vacuo. The residue obtained was subjected to silica gel flash column chromatography, eluting with a gradient of EtOAc and heptane to obtain the title compound as a solid (2 g). HPLC/MS (method 1): Rt: 1.963 min; m/z=421 (M+1)+.

Step-3: Synthesis of N-[5-(4-aminophenyl)-2-ethyl-pyrazol-3-yl]-4-(trifluoromethoxy) benzamide To a stirred solution of N-[2-ethyl-5-(4-nitrophenyl)pyrazol-3-yl]-4-(trifluoromethoxy)benzamide (2.0 g) in Isopropyl alcohol (20.0 mL) were subsequently added bispinacolato diborane (3.76 g) and pottasium t-butoxide (0.639 g) and the mixture was heated at 110° C. for 4 h. The mixture was subsequently cooled to ambient temperature, diluted with water and extracted with EtOAc. The organic extracts were dried over sodium sulfate and concentrated under reduced pressure. The resultant residue subjected to silica gel flash column chromatography eluting with a gradient of EtOAc and heptane to get the title compound as a solid (1.8 g). HPLC/MS (method 1): Rt: 1.739 min; m/z=390.65 (M+1)+.

Step-4: Synthesis of (4-nitrophenyl) N-[4-[1-ethyl-5-[[4-(trifluoromethoxy)benzoyl]amino]pyrazol-3-yl]phenyl]carbamate To a stirred solution of N-[5-(4-aminophenyl)-2-ethyl-pyrazol-3-yl]-4-(trifluoromethoxy) Benzamide (2.0 g) in THF (20 mL) was added (4-nitrophenyl) carbonochloridate (1.136 g) and the mixture was stirred at 0° C. for 4 h. The reaction mixture was evaporated in vacuo. and the residue obtained was subjected to heptane tituration, filtered and evaporated under vacuo. to obtain the title compound as a solid (2.5 g).

Step-5: Synthesis of [(2S,3R,4R,5S,6S)-3,4,5-trimethoxy-6-methyl-tetrahydropyran-2-yl] N-[4-[1-ethyl-5-[[4-(trifluoromethoxy)benzoyl]amino]pyrazol-3-yl]phenyl]carbamate (C-33)

To a mixture of (4-nitrophenyl) N-[4-[1-ethyl-5-[[4-(trifluoromethoxy)benzoyl]amino]pyrazol-3-yl]phenyl]carbamate (1.0 g) and (2R,3R,4R,5S,6S)-3,4,5-trimethoxy-6-methyl-tetrahydropyran-2-ol (0.446 g) in MeCN (10 mL) were subsequently added K3PO4 hydrate (0.763 g) and diisopropyl amine (0.464 g) at 0° C. The reaction mass was stirred at ambient temperature for 12 h. The mixture was diluted with water and extracted with EtOAc; and the organic extracts were dried over sodium sulfate and concentrated under reduced pressure. The resultant residue subjected to Prep. HPLC to get the title compound as a solid (0.12 g). HPLC/MS (method 1): Rt: 1.909 min; m/z=622 (M+1)+; 1H NMR (300 MHz, DMSO-d6) δ 10.46 (s, 1H), 9.89 (s, 1H), 8.18-8.07 (m, 2H), 7.78-7.70 (m, 2H), 7.70-7.47 (m, 4H), 6.66 (s, 1H), 5.97 (d, J=2.1 Hz, 1H), 4.07 (q, J=7.2 Hz, 2H), 3.75 (t, J=2.7 Hz, 1H), 3.64 (dd, J=9.5, 6.1 Hz, 1H), 3.60-3.48 (m, 1H), 3.44 (d, J=5.9 Hz, 9H), 3.06 (t, J=9.3 Hz, 1H), 1.36 (t, J=7.2 Hz, 3H), 1.19 (d, J=6.2 Hz, 3H).

Example C-34

Step 1: Synthesis of N-[5-(4-bromophenyl)-2-ethyl-pyrazol-3-yl]-N-methyl-4-(trifluoromethoxy)benzamide To a stirred solution of N-[5-(4-bromophenyl)-2-ethyl-pyrazol-3-yl]-4-(trifluoromethoxy) Benzamide (0.3 g) in N,N-Dimethylformamide (3 mL) were subsequently added methyl iodide (0.103 g) and Pottasium carbonate (0.182 g) at ambient temperature. The reaction mixture was heated at 85° C. for 6 h and after completion of the reaction, reaction mass was diluted with water. The mixture was extracted with EtOAc and the organic extracts dried over anhydrous Sodium sulphate; and evaporated in vacuo. The residue obtained was subjected to silica gel flash column chromatography, eluting with a gradient of EtOAc and heptane to obtain the title compound as a solid (0.24 g). HPLC/MS (method 1): Rt: 2.240 min; m/z=469.15 (M+1)+.

Step 2: Synthesis of N-[2-ethyl-5-(4-vinylphenyl)pyrazol-3-yl]-N-methyl-4-(trifluoromethoxy)benzamide was achieved following method similar to step 3 of C-1.

HPLC/MS (method 1): Rt: 2.176 min; m/z=415.55 (M+1)+.

Step 3: Synthesis of N-[2-ethyl-5-(4-formylphenyl)pyrazol-3-yl]-N-methyl-4-(trifluoromethoxy)benzamide was achieved following method similar to step 4 of C-1. HPLC/MS (method 1): Rt: 1.973 min; m/z=417.35 (M+1)+.

Step 4: Synthesis of N-[2-ethyl-5-[4-[(E)-[(2-isopropylphenyl) carbamothioylhydrazono]methyl]phenyl]pyrazol-3-yl]-N-methyl-4-(trifluoromethoxy) benzamide (C-34) was achieved following method similar to step 5 of C-1.

HPLC/MS (method 1): Rt: 2.144 min; m/z=608.50 (M+1)+; 1H NMR (500 MHz, DMSO-d6) δ 11.78 (s, 1H), 9.99 (s, 1H), 8.14 (s, 1H), 7.90 (d, J=8.1 Hz, 2H), 7.73 (d, J=7.9 Hz, 2H), 7.52 (s, 2H), 7.36 (d, J=7.7 Hz, 1H), 7.30 (ddd, J=8.0, 5.3, 3.4 Hz, 3H), 7.26-7.19 (m, 2H), 6.80 (s, 1H), 3.9-4 (s, 2H), 3.3 (s, 3H), 3.13 (p, J=6.9 Hz, 1H), 1.26 (s, 3H), 1.19 (d, J=6.9 Hz, 6H).

Example C-40

[(2S,3R,4R,5S,6S)-3,4,5-trimethoxy-6-methyl-tetrahydropyran-2-yl] N-[4-[1-ethyl-5-[[4-(trifluoromethoxy)phenyl]methylamino]pyrazol-3-yl]phenyl]carbamate (C-40)

Step-1: Synthesis of 2-ethyl-5-(4-nitrophenyl)pyrazol-3-amine

To a stirred solution of 3-(4-nitrophenyl)-3-oxo-propanenitrile (1.3 g) in ethanol (25 mL) were added ethylhydrazine dihydrochloride (1.364 g) and diisopropyl ethylamine (2.65 g) at ambient temperature. The reaction mixture was heated at 85° C. for 12 h and after completion of the reaction ethanol was removed under reduced pressure, crude was dissloved in water. The mixture was extracted with EtOAc and the organic extracts dried over anhydrous Sodium sulphate and evaporated in vacuo. The residue obtained was subjected to silica gel flash column chromatography, eluting with a gradient of EtOAc and heptane to obtain the title compound as a solid (1.54 g). HPLC/MS (method 1): Rt: 0.816 min; m/z=232.9 (M+1)+.

Step-2: Synthesis of (E)-N-[2-ethyl-5-(4-nitrophenyl)pyrazol-3-yl]-1-[4 (trifluoromethoxy)phenyl]methanimine To a stirred solution of 2-ethyl-5-(4-nitrophenyl)pyrazol-3-amine (1.54 g) in ethanol (20 mL) was added 4-(trifluoromethoxy)benzaldehyde (1.57 g) and the reaction mixture was stirred at 60° C. for 2 h. The precipitated product was filtered off under suction and triturated with Diisopropyl ether, product was filtered off and evaporated in vacuo to obtain the title compound as a solid (0.9 g). HPLC/MS (method 1): Rt: 1.484 min; m/z=404.8 (M+1)+.

Step-3: Synthesis of 2-ethyl-5-(4-nitrophenyl)-N-[[4-(trifluoromethoxy)phenyl]methyl]pyrazol-3-amine To a stirred solution of (E)-N-[2-ethyl-5-(4-nitrophenyl) pyrazol-3-yl]-1-[4 (trifluoromethoxy)phenyl]methanimine (0.9 g) in ethanol (15 mL) at 0° C. was subsequently added sodium borohydride (0.126 g) and the mixture was stirred at ambient temperature for 4 h. The mixture was evaporated in vacuo, diluted with water and extracted with EtOAc. The organic extracts were dried over Sodium sulfate and concentrated under reduced pressure to get the title compound as a solid (0.77 g). HPLC/MS (method 1): Rt: 1.322 min; m/z=407 (M+1)+.

Step-4: Synthesis of 5-(4-aminophenyl)-2-ethyl-N-[[4-(trifluoromethoxy)phenyl]methyl]pyrazol-3-amine To a stirred solution of 2-ethyl-5-(4-nitrophenyl)-N-[[4-(trifluoromethoxy) phenyl]methyl]pyrazol-3-amine (0.77 g) in methanol (30.0 mL) was subsequently added tin (II) chloride dihydrate (1.282 g) and mixture was stirred at 70° C. for 12 h. The mixture was diluted with 1 N NaOH solution and extracted with EtOAc. The organic extracts were dried over Sodium sulfate and concentrated under reduced pressure to obtain the title compound as a solid (0.71 g). HPLC/MS (method 1): Rt: 0.956 min; m/z=377 (M+1)+.

Step-5: Synthesis of (4-nitrophenyl) N-[4-[1-ethyl-5-[[4 (trifluoromethoxy)phenyl]methylamino]pyrazol-3-yl]phenyl] carbamate To a stirred solution of 5-(4-aminophenyl)-2-ethyl-N—[[4 (trifluoromethoxy)phenyl]methyl]pyrazol-3-amine (0.71 g) in THF (8 mL) was added (4-nitrophenyl) carbonochloridate (0.380 g) and the mixture was stirred at 0° C. for 4 h. The reaction mixture was evaporated in vacuo. and the residue obtained was subjected to heptane tituration, filtered and evaporated under vacuo. to obtain the title compound as a solid (1 g).

HPLC/MS (method 1): Rt: 1.178 min; m/z=542.1 (M+1)+.

Step-6: Synthesis of [(2S,3R,4R,5S,6S)-3,4,5-trimethoxy-6-methyl-tetrahydropyran-2-yl] N-[4-[1-ethyl-5-[[4-(trifluoromethoxy)phenyl]methylamino]pyrazol-3-yl]phenyl]carbamate (C-40)

To a mixture of (4-nitrophenyl) N-[4-[1-ethyl-5-[[4 (trifluoromethoxy)phenyl]methylamino]pyrazol-3-yl]phenyl] carbamate (0.3 g) and (2R,3R,4R,5S,6S)-3,4,5-trimethoxy-6-methyl-tetrahydropyran-2-ol (0.137 g) in MeCN (9.0 mL) were subsequently added Tripotassium phosphate hydrate (0.294 g) and Diisopropyl amine (0.179 g) at 0° C. The reaction mass was stirred at ambient temperature for 12 h and the mixture was diluted with water and extracted with EtOAc. The organic extracts were dried over Sodium sulfate and concentrated under reduced pressure. The resultant residue subjected to Prep. HPLC to get the title compound as a solid (0.08 g) HPLC/MS (method 1): Rt: 1.111 min; m/z=609.2 (M+1)+.

Example C-47

Synthesis of 5-[4-[(E)-[(Z)-[3-(2-isopropylphenyl)-4-oxo-thiazolidin-2-ylidene]hydrazono]methyl]phenyl]-2-methyl-N-[4-(trifluoromethoxy)phenyl]pyrazole-3-carboxamide Step 1: Synthesis of 5-(4-formylphenyl)-2-methyl-pyrazole-3-carboxylic acid was achieved following method similar to step 3 of C-15.

HPLC/MS (method 2): Rt: 0.857 min; m/z=231 (M+1)+.

Step 2: Synthesis of 5-[4-[(E)-[(2-isopropylphenyl)carbamothioylhydrazono]methyl]phenyl]-2-methyl-pyrazole-3-carboxylic acid was achieved following method similar to step 5 of C-1. H PLC/MS (method 2): Rt: 1.14 min; m/z=422 (M+1)+.

Step 3: Synthesis of 5-[4-[(E)-[(2-isopropylphenyl)carbamothioylhydrazono]methyl]phenyl]-2-methyl-pyrazole-3-carboxylic acid was achieved following method similar step of C-2. HPLC/MS (method 2): Rt: 1.22 min; m/z=462 (M+1)+.

Step 4: Synthesis of 5-[4-[(E)-[(Z)-[3-(2-isopropylphenyl)-4-oxo-thiazolidin-2-ylidene]hydrazono]methyl]phenyl]-2-methyl-N-[4-(trifluoromethoxy)phenyl]pyrazole-3-carboxamide was achieved following method similar to step 5 of C-1.

HPLC/MS (method 2): Rt: 1.48 min; m/z=621 (M+1)+.

Example C-52

Step-1: Synthesis of Ethyl 4-(4-bromophenyl)-2,4-dioxo-butanoate

To a stirred solution of 1-(4-bromophenyl)ethanone (5.0 g) in toluene (80.0 mL) was added sodium hydride (1.2 g) at 0° C. The reaction mixture was stirred at ambient temaperature for 10 min. The reaction mixture cooled to 0° C. and diethyl oxalate (4.40 g) was added. The reaction mixture was heated at 50° C. for 3 h. The reaction mixture was quench with ammonium chloride solution (100 mL). The mixture was extracted with EtOAc and the organic extracts dried over anhydrous Sodium sulphate and evaporated in vacuo and the residue obtained was subjected to silica gel flash column chromatography, eluting with a gradient of EtOAc and heptane to obtain the title compound as a solid (7.1 g) HPLC/MS (method 1): Rt: 2.02 min; m/z=298.5 (M−1)+.

Step-2: Synthesis of Ethyl 5-(4-bromophenyl)-2-methyl-pyrazole-3-carboxylate

To a stirred solution of ethyl 4-(4-bromophenyl)-2,4-dioxo-butanoate (7.0 g) in ethanol (100 mL) was added acetic acid (2.0 mL) & methylhydrazine 85% in water (7.0 mL) at 0° C. The reaction mixture was heated at 90° C. for 4 h. After completion of the reaction ethanol was removed under reduced pressure, crude was dissloved in water (100 mL). The mixture was extracted with EtOAc and the organic extracts dried over anhydrous sodium sulphate and evaporated in vacuo and the residue obtained was subjected to silica gel flash column chromatography, eluting with a gradient of EtOAc and heptane to obtain the title compound as a solid (4.0 g). HPLC/MS (method 1): Rt: 2.2 min; m/z=310 (M+1)+.

Step-3: Synthesis of [5-(4-bromophenyl)-2-methyl-pyrazol-3-yl]methanol

To a stirred solution of ethyl 5-(4-bromophenyl)-2-methyl-pyrazole-3-carboxylate (4.0 g) in THF (50 mL) was 1M solution of lithium aluminium hydride in THF (15.0 mL) at 0° C. The reaction mixture was stirred at ambient temaperature for 4h. The reaction mixture was quench with saturated sodium sulphate solution (100 mL). The mixture was extracted with EtOAc and the organic extracts dried over anhydrous sodium sulphate and evaporated in vacuo to obtain the title compound as a solid (3.2 g) H PLC/MS (method 1): Rt: 1.6 min; m/z=268 (M+1)+.

Step-4: Synthesis of 3-(4-bromophenyl)-5-(chloromethyl)-1-methyl-pyrazole

To a stirred solution of [5-(4-bromophenyl)-2-methyl-pyrazol-3-yl]methanol (0.4 g) in DCM (8.0 mL) was methanesulfonyl chloride (0.206 g) at 0° C. The reaction mixture was stirred at ambient temaperature for 4h. The reaction mixture was quench with water (40 mL). The mixture was extracted with EtOAc and the organic extracts dried over anhydrous Sodium sulphate and evaporated in vacuo to obtain the title compound as a solid (0.4 g). HPLC/MS (method 1): Rt: 2.02 min; m/z=286 (M+1)+.

Step-5: Synthesis of 3-(4-bromophenyl)-1-methyl-5-[[4-(trifluoromethoxy)phenoxy]methyl]pyrazole To a stirred solution of 3-(4-bromophenyl)-5-(chloromethyl)-1-methyl-pyrazole (0.350 g) in MeCN (4.0 mL) was added K2CO3 (0.333 g) and 4-(trifluoromethoxy)phenol (0.196 g) at ambient temperature. The reaction mixture was heated at 90° C. for 4h. The reaction mixture was dissloved in water (50 mL). The mixture was extracted with EtOAc and the organic extracts dried over anhydrous sodium sulphate and evaporated in vacuo and the residue obtained was subjected to silica gel flash column chromatography, eluting with a gradient of EtOAc and heptane to obtain the title compound as a solid (0.38 g). HPLC/MS (method 1): Rt: 2.2 min; m/z=428 (M+1)+.

Step-6: Synthesis of 1-methyl-5-[[4-(trifluoromethoxy)phenoxy]methyl]-3-(4-vinylphenyl)pyrazole was achieved following method similar to step 3 of C-1. HPLC/MS (method 1): Rt: 2.18 min; m/z=375 (M+1)+.

Step-7: Synthesis of 4-[1-methyl-5-[[4-(trifluoromethoxy) phenoxy]methyl]pyrazol-3-yl]benzaldehyde was achieved following method similar to step 4 of C-1.

HPLC/MS (method 1): Rt: 2.08 min; m/z=375 (M−1)+.

Step-8: Synthesis of 1-(2-isopropylphenyl)-3-[(E)-[4-[1-methyl-5-[[4-(trifluoromethoxy)phenoxy]methyl]pyrazol-3-yl]phenyl]methyleneamino]thiourea (C-52) was achieved following method similar to step 5 of C-1.

HPLC/MS (method 1): Rt: 2.1 min; m/z=566(M−1)+; 1H NMR (500 MHz, DMSO-d6) δ 11.80 (s, 1H), 10.02 (s, 1H), 8.15 (s, 1H), 7.93 (d, J=8.2 Hz, 2H), 7.84-7.79 (m, 2H), 7.36 (m,4H), 7.30 (m,4H), 6.95 (s, 1H), 5.25 (s, 2H), 3.91 (s, 3H), 3.13 (p, J=6.9 Hz, 1H), 1.19 (d, J=6.9 Hz, 6H).

Example C-57

Synthesis of N-[3-[4-[(E)-[(2-isopropylphenyl)carbamothioylhydrazono]methyl]phenyl]-1H-pyrazol-5-yl]-4-(trifluoromethoxy)benzamide (C-57)

Step-1: Synthesis of methyl 4-(5-amino-1H-pyrazol-3-yl) benzoate

To a stirred solution of methyl 4-(2-cyanoacetyl)benzoate (2.4 g) in ethanol (35.0 mL) was added hydrazine hydrate (0.6 mL) at ambient temperature. The reaction mixture was heated at 80° C. for 3 h. The progress of the reaction was monitored by TLC. After the completion of reaction, the excess ethanol was removed. The reaction mixture was diluted with water (75 mL) then extracted with ethyl acetate (100 mL). The organic layer was dried over sodium sulphate and concentrated in vacuo to offer the desired product as solid (1.82 g).

1H NMR (500 MHz, DMSO-d6) δ 11.85 (bs, 1H), 7.95 (d, J=8.0 Hz, 2H), 7.80 (d, J=8.1 Hz, 2H), 5.80 (bs, 1H), 5.22 (bs, 2H), 3.86 (s, 3H).

Step 2: Synthesis of methyl 4-[5-[[4-(trifluoromethoxy)benzoyl]amino]-1H-pyrazol-3-yl]benzoate was achieved following method similar to step 2 of C-1. HPLC/MS (method 1): Rt: 1.867 min; m/z=406 (M+1)+.

Step 3: Synthesis of N-[3-[4-(hydroxymethyl)phenyl]-1H-pyrazol-5-yl]-4-(trifluoromethoxy)benzamide To a stirred solution of methyl 4-[5-[[4-(trifluoromethoxy)benzoyl]amino]-1H-pyrazol-3-yl]benzoate (0.5 g) in THF (10.0 mL) was added 1M LAH solution in THF (1.3 mL) at ambient temperature. The reaction mixture was stirred at ambient temperature for 3h. The progress of the reaction was monitored by TLC analysis. After the completion of reaction, the reaction mixture was quenched with saturated ammonium chloride solution (50 mL) then extracted with ethyl acetate (50 mL×2). The combined organic layers were dried over sodium sulphate and concentrated in vacuo to offer the desired product as pure white solid (0.31 g). HPLC/MS (method 1): Rt: 1.621 min; m/z=378 (M+1)+

Step 4: Synthesis of N-[3-(4-formylphenyl)-1H-pyrazol-5-yl]-4-(trifluoromethoxy) benzamide To a stirred solution of N-[3-[4-(hydroxymethyl)phenyl]-1H-pyrazol-5-yl]-4-(trifluoromethoxy)benzamide (0.2 g) in THF (10 mL) was added Dess Martin periodinane (0.337 g) at ambient temperature and stirred for 3 h. The progress of the reaction was monitored by TLC analysis. After the completion of reaction, the reaction mixture was quenched with saturated sodium bicarbonate solution (50 mL) then extracted with ethyl acetate (50 mL). The organic layer was dried over sodium sulphate and concentrated in vacuo to offer the desired product. The crude product was purified by column chromatography using ethyl acetate and heptane as eluent to offer the desired product as off-white solid (0.15 g). HPLC/MS (method 1): Rt: 1.781 min; m/z=374 (M−1)+

Step 5: Synthesis of N-[3-[4-[(E)-[(2-isopropylphenyl)carbamothioylhydrazono]methyl]phenyl]-1H-pyrazol-5-yl]-4-(trifluoromethoxy) benzamide (C-57) was achieved following method similar to step 5 of C-1

HPLC/MS (method 1): Rt: 2.016 min; m/z=567 (M+1)+; 1H NMR (500 MHz, DMSO-d6) δ 13.08 (s, 1H), 11.82 (s, 1H), 11.06 (s, 1H), 10.06 (s, 1H), 8.16 (dd, J=6.3, 2.6 Hz, 3H), 8.00 (d, J=8.1 Hz, 2H), 7.82 (d, J=8.1 Hz, 2H), 7.51 (d, J=8.1 Hz, 2H), 7.37 (dd, J=7.7, 1.5 Hz, 1H), 7.31 (ddd, J=7.8, 6.6, 2.1 Hz, 1H), 7.27-7.19 (m, 2H), 7.14 (s, 1H), 3.21-3.07 (m, 1H), 1.20 (d, J=6.9 Hz, 6H).

Example C-58

Synthesis of N-[3-[4-[(E)-[(Z)-[3-(2-isopropylphenyl)-4-oxo-thiazolidin-2-ylidene]hydrazono]methyl]phenyl]-1H-pyrazol-5-yl]-4-(trifluoromethoxy)benzamide (C-58) was achieved following method similar steps of C-2.

HPLC/MS (method 1): Rt: 2.069 min; m/z=607 (M+1)+; 1H NMR (500 MHz, DMSO-d6) δ 13.11 (s, 1H), 11.06 (s, 1H), 8.34 (s, 1H), 8.16 (d, J=8.5 Hz, 2H), 7.86-7.80 (m, 4H), 7.51-7.46 (m, 4H), 7.36-7.28 (m, 2H), 7.15 (s, 1H), 4.20 (q, J=60, 15 Hz, 2H), 2.81-2.79 (m, 1H), 1.18-1.14 (m, 6H).

Example C-60

Synthesis of N-[4-chloro-3-[4-[(E)-[(2-isopropylphenyl)carbamothioylhydrazono]methyl]phenyl]-1H-pyrazol-5-yl]-4-(trifluoromethoxy)benzamide (C-60)

Step 1: methyl 4-(5-amino-4-chloro-1H-pyrazol-3-yl)benzoate

To a stirred solution of methyl 4-(5-amino-1H-pyrazol-3-yl)benzoate (1.0 g) in dichloroethane (20 mL) was added N-chlorosuccinimide (0.675 g) at ambient temperature and stirred for 3 h. The progress of the reaction was monitored by TLC analysis. After completion of reaction, the reaction mixture was diluted with water (50 mL) then extracted with dichloromethane (50 mL). The organic layer was filtered to remove the insoluble impurities then the filtrate was concentrated in vacuo after drying over sodium sulphate, to afford the product as pale yellow solid (0.872 g).

HPLC/MS (method 1): Rt: 1.493 min; m/z=250 (M−1)+

Step 2: Synthesis of methyl 4-[4-chloro-5-[[4-(trifluoromethoxy)benzoyl]amino]-1H-pyrazol-3-yl]benzoate was achieved following method similar to step 2 of C-1.

HPLC/MS (method 1): Rt: 1.89 min; m/z=438 (M−1)+

Step 3: Synthesis of N-[4-chloro-3-[4-(hydroxymethyl)phenyl]-1H-pyrazol-5-yl]-4-(trifluoromethoxy)benzamide was achieved following method similar to step 3 of C-57.

HPLC/MS (method 1): Rt: 1.664 min; m/z=410 (M−1)+

Step 4: Synthesis of N-[4-chloro-3-(4-formylphenyl)-1H-pyrazol-5-yl]-4-(trifluoromethoxy)benzamide was achieved following method similar to step 4 of C-57.

HPLC/MS (method 1): Rt: 1.813 min; m/z=408 (M−1)+

Step 5: Synthesis of N-[4-chloro-3-[4-[(E)-[(2-isopropylphenyl)carbamothioylhydrazono]methyl]phenyl]-1H-pyrazol-5-yl]-4-(trifluoromethoxy)benzamide was achieved following method similar to step 5 of C-1.

HPLC/MS (method 1): Rt: 2.325 min; m/z=601 (M+1)+; 1H NMR (500 MHz, DMSO-d6) δ 13.60 (s, 1H), 11.88 (s, 1H), 10.48 (s, 1H), 10.07 (s, 1H), 8.14 (d, J=8.4 Hz, 2H), 8.11-8.04 (m, 2H), 7.88 (d, J=8.1 Hz, 2H), 7.56 (d, J=8.3 Hz, 2H), 7.37 (dd, J=7.8, 1.5 Hz, 1H), 7.31 (td, J=7.8, 7.3, 2.0 Hz, 1H), 7.27-7.16 (m, 3H), 3.14 (p, J=6.8 Hz, 1H), 1.20 (d, J=6.9 Hz, 6H).

Example C-63

Synthesis of N-[5-[4-[(E)-[(2-isopropylphenyl)carbamothioylhydrazono]methyl]phenyl]-2-methyl-1,2,4-triazol-3-yl]-4-(trifluoromethoxy)benzamide (C-62)

Step 1: Synthesis of N-[3-(4-bromophenyl)-1H-1,2,4-triazol-5-yl]-4-(trifluoromethoxy)benzamide To a stirred solution of 4-(trifluoromethyl)benzoic acid (3.104 g) in DMF (75.0 mL) was added HATU (10.497 g) and DIPEA (6.461 mL) at 0° C. After stirring the reaction mixture for 1 h, 3-(4-bromophenyl)-1H-1,2,4-triazol-5-amine (3.0 g) was added at 0° C. The mixture was stirred at room temperature for 16 h. The reaction mixture was diluted with brine (NaCl aq. Solution) and extracted with EtOAc. The organic phase was dried over sodium sulfate, concentrated under reduced pressure and resultant residue subjected to silica gel flash column chromatography, eluting with a gradient of EtOAc and cyclohexane to obtain the title compound as a solid (2.38 g). HPLC/MS (method 2): Rt: 1.359 min; m/z=426.9 (M+1)+

Step 2: Synthesis of N-[5-(4-bromophenyl)-2-methyl-1,2,4-triazol-3-yl]-4-(trifluoromethoxy)benzamide To a stirred solution of N-[3-(4-bromophenyl)-1H-1,2,4-triazol-5-yl]-4-(trifluoromethoxy)benzamide (1.7 g) in DMF (45.0 mL), sodium hydride (60%, 0.478 g) was added at 0° C. The reaction mixture was stirred 1 h at 0° C. followed by the addition of iodomethane (0.248 mL). After stirring the mixture at room temperature over night, water was added and the mixture was cooled down. The resulting precipitate was filtered and subjected to silica gel flash column chromatography, eluting with a gradient of EtOAc and cyclohexane to obtain the title compound as a solid (0.77 g). HPLC/MS (method 2): Rt: 1.230 min; m/z=440.9 (M+1)+.

Step 3: Synthesis of N-[2-methyl-5-[4-[(E)-prop-1-enyl]phenyl]-1,2,4-triazol-3-yl]-4-(trifluoromethoxy)benzamide A solution of N-[5-(4-bromophenyl)-2-methyl-1,2,4-triazol-3-yl]-4-(trifluoromethoxy) benzamide (0.77 g), [(E)-prop-1-enyl]boronic acid (0.33 g), potassium carbonate (0.603 g), water (1.5 mL) in 1,2-dimethoxyethane (30 mL) was set under argon atmosphere. Pd(dppf)Cl2 (0.064 g) was added to the reaction mixture and stirred for 48 h at 100° C. The solvent was removed under reduced pressure and the residue obtained was subjected to silica gel flash column chromatography eluting with a gradient of EtOAc and cyclohexane to obtain the title compound as a solid (0. 520 g). HPLC/MS (method 2): Rt: 1.259 min; m/z=402.9 (M+1)+.

Step 4: Synthesis of N-[5-(4-formylphenyl)-2-methyl-1,2,4-triazol-3-yl]-4-(trifluoromethoxy)benzamide was achieved following method similar to step 4 of C-1.

HPLC/MS (method 2): Rt: 1.093 min; m/z=390.8 (M+1)+

Step 5: Synthesis of N-[5-[4-[(E)-[(2-isopropylphenyl)carbamothioylhydrazono]methyl]phenyl]-2-methyl-1,2,4-triazol-3-yl]-4-(trifluoromethoxy)benzamide was achieved following method similar to step 5 of C-1.

HPLC/MS (method 2): Rt: 1.303 min; m/z=582.0 (M+1)+. 1H NMR (400 MHz, Chloroform-d) δ 11.08 (s, 1H), 8.98 (s, 1H), 8.14-8.08 (m, 2H), 7.93-7.87 (m, 2H), 7.71 (s, 1H), 7.54 (dd, J=7.5, 1.2 Hz, 1H), 7.45-7.21 (m, 8H), 3.90 (s, 3H), 3.15 (p, J=6.9 Hz, 1H), 1.25 (dd, J=6.9, 2.9 Hz, 6H).

Example C-64

Synthesis of N-[5-[4-[(E)-[(Z)-[3-(2-isopropylphenyl)-4-oxo-thiazolidin-2-ylidene]hydrazono]methyl]phenyl]-2-methyl-1,2,4-triazol-3-yl]-4-(trifluoromethoxy)benzamide was achieved following method similar step of C-2.

HPLC/MS (method 2): Rt: 1.331 min; m/z=622.1 (M+1)+. 1H NMR (400 MHz, Chloroform-d) δ 9.57 (s, 1H), 8.27 (s, 1H), 8.08 (d, J=7.5 Hz, 2H), 7.98 (d, J=8.1 Hz, 2H), 7.78 (d, J=8.2 Hz, 2H), 7.50-7.45 (m, 2H), 7.33 (dt, J=7.8, 4.4 Hz, 1H), 7.29-7.23 (m, 2H), 7.17 (dt, J=7.8, 1.0 Hz, 1H), 4.01 (d, J=2.9 Hz, 2H), 3.91 (s, 3H), 2.82 (hept, J=6.8 Hz, 1H), 1.22 (dd, J=6.9, 4.2 Hz, 6H).

Example C-68

Synthesis of N-[2-methyl-5-[4-[(E)-[(2S,3R,4R,5S,6S)-3,4,5-trimethoxy-6-methyl-tetrahydropyran-2-yl]oxyiminomethyl]phenyl]-1,2,4-triazol-3-yl]-4-(trifluoromethoxy)benzamide was achieved following method similar step of C-32.

HPLC/MS (method 2): Rt: 1.213 min; m/z=594 (M+1)+. 1H NMR (400 MHz, Chloroform-d) δ 8.15 (d, J=7.9 Hz, 3H), 7.95 (d, J=8.0 Hz, 2H), 7.70 (d, J=8.0 Hz, 2H), 7.29 (d, J=7.8 Hz, 2H), 3.93 (s, 3H), 3.58-3.48 (m, 14H), 1.31 (dd, J=6.2, 1.4 Hz, 4H).
(I)
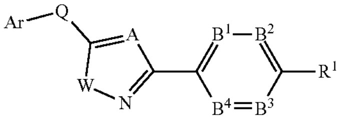
TABLE C
wherein i-Pr is isopropyl group.
| No | Ar—Q | 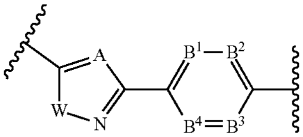 | $R^1$ | HPLC/ MS | Rt min |
|---|---|---|---|---|---|
| C-1 | 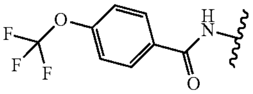 [SMILES: *NC(=O)c1ccc(OC(F)(F)F)cc1] | 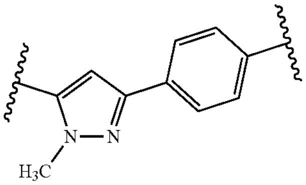 | 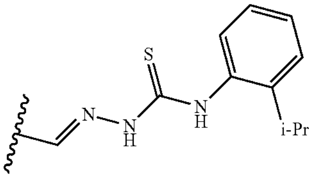 | 581 (method 1) | 2.16 |
| C-2 | 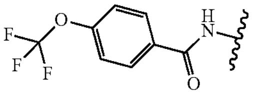 [SMILES: *NC(=O)c1ccc(OC(F)(F)F)cc1] | 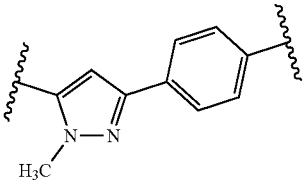 [SMILES: *c1ccc(-c2cc(*)n(C)n2)cc1] | 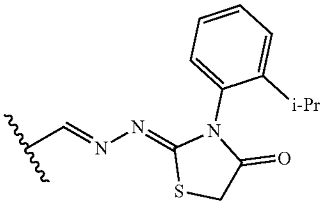 [SMILES: */C=N/N=C1\SCC(=O)N1c1ccccc1C(C)C] | 621 (method 1) | 2.25 |
| C-3 | 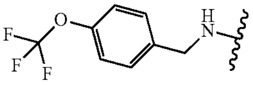 [SMILES: *NCc1ccc(OC(F)(F)F)cc1] | 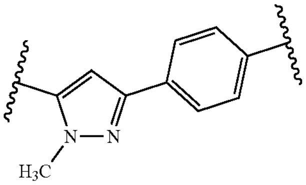 [SMILES: *c1ccc(-c2cc(*)n(C)n2)cc1] | 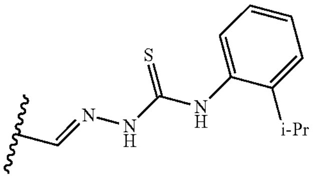 | 567 (method 1) | 2.12 |
| C-4 | 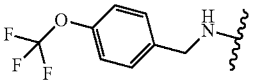 [SMILES: *NCc1ccc(OC(F)(F)F)cc1] | 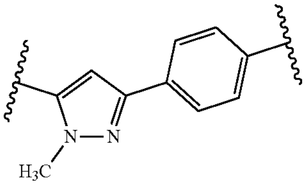 | 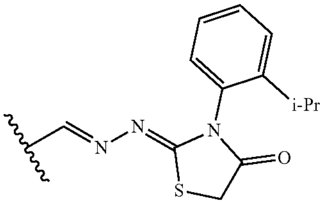 [SMILES: */C=N/N=C1\SCC(=O)N1c1ccccc1C(C)C] | 607 (method 1) | 2.16 |
| C-5 | 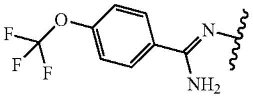 | 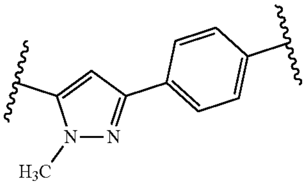 [SMILES: *c1ccc(-c2cc(*)n(C)n2)cc1] | 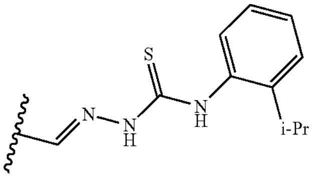 [SMILES: */C=N/NC(=S)Nc1ccccc1C(C)C] | 580 (method 1) | 2.10 |

TABLE C-continued
wherein i-Pr is isopropyl group.
| No | Ar—Q | 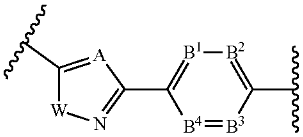 | R¹ | HPLC/MS | Rt min |
|---|---|---|---|---|---|
| C-6 | 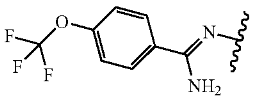 | 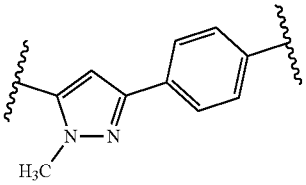 [SMILES: *c1ccc(-c2cc(*)n(C)n2)cc1] | 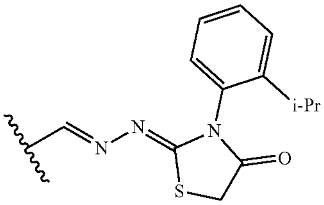 [SMILES: */C=N/N=C1\SCC(=O)N1c1ccccc1C(C)C] | 620 (method 1) | 2.17 |
| C-7 | 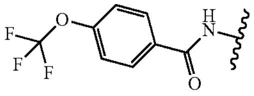 [SMILES: *NC(=O)c1ccc(OC(F)(F)F)cc1] | 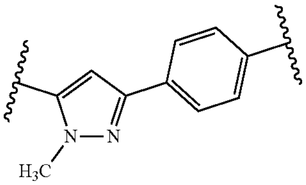 [SMILES: *c1ccc(-c2cc(*)n(C)n2)cc1] | 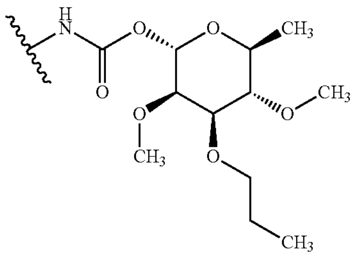 [SMILES: *NC(=O)O[C@@H]1O[C@@H](C)[C@H](OC)[C@@H](OCCC)[C@H]1OC] | 637 (method 2) | 1.28 |
| C-8 | 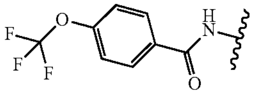 [SMILES: *NC(=O)c1ccc(OC(F)(F)F)cc1] | 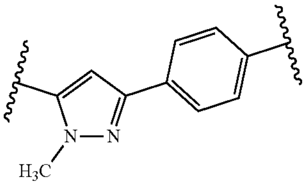 [SMILES: *c1ccc(-c2cc(*)n(C)n2)cc1] | 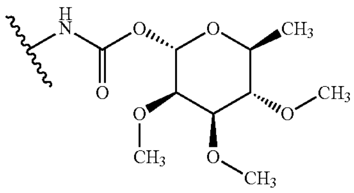 [SMILES: *NC(=O)O[C@@H]1O[C@@H](C)[C@H](OC)[C@@H](OC)[C@H]1OC] | 609 (method 2) | 1.20 |
| C-9 | 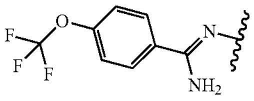 | 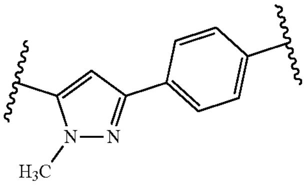 | 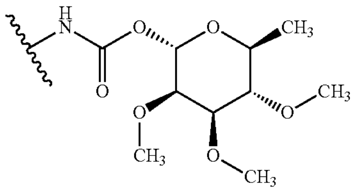 [SMILES: *NC(=O)O[C@@H]1O[C@@H](C)[C@H](OC)[C@@H](OC)[C@H]1OC] | 608 (method 1) | 1.78 |
| C-10 | 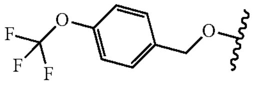 [SMILES: *OCc1ccc(OC(F)(F)F)cc1] | 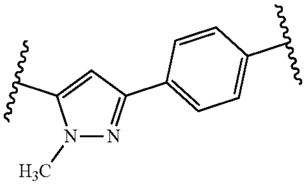 [SMILES: *c1ccc(-c2cc(*)n(C)n2)cc1] | 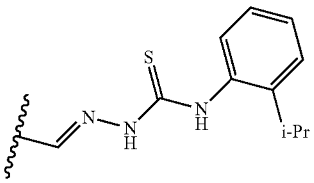 [SMILES: */C=N/NC(=S)Nc1ccccc1C(C)C] | 568 (method 1) | 2.25 |
| C-11 | 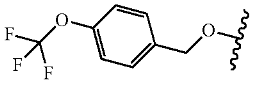 [SMILES: *OCc1ccc(OC(F)(F)F)cc1] | 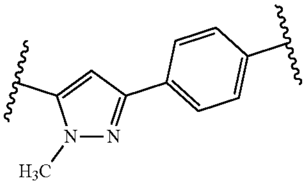 | 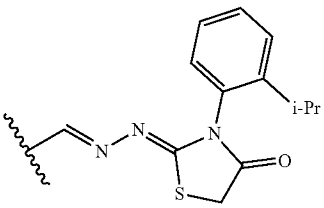 [SMILES: */C=N/N=C1\SCC(=O)N1c1ccccc1C(C)C] | 608 (method 1) | 2.27 |

TABLE C-continued
wherein i-Pr is isopropyl group.
| No | Ar—Q | 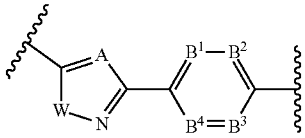 | $R^1$ | HPLC/MS | Rt min |
|---|---|---|---|---|---|
| C-12 | 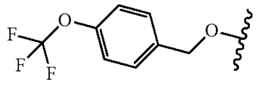 [SMILES: *OCc1ccc(OC(F)(F)F)cc1] | 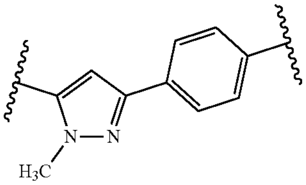 | 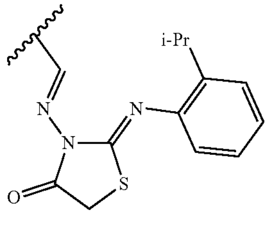 [SMILES: */C=N/N1C(=O)CS/C1=N\c1ccccc1C(C)C] | 608 (method 1) | 2.36 |
| C-13 | 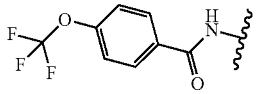 [SMILES: *NC(=O)c1ccc(OC(F)(F)F)cc1] | 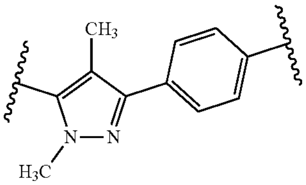 [SMILES: *c1ccc(-c2nn(C)c(*)c2C)cc1] | 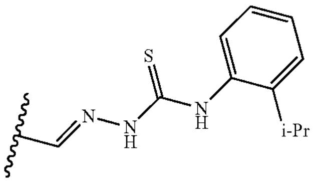 [SMILES: */C=N/NC(=S)Nc1ccccc1C(C)C] | 595 (method 2) | 1.34 |
| C-14 | 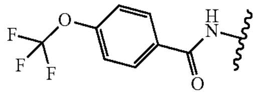 [SMILES: *NC(=O)c1ccc(OC(F)(F)F)cc1] | 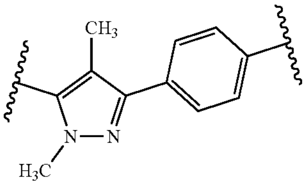 [SMILES: *c1ccc(-c2nn(C)c(*)c2C)cc1] | 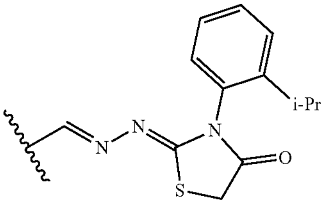 [SMILES: */C=N/N=C1\SCC(=O)N1c1ccccc1C(C)C] | 635 (method 2) | 1.37 |
| C-15 | 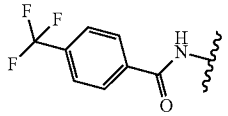 [SMILES: *NC(=O)c1ccc(C(F)(F)F)cc1] | 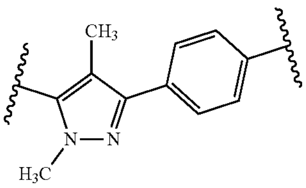 | 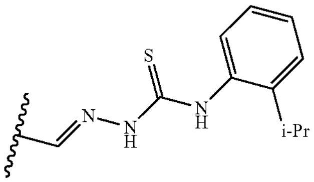 [SMILES: */C=N/NC(=S)Nc1ccccc1C(C)C] | 579 (method 2) | 1.32 |
| C-16 | 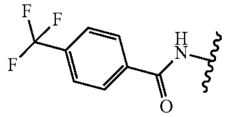 [SMILES: *NC(=O)c1ccc(C(F)(F)F)cc1] | 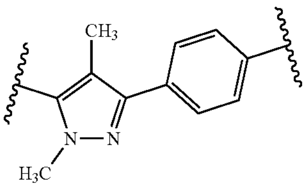 | 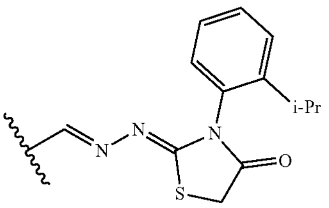 [SMILES: */C=N/N=C1\SCC(=O)N1c1ccccc1C(C)C] | 619 (method 2) | 1.35 |
| C-17 | 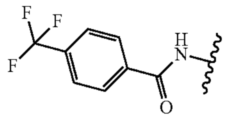 [SMILES: *NC(=O)c1ccc(C(F)(F)F)cc1] | 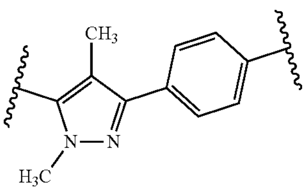 [SMILES: *c1ccc(-c2nn(C)c(*)c2C)cc1] | 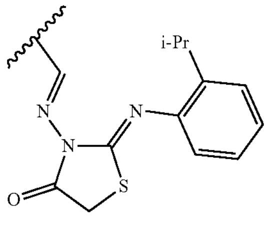 [SMILES: */C=N/N1C(=O)CS/C1=N\c1ccccc1C(C)C] | 619 (method 2) | 1.37 |

TABLE C-continued
wherein i-Pr is isopropyl group.
| No | Ar—Q | 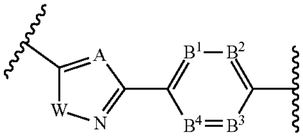 | $R^1$ | HPLC/MS | Rt min |
|---|---|---|---|---|---|
| C-18 | 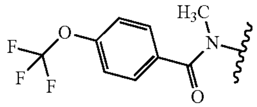 [SMILES: *N(C)C(=O)c1ccc(OC(F)(F)F)cc1] | 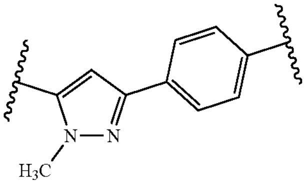 [SMILES: *c1ccc(-c2cc(*)n(C)n2)cc1] | 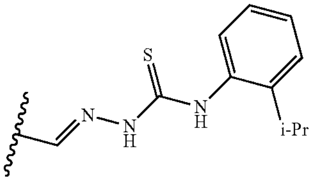 [SMILES: */C=N/NC(=S)Nc1ccccc1C(C)C] | 595 (method 1) | 2.10 |
| C-19 | 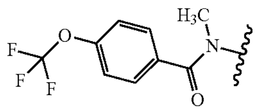 [SMILES: *N(C)C(=O)c1ccc(OC(F)(F)F)cc1] | 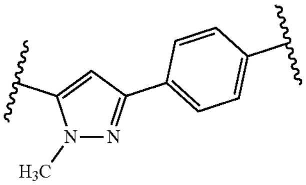 | 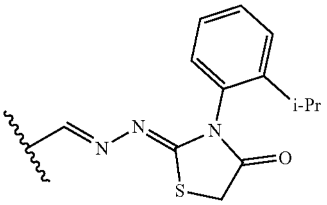 [SMILES: */C=N/N=C1\SCC(=O)N1c1ccccc1C(C)C] | 634 (method 1) | 2.08 |
| C-20 | 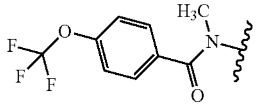 [SMILES: *N(C)C(=O)c1ccc(OC(F)(F)F)cc1] | 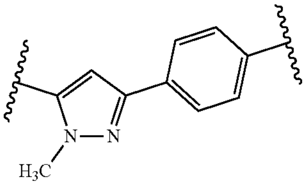 [SMILES: *c1ccc(-c2cc(*)n(C)n2)cc1] | 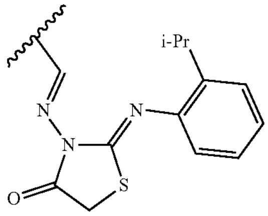 [SMILES: */C=N/N1C(=O)CS/C1=N\c1ccccc1C(C)C] | 634 (method 1) | 2.11 |
| C-21 | 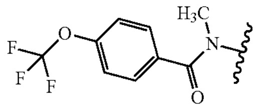 [SMILES: *N(C)C(=O)c1ccc(OC(F)(F)F)cc1] | 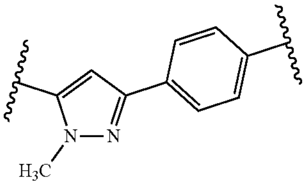 [SMILES: *c1ccc(-c2cc(*)n(C)n2)cc1] | 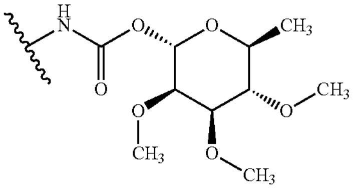 [SMILES: *NC(=O)O[C@@H]1O[C@@H](C)[C@H](OC)[C@@H](OC)[C@H]1OC] | 622 (method 1) | 1.82 |
| C-22 | 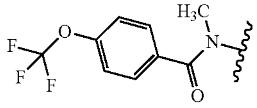 [SMILES: *N(C)C(=O)c1ccc(OC(F)(F)F)cc1] | 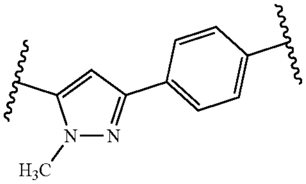 [SMILES: *c1ccc(-c2cc(*)n(C)n2)cc1] | 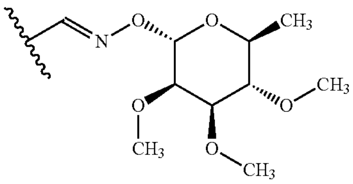 | 606 (method 1) | 1.96 |
| C-23 | 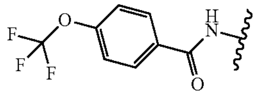 [SMILES: *NC(=O)c1ccc(OC(F)(F)F)cc1] | 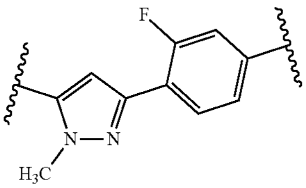 [SMILES: *c1ccc(-c2cc(*)n(C)n2)c(F)c1] | 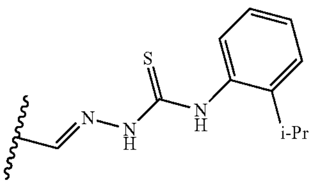 [SMILES: */C=N/NC(=S)Nc1ccccc1C(C)C] | 596 (method 1) | 2.10 |
| C-24 | 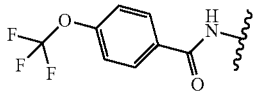 [SMILES: *NC(=O)c1ccc(OC(F)(F)F)cc1] | 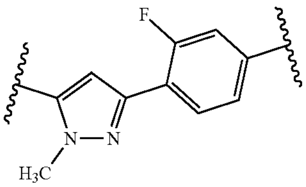 [SMILES: *c1ccc(-c2cc(*)n(C)n2)c(F)c1] | 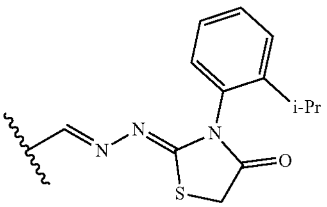 [SMILES: */C=N/N=C1\SCC(=O)N1c1ccccc1C(C)C] | 638 (method 1) | 2.16 |

TABLE C-continued
wherein i-Pr is isopropyl group.
| No | Ar—Q | 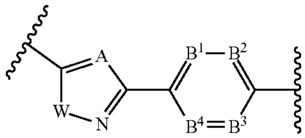 | $R^1$ | HPLC/ MS | Rt min |
|---|---|---|---|---|---|
| C-25 | 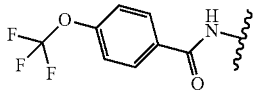 [SMILES: *NC(=O)c1ccc(OC(F)(F)F)cc1] | 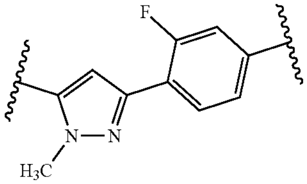 [SMILES: *c1ccc(-c2cc(*)n(C)n2)c(F)c1] | 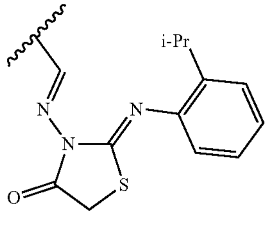 [SMILES: */C=N/N1C(=O)CS/C1=N\c1ccccc1C(C)C] | 638 (method 1) | 2.19 |
| C-26 | 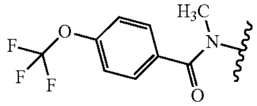 [SMILES: *N(C)C(=O)c1ccc(OC(F)(F)F)cc1] | 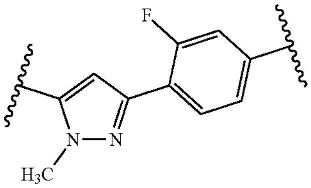 [SMILES: *c1ccc(-c2cc(*)n(C)n2)c(F)c1] | 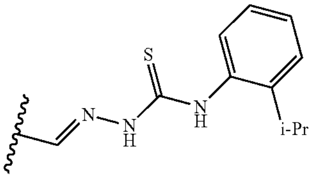 [SMILES: */C=N/NC(=S)Nc1ccccc1C(C)C] | 611 (method 1) | 2.11 |
| C-27 | 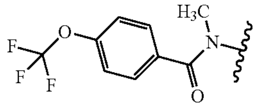 [SMILES: *N(C)C(=O)c1ccc(OC(F)(F)F)cc1] | 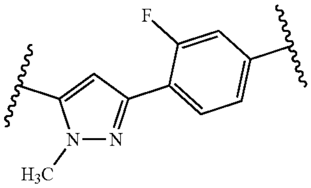 [SMILES: *c1ccc(-c2cc(*)n(C)n2)c(F)c1] | 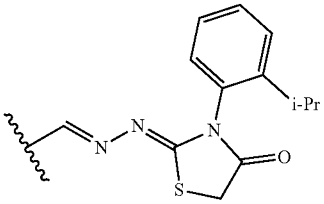 [SMILES: */C=N/N=C1\SCC(=O)N1c1ccccc1C(C)C] | 652 (method 1) | 2.19 |
| C-28 | 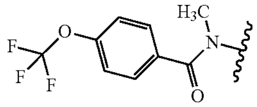 [SMILES: *N(C)C(=O)c1ccc(OC(F)(F)F)cc1] | 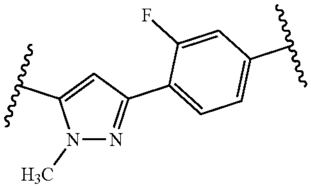 [SMILES: *c1ccc(-c2cc(*)n(C)n2)c(F)c1] | 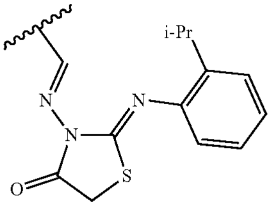 [SMILES: */C=N/N1C(=O)CS/C1=N\c1ccccc1C(C)C] | 652 (method 1) | 2.20 |
| C-29 | 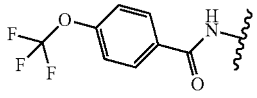 [SMILES: *NC(=O)c1ccc(OC(F)(F)F)cc1] | 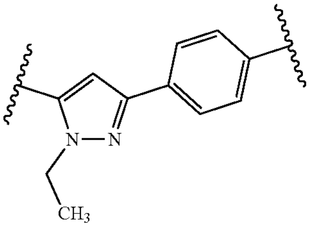 [SMILES: *c1ccc(-c2cc(*)n(CC)n2)cc1] | 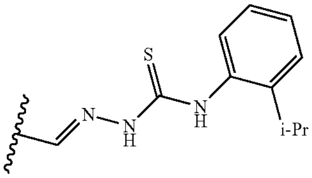 [SMILES: */C=N/NC(=S)Nc1ccccc1C(C)C] | 593 (method 1) | 2.11 |
| C-30 | 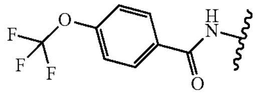 | 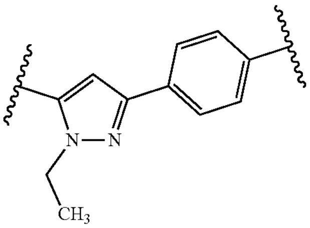 [SMILES: *c1ccc(-c2cc(*)n(CC)n2)cc1] | 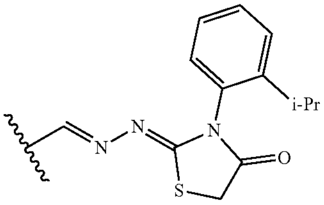 [SMILES: */C=N/N=C1\SCC(=O)N1c1ccccc1C(C)C] | 633 (method 1) | 2.16 |

TABLE C-continued
wherein i-Pr is isopropyl group.
| No | Ar—Q | 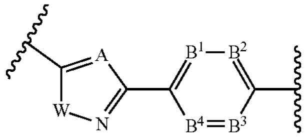 | $R^1$ | HPLC/MS | Rt min |
|---|---|---|---|---|---|
| C-31 | 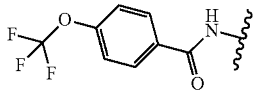 [SMILES: *NC(=O)c1ccc(OC(F)(F)F)cc1] | 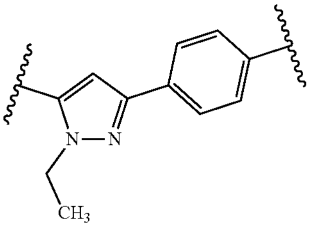 [SMILES: *c1ccc(-c2cc(*)n(CC)n2)cc1] | 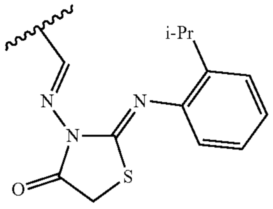 [SMILES: */C=N/N1C(=O)CS/C1=N\c1ccccc1C(C)C] | 634 (method 1) | 2.21 |
| C-32 | 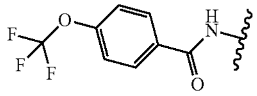 [SMILES: *NC(=O)c1ccc(OC(F)(F)F)cc1] | 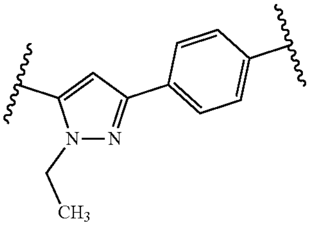 [SMILES: *c1ccc(-c2cc(*)n(CC)n2)cc1] | 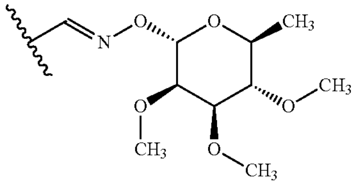 [SMILES: */C=N/O[C@@H]1O[C@@H](C)[C@H](OC)[C@@H](OC)[C@H]1OC] | 605 (method 1) | 2.06 |
| C-33 | 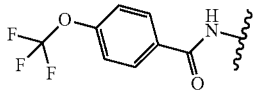 | 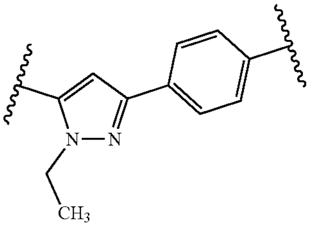 [SMILES: *c1ccc(-c2cc(*)n(CC)n2)cc1] | 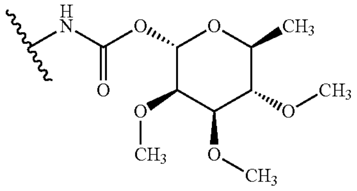 [SMILES: *NC(=O)O[C@@H]1O[C@@H](C)[C@H](OC)[C@@H](OC)[C@H]1OC] | 622 (method 1) | 1.91 |
| C-34 | 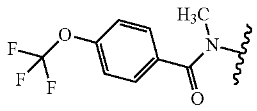 [SMILES: *N(C)C(=O)c1ccc(OC(F)(F)F)cc1] | 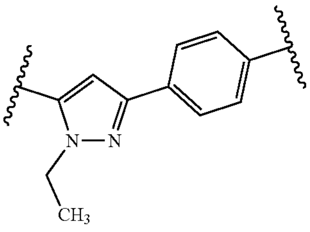 [SMILES: *c1ccc(-c2cc(*)n(CC)n2)cc1] | 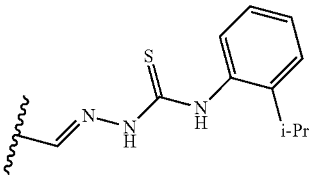 [SMILES: */C=N/NC(=S)Nc1ccccc1C(C)C] | 609 (method 1) | 2.14 |
| C-35 | 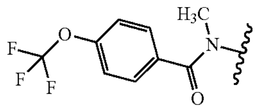 [SMILES: *N(C)C(=O)c1ccc(OC(F)(F)F)cc1] | 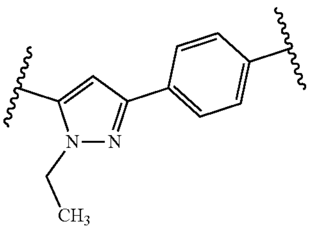 [SMILES: *c1ccc(-c2cc(*)n(CC)n2)cc1] | 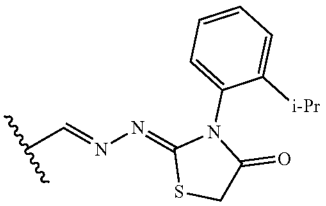 [SMILES: */C=N/N=C1\SCC(=O)N1c1ccccc1C(C)C] | 649 (method 1) | 2.22 |
| C-36 | 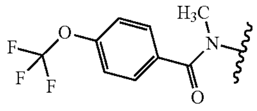 [SMILES: *N(C)C(=O)c1ccc(OC(F)(F)F)cc1] | 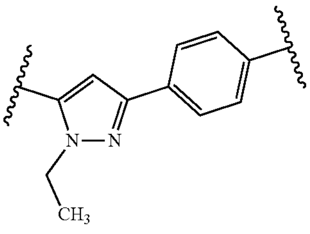 [SMILES: *c1ccc(-c2cc(*)n(CC)n2)cc1] | 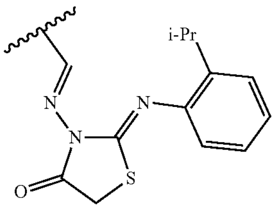 [SMILES: */C=N/N1C(=O)CS/C1=N\c1ccccc1C(C)C] | 649 (method 1) | 2.22 |

TABLE C-continued
wherein i-Pr is isopropyl group.
| No | Ar—Q | 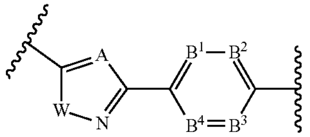 | $R^1$ | HPLC/ MS | Rt min |
|---|---|---|---|---|---|
| C-37 | 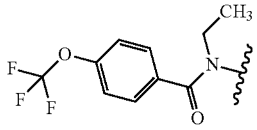 [SMILES: *N(CC)C(=O)c1ccc(OC(F)(F)F)cc1] | 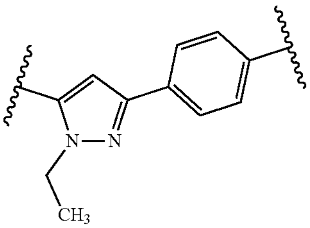 [SMILES: *c1ccc(-c2cc(*)n(CC)n2)cc1] | 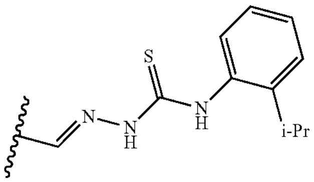 [SMILES: */C=N/NC(=S)Nc1ccccc1C(C)C] | 623 (method 1) | 2.21 |
| C-38 | 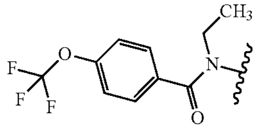 [SMILES: *N(CC)C(=O)c1ccc(OC(F)(F)F)cc1] | 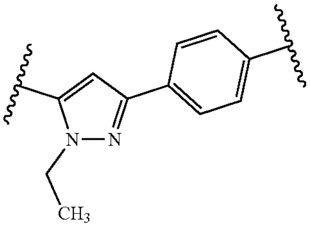 [SMILES: *c1ccc(-c2cc(*)n(CC)n2)cc1] | 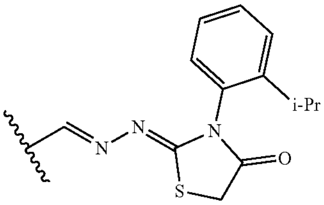 [SMILES: */C=N/N=C1\SCC(=O)N1c1ccccc1C(C)C] | 663 (method 1) | 2.27 |
| C-39 | 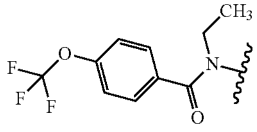 [SMILES: *N(CC)C(=O)c1ccc(OC(F)(F)F)cc1] | 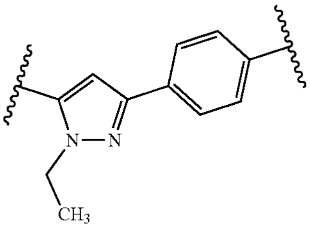 [SMILES: *c1ccc(-c2cc(*)n(CC)n2)cc1] | 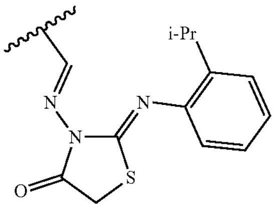 [SMILES: */C=N/N1C(=O)CS/C1=N\c1ccccc1C(C)C] | 663 (method 1) | 2.32 |
| C-40 | 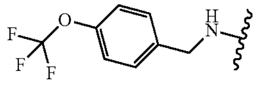 [SMILES: *NCc1ccc(OC(F)(F)F)cc1] | 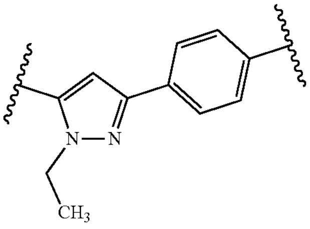 [SMILES: *c1ccc(-c2cc(*)n(CC)n2)cc1] | 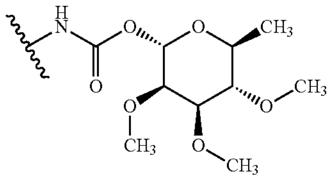 [SMILES: *NC(=O)O[C@@H]1O[C@@H](C)[C@H](OC)[C@@H](OC)[C@H]1OC] | 609 (method 2) | 1.11 |
| C-41 | 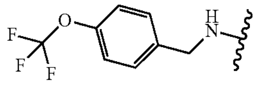 [SMILES: *NCc1ccc(OC(F)(F)F)cc1] | 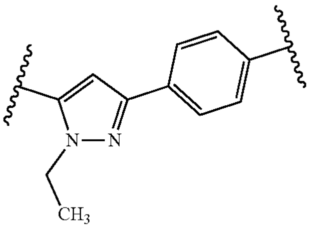 [SMILES: *c1ccc(-c2cc(*)n(CC)n2)cc1] | 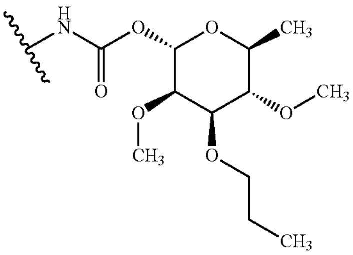 [SMILES: *NC(=O)O[C@@H]1O[C@@H](C)[C@H](OC)[C@@H](OCCC)[C@H]1OC] | 637 (method 2) | 1.20 |
| C-42 | 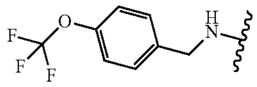 [SMILES: *NCc1ccc(OC(F)(F)F)cc1] | 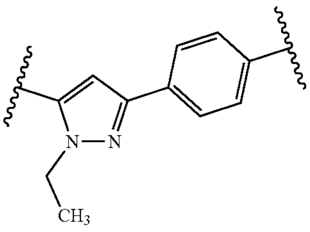 [SMILES: *c1ccc(-c2cc(*)n(CC)n2)cc1] | 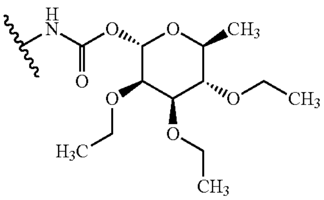 [SMILES: *NC(=O)O[C@@H]1O[C@@H](C)[C@H](OCC)[C@@H](OCC)[C@H]1OCC] | 651 (method 2) | 1.24 |

TABLE C-continued
wherein i-Pr is isopropyl group.
| No | Ar—Q | 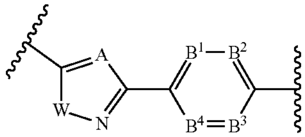 | $R^1$ | HPLC/ MS | Rt min |
|---|---|---|---|---|---|
| C-43 | 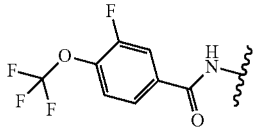 [SMILES: *NC(=O)c1ccc(OC(F)(F)F)c(F)c1] | 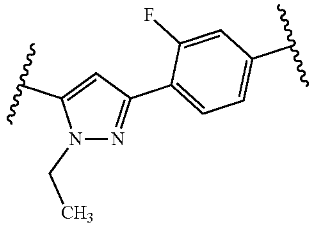 [SMILES: *c1ccc(-c2cc(*)n(CC)n2)c(F)c1] | 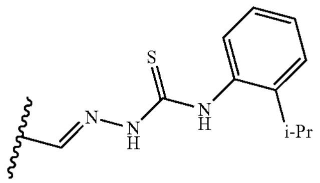 [SMILES: */C=N/NC(=S)Nc1ccccc1C(C)C] | 629 (method 1) | 2.14 |
| C-44 | 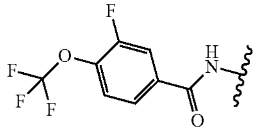 [SMILES: *NC(=O)c1ccc(OC(F)(F)F)c(F)c1] | 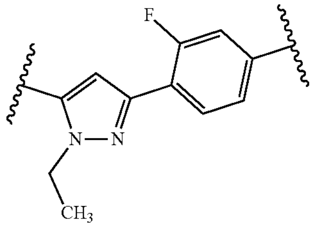 [SMILES: *c1ccc(-c2cc(*)n(CC)n2)c(F)c1] | 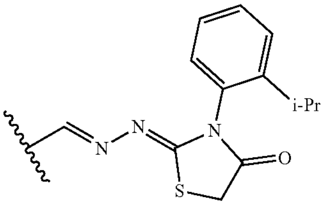 [SMILES: */C=N/N=C1\SCC(=O)N1c1ccccc1C(C)C] | 670 (method 1) | 2.21 |
| C-45 | 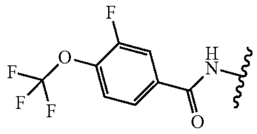 [SMILES: *NC(=O)c1ccc(OC(F)(F)F)c(F)c1] | 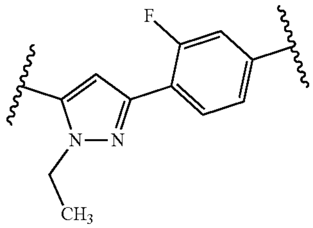 [SMILES: *c1ccc(-c2cc(*)n(CC)n2)c(F)c1] | 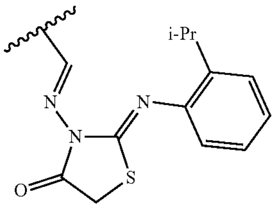 [SMILES: */C=N/N1C(=O)CS/C1=N\c1ccccc1C(C)C] | 670 (method 1) | 2.25 |
| C-46 | 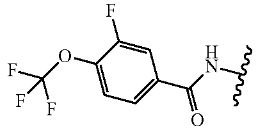 [SMILES: *NC(=O)c1ccc(OC(F)(F)F)c(F)c1] | 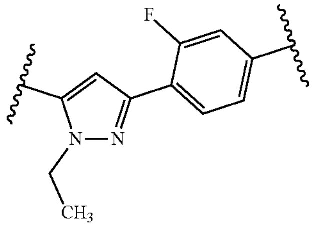 [SMILES: *c1ccc(-c2cc(*)n(CC)n2)c(F)c1] | 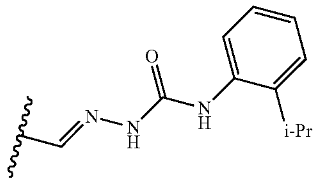 | 615 (method 1) | 2.06 |
| C-47 | 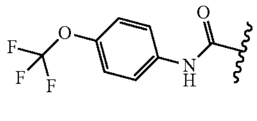 [SMILES: *C(=O)Nc1ccc(OC(F)(F)F)cc1] | 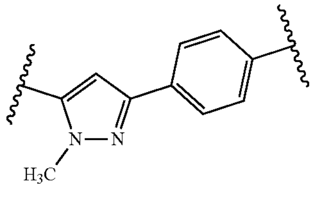 | 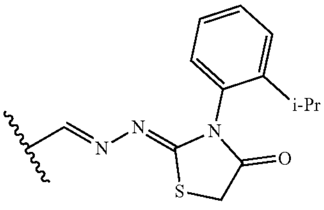 [SMILES: */C=N/N=C1\SCC(=O)N1c1ccccc1C(C)C] | 621 (method 2) | 1.48 |
| C-48 | 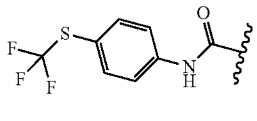 [SMILES: *C(=O)Nc1ccc(SC(F)(F)F)cc1] | 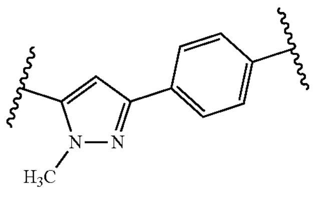 [SMILES: *c1ccc(-c2cc(*)n(C)n2)cc1] | 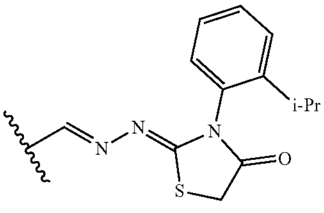 [SMILES: */C=N/N=C1\SCC(=O)N1c1ccccc1C(C)C] | 637 (method 2) | 1.52 |

TABLE C-continued
wherein i-Pr is isopropyl group.
| No | Ar—Q | 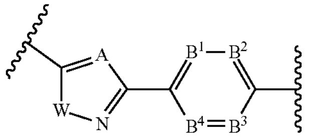 | $R^1$ | HPLC/ MS | Rt min |
|---|---|---|---|---|---|
| C-49 | 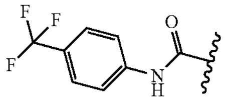 [SMILES: *C(=O)Nc1ccc(C(F)(F)F)cc1] | 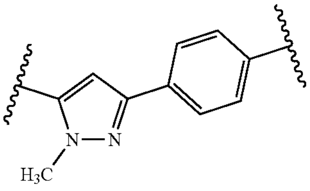 | 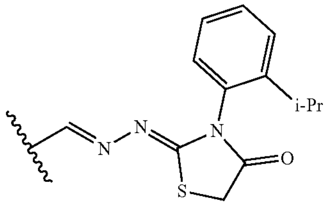 [SMILES: */C=N/N=C1\SCC(=O)N1c1ccccc1C(C)C] | 605 (method 2) | 1.47 |
| C-50 | 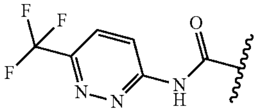 [SMILES: *C(=O)Nc1ccc(C(F)(F)F)nn1] | 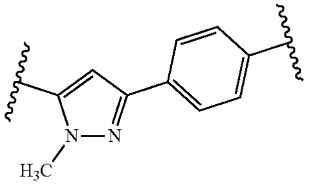 [SMILES: *c1ccc(-c2cc(*)n(C)n2)cc1] | 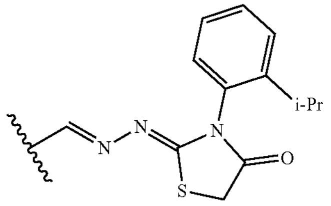 [SMILES: */C=N/N=C1\SCC(=O)N1c1ccccc1C(C)C] | 607 (method 2) | 1.39 |
| C-51 | 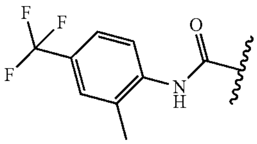 [SMILES: *C(=O)Nc1ccc(C(F)(F)F)cc1C] | 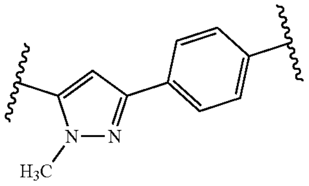 [SMILES: *c1ccc(-c2cc(*)n(C)n2)cc1] | 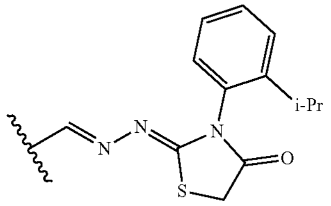 [SMILES: */C=N/N=C1\SCC(=O)N1c1ccccc1C(C)C] | 619 (method 2) | 1.46 |
| C-52 | 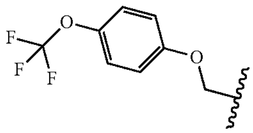 | 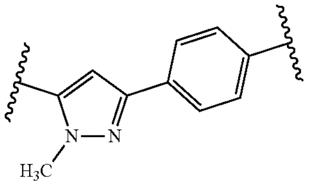 [SMILES: *c1ccc(-c2cc(*)n(C)n2)cc1] | 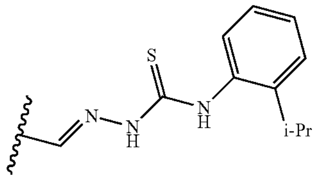 | 566 (method 1) | 2.10 |
| C-53 | 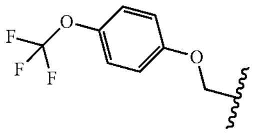 [SMILES: *COc1ccc(OC(F)(F)F)cc1] | 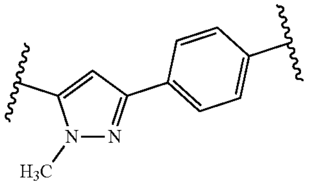 | 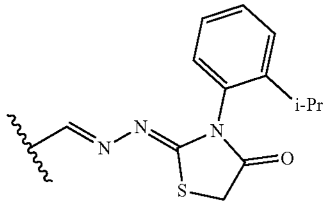 [SMILES: */C=N/N=C1\SCC(=O)N1c1ccccc1C(C)C] | 608 (method 1) | 2.22 |
| C-54 | 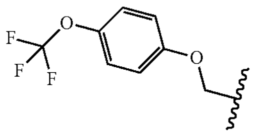 [SMILES: *COc1ccc(OC(F)(F)F)cc1] | 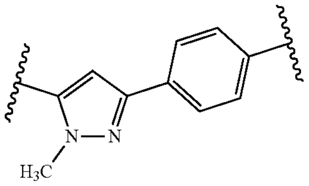 [SMILES: *c1ccc(-c2cc(*)n(C)n2)cc1] | 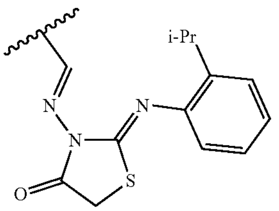 [SMILES: */C=N/N1C(=O)CS/C1=N\c1ccccc1C(C)C] | 608 (method 1) | 2.31 |

TABLE C-continued
wherein i-Pr is isopropyl group.
| No | Ar—Q | 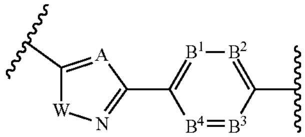 | R[1] | HPLC/ MS | Rt min |
|---|---|---|---|---|---|
| C-55 | 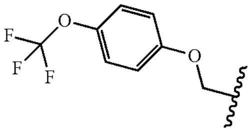 [SMILES: *COc1ccc(OC(F)(F)F)cc1] | 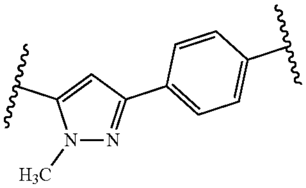 | 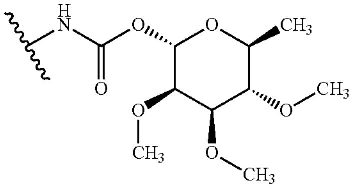 [SMILES: *NC(=O)O[C@@H]1O[C@@H](C)[C@H](OC)[C@@H](OC)[C@H]1OC] | 594 (method 1) | 2.03 |
| C-56 | 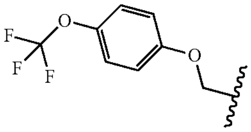 [SMILES: *COc1ccc(OC(F)(F)F)cc1] | 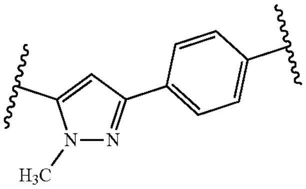 [SMILES: *c1ccc(-c2cc(*)n(C)n2)cc1] | 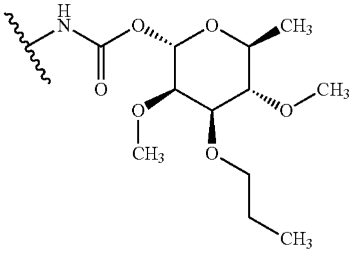 [SMILES: *NC(=O)O[C@@H]1O[C@@H](C)[C@H](OC)[C@@H](OCCC)[C@H]1OC] | 624 (method 1) | 2.10 |
| C-57 | 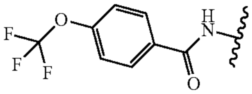 [SMILES: *NC(=O)c1ccc(OC(F)(F)F)cc1] | 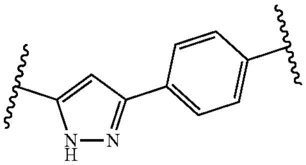 [SMILES: *c1ccc(-c2cc(*)[nH]n2)cc1] | 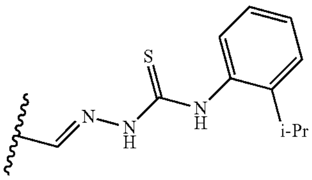 | 565 (method 1) | 2.02 |
| C-58 | 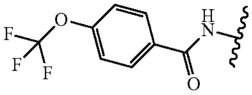 [SMILES: *NC(=O)c1ccc(OC(F)(F)F)cc1] | 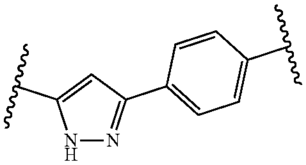 [SMILES: *c1ccc(-c2cc(*)[nH]n2)cc1] | 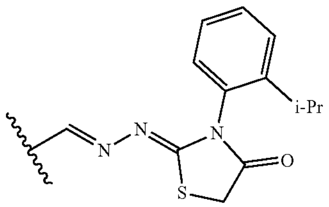 [SMILES: */C=N/N=C1\SCC(=O)N1c1ccccc1C(C)C] | 607 (method 1) | 2.06 |
| C-59 | 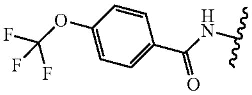 [SMILES: *NC(=O)c1ccc(OC(F)(F)F)cc1] | 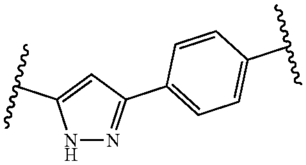 [SMILES: *c1ccc(-c2cc(*)[nH]n2)cc1] | 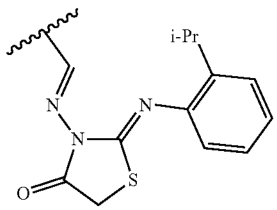 [SMILES: */C=N/N1C(=O)CS/C1=N\c1ccccc1C(C)C] | 607 (method 1) | 2.11 |
| C-60 | 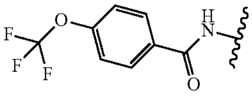 | 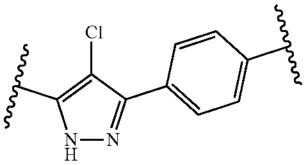 [SMILES: *c1ccc(-c2n[nH]c(*)c2Cl)cc1] | 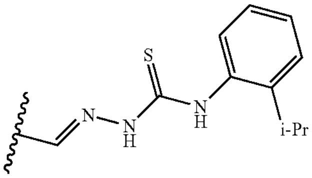 | 601 (method 1) | 2.33 |

TABLE C-continued
wherein i-Pr is isopropyl group.
| No | Ar—Q | 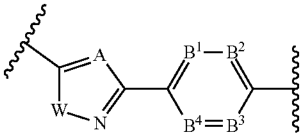 | R¹ | HPLC/ MS | Rt min |
|---|---|---|---|---|---|
| C-61 | 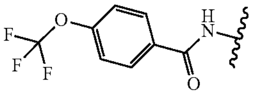 [SMILES: *NC(=O)c1ccc(OC(F)(F)F)cc1] | 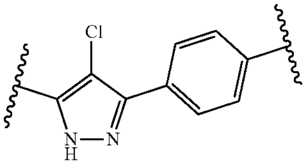 [SMILES: *c1ccc(-c2n[nH]c(*)c2Cl)cc1] | 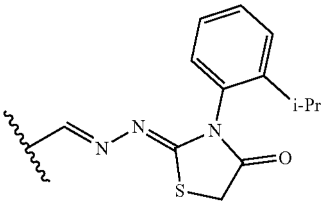 [SMILES: */C=N/N=C1\SCC(=O)N1c1ccccc1C(C)C] | 641 (method 1) | 2.04 |
| C-62 | 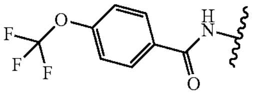 [SMILES: *NC(=O)c1ccc(OC(F)(F)F)cc1] | 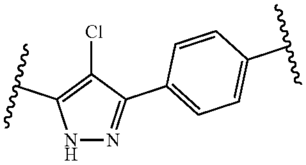 [SMILES: *c1ccc(-c2n[nH]c(*)c2Cl)cc1] | 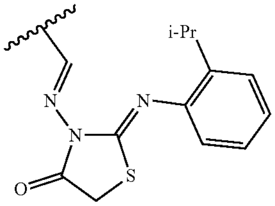 [SMILES: */C=N/N1C(=O)CS/C1=N\c1ccccc1C(C)C] | 641 (method 1) | 2.07 |
| C-63 | 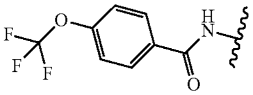 [SMILES: *NC(=O)c1ccc(OC(F)(F)F)cc1] | 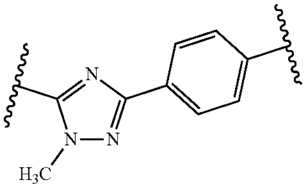 [SMILES: *c1ccc(-c2nc(*)n(C)n2)cc1] | 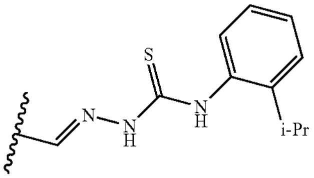 | 582 (method 2) | 1.30 |
| C-64 | 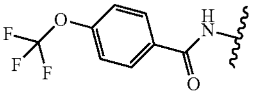 [SMILES: *NC(=O)c1ccc(OC(F)(F)F)cc1] | 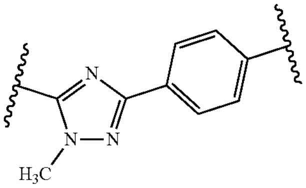 [SMILES: *c1ccc(-c2nc(*)n(C)n2)cc1] | 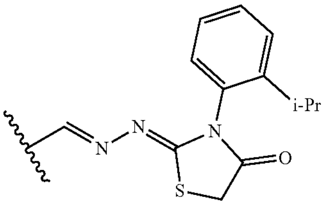 [SMILES: */C=N/N=C1\SCC(=O)N1c1ccccc1C(C)C] | 622 (method 2) | 1.34 |
| C-65 | 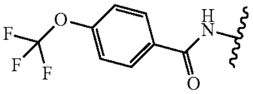 [SMILES: *NC(=O)c1ccc(OC(F)(F)F)cc1] | 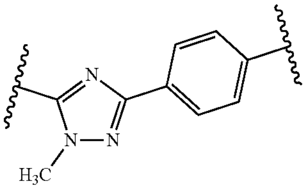 [SMILES: *c1ccc(-c2nc(*)n(C)n2)cc1] | 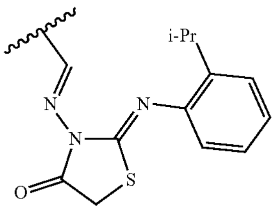 [SMILES: */C=N/N1C(=O)CS/C1=N\c1ccccc1C(C)C] | 622 (method 2) | 1.35 |
| C-66 | 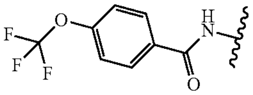 [SMILES: *NC(=O)c1ccc(OC(F)(F)F)cc1] | 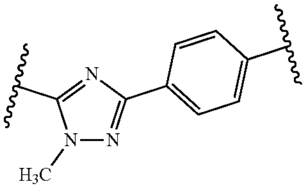 | 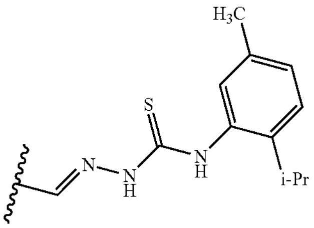 [SMILES: */C=N/NC(=S)Nc1cc(C)ccc1C(C)C] | 596 (method 2) | 1.34 |

TABLE C-continued
wherein i-Pr is isopropyl group.
| No | Ar—Q | 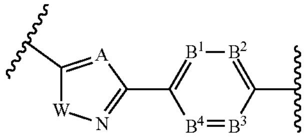 | $R^1$ | HPLC/MS | Rt min |
|---|---|---|---|---|---|
| C-67 | 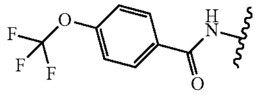 [SMILES: *NC(=O)c1ccc(OC(F)(F)F)cc1] | 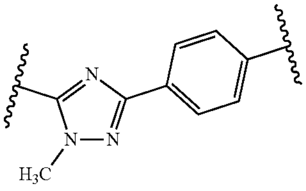 [SMILES: *c1ccc(-c2nc(*)n(C)n2)cc1] | 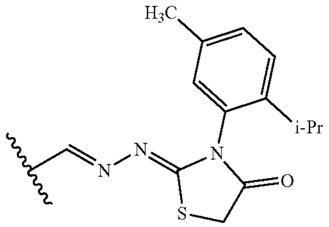 [SMILES: */C=N/N=C1\SCC(=O)N1c1cc(C)ccc1C(C)C] | 636 (method 2) | 1.37 |
| C-68 | 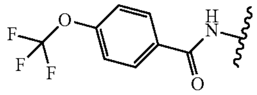 [SMILES: *NC(=O)c1ccc(OC(F)(F)F)cc1] | 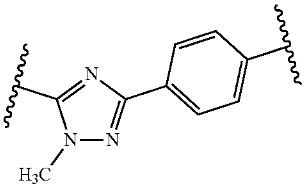 [SMILES: *c1ccc(-c2nc(*)n(C)n2)cc1] | 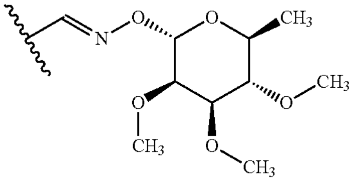 [SMILES: */C=N/O[C@@H]1O[C@@H](C)[C@H](OC)[C@@H](OC)[C@H]1OC] | 594 (method 2) | 1.21 |
| C-69 | 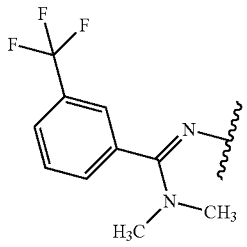 [SMILES: */N=C(/c1cccc(C(F)(F)F)c1)N(C)C] | 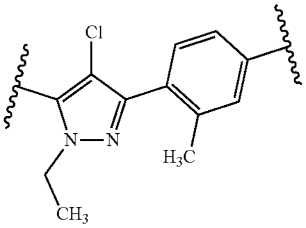 [SMILES: *c1ccc(-c2nn(CC)c(*)c2Cl)c(C)c1] | 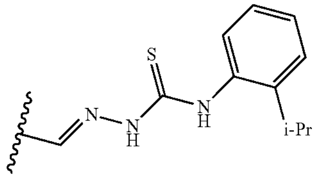 [SMILES: */C=N/NC(=S)Nc1ccccc1C(C)C] | 654 (method 1) | 2.21 |
| C-70 | 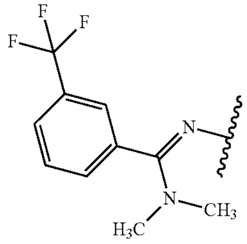 [SMILES: */N=C(/c1cccc(C(F)(F)F)c1)N(C)C] | 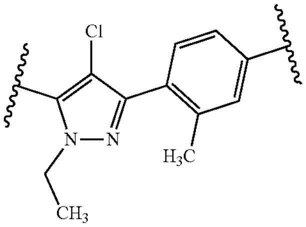 [SMILES: *c1ccc(-c2nn(CC)c(*)c2Cl)c(C)c1] | 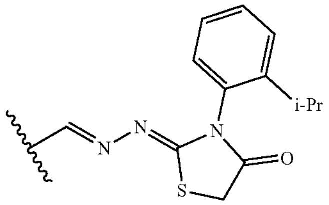 [SMILES: */C=N/N=C1\SCC(=O)N1c1ccccc1C(C)C] | 694 (method 1) | 2.33 |
| C-71 | 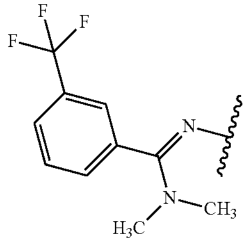 [SMILES: */N=C(/c1cccc(C(F)(F)F)c1)N(C)C] | 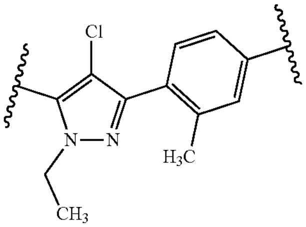 [SMILES: *c1ccc(-c2nn(CC)c(*)c2Cl)c(C)c1] | 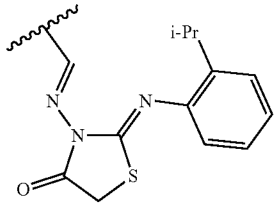 [SMILES: */C=N/N1C(=O)CS/C1=N\c1ccccc1C(C)C] | 694 (method 1) | 2.43 |
| C-72 | 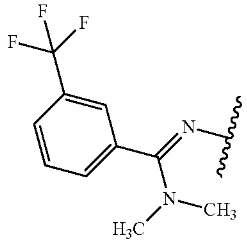 [SMILES: */N=C(/c1cccc(C(F)(F)F)c1)N(C)C] | 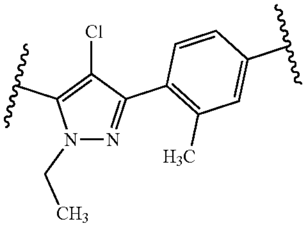 [SMILES: *c1ccc(-c2nn(CC)c(*)c2Cl)c(C)c1] | 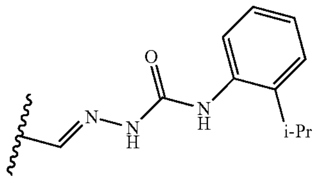 | 638 (method 1) | 2.30 |

TABLE C-continued wherein i-Pr is isopropyl group.

| No | Ar—Q | 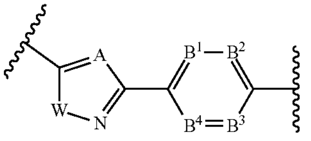 | $R^1$ | HPLC/ MS | Rt min |
|---|---|---|---|---|---|
| C-73 | 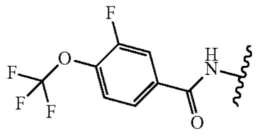 [SMILES: *NC(=O)c1ccc(OC(F)(F)F)c(F)c1] | 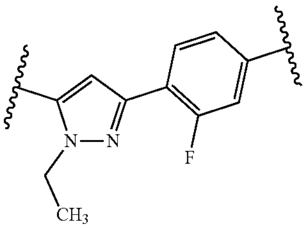 [SMILES: *c1ccc(-c2cc(*)n(CC)n2)c(F)c1] | 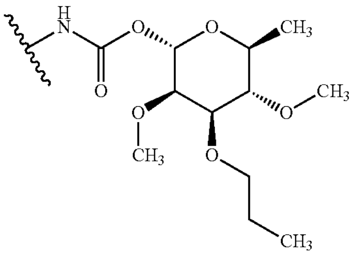 [SMILES: *NC(=O)O[C@@H]1O[C@@H](C)[C@H](OC)[C@@H](OCCC)[C@H]1OC] | 687 (method 1) | 2.08 |

BIOLOGICAL EXAMPLE

Example B1: Action on Yellow Fever Mosquito (*Aedes aegypti*)

For evaluating control of yellow fever mosquito (*Aedes aegypti*) the test unit consisted of 96-well-microtiter plates containing 200 μl of tap water per well and 5-15 freshly hatched *A. aegypti* larvae.

The active compounds or mixtures were formulated using a solution containing 75% (v/v) water and 25% (v/v) DMSO. Different concentrations of formulated compounds or mixtures were sprayed onto the insect diet at 2.5 μl using a custom built micro atomizer, at two replications.

For experimental mixtures in these tests identical volumes of both mixing partners at the desired concentrations respectively, were mixed together.

After application, microtiter plates were incubated at 28+1° C., 80+5% RH for 2 days. Larval mortality was then visually assessed.

In this test, compounds C-1, C-2, C-3, C-4, C-5, C-6, C-7, C-8, C-9, C-11, C-12, C-14, C-16, C-17, C-18, C-19, C-20, C-23, C-24, C-25, C-26, C-27, C-28, C-29, C-30, C-31, C-32, C-33, C-34, C-35, C-36, C-37, C-38, C-39, C-40, C-41, C-47, C-48, C-49, C-50, C-51, C-52, C-53, C-54, C-57, C-58, C-59, C-64, C-65, C-66, at 800 ppm showed at least 50% mortality in comparison with untreated controls.

Example B2: Action on Orchid Thrips (*Dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus Kinetic® HV at a rate of 0.01% v/v.

Thrips potency of each compound was evaluated by using a floral-immersion technique. All petals of individual, intact orchid flowers were dipped into treatment solution and allowed to dry in Petri dishes. Treated petals were placed into individual re-sealable plastic along with about 20 adult thrips. All test arenas were held under continuous light and a temperature of about 28° C. for duration of the assay. After 3 days, the numbers of live thrips were counted on each petal. The percent mortality was recorded 72 hours after treatment.

In this test, compounds C-1, C-2, C-3, C-5, C-10, C-11, C-13, C-14, C-15, C-16, C-17, C-18, C-19, C-20, C-23, C-24, C-25, C-27, C-28, C-29, C-30, C-31, C-34, C-35, C-36, C-37, C-38, C-39, C-50, C-52, C-53, C-57, C-58, C-59, C-62, C-63, C-64, C-65, C-66, at 500 ppm showed at least 75% mortality in comparison with untreated controls.

Example B3: Action on Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% (v/v) water and 25% (v/v) DMSO. Different concentrations of formulated compounds were sprayed onto the insect diet at 5 μl, using a custom built micro atomizer, at two replications.

After application, microtiter plates were incubated at about 25+1° C. and about 75+5% relative humidity for 5 days. Egg and larval mortality was then visually assessed.

In this test, compounds C-1, C-2, C-3, C-4, C-5, C-6, C-7, C-8, C-9, C-10, C-11, C-12, C-14, C-15, C-16, C-17, C-18, C-19, C-20, C-21, C-22, C-23, C-24, C-25, C-26, C-27, C-28, C-29, C-30, C-31, C-32, C-33, C-34, C-35, C-36, C-37, C-38, C-39, C-40, C-41, C-42, C-50, C-52, C-53, C-54, C-57, C-58, C-59, C-62, C-63, C-64, C-65, C-66, C-67 at 800 ppm showed at least 75% mortality in comparison with untreated controls.

Example B4: Action on Silverleaf Whitefly (*Bemisia argentifolii*) (Adults)

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 5 or 10 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, compounds C-1, C-2, C-10, C-36, C-38, C-39, C-52, C-65, at 300 ppm showed at least 75% mortality in comparison with untreated controls.

Example B5: Action on Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 μl, using a custom-built micro atomizer, at two replications.

After application, microtiter plates were incubated at about 28+1° C. and about 80+5% relative humidity for 5 days. Egg and larval mortality were then visually assessed.

In this test, compounds C-1, C-2, C-3, C-4, C-5, C-6, C-7, C-10, C-11, C-12, C-14, C-15, C-16, C-17, C-18, C-19, C-20, C-22, C-23, C-24, C-25, C-28, C-29, C-30, C-31, C-32, C-33, C-34, C-35, C-36, C-37, C-38, C-39, C-40, C-41, C-42, C-47, C-49, C-50, C-51, C-52, C-53, C-54, C-57, C-58, C-59, C-62, C-63, C-64, C-65, C-66, C-67 at 800 ppm showed at least 75% mortality in comparison with untreated controls.

Example B6: Action on Diamond Back Moth (*Plutella xylostella*)

The active compound is dissolved at the desired concentration in a mixture of 1:1 (v/v) distilled water: acetone. Surfactant (Kinetic® HV) is added at a rate of 0.01% (v/v). The test solution is prepared at the day of use.

Leaves of cabbage were dipped in test solution and air-dried. Treated leaves were placed in petri dishes lined with moist filter paper and inoculated with ten 3rd instar larvae. Mortality was recorded 72 hours after treatment. Feeding damages were also recorded using a scale of 0-100%.

In this test, compounds C-1, C-2, C-3, C-4, C-5, C-6, C-7, C-9, C-10, C-11, C-12, C-13, C-14, C-15, C-16, C-17, C-18, C-19, C-20, C-22, C-23, C-24, C-25, C-26, C-27, C-28, C-29, C-30, C-31, C-32, C-33, C-34, C-35, C-36, C-37, C-38, C-39, C-40, C-41, C-42, C-47, C-50, C-51, C-52, C-53, C-54, C-55, C-56, C-57, C-58, C-59, C-62, C-63, C-64, C-65, C-66, C-67, at 500 ppm showed at least 75% mortality in comparison with untreated controls.

Example B7: Action on Southern Armyworm (*Spodoptera eridania*), 2nd Instar Larvae The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Lima bean plants (variety Sieve) were grown 2 plants to a pot and selected for treatment at the 1st true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, compounds C-1, C-2, C-3, C-4, C-5, C-6, C-10, C-1, C-12, C-13, C-14, C-15, C-16, C-17, C-18, C-19, C-20, C-23, C-24, C-25, C-27, C-28, C-29, C-30, C-31, C-32, C-34, C-35, C-36, C-37, C-38, C-39, C-41, C-42, C-43, C-45, C-47, C-51, C-52, C-53, C-54, C-56, C-62, C-64, C-65, C-66 at 300 ppm showed at least 75% mortality in comparison with untreated controls.

We claim:

1. A compound of formula I (I)

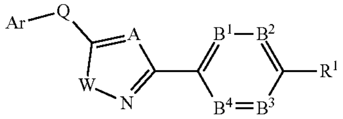

wherein

A is N or $CR^A$;

$B^1$ is N or $CR^{B1}$;

$B^2$ is N or $CR^{B2}$;

$B^3$ is N or $CR^{B3}$;

$B^4$ is N or $CR^{B4}$;

W is O, $S(=O)_m$, or $NR^6$;

$R^A$ is H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxyl-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, or $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, or $R^A$ is C(=O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(=O)—$NR^bR^c$, C(=O)—$R^d$, $SO_2NR^bR^c$, $S(=O)_mR^e$, phenyl, phenoxy, phenylcarbonyl, phenylthiol, or —$CH_2$-phenyl, wherein the phenyl rings are unsubstituted or substituted with $R^f$;

$R^{B1}$, $R^{B2}$, $R^{B3}$, and $R^{B4}$ independently of each other are H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, C1-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, or $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, or $R^{B1}$, $R^{B2}$, $R^{B3}$, and $R^{B4}$ independently of each other are C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$, phenyl, phenoxy, phenylcarbonyl, phenylthiol, or —$CH_2$-phenyl, wherein the phenyl rings are unsubstituted or substituted with $R^f$;

Q is —$C(R^4R^5)$—O—, —C(═O)—O—, —$S(═O)_m$—$C(R^7R^8)$—, —$N(R^2)$—$S(═O)_m$—, —$N(R^2)$—$C(R^9R^{10})$—, —C(═O)—$C(R^{19}R^{20})$—, —$N(R^2)$—C(═O)—, —$N(R^2)$—C(═S)—, —$C(R^{13}R^{14})$—$C(R^{15}R^{16})$—, —N═C(X)—, or —$N(R^2)$—C(═NR)—; wherein Ar is bound to either side of Q;

m is 0, 1, or 2;

X is H, halogen, $SR^7$, $OR^8$, or $N(R^3)_2$;

R is H, CN, $C_1$-$C_6$-alkyl, $C_2$-$C_6$-alkenyl, $C_2$-$C_6$-alkynyl, or $C_3$-$C_6$-cycloalkyl, wherein the alkyl, alkenyl, and cycloalkyl moieties are unsubstituted or substituted with halogen, or R is selected from $OR^8$ or $N(R^3)_2$;

$R^3$ is H, C1-$C_6$-alkyl, or C1-$C_6$-alkoxy-$C_1$-$C_4$-alkyl;

$R^2$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, or $C_3$-$C_6$-cycloalkyl-$C_1$-$C_4$-alkyl, or $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, or $R^2$ is C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, $S(═O)_m$ $R^e$, phenyl, or —$CH_2$-phenyl, wherein the phenyl rings are unsubstituted or substituted with $R^f$;

$R^4$, $R^5$, $R^7$, $R^8$, $R^9$, $R^{10}$, $R^{13}$, $R^{14}$, $R^{15}$, $R^{16}$, $R^{19}$, $R^{20}$ independently of each other are H, halogen, $C_1$-$C_6$-alkyl, $C_2$-$C_6$-alkenyl, $C_2$-$C_6$-alkynyl, $C_1$-$C_6$-alkoxyl-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, or $R^4$, $R^5$, $R^7$, $R^8$, $R^9$, $R^{10}$, $R^{13}$, $R^{14}$, $R^{15}$, $R^{16}$, $R^{19}$, $R^{20}$ independently of each other are C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, $S(═O)_mR^e$, phenyl, or —$CH_2$-phenyl, wherein the phenyl rings are unsubstituted or substituted with $R^f$;

$R^6$ is H, $C_1$-$C_6$-alkyl, $C_2$-$C_6$-alkenyl, $C_2$-$C_6$-alkynyl, $C_1$-$C_6$-alkoxyl-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, or $R^6$ is C(═O)—$OR^a$, $C_1$-$C_6$-alkylene-$NR^bR^c$, $C_1$-$C_5$-alkylene-CN, C(═O)—$NR^bR^c$, C(═O)—$R^d$, $SO_2NR^bR^c$, or $S(═O)_m$ $R^e$, phenyl, —$CH_2$—C(═O)—$OR^a$, or —$CH_2$-phenyl, wherein the phenyl rings are unsubstituted or substituted with $R^f$;

Ar is phenyl or 5- or 6-membered hetaryl, which are unsubstituted or substituted with $R^A$r, wherein $R^{Ar}$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxyl-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, or $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $R^{Ar}$ is C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$, phenyl, phenoxy, phenylcarbonyl, phenylthio or —$CH_2$-phenyl, wherein the phenyl rings are unsubstituted or substituted with $R^f$;

$R^1$ is a moiety selected from the group consisting of YZT-1 to YZT-8, wherein

denotes attachment to the 6 membered ring:

YZT-1

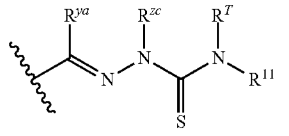

YZT-2

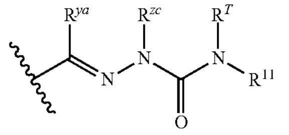

YZT-3

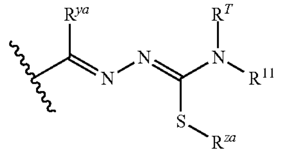

YZT-4

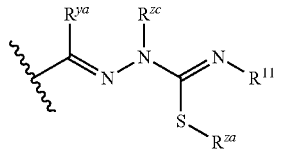

YZT-5

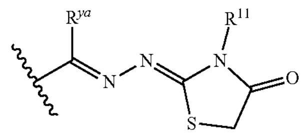

-continued

YZT-6

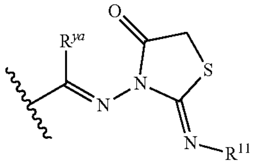

YZT-7

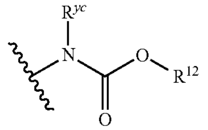

YZT-8

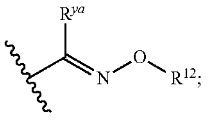

$R^{11}$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, or $R^{11}$ is $C_1$-$C_6$-alkylene-$NR^bR^c$, $C_1$-$C_6$-alkylene-CN, C(═O)—$NR^bR^c$, C(═O)—$R^d$, aryl, aryl-carbonyl, aryl-$C_1$-$C_4$-alkyl, aryloxy-$C_1$-$C_4$-alkyl, hetaryl, carbonyl-hetaryl, hetaryl-$C_1$-$C_4$-alkyl or hetaryloxy-$C_1$-$C_4$-alkyl, wherein when the aryl groups are a phenyl, the phenyl groups are unsubstituted or substituted with $R^9$ and wherein the hetaryl is a 5- or 6-membered monocyclic hetaryl or a 8-, 9-, or 10-membered bicyclic hetaryl;

$R^{12}$ is a radical of the formula $A^1$;

($A^1$)

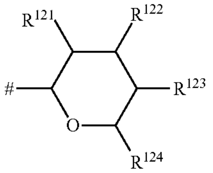

wherein # indicates the point of attachment to the remainder of R1;

$R^{121}$, $R^{122}$, $R^{123}$ independently of each other are H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy, $C_2$-$C_6$-alkenyloxy, $C_2$-$C_6$-alkynyloxy, $C_1$-$C_6$-alkoxy-$C_1$-$C_4$-alkoxy, $C_1$-$C_6$-alkylcarbonyloxy, $C_1$-$C_6$-alkenylcarbonyloxy, or $C_3$-$C_6$-cycloalkylcarbonyloxy, wherein the alkyl, alkoxy, alkenyl, alkenyloxy, alkynyl, alkynyloxy, and cycloalkyl moieties are unsubstituted or substituted with halogen, or $R^{121}$, $R^{122}$, $R^{123}$ independently of each other are $NR^bR^c$, or one of $R^{121}$, $R^{122}$, or $R^{123}$ may be oxo;

$R^{124}$ is H, C1-$C_6$-alkyl, C1-$C_6$-alkoxy-C1-$C_4$-alkyl, C1-$C_6$-alkoxy, or $C_2$-$C_6$-alkenyloxy, wherein the alkyl, alkoxy, alkenyl and alkenyloxy moieties are unsubstituted or substituted with halogen;

and where $R^{ya}$ is H, halogen, $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_1$-$C_4$-alkyl-$C_3$-$C_6$-cycloalkyl, or $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, or wherein $R^{ya}$ is C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, or $S(═O)_mR^e$, phenyl, or —$CH_2$-phenyl, wherein the phenyl rings are unsubstituted or substituted with $R^f$;

$R^{yc}$, $R^{zc}$ are, identical or different, H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, C1-$C_4$-alkyl-$C_3$-$C_6$-cycloalkyl, or C1-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen;

$R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl wherein the alkyl, alkoxy, alkenyl, alkynyl, cycloalkyl and cycloalkoxy moieties are unsubstituted or substituted with halogen, or wherein $R^T$ is C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, or $S(═O)_mR^e$, phenyl, or —$CH_2$-phenyl, wherein the phenyl rings are unsubstituted or substituted with $R^f$;

$R^{zc}$ together with $R^T$ if present, may form $C_1$-$C_6$-alkylene or a linear $C_2$-$C_6$-alkenylene group, where wherein when the $C_1$-$C_6$-alkylene is linear and in the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^{za}$ is H, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkoxy, or $C_1$-$C_4$-alkyl-$C_3$-$C_6$-cycloalkyl, wherein the alkyl, alkoxy, alkenyl, alkynyl, cycloalkyl and cycloalkoxy moieties are unsubstituted or substituted with halogen, or $R^{za}$ is $C_1$-$C_6$-alkylene-$NR^bR^c$, $C_1$-$C_6$-alkylene-CN, C(═O)—$NR^bR^c$, C(═O)—$R^d$, phenyl, phenylcarbonyl, or —$CH_2$-phenyl, wherein the phenyl rings are unsubstituted or substituted with $R^f$;

$R^{za}$ together with $R^T$ if present, may form $C_1$-$C_6$-alkylene or a linear $C_2$-$C_6$-alkenylene group, wherein when the $C_1$-$C_6$-alkylene is linear and in the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^a$, $R^b$, $R^c$ are, identical or different, H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, or $R^a$, $R^b$, $R^c$ are, identical or different, $C_1$-$C_6$-alkylene-CN, phenyl, or —$CH_2$-phenyl, wherein the phenyl rings are unsubstituted or substituted with $R^f$;

$R^d$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, or $R^d$ is phenyl, or —$CH_2$-phenyl, wherein the phenyl rings are unsubstituted or substituted with $R^f$;

$R^e$ is $C_1$-$C_6$-alkyl, $C_3$-$C_6$-cycloalkyl, $C_3$-$C_6$-cycloalkyl-$C_1$-$C_4$-alkyl, wherein the alkyl, and cycloalkyl moieties are unsubstituted or substituted with halogen, or phenyl and —$CH_2$-phenyl, wherein the phenyl rings are unsubstituted or substituted with $R^f$;

$R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxyl-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, or $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, or $R^f$ is C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$;

$R^g$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxyl-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, or $C_3$-$C_6$-cycloalkoxy-$C_1$-$C_4$-alkyl-, wherein the alkyl, alkoxy, alkenyl, alkynyl, cycloalkyl and cycloalkoxy moieties are unsubstituted or substituted with halogen, or $R^g$ is C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(=O)_mR^e$;

$R^h$ is halogen, OH, $C_1$-$C_6$-alkyl, $C_3$-$C_6$-cycloalkyl, or CN;

and N-oxides, stereoisomers, tautomers and agriculturally or veterinarily acceptable salts thereof, wherein the compound tert-butyl-N-[4-(5-[3-(aminocarbonyl)-2,4-difluorophenoxy]methyl-1,2,4-oxadiazol-3-yl)phenyl]carbamate is excluded.

2. The compound of formula I according to claim 1, wherein W is $NR^6$, A is $CR^A$, $B^1$ is $CR^{B1}$, $B^2$ is $CR^{B2}$, $B^3$ is $CR^{B3}$, and $B^4$ is $CR^{B4}$.

3. The compound of formula I according to claim 1, wherein W is O, A is N, $B^1$ is $CR^{B1}$, $B^2$ is $CR^{B2}$, $B^3$ is $CR^{B3}$, and $B^4$ is $CR^{B4}$.

4. The compound of formula I according to claim 1, wherein W is $S(═O)_m$, A is $CR^A$, $B^1$ is N, $B^2$ is $CR^{B2}$, $B^3$ is $CR^{B3}$, $B^4$ is $CR^{B4}$.

5. The compound of formula I according to claim 1, wherein W is $NR^6$, A is $CR^A$, $B^1$ is $CR^{B1}$, $B^2$ is N, $B^3$ is $CR^{B3}$, and $B^4$ is $CR^{B4}$.

6. The compound of formula I according to claim 1, wherein W is $NR^6$, A is $CR^A$, $B^1$ is $CR^{B1}$, $B^2$ is N, $B^3$ is N, and $B^4$ is $CR^{B4}$.

7. The compound of formula I according to claim 1, wherein W is $S(═O)_m$, A is N, $B^1$ is N, $B^2$ is $CR^{B2}$, $B^3$ is $CR^{B3}$, $B^4$ is $CR^{B4}$.

8. The compound of formula I according to claim 1, wherein Ar is a formula Ar-i to Ar-22

Ar-1

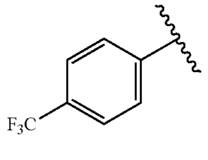

-continued

Ar-2

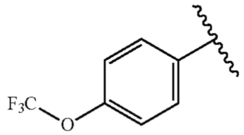

Ar-3

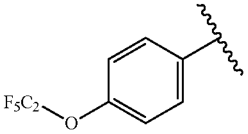

Ar-4

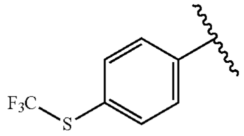

Ar-5

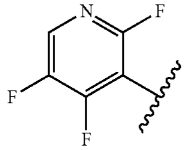

Ar-6

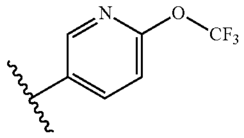

Ar-7

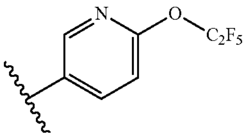

Ar-8

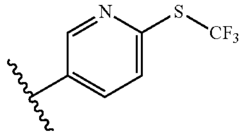

Ar-9

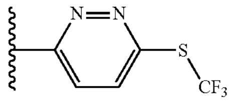

Ar-10

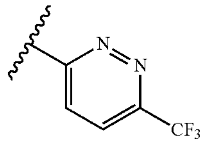

Ar-11

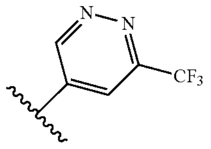

Ar-12

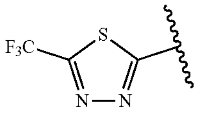

-continued

Ar-13

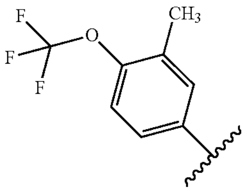

Ar-14

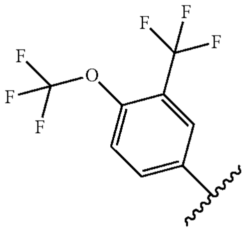

Ar-15

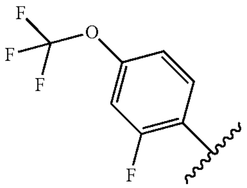

Ar-16

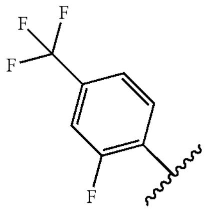

Ar-17

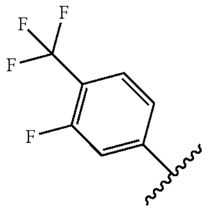

Ar-18

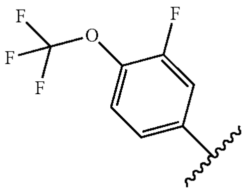

-continued

Ar-19

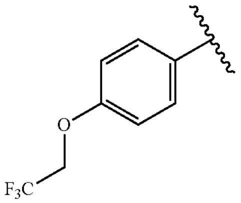

Ar-20

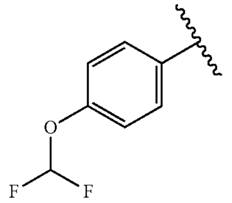

Ar-21

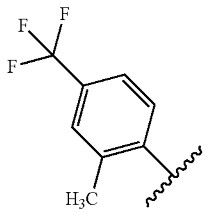

Ar-22

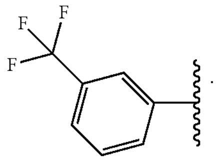

9. A composition comprising at least one compound of formula I according to claim 1, an N-oxide or an agriculturally acceptable salt thereof, and a further active substance.

10. A method for combating or controlling invertebrate pests, comprising contacting said pest or its food supply, habitat or breeding grounds with a pesticidally effective amount of at least one compound according to claim 1.

11. A method for protecting growing plants from attack or infestation by invertebrate pests, comprising contacting the plants, or soil or water wherein the plants are growing, with a pesticidally effective amount of at least one compound according to claim 1.

12. A seed comprising the compound according to claim 1, or enantiomers, diastereomers, or salts thereof in an amount of from 0.1 g to 10 kg per 100 kg of seed.

13. A method for treating or protecting an animal from infestation or infection by invertebrate pests comprising contacting the animal with a pesticidally effective amount of at least one compound of formula I according to claim 1, stereoisomers thereof, and/or veterinarily acceptable salts thereof.

* * * * *